US012004494B2

(12) United States Patent
Rosenthal et al.

(10) Patent No.: US 12,004,494 B2
(45) Date of Patent: Jun. 11, 2024

(54) SIGLEC TRANSGENIC MICE AND METHODS OF USE THEREOF

(71) Applicant: Alector LLC, South San Francisco, CA (US)

(72) Inventors: Arnon Rosenthal, Woodside, CA (US); Seung-Joo Lee, San Francisco, CA (US)

(73) Assignee: ALECTOR LLC, South San Francisco, CA (US)

( * ) Notice: Subject to any disclaimer, the term of this patent is extended or adjusted under 35 U.S.C. 154(b) by 388 days.

(21) Appl. No.: 17/475,116

(22) Filed: Sep. 14, 2021

(65) Prior Publication Data

US 2022/0000083 A1  Jan. 6, 2022

Related U.S. Application Data

(62) Division of application No. 15/836,089, filed on Dec. 8, 2017, now Pat. No. 11,147,249.

(60) Provisional application No. 62/431,661, filed on Dec. 8, 2016.

(51) Int. Cl.
| | | |
|---|---|---|
| *A01K 67/027* | (2024.01) | |
| *A01K 67/0275* | (2024.01) | |
| *A01K 67/0276* | (2024.01) | |
| *C07K 14/705* | (2006.01) | |
| *C12N 15/85* | (2006.01) | |

(52) U.S. Cl.
CPC ...... *A01K 67/0276* (2013.01); *A01K 67/0275* (2013.01); *C07K 14/7056* (2013.01); *C07K 14/70596* (2013.01); *C12N 15/8509* (2013.01); *A01K 2207/15* (2013.01); *A01K 2217/05* (2013.01); *A01K 2217/052* (2013.01); *A01K 2217/07* (2013.01); *A01K 2217/15* (2013.01); *A01K 2227/105* (2013.01); *A01K 2267/01* (2013.01); *A01K 2267/03* (2013.01)

(58) Field of Classification Search
None
See application file for complete search history.

(56) References Cited

U.S. PATENT DOCUMENTS

| | | |
|---|---|---|
| 4,469,863 A | 9/1984 | Ts'o et al. |
| 4,873,191 A | 10/1989 | Wagner et al. |
| 5,175,384 A | 12/1992 | Krimpenfort et al. |
| 5,536,821 A | 7/1996 | Agrawal et al. |
| 5,541,306 A | 7/1996 | Agrawal et al. |
| 5,602,229 A | 2/1997 | Malabarba et al. |
| 5,614,622 A | 3/1997 | Iyer et al. |
| 5,637,683 A | 6/1997 | Usher et al. |
| 5,637,684 A | 6/1997 | Cook et al. |
| 5,700,922 A | 12/1997 | Cook |
| 5,717,083 A | 2/1998 | Cook et al. |
| 5,719,262 A | 2/1998 | Buchardt et al. |
| 5,739,308 A | 4/1998 | Kandimalla et al. |
| 5,739,314 A | 4/1998 | Roy et al. |
| 5,773,601 A | 6/1998 | Agrawal |
| 5,886,165 A | 3/1999 | Kandimalia et al. |
| 5,929,226 A | 7/1999 | Padmapriya et al. |
| 5,955,599 A | 9/1999 | Iyer et al. |
| 5,962,674 A | 10/1999 | Iyer et al. |
| 5,977,296 A | 11/1999 | Nielsen et al. |
| 6,037,521 A | 3/2000 | Sato et al. |
| 6,066,778 A | 5/2000 | Ginsburg et al. |
| 6,117,992 A | 9/2000 | Iyer |
| 6,140,482 A | 10/2000 | Iyer et al. |
| 6,455,308 B1 | 9/2002 | Freier |
| 11,147,249 B2 | 10/2021 | Arnon et al. |
| 2018/0160661 A1 | 6/2018 | Arnon et al. |

FOREIGN PATENT DOCUMENTS

| | | |
|---|---|---|
| WO | WO-1995002697 A1 | 1/1995 |
| WO | WO-1999032619 A1 | 7/1999 |
| WO | WO-2000044895 A1 | 8/2000 |
| WO | WO-2000056746 A2 | 9/2000 |
| WO | WO-2000075372 A1 | 12/2000 |
| WO | WO-2001014398 A1 | 3/2001 |
| WO | WO-2001029058 A1 | 4/2001 |

(Continued)

OTHER PUBLICATIONS

Alphey et aL, "High Resolution Crystal Structures of Siglec-7-Insights into Ligand Specificity in the Siglec Family", The Journal of Biological Chemistry, vol. 278, No. 5, Jan. 31, 2003, pp. 3372-3377.

Ariga et al., "Role of Ganglioside Metabolism in the Pathogenesis of Alzheimer's Disease—A Review", Journal of Lipid Research, vol. 49, 2008, pp. 1157-1175.

Attrill et al., "Siglec-7 Undergoes a Major Conformational Change When Complexed with the a(2,8)-Disialylganglioside GT1b", The Journal of Biological Chemistry, vol. 281, No. 43, Oct. 27, 2006, pp. 32774-32783.

(Continued)

*Primary Examiner* — Michael D Burkhart
(74) *Attorney, Agent, or Firm* — MORRISON & FOERSTER LLP

(57) ABSTRACT

Provided herein are transgenic non-human animals whose genomes comprise two or more human genes selected from CD33, Siglec-5, Siglec-7, Siglec-9, Siglec-11, Siglec-14, and Siglec-16, to methods of screening candidate agents that bind to and/or modulate the function and/or activity of at least one of the human genes in the transgenic non-human animals, and to methods of screening candidate agents to determine their effect on one or more activities and/or functions associated with expression of at least one of the human genes in the transgenic non-human animals. Further provided herein are methods of recapitulating a human Siglec immune system in a non-human animal, and methods of generating a non-human animal disease model comprising a human Siglec repertoire.

22 Claims, 40 Drawing Sheets
(32 of 40 Drawing Sheet(s) Filed in Color)
Specification includes a Sequence Listing.

(56) References Cited

FOREIGN PATENT DOCUMENTS

WO    WO-2001036646 A1    5/2001

OTHER PUBLICATIONS

Beattie et al., "ProNGF Induces p75-Mediated Death of Oligodendrocytes following Spinal Cord Injury", Neuron, vol. 36, No. 3, Oct. 24, 2002, pp. 375-386.
Bennett et al., "New Tools for Studying Microglia in the Mouse and Human CNS", PNAS, vol. 113, No. 12, Feb. 16, 2016, pp. E1738-E1746.
Blesa et al., "Parkinson's Disease: Animal Models and Dopaminergic Cell Vulnerability", Frontiers in Neuroanatomy, vol. 8, No. 155, Dec. 2014, pp. 1-12.
Bradley et al., "Formation of Germ-Line Chimaeras from Embryo-Derived Teratocarcinoma Ce!! Lines", Nature, vol. 309, May 17, 1984, pp. 255-256.
Cowan et al., "Antibody-Based Therapy of Acute Myeloid Leukemia with Gemtuzumab Ozogamicin", Frontiers in Bioscience, vol. 18, Jun. 2013, pp. 1311-1334.
Crocker et aL, "Molecular Analysis of Sialoside Binding to Sialoadhesin by NMR and Site-Directed Mutagenesis", Biochemical Journal, vol. 341, 1999, pp. 355-361.
Crocker et aL, "Siglecs, Sialic Acids and Innate Immunity", Trends in Immunology, vol. 22, No. 6, Jun. 2001, pp. 337-342.
Crocker et al., "Siglecs and Their Roles in the Immune System", Nature Reviews, Immunology, vol. 7, Apr. 2007, pp. 255-266.
Cruts et aL, "Loss of Progranulin Function in Frontotemporal Lobar Degeneration", Trends Genetics, vol. 24, No. 4, 2008, pp. 186-194.
Evans et aL, "Establishment in Culture of Pluripotential Cells from Mouse Embryos", Nature, vol. 292, Jul. 9, 1981, pp. 154-156.
Gordon et aL, "Genetic Transformation of Mouse Embryos by Microinjection of Purified DNA", Proceedings of the National Academy of Sciences, vol. 77, No. 12, Dec. 1980, pp. 7380-7384.
Gossler et aL, "Transgenesis by Means of Blastocyst-Derived Embryonic Stem Cell Lines", Proceedings of the National Academy of Sciences, vol. 83, Dec. 1986, pp. 9065-9069.
Gotz et al., "Animal Models for Alzheimer's Disease and Frontotemporal Dementia: A Perspective", ASN Neuro, vol. 1, No. 4, 2009, pp. 251-264.
Gotz et al., "Animal Models of Alzheimer's Disease and Frontotemporal Dementia", Nature Reviews Neuroscience, vol. 9, Jul. 2008, pp. 532-544.
Green et al., "Antibody engineering via genetic engineering of the mouse: XenoMouse strains are a vehicle for the facile generation of therapeutic human monoclonal antibodies", J Immunol Methods, vol. 231, Issues 1-2, Dec. 10, 1999, pp. 11-23.
Gunten et al., "Basic and Clinical Immunology of Siglecs", Annals of the New York Academy of Sciences, vol. 1143, Nov. 2008, pp. 61-82.
Harrington et al., "Secreted proNGF is a Pathophysiological Death-Inducing Ligand after Adult CNS Injury", PNAS, vol. 101, No. 16, Apr. 20, 2004, pp. 6226-6230.
Hutton et al., "Association of Missense and 5'-Splice-Site Mutations in Tau with the Inherited Dementia FTDP-17", Nature, vol. 393, Jun. 18, 1998, pp. 702-705.
Koson et al., "Truncated Tau Expression Levels Determine Life Span of a Rat Model of Tauopathy without Causing Neuronal Loss or Correlating with Terminal Neurofibriilary Tangle Load", European Journal of Neuroscience, vol. 28, 2008, pp. 239-246.
Laird et al., "Progranulin is Neurotrophic in Vivo and Protects against a Mutant TOP-43 Induced Axonopathy", PLoS One, vol. 5, No. 10, Oct. 2010, pp. 1-7.
Lo, Cecilia W., "Transformation by Iontophoretic Microinjection of DNA: Multiple Integrations without Tandem Insertions", Molecular and Cellular Biology, vol. 3, 1983, pp. 1803-1814.
Luk et aL, "Pathological a-Synuclein Transmission Initiates Parkinson-like Neurodegeneration in Non-transgenic Mice", Science, vol. 338, Nov. 16, 2012, pp. 949-953.
MacAuley et al., "Siglec-Mediated Regulation of Immune Cell Function in Disease", Nature Reviews Immunology, vol. 14, No. 10, Oct. 2014, pp. 653-666.
MacDonald et al., "Precise and in situ genetic humanization of 6 Mb of mouse immunoglobulin genes", Proc Natl Acad Sci USA, vol. 111, Issue 14, Apr. 8, 2014, pp. 5147-5152.
May et al., "Crystal Structure of the N-Terminal Domain of Sialoadhesin in Complex with 3' Sialyllactose at 1.85 A Resolution", Molecular Cell, vol. 1, Apr. 1998, pp. 719-728.
McMillan et al., "CD33-Related Sialic-Acid-Binding Immunoglobulin-Like Lectins in Health and Disease", Carbohydrate Research, vol. 343, 2008, pp. 2050-2056.
Neary et aL, "Frontotemporal Lobar Degeneration: A Consensus on Clinical Diagnostic Criteria", Neurology, vol. 51, Dec. 1998, pp. 1546-1554.
Neumann et al., "TDP-43 Proteinopathy in Frontoternporal Lobar Degeneration and Arnyotrophic Lateral Sclerosis", Arch Neurol., vol. 64, No. 10, Oct. 2007, pp. 1388-1394.
O'Reilly et ai., "Siglecs as Targets for Therapy in Immune Celi Mediated Disease", Trends Pharmacoi Sci., vol. 30, No. 5, May 2009, pp. 240-248.
Philips et a!., "Rodent Models of Arnyotrophic Lateral Sclerosis", Current Protocols in Pharmacology, vol. 69, 2016, pp. 1-26.
Putten et al., "Efficient Insertion of Genes into the Mouse Germ Line via Retroviral Vectors", Proceedings of the National Academy of Sciences USA, vol. 82, 1985, pp. 6148-6152.
Ramaswamy et al., "Animal Models of Huntington's Disease", ILAR Journal, vol. 48, No. 4, 2007, pp. 356-373.
Ratnavalli et al., "The Prevalence of Frontotemporal Dementia", Neurology, vol. 58, 2002, pp. 1615-1621.
Robertson et al., "Germ-Line Transmission of Genes Introduced into Cultured Pluripotential Cells by Retroviral Vector", Nature, vol. 323, Oct. 2, 1986, pp. 445-448.
Schymick et al., "Progranulin Mutations and Amyotrophic Lateral Sclerosis or Amyotrophic Lateral Scierosis-Frontotemporal Dementia Phenotypes", Journal of Neurology, Neurosurgery and Psychiatry, vol. 78, 2007, pp. 754-756.
Svennerholm, Lars, "The Gangliosides", Journal of Lipid Research, vol. 5, 1964, pp. 144-155.
Thompson et al., "Germ Line Transmission and Expression of a Corrected HPRT Gene Produced by Gene Targeting in Embryonic Stem Cells", Cell, vol. 56, Jan. 27, 1989, pp. 313-321.
Varki et al., "Siglecs—The Major Subfamily of I-Type Lectins", Glycobiology, vol. 16, No. 1, 2006, pp. 1R-27R.
Jaenisch, (1988). "Transgenic animals," Science, 240:1468-74. Abstract Only.
Van der Putten et al., (1985). "Efficient insertion of genes into the mouse germ line via retroviral vectors," PNAS, 82:6148-6152.
Von Gunten et al., (2008). "Basic and clinical immunology of Siglecs," Ann NY Acad Sci., 1143:61-82, 25 pages.

FIG. 2

| Receptor | Fluorophore | Cell Type |
|---|---|---|
| Live Cells | Aqua Dye | Exclude Dead Cells |
| mCD3 | PerCp-Cy5.5 | T-cells |
| mCD11b | Pacific Blue | Myeloid |
| mNK1.1 | APC-Cy7 | Natural Killer Cells |
| mLy6G | PE-Cy7 | Neutrophils/G-MDSC |
| mLy6C | Alexa 488 | Mono/Macrophage/Neutrophil/Mo-MDSC |
| hCD33 | APC | Alector BAC-Tg Target Myeloid/MDSC |
| hSiglec-7 or 9 | PE | Alector BAC-Tg Target Myeloid/MDSC |

FIG. 8

| Receptor | Fluorophore | Cell Type |
|---|---|---|
| Live Cells | Aqua Dye | Exclude Dead Cells |
| mCD11b | PerCpCy5.5 | Microglia High |
| mCD45 | PE-Cy7 | Microglia Mid |
| mF4/80 | Pacific Blue | Microglia+ |
| hCD33 | APC | Afector BAC-Tg Target |

FIG. 22

SIGLEC TRANSGENIC MICE AND METHODS OF USE THEREOF

CROSS-REFERENCE TO RELATED APPLICATIONS

This application is a divisional of U.S. application Ser. No. 15/836,089, filed Dec. 8, 2017, which claims the benefit of U.S. Provisional Application No. 62/431,661, filed Dec. 8, 2016, each of which is herein incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 735022001310SEQLIST.TXT, date recorded: Sep. 9, 2021, size 135,153 bytes).

FIELD OF THE INVENTION

The present disclosure relates to transgenic non-human animals whose genomes comprise two or more human genes selected from CD33, Siglec-5, Siglec-7, Siglec-9, Siglec-11, Siglec-14, and Siglec-16, and to uses of such transgenic non-human animals.

BACKGROUND

Sialic acid-binding Ig-like lectinproteins (Siglecs) are type 1, immunoglobulin-like, transmembrane proteins expressed on immune and hematopoietic cells, including immature and mature myeloid cells, such as monocytes, macrophages, dendritic cells, neutrophils, and microglial cells, as well as lymphoid cells, such as natural killer cells, and subsets of T cells (Crocker et al. (2007) Nat Rev Immunol. 7:255-266; O'Reilly and Paulson (2009) Trends in Pharm. Sci. 30:5:240-248; and Macauley et al. (2014) Nat. Rev. Imm 14: 653-666). The Siglec family of lectins binds sialic acid residues of glycoproteins and glycolipids. One potential glycolipid binding target for Siglec proteins is gangliosides; that is, glycolipids that consist of a ceramide linked to a sialylated glycan. Most gangliosides share a common lacto-ceramide core and one or more sialic acid residues. Diversity in the Siglec ligands is generated by the addition of other neutral sugars and sialic acid in different linkages, either branched or terminal, and modification of sialic acid itself.

Fourteen Siglec proteins have been identified in humans and nine in mice that are comprised of 2-17 extracellular Ig domains including an amino-terminal V-set domain that contains the sialic acid-binding site. These include CD33 (also known as Siglec-3), Siglec-5, Siglec-7, Siglec-9, and Siglec-11. These proteins have been implicated in immune system function in health and disease. The sialic acid-binding region is located on the V-set Ig-like domain, which contains a two aromatic residues and one arginine motif highly conserved in all Siglecs (Crocker et al. (2007) Nat Rev Immunol. 7:255-266; McMillan and Crocker (2008) Carbohydr Res. 343:2050-2056; Von Gunten and Bochner (2008) Ann NY Acad Sci. 1143:61-82; May et al. (1998) Mol Cell. 1:719-728; Crocker et al. (1999) Biochem J. 341:355-361; and Crocker and Varki (2001) Trends Immunol. 2:337-342). The binding sites to sialylated ligands have been mapped by crystal structures with and without ligand bound (Attrill et al., (2006) J. Biol. Chem. 281 32774-32783; Alphey et al. (2003) J. Biol. Chem. 278:5 3372-3377; Varki et al., Glycobiology, 16 pp. 1R-27R; and May et al. (1998) Mol. Cell 1:5:719-728). Since cell membranes are rich in sialic acids, ligand binding by Siglecs can occur in cis and in trans, both affecting their functional properties. Each Siglec has a distinct preference for binding the diverse types of sialylated glycans that are found on the surface of mammalian cells (Crocker et al. (2007) Nat Rev Immunol. 7:255-266; and Crocker et al. (2007) Nat Rev Immunol. 7:255-266). Most Siglec proteins, including CD33, Siglec-7 and Siglec-9, contain one or more immunoreceptor tyrosine-based inhibitory motif (ITIM) sequences in their cytoplasmic tails, which enable them as inhibitory receptors and negative regulators of immune functions through recruitment of the tyrosine phosphatases SHP1 and SHP2 (Crocker et al. (2007) Nat Rev Immunol. 7:255-266; McMillan and Crocker (2008) Carbohydr Res. 343:2050-2056; and Von Gunten and Bochner (2008) Ann NY Acad Sci. 1143:61-82). Certain Siglecs contain immunoreceptor tyrosine-based activating motif (ITAM) sequences in their cytoplasmic tails, which enable them to act as activating receptors and positive regulators of immune function through predicted recruitment of spleen tyrosine kinase (Syk) (Macauley S M. et al., (2014) *Nature Reviews Immunology* 14, 653-666). The Siglec protein family is associated with multiple human diseases including, autoimmunity, susceptibility to infection, multiple types of cancer including lymphoma, leukemia and acute myeloid leukemia, systemic lupus erythematosus, rheumatoid arthritis, neurodegenerative disorders, asthma, allergy, sepsis, chronic obstructive pulmonary disease, graft-versus-host disease, eosinophilia, and osteoporosis (Macauley S M. et al., (2014) *Nature Reviews Immunology* 14, 653-666).

Genome-wide association studies (GWAS) performed on extended cohorts (e.g., thousands of individuals) identified two single nucleotide polymorphism (SNP) variants, rs3865444$^C$ (also known as rs3826656) and rs3865444$^A$, in CD33 as genetic modulators of risk for late onset Alzheimer's disease (AD). The minor allele rs3865444$^A$ SNP has been associated with significantly reduced CD33 protein levels and was reported to confer protection against AD. In contrast, the rs3865444$^C$ risk allele has been associated with a 7-fold increase in cell surface expression of CD33 in the monocytes of young and older individuals homozygous for this allele, while the heterozygous carriers of the rs3865444$^{AC}$ variant displayed a 3-4 fold increase in CD33 cell surface expression. CD33 is also expressed at all three stages of activation in microglia and macrophages in the human brain, but there is no effect of age on CD33 surface expression. rs3865444$^C$ homozygosity and heterozygosity were also associated with reduced phagocytic ability of monocyte internalization of amyloid beta 42 (Abeta 42) peptide, accumulation of neuritic amyloid pathology and fibrillar amyloid on in vivo imaging, and increased numbers of activated human microglia that may be less functional and fail to clear amyloid beta plaques, indicating that the rs3865444$^C$ allele may be dominant for functional traits and have a role in amyloid accumulation in the presymptomatic phase of Alzheimer's disease (AD). CD33 mRNA and protein levels as well as the number of CD33-positive microglia were shown to increase in AD brains relative to age-matched controls. However, AD brains from carriers of the rs3865444$^{AA}$ allele of the CD33 SNP rs3865444, were still associated with lower levels of both CD33 microglial expression and the levels of insoluble Abeta 42 peptide compared to AD brains from carrier of the rs3865444$^C$ non-protective allele. Increased number of CD33-immunoreactive microglia was shown to be positively correlated with insoluble Abeta 42 levels and the amyloid plaque burden in AD cases.

While Siglec proteins, including CD33, are known to be associated with multiple human diseases, in vivo study of these proteins, and their potential roles in human disease, remains challenging as no suitable animal model for studying human Siglecs has been developed. A major limitation in developing animal models useful for the study of in vivo Siglec protein functions is that mammalian Siglecs, such as CD33, are highly divergent evolutionarily. This high evolutionary divergence observed between mammalian Siglecs indicates that key features of the human Siglecs, such as ITIM and ligand binding domains, may not be structurally conserved. Moreover, expression patterns and protein-protein interactions of the human Siglecs, including physical associations among Siglec proteins, may not be conserved in other mammalian species. Due to the high likelihood of both structural and functional differences in mammalian Siglec proteins, indicated by low evolutionary conservation of these proteins across mammalian species, current animal models are unsuitable proxies for the in vivo study of the functions and interactions of human Siglec proteins, as well as their role in human diseases.

All references cited herein, including patent applications, patent publications, and non-patent literature are herein incorporated by reference in their entirety, as if each individual reference were specifically and individually indicated to be incorporated by reference.

BRIEF SUMMARY

There is a need for suitable animal models useful for the in vivo study of human Siglec protein functions, including animal models coordinately expressing multiple human Siglec proteins in relevant cell types. Additionally, there is a need for animal models suitable for testing candidate agents targeting human Siglec proteins in vivo, and for animal disease models which express some or all of the human Siglec genes to study the association of various human Siglec proteins and disease (e.g., Alzheimer's disease and cancer). Accordingly, the present disclosure relates, in part, to transgenic non-human animals (e.g., mice) harboring multiple human Siglec genes which effectively express human Siglec proteins in myeloid and/or natural killer (NK) cell lineages. These transgenic animals are useful for the investigation and establishment of functional and pathological properties of human Siglec genes in vivo, and to the development of therapeutics that target human Siglec genes and their products. The present disclosure is based, in part, on the surprising finding that transgenic animals were generated that coordinately expressed multiple human Siglec proteins (See e.g., Examples 1 and 2), and further, that expression of these Siglec proteins in the transgenic animals at least partially recapitulated the highly coordinated expression pattern of these proteins observed with the relevant corresponding human cells (See e.g., Examples 2 and 3).

Accordingly, certain aspects of the present disclosure relate to a transgenic non-human animal whose genome comprises two or more human genes, wherein the two or more human genes are selected from the group consisting of CD33, Siglec-5, Siglec-7, Siglec-9, Siglec-11, Siglec-14, and Siglec-16, wherein the two or more human genes are expressed in one or more cells of the transgenic non-human animal, and wherein the one of more cells selected from the group consisting of myeloid cells, natural killer (NK) cells, T cells, microglia, and any combination thereof.

In some embodiments that may be combined with any of the preceding embodiments, the transgenic non-human animal is a rodent. In some embodiments that may be combined with any of the preceding embodiments, the transgenic non-human animal is a mouse. In some embodiments that may be combined with any of the preceding embodiments, the genome comprises the human genes Siglec-5 and Siglec-14. In some embodiments that may be combined with any of the preceding embodiments, the genome comprises the human genes Siglec-11 and Siglec-16. In some embodiments that may be combined with any of the preceding embodiments, the genome comprises at least three human genes. In some embodiments that may be combined with any of the preceding embodiments, the genome comprises the human genes CD33, Siglec-7, and Siglec-9. In some embodiments that may be combined with any of the preceding embodiments, the genome comprises the human genes CD33, Siglec-5, Siglec-7, Siglec-9, Siglec-11, Siglec-14, and Siglec-16. In some embodiments that may be combined with any of the preceding embodiments, one or more of the human genes comprise all intronic and exonic sequences of the one or more genes. In some embodiments that may be combined with any of the preceding embodiments, one or more of the human genes comprise at least one flanking sequence at the 5' and/or 3' end of the one or more genes. In some embodiments that may be combined with any of the preceding embodiments, the flanking sequence is at least 10,000 base pairs in length. In some embodiments that may be combined with any of the preceding embodiments, the flanking sequence comprises one or more human transcriptional regulatory elements. In some embodiments that may be combined with any of the preceding embodiments, the one or more human transcriptional regulatory elements directs expression of one or more of the human CD33, Siglec-5, Siglec-7, Siglec-9, Siglec-11, Siglec-14, and/or Siglec-16 genes. In some embodiments that may be combined with any of the preceding embodiments, the one or more human transcriptional regulatory elements directs coordinate expression of at least two of the human CD33, Siglec-5, Siglec-7, Siglec-9, Siglec-11, Siglec-14, and/or Siglec-16 genes. In some embodiments that may be combined with any of the preceding embodiments, the human CD33 gene encodes a polypeptide at least 95% identical to a polypeptide encoded by the nucleic acid sequence of SEQ ID NO: 15. In some embodiments that may be combined with any of the preceding embodiments, the human CD33 gene encodes a polypeptide at least 95% identical to a sequence selected from the group consisting of SEQ ID NOS: 1-3. In some embodiments that may be combined with any of the preceding embodiments, the human CD33 gene comprises one or more single nucleotide polymorphisms (SNPs) selected from the group consisting of: (a) SNP rs3865444$^{AC}$; (b) SNP rs3865444$^{CC}$; (c) SNP rs3865444$^{AA}$; (d) SNP rs35112940$^{GG,\ AA,\ AG}$; (e) SNP rs12459419$^{CC,\ CT\ or\ TT}$; and (f) any combination thereof. In some embodiments that may be combined with any of the preceding embodiments, the human Siglec-5 gene encodes a polypeptide at least 95% identical to a polypeptide encoded by the nucleic acid sequence of SEQ ID NO: 16. In some embodiments that may be combined with any of the preceding embodiments, the human Siglec-5 gene encodes a polypeptide at least 95% identical to SEQ ID NO: 4. In some embodiments that may be combined with any of the preceding embodiments, the human Siglec-7 gene encodes a polypeptide at least 95% identical to a polypeptide encoded by the nucleic acid sequence of SEQ ID NO: 17. In some embodiments that may be combined with any of the preceding embodiments, the human Siglec-7 gene encodes a polypeptide at least 95% identical to a sequence selected from the group consisting of SEQ ID NOS: 5-8. In some embodiments that may be combined with any of the preceding embodiments, the human Siglec-9 gene encodes a polypeptide at least 95% identical to a polypeptide encoded by the nucleic acid sequence of SEQ ID NO: 18. In some embodiments that may be combined with any of the preceding embodiments, the human Siglec-9 gene encodes a polypeptide at least 95% identical to SEQ ID NO: 9 or SEQ ID NO: 10. In some embodiments that may be combined with any of the preceding embodiments, the human Siglec-11 encodes a polypeptide at least 95% identical to a polypeptide encoded by the nucleic acid sequence of SEQ ID NO: 19. In some embodiments that may be combined with any of the preceding embodiments, the human Siglec-11 gene encodes a polypeptide at least 95% identical to SEQ ID NO: 11 or SEQ ID NO: 12. In some embodiments that may be combined with any of the preceding embodiments, the human Siglec-14 gene encodes a polypeptide at least 95% identical to a polypeptide encoded by the nucleic acid sequence of SEQ ID NO: 20. In some embodiments that may be combined with any of the preceding embodiments, the human Siglec-14 gene encodes a polypeptide at least 95% identical to SEQ ID NO: 13. In some embodiments that may be combined with any of the preceding embodiments, the human Siglec-16 gene encodes a polypeptide at least 95% identical to a polypeptide encoded by the nucleic acid sequence of SEQ ID NO: 21. In some embodiments that may be combined with any of the preceding embodiments, the human Siglec-16 gene encodes a polypeptide at least 95% identical to SEQ ID NO: 14. In some embodiments that may be combined with any of the preceding embodiments, the myeloid cells are selected from the group consisting of myeloid-derived suppressor cells, granulocyte-like myeloid-derived suppressor cells, monocyte-like myeloid-derived suppressor cells, monocytes, macrophages, bone marrow-derived macrophages, M1 macrophages, activated M1 macrophages, M2 macrophages, neutrophils, M1 neutrophils, activated M1 neutrophils, M2 neutrophils, basophils, eosinophils, erythrocytes, dendritic cells, bone marrow-derived dendritic cells, megakaryocytes, and any combination thereof. In some embodiments that may be combined with any of the preceding embodiments, the NK cells are selected from the group consisting of M1 NK cells, activated M1 NK cells, M2 NK cells, and any combination thereof. In some embodiments that may be combined with any of the preceding embodiments, the T cells are selected from the group consisting of T helper cells, cytotoxic T cells, regulatory T cells (Tregs), and any combination thereof. In some embodiments that may be combined with any of the preceding embodiments, the microglia are selected from the group consisting of brain microglial, M1 microglia, activated M1 microglia, M2 microglia, and any combination thereof. In some embodiments that may be combined with any of the preceding embodiments, expression of the two or more human genes in the one or more cells of the transgenic non-human animal recapitulates the expression pattern of the two or more human genes in a corresponding human cell. In some embodiments that may be combined with any of the preceding embodiments, the one or more cells of the transgenic non-human animal are one or more cells selected from the group consisting of monocytes, macrophages, dendritic cells, and microglia. In some embodiments that may be combined with any of the preceding embodiments, the corresponding human cell is a human cell selected from the group consisting of a monocyte, a macrophage, a dendritic cell, and a microglial cell. In some embodiments that may be combined with any of the preceding embodiments, the two or more human genes are co-expressed. In some embodiments that may be combined with any of the preceding embodiments, co-expression of the two or more human genes suppresses one or more myeloid immune cell functions. In some embodiments that may be combined with any of the preceding embodiments, the one or more myeloid immune cell functions are selected from the group consisting of: (a) phagocytosis; (b) antigen presentation; (c) immune cell recruitment; (d) immune cell maturation, migration, proliferation, differentiation, and/or survival; (e) modulation of adaptive immune cells such as B cells and T cells; (f) expression and/or secretion of one or more cytokines and/or chemokines; (g) tumor infiltration, tumor cell recognition, and/or tumor cell killing; (h) releasing granules (degranulation) or neutrophil extracellular traps (NETs); (i) anti-parasitic activities; (j) bactericidal activities; (k) clearance of cellular debris and/or protein aggregates; and (1) any combination thereof. In some embodiments that may be combined with any of the preceding embodiments, expression of the two or more human genes humanizes the Siglec repertoire on the one or more cells of the transgenic non-human animal. In some embodiments that may be combined with any of the preceding embodiments, the mouse comprises a genome comprising one or more non-functional murine genes, wherein the one or more non-functional murine genes are selected from the group consisting of murine CD33, murine Siglec-5, murine Siglec-7, murine Siglec-9, murine Siglec-11, and any combination thereof. In some embodiments that may be combined with any of the preceding embodiments, the mouse comprises a genome comprising a non-functional murine CD33 gene, a non-functional murine Siglec-5 gene, a non-functional murine Siglec-7 gene, a non-functional murine Siglec-9 gene, and a non-functional murine Siglec-11 gene. In some embodiments that may be combined with any of the preceding embodiments, the transgenic non-human animal is predisposed to develop one or more diseases. In some embodiments that may be combined with any of the preceding embodiments, the transgenic non-human animal is treated or interbred to generate one or more animal disease models. In some embodiments that may be combined with any of the preceding embodiments, the one or more diseases are selected from the group consisting of neurodegenerative diseases, immune-related diseases, infectious diseases, and proliferative disorders. In some embodiments that may be combined with any of the preceding embodiments, the neurodegenerative diseases are one or more diseases selected from the group consisting of dementia, frontotemporal dementia (FTD), Alzheimer's disease, Parkinson's disease, amyotrophic lateral sclerosis (ALS), Huntington's disease, taupathy disease, and multiple sclerosis. In some embodiments that may be combined with any of the preceding embodiments, the disease is Alzheimer's disease.

Other aspects of the present disclosure relate to a method of screening candidate agents, the method comprising i) administering one or more candidate agents to a transgenic non-human animal, wherein the genome of the transgenic non-human animal comprises two or more human genes, wherein the two or more human genes are selected from the group consisting of CD33, Siglec-5, Siglec-7, Siglec-9, Siglec-11, Siglec-14, and Siglec-16, wherein the two or more human genes are expressed in one or more cells of the transgenic non-human animal, and wherein the one of more cells selected from the group consisting of myeloid cells, natural killer (NK) cells, T cells, microglia, and any combination thereof; and ii) determining whether the one or more candidate agents bind to and/or modulates the function and/or activity of at least one of the two or more human genes in the transgenic non-human animal.

Other aspects of the present disclosure relate to a method of screening candidate agents, the method comprising i) administering one or more candidate agents to a transgenic non-human animal, wherein the genome of the transgenic non-human animal comprises two or more human genes, wherein the two or more human genes are selected from the group consisting of CD33, Siglec-5, Siglec-7, Siglec-9, Siglec-11, Siglec-14, and Siglec-16, wherein the two or more human genes are expressed in one or more cells of the transgenic non-human animal, and wherein the one of more cells selected from the group consisting of myeloid cells, natural killer (NK) cells, T cells, microglia, and any combination thereof; and ii) determining the effect of the one or more candidate agents on one or more activities and/or functions associated with the expression of at least one of the two or more human genes in the transgenic non-human animal.

In some embodiments that may be combined with any of the preceding embodiments, the candidate agent inhibits one or more activities and/or functions associated with the expression of human CD33, human Siglec-5, human Siglec-7, human Siglec-9, human Siglec-11, human Siglec-14, and/or human Siglec-16 genes in the transgenic non-human animal. In some embodiments that may be combined with any of the preceding embodiments, the one or more candidate agents are two or more candidate agents. In some embodiments that may be combined with any of the preceding embodiments, the two or more candidate agents target two or more of the human genes. In some embodiments that may be combined with any of the preceding embodiments, each of the two or more candidate agents targets a human gene selected from the group consisting of CD33, Siglec-5, Siglec-7, Siglec-9, Siglec-11, Siglec-14, and Siglec-16, and wherein each of the two or more candidate agents targets a different human gene. In some embodiments that may be combined with any of the preceding embodiments, the one or more activities and/or functions associated with expression of the two or more human genes are selected from the group consisting of: (a) immune cell suppression; (b) decreased expression of one or more pro-inflammatory cytokines, optionally wherein the one or more pro-inflammatory cytokines are selected from a group consisting IFN-α4, IFN-beta, IL-113, IL-1alpha, TNF-α, IL-6, IL-8, CRP, IL-20 family members, LIF, IFN-gamma, OSM, CNTF, GM-CSF, IL-11, IL-12, IL-17, IL-18, CRP, MCP-1, and MIP-1-beta; (c) decreased expression of one or more pro-inflammatory cytokines in one or more cells selected from the group consisting of macrophages, neutrophils, NK cells, dendritic cells, bone marrow-derived dendritic cells, monocytes, osteoclasts, T cells, T helper cells, cytotoxic T cells, granulocytes, and microglial cells; (d) increased expression of one or more anti-inflammatory cytokines, optionally wherein the one or more anti-inflammatory cytokines are selected from the group consisting of IL4, IL10, IL13, IL35, IL16, TGF-beta, IL1ra, G-CSF, and soluble receptors for TNF, IFN-beta1a, IFN-beta1b, and IL6; (e) increased expression of one or more anti-inflammatory cytokines in one or more cells selected from the group consisting of macrophages, neutrophils, NK cells, dendritic cells, bone marrow-derived dendritic cells, monocytes, osteoclasts, T cells, T helper cells, cytotoxic T cells, granulocytes, and microglial cells; (f) inhibition of extracellular signal-regulated kinase (ERK) phosphorylation; (g) decreasing tyrosine phosphorylation on one or more cellular proteins, optionally, wherein the one or more cellular proteins comprise ZAP-70 and the tyrosine phosphorylation occurs on Tyr-319 of ZAP-70; (h) decreased expression of C—C chemokine receptor 7 (CCR7); (i) inhibition of microglial cell chemotaxis toward CCL19-expressing and CCL21-expressing cells; (j) decreasing T cell proliferation induced by one or more cells selected from the group consisting of dendritic cells, bone marrow-derived dendritic cells, monocytes, microglia, M1 microglia, activated M1 microglia, M2 microglia, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, and M2 NK cells; (k) inhibition of osteoclast production, decreased rate of osteoclastogenesis, or both; (l) decreasing survival of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; (m) decreasing proliferation of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; (n) inhibiting migration of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; (o) inhibiting one or more functions of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; (p) inhibiting maturation of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; (q) inhibition of one or more types of clearance selected from the group consisting of apoptotic neuron clearance, nerve tissue debris clearance, non-nerve tissue debris clearance, bacteria clearance, other foreign body clearance, disease-causing protein clearance, disease-causing peptide clearance, and tumor cell clearance; optionally wherein the disease-causing protein is selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides and the tumor cell is from a cancer selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer; (r) inhibition of phagocytosis of one or more of apoptotic neurons, nerve tissue debris, non-nerve tissue debris, bacteria, other foreign bodies, disease-causing proteins, disease-causing peptides, disease-causing nucleic acids, or tumor cells; optionally wherein the disease-causing nucleic acids are antisense GGCCCC (G2C4) repeat-expansion RNA, the disease-causing proteins are selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and the tumor cells are from a cancer selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, or thyroid cancer; (s) inhibition of tumor cell killing by one or more of microglia, macrophages, neutrophils, NK cells, dendritic cells, bone marrow-derived dendritic cells, neutrophils, T cells, T helper cells, or cytotoxic T cells; (t) inhibiting anti-tumor cell proliferation activity of one or more of microglia, macrophages, neutrophils, NK cells, dendritic cells, bone marrow-derived dendritic cells, neutrophils, T cells, T helper cells, or cytotoxic T cells; (u) inhibition of anti-tumor cell metastasis activity of one or more of microglia, macrophages, neutrophils, NK cells, dendritic cells, bone marrow-derived dendritic cells, neutrophils, T cells, T helper cells, or cytotoxic T cells; (v) inhibition of one or more ITAM motif containing receptors, optionally wherein the one or more ITAM motif containing receptors are selected from the group consisting of TREM1, TREM2, Sirp beta, FcgR, DAP10, and DAP12; (w) inhibition of signaling by one or more pattern recognition receptors (PRRs), optionally wherein the one or more PRRs are selected from the group consisting of receptors that identify pathogen-associated molecular patterns (PAMPs), receptors that identify damage-associated molecular patterns (DAMPs), and any combination thereof; (x) inhibition of one or more receptors comprising the motif $D/Ex_{0-2}YxxL/IX_{6-8}YxxL/I$ (SEQ ID NO: 22); (y) inhibition of signaling by one or more Toll-like receptors; (z) inhibition of the JAK-STAT signaling pathway; (aa) inhibition of nuclear factor kappa-light-chain-enhancer of activated B cells (NFκB); (bb) de-phosphorylation of an ITAM motif containing receptor; (cc) decreased expression of one or more inflammatory receptors, optionally wherein the one or more inflammatory receptors comprise CD86 and the one or more inflammatory receptors are expressed on one or more of microglia, macrophages, neutrophils, NK cells, dendritic cells, bone marrow-derived dendritic cells, neutrophils, T cells, T helper cells, or cytotoxic T cells; (dd) decreasing expression of one or more ITAM-dependent genes, optionally wherein the one more ITAM-dependent genes are activated by nuclear factor of activated T cells (NFAT) transcription factors; (ee) promoting differentiation of one or more of immunosuppressor dendritic cells, immunosuppressor macrophages, immunosuppressor neutrophils, immunosuppressor NK cells, myeloid derived suppressor cells, tumor-associated macrophages, tumor-associated neutrophils, tumor-associated NK cells, and regulatory T cells; (ff) rescuing functionality of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells; (gg) increasing infiltration of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells into tumors; (hh) increasing the number of tumor-promoting myeloid/granulocytic immune-suppressive cells in a tumor, in peripheral blood, or other lymphoid organ; (ii) enhancing tumor-promoting activity of myeloid-derived suppressor cells; (jj) increasing expression of tumor-promoting cytokines in a tumor or in peripheral blood, optionally wherein the tumor-promoting cytokines are TGF-beta or IL-10; (kk) increasing tumor infiltration of tumor-promoting FoxP3+ regulatory T lymphocytes; (ll) enhancing tumor-promoting activity of myeloid-derived suppressor cells (MDSC); (mm) decreasing activation of tumor-specific T lymphocytes with tumor killing potential; (nn) decreasing infiltration of tumor-specific NK cells with tumor killing potential; (oo) decreasing the tumor killing potential of NK cells; (pp) decreasing infiltration of tumor-specific B lymphocytes with potential to enhance immune response; (qq) decreasing infiltration of tumor-specific T lymphocytes with tumor killing potential; (rr) increasing tumor volume; (ss) increasing tumor growth rate; (tt) increasing metastasis; (uu) increasing rate of tumor recurrence; (vv) decreasing efficacy of one or more immune-therapies that modulate anti-tumor T cell responses, optionally wherein the one or more immune-therapies are immune-therapies that target one or more target proteins selected from the group consisting of PD1/PDLL, CTLA4, CD40, OX40, ICOS, CD28, CD137/4-1BB, CD27, GITR, PD-L1, CTLA4, PD-L2, PD-1, B7-H3, B7-H4, HVEM, BTLA, KIR, GALS, TIM3, A2AR, LAG, DR-5, and any combination thereof, or cancer vaccines; (ww) inhibition of PLCγ/PKC/calcium mobilization; (xx) inhibition of PI3K/Akt, Ras/MAPK signaling; and (yy) any combination thereof. In some embodiments that may be combined with any of the preceding embodiments, the transgenic non-human animal suffers from a disease, disorder, and/or injury. In some embodiments that may be combined with any of the preceding embodiments, administering the one or more candidate agents reduces or eliminates one or more signs and/or symptoms of the disease, disorder, and/or injury. In some embodiments that may be combined with any of the preceding embodiments, the disease, disorder, and/or injury is one or more of autoimmunity, susceptibility to infection, cancer, proliferative disorders, and neurodegenerative disorders. In some embodiments that may be combined with any of the preceding embodiments, the disease, disorder, and/or injury is one or more of dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV infection, and *Haemophilus influenza* infection. In some embodiments that may be combined with any of the preceding embodiments, the effect of the one or more candidate agents is selected from the group consisting of: (a) reducing cell surface levels of one or more polypeptides encoded by the human CD33, Siglec-5, Siglec-7, Siglec-9, Siglec-11, Siglec-14, or Siglec-16 genes; (b) competing for binding with a natural ligand of one or more polypeptides encoded by the human CD33, Siglec-5, Siglec-7, Siglec-9, Siglec-11, Siglec-14, or Siglec-16 genes; (c) reducing T cell proliferation and/or phagocytosis; (d) increasing the survival of macrophages, neutrophils, NK cells, and/or dendritic cells; (e) inducing CCR7 and/or F-actin in microglia, macrophages, neutrophils, NK cells, and/or dendritic cells; (f) increasing expression of one or more inflammatory cell surface markers on macrophages, neutrophils, and/or NK cells; (g) suppressing myeloid-derived suppressor cell (MDSC) proliferation, activation, and/or function; (h) reducing IL-10 secretion from one or more myeloid cells; (i) inducing SYK and/or ERK activation and/or phosphorylation; and (j) any combination thereof. In some embodiments that may be combined with any of the preceding embodiments, the transgenic non-human animal is a rodent. In some embodiments that may be combined with any of the preceding embodiments, the transgenic non-human animal is a mouse. In some embodiments that may be combined with any of the preceding embodiments, the genome comprises the human genes Siglec-5 and Siglec-14. In some embodiments that may be combined with any of the preceding embodiments, the genome comprises the human genes Siglec-11 and Siglec-16. In some embodiments that may be combined with any of the preceding embodiments, the genome comprises three or more human genes. In some embodiments that may be combined with any of the preceding embodiments, the genome comprises the human genes CD33, Siglec-7, and Siglec-9. In some embodiments that may be combined with any of the preceding embodiments, the genome comprises the human genes CD33, Siglec-5, Siglec-7, Siglec-9, Siglec-11, Siglec-14, and Siglec-16. In some embodiments that may be combined with any of the preceding embodiments, one or more of the human genes comprise all intronic and exonic sequences of the one or more genes. In some embodiments that may be combined with any of the preceding embodiments, one or more of the human genes comprise at least one flanking sequence at the 5' and/or 3' end of the one or more genes. In some embodiments that may be combined with any of the preceding embodiments, the flanking sequence is at least 10,000 base pairs in length. In some embodiments that may be combined with any of the preceding embodiments, the flanking sequence comprises one or more human transcriptional regulatory elements. In some embodiments that may be combined with any of the preceding embodiments, the one or more human transcriptional regulatory elements direct expression of one or more of human CD33, Siglec-5, Siglec-7, Siglec-9, Siglec-11, Siglec-14, and/or Siglec-16 genes. In some embodiments that may be combined with any of the preceding embodiments, the one or more human transcriptional regulatory elements direct coordinate expression of two or more of human CD33, Siglec-5, Siglec-7, Siglec-9, Siglec-11, Siglec-14, and/or Siglec-16 genes. In some embodiments that may be combined with any of the preceding embodiments, the human CD33 encodes a polypeptide at least 95% identical to a polypeptide encoded by the nucleic acid sequence of SEQ ID NO: 15. In some embodiments that may be combined with any of the preceding embodiments, the human CD33 gene encodes a polypeptide at least 95% identical to a sequence selected from the group consisting of SEQ ID NOS: 1-3. In some embodiments that may be combined with any of the preceding embodiments, the human CD33 gene comprises one or more single nucleotide polymorphisms (SNPs) selected from the group consisting of: (a) SNP rs3865444$^{AC}$; (b) SNP rs3865444$^{CC}$; (c) SNP rs3865444$^{AA}$; (d) SNP rs35112940$^{GG,\ AA,\ AG}$; (e) SNP rs12459419$^{CC,\ CT\ or\ TT}$; and (f) any combination thereof. In some embodiments that may be combined with any of the preceding embodiments, the human Siglec-5 gene encodes a polypeptide at least 95% identical to a polypeptide encoded by the nucleic acid sequence of SEQ ID NO: 16. In some embodiments that may be combined with any of the preceding embodiments, the human Siglec-5 gene encodes a polypeptide at least 95% identical to SEQ ID NO: 4. In some embodiments that may be combined with any of the preceding embodiments, the human Siglec-7 gene encodes a polypeptide at least 95% identical to a polypeptide encoded by the nucleic acid sequence of SEQ ID NO: 17. In some embodiments that may be combined with any of the preceding embodiments, the human Siglec-7 gene encodes a polypeptide at least 95% identical to a sequence selected from the group consisting of SEQ ID NOS: 5-8. In some embodiments that may be combined with any of the preceding embodiments, the human Siglec-9 gene encodes a polypeptide at least 95% identical to a polypeptide encoded by the nucleic acid sequence of SEQ ID NO: 18. In some embodiments that may be combined with any of the preceding embodiments, the human Siglec-9 gene encodes a polypeptide at least 95% identical to SEQ ID NO: 9 or SEQ ID NO: 10. In some embodiments that may be combined with any of the preceding embodiments, the human Siglec-11 encodes a polypeptide at least 95% identical to a polypeptide encoded by the nucleic acid sequence of SEQ ID NO: 19. In some embodiments that may be combined with any of the preceding embodiments, the human Siglec-11 gene encodes a polypeptide at least 95% identical to SEQ ID NO: 11 or SEQ ID NO: 12. In some embodiments that may be combined with any of the preceding embodiments, the human Siglec-14 gene encodes a polypeptide at least 95% identical to a polypeptide encoded by the nucleic acid sequence of SEQ ID NO: 20. In some embodiments that may be combined with any of the preceding embodiments, the human Siglec-14 gene encodes a polypeptide at least 95% identical to SEQ ID NO: 13. In some embodiments that may be combined with any of the preceding embodiments, the human Siglec-16 gene encodes a polypeptide at least 95% identical to a polypeptide encoded by the nucleic acid sequence of SEQ ID NO: 21. In some embodiments that may be combined with any of the preceding embodiments, the human Siglec-16 gene encodes a polypeptide at least 95% identical to SEQ ID NO: 14. In some embodiments that may be combined with any of the preceding embodiments, the myeloid cells are selected from the group consisting of myeloid-derived suppressor cells, granulocyte-like myeloid-derived suppressor cells, monocyte-like myeloid-derived suppressor cells, monocytes, macrophages, bone marrow-derived macrophages, M1 macrophages, activated M1 macrophages, M2 macrophages, neutrophils, M1 neutrophils, activated M1 neutrophils, M2 neutrophils, basophils, eosinophils, erythrocytes, dendritic cells, bone marrow-derived dendritic cells, megakaryocytes, and any combination thereof. In some embodiments that may be combined with any of the preceding embodiments, the NK cells are selected from the group consisting of M1 NK cells, activated M1 NK cells, M2 NK cells, and any combination thereof. In some embodiments that may be combined with any of the preceding embodiments, the T cells are selected from the group consisting of T helper cells, cytotoxic T cells, regulatory T cells (Tregs), and any combination thereof. In some embodiments that may be combined with any of the preceding embodiments, the microglia are selected from the group consisting of brain microglial, M1 microglia, activated M1 microglia, M2 microglia, and any combination thereof. In some embodiments that may be combined with any of the preceding embodiments, expression of the two or more human genes in the one or more cells of the transgenic non-human animal recapitulates the expression pattern of the two or more human genes in a corresponding human cell. In some embodiments that may be combined with any of the preceding embodiments, the one or more cells of the transgenic non-human animal are one or more cells selected from the group consisting of monocytes, macrophages, dendritic cells, and microglia. In some embodiments that may be combined with any of the preceding embodiments, the corresponding human cell is a human cell selected from the group consisting of a monocyte, a macrophage, a dendritic cell, and a microglial cell. In some embodiments that may be combined with any of the preceding embodiments, the two or more human genes are co-expressed. In some embodiments that may be combined with any of the preceding embodiments, co-expression of the two or more human genes suppresses one or more myeloid immune cell functions. In some embodiments that may be combined with any of the preceding embodiments, the one or more myeloid immune cell functions are selected from the group consisting of: (a) phagocytosis; (b) antigen presentation; (c) immune cell recruitment; (d) immune cell maturation, migration, proliferation, differentiation, and/or survival; (e) modulation of adaptive immune cells such as B cells and T cells; (f) expression and/or secretion of one or more cytokines and/or chemokines; (g) tumor infiltration, tumor cell recognition, and/or tumor cell killing; (h) releasing granules (degranulation) or neutrophil extracellular traps (NETs); (i) anti-parasitic activities; (j) bactericidal activities; (k) clearance of cellular debris and/or protein aggregates; and (1) any combination thereof. In some embodiments that may be combined with any of the preceding embodiments, expression of the two or more human genes humanizes the Siglec repertoire on the one or more cells of the transgenic non-human animal. In some embodiments that may be combined with any of the preceding embodiments, the mouse comprises a genome comprising one or more non-functional murine genes, wherein the one or more non-functional murine genes are selected from the group consisting of murine CD33, murine Siglec-5, murine Siglec-7, murine Siglec-9, murine Siglec-11, and any combination thereof. In some embodiments that may be combined with any of the preceding embodiments, the mouse comprises a genome comprising a non-functional murine CD33 gene, a non-functional murine Siglec-5 gene, a non-functional murine Siglec-7 gene, a non-functional murine Siglec-9 gene, and a non-functional murine Siglec-11 gene.

Other aspects of the present disclosure relate to a method for recapitulating a human Siglec immune system in a non-human animal, the method comprising generating a transgenic non-human animal whose genome comprises two or more human genes, wherein the two or more human genes are selected from the group consisting of CD33, Siglec-5, Siglec-7, Siglec-9, Siglec-11, Siglec-14, and Siglec-16, wherein the two or more human genes are coordinately expressed in one or more cells of the transgenic non-human animal, and wherein the one of more cells selected from the group consisting of myeloid cells, natural killer (NK) cells, T cells, microglia, and any combination thereof.

In some embodiments that may be combined with any of the preceding embodiments, the transgenic non-human animal is a rodent. In some embodiments that may be combined with any of the preceding embodiments, the transgenic non-human animal is a mouse. In some embodiments that may be combined with any of the preceding embodiments, the genome comprises the human genes Siglec-5 and Siglec-14. In some embodiments that may be combined with any of the preceding embodiments, the genome comprises the human genes Siglec-11 and Siglec-16. In some embodiments that may be combined with any of the preceding embodiments, the genome comprises three or more human genes. In some embodiments that may be combined with any of the preceding embodiments, the genome comprises the human genes CD33, Siglec-7, and Siglec-9. In some embodiments that may be combined with any of the preceding embodiments, the genome comprises seven human genes. In some embodiments that may be combined with any of the preceding embodiments, the genome comprises the human genes CD33, Siglec-5, Siglec-7, Siglec-9, Siglec-11, Siglec-14, and Siglec-16. In some embodiments that may be combined with any of the preceding embodiments, one or more of the human genes comprise all intronic and exonic sequences of the one or more genes. In some embodiments that may be combined with any of the preceding embodiments, one or more of the human genes comprise at least one flanking sequence at the 5' and/or 3' end of the one or more genes. In some embodiments that may be combined with any of the preceding embodiments, the flanking sequence is at least 10,000 base pairs in length. In some embodiments that may be combined with any of the preceding embodiments, the flanking sequence comprises one or more human transcriptional regulatory elements. In some embodiments that may be combined with any of the preceding embodiments, the one or more human transcriptional regulatory elements directs expression of one or more of human CD33, Siglec-5, Siglec-7, Siglec-9, Siglec-11, Siglec-14, and/or Siglec-16 genes. In some embodiments that may be combined with any of the preceding embodiments, the one or more human transcriptional regulatory elements directs coordinate expression of at least two of human CD33, Siglec-5, Siglec-7, Siglec-9, Siglec-11, Siglec-14, and/or Siglec-16 genes. In some embodiments that may be combined with any of the preceding embodiments, the human CD33 gene encodes a polypeptide at least 95% identical to a polypeptide encoded by the nucleic acid sequence of SEQ ID NO: 15. In some embodiments that may be combined with any of the preceding embodiments, the human CD33 gene encodes a polypeptide at least 95% identical to a sequence selected from the group consisting of SEQ ID NOS: 1-3. In some embodiments that may be combined with any of the preceding embodiments, the human CD33 gene comprises one or more single nucleotide polymorphisms (SNPs) selected from the group consisting of: (a) SNP rs3865444$^{AC}$; (b) SNP rs3865444$^{CC}$; (c) SNP rs3865444$^{AA}$; (d) SNP rs35112940$^{GG, AA, AG}$; (e) SNP rs12459419$^{CC, CT\ or\ TT}$; and (f) any combination thereof. In some embodiments that may be combined with any of the preceding embodiments, the human Siglec-5 gene encodes a polypeptide at least 95% identical to a polypeptide encoded by the nucleic acid sequence of SEQ ID NO: 16. In some embodiments that may be combined with any of the preceding embodiments, the human Siglec-5 gene encodes a polypeptide at least 95% identical to SEQ ID NO: 4. In some embodiments that may be combined with any of the preceding embodiments, the human Siglec-7 gene encodes a polypeptide at least 95% identical to a polypeptide encoded by the nucleic acid sequence of SEQ ID NO: 17. In some embodiments that may be combined with any of the preceding embodiments, the human Siglec-7 gene encodes a polypeptide at least 95% identical to a sequence selected from the group consisting of SEQ ID NOS: 5-8. In some embodiments that may be combined with any of the preceding embodiments, the human Siglec-9 gene encodes a polypeptide at least 95% identical to a polypeptide encoded by the nucleic acid sequence of SEQ ID NO: 18. In some embodiments that may be combined with any of the preceding embodiments, the human Siglec-9 gene encodes a polypeptide at least 95% identical to SEQ ID NO: 9 or SEQ ID NO: 10. In some embodiments that may be combined with any of the preceding embodiments, the human Siglec-11 encodes a polypeptide at least 95% identical to a polypeptide encoded by the nucleic acid sequence of SEQ ID NO: 19. In some embodiments that may be combined with any of the preceding embodiments, the human Siglec-11 gene encodes a polypeptide at least 95% identical to SEQ ID NO: 11 or SEQ ID NO: 12. In some embodiments that may be combined with any of the preceding embodiments, the human Siglec-14 gene encodes a polypeptide at least 95% identical to a polypeptide encoded by the nucleic acid sequence of SEQ ID NO: 20. In some embodiments that may be combined with any of the preceding embodiments, the human Siglec-14 gene encodes a polypeptide at least 95% identical to SEQ ID NO: 13. In some embodiments that may be combined with any of the preceding embodiments, the human Siglec-16 gene encodes a polypeptide at least 95% identical to a polypeptide encoded by the nucleic acid sequence of SEQ ID NO: 21. In some embodiments that may be combined with any of the preceding embodiments, the human Siglec-16 gene encodes a polypeptide at least 95% identical to SEQ ID NO: 14. In some embodiments that may be combined with any of the preceding embodiments, the two or more human genes are expressed in a myeloid cell, a natural killer (NK) cell, or both a myeloid cell and an NK cell of the transgenic non-human animal. In some embodiments that may be combined with any of the preceding embodiments, the myeloid cells are selected from the group consisting of myeloid-derived suppressor cells, granulocyte-like myeloid-derived suppressor cells, monocyte-like myeloid-derived suppressor cells, monocytes, macrophages, bone marrow-derived macrophages, M1 macrophages, activated M1 macrophages, M2 macrophages, neutrophils, M1 neutrophils, activated M1 neutrophils, M2 neutrophils, basophils, eosinophils, erythrocytes, dendritic cells, bone marrow-derived dendritic cells, megakaryocytes, and any combination thereof. In some embodiments that may be combined with any of the preceding embodiments, the NK cells are selected from the group consisting of M1 NK cells, activated M1 NK cells, M2 NK cells, and any combination thereof. In some embodiments that may be combined with any of the preceding embodiments, the T cells are selected from the group consisting of T helper cells, cytotoxic T cells, regulatory T cells (Tregs), and any combination thereof. In some embodiments that may be combined with any of the preceding embodiments, the microglia are selected from the group consisting of brain microglial, M1 microglia, activated M1 microglia, M2 microglia, and any combination thereof. In some embodiments that may be combined with any of the preceding embodiments, coordinate expression of the two or more human genes suppresses one or more myeloid immune cell functions. In some embodiments that may be combined with any of the preceding embodiments, the one or more myeloid immune cell functions are selected from the group consisting of: (a) phagocytosis; (b) antigen presentation; (c) immune cell recruitment; (d) immune cell maturation, migration, proliferation, differentiation, and/or survival; (e) modulation of adaptive immune cells such as B cells and T cells; (f) expression and/or secretion of one or more cytokines and/or chemokines; (g) tumor infiltration, tumor cell recognition, and/or tumor cell killing; (h) releasing granules (degranulation) or neutrophil extracellular traps (NETs); (i) anti-parasitic activities; (j) bactericidal activities; (k) clearance of cellular debris and/or protein aggregates; and (l) any combination thereof. In some embodiments that may be combined with any of the preceding embodiments, coordinate expression of the two or more human genes humanizes the Siglec repertoire on the one or more cells of the transgenic non-human animal. In some embodiments that may be combined with any of the preceding embodiments, the mouse comprises a genome that does not encode at least one murine gene, wherein the murine gene is selected from the group consisting of murine CD33, murine Siglec-5, murine Siglec-7, murine Siglec-9 and murine Siglec-11. In some embodiments that may be combined with any of the preceding embodiments, the mouse comprises a genome comprising one or more non-functional murine genes, wherein the one or more non-functional murine genes are selected from the group consisting of murine CD33, Siglec-5, murine Siglec-7, murine Siglec-9, murine Siglec-11, and any combination thereof.

Other aspects of the present disclosure relate to a method of generating a non-human animal disease model with a human Siglec repertoire, the method comprising introducing one or more genetic determinants of a disease into the genome of the non-human animal of any of the preceding embodiments. In some embodiments, the one or more genetic determinants are introduced into the genome of the non-human animal by mating. In some embodiments, the one or more genetic determinants are introduced into the genome of the non-human animal by mating with a disease model non-human animal. In some embodiments, the one or more genetic determinants are introduced into the genome of the non-human animal by genetic manipulation. In some embodiments, the disease is selected from the group consisting of cancer, proliferative disorders, infectious diseases, and neurodegenerative disorders such as Alzheimer's disease. In some embodiments, the genetic determinant is a polynucleotide encoding a polypeptide comprising one or more mutations, wherein the polypeptide is selected from the group consisting of amyloid precursor protein (APP), presenilin 1 (PS1), presenilin 2 (PS2), alpha-synuclein, serine/threonine-protein kinase PINK1, parkin, leucine-rich repeat serine/threonine protein kinase 2 (LRRK2), protein deglycase (DJ-1), probable cation-transporting ATPase 13A2 (ATP13A2), superoxide dismutase (SOD1), TAR DNA-binding protein 43 (TDP-43), RNA-binding protein FUS, huntingtin (HTT), translation endoplasmic reticulum ATPase (VCP), microtubule-associated protein tau (MAPT), progranulin, protein C9orf72, charged multivesicular body protein 2b (CHMP2B), and any combinations thereof.

It is to be understood that one, some, or all of the properties of the various embodiments described herein may be combined to form other embodiments of the present invention. These and other aspects of the invention will become apparent to one of skill in the art.

BRIEF DESCRIPTION OF THE DRAWINGS

The patent or application file contains at least one drawing executed in color. Copies of this patent or patent application publication with color drawings will be provided by the office upon request and payment of the necessary fee.

FIG. 2 shows glycan-binding specificities of human Siglec proteins. This figure shows a summary of the most commonly reported specificities for the most commonly studied sialylated glycans. Relative binding within studies of each Siglec is indicated as ++, strong binding; +, detectable binding; and –, very weak or undetectable binding. Not shown is the recently reported strong-binding preference of hSiglec-8 and mSiglec-F for 6'-sulfated-sialyl-Lewis x (sLex) and of hSiglec-9 for 6-sulfated-sLex. With a few exceptions (CD22 and MAG), results of binding specificity studies of human Siglecs by different investigators using different assays have varied significantly. In addition to assay formats and glycan linker issues, the density and arrangement of the ligands studied could be responsible for this variation (Varki et al., (2006) Glycobiol. 16:1R-27R).

FIG. 7A shows results of FACS analysis demonstrating human CD33 and human Siglec-9 expression on CD11b-positive and CD11b-negative primary cells from non-transgenic and BACRP11-891J20 transgenic mice. Numbers indicate the percentage of cells with staining with an antibody to CD33 or Siglec-9 as indicated (black line) above isotype control background levels (represented by grey area). Arrows indicate animals with transgene expression above background levels in CD11b+ peripheral blood cells. FIG. 7B shows results of FACS analysis demonstrating human CD33 and human Siglec-9 co-expression on CD11b-positive cells in sera from non-transgenic and BACRP11-891J20 transgenic mice. Arrows indicate transgenic animals with transgene expression significantly above background seen with naïve sera.

FIG. 8 shows the antibody panel for FACS expression analysis of human CD33, human Siglec-7, and human Siglec-9 on peripheral blood or spleen cells from non-transgenic and BACRP11-891J20 transgenic mice.

FIG. 22 shows the antibody panel for FACS expression analysis of human CD33 on brain microglia from BACRP11-891J20 transgenic mice.

FIG. 35A shows results of FACS analysis demonstrating the expression pattern of human Siglec-5 and human Siglec-7 on primary dendritic cells (hDC) from peripheral blood of a human patient stained with an isotype control antibody (blue line) or an anti-human Siglec-5 antibody or anti-human Siglec-7 antibody (red lines). FIG. 35B shows results of FACS analysis demonstrating the expression pattern of human Siglec-5 and human Siglec-I on primary bone marrow-derived dendritic cells from control non-transgenic mice (#25 and #42) and BACCTD-2026P14 transgenic mice (#26, #27, #30, #40, and #41) stained with an isotype control antibody (blue line) or an anti-human Siglec-5 antibody or anti-human Siglec-7 antibody (red lines).

DETAILED DESCRIPTION

Figure 1:
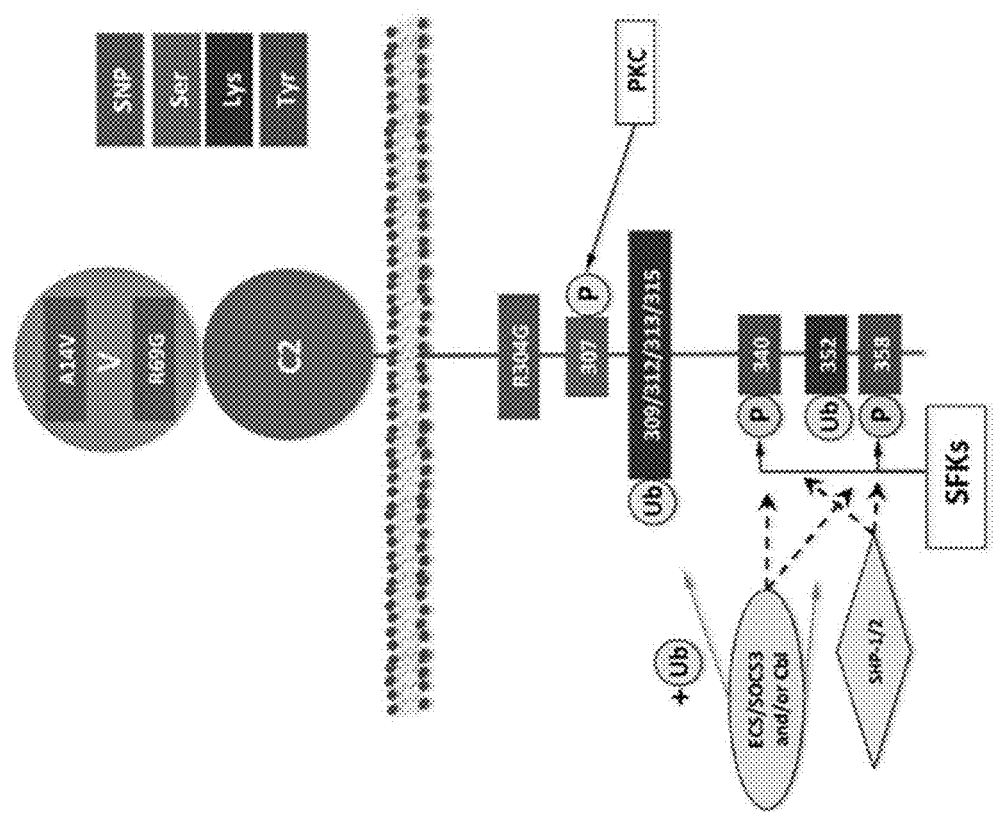
FIG. 1 shows the structure of CD33, and a scheme depicting the domain structure of CD33 as well as individual amino acids that have been implicated in phosphorylation or ubiquitination events or that have been identified as residues of relatively frequent non-synonymous single nucleotide polymorphisms (SNPs). Abbreviations: CBL: casitas B-lineage lymphoma E3 ubiquitin ligase; C2: C2-set Ig-like domain; ECS: Elongin B/C-Cullin-5 SPRY domain ubiquitin ligase; P: phospho-; PKC: protein kinase C; SFKs: Src-family kinases; SHP-1/2: Src homology region 2 domain-containing phosphatase-1 and –2; SOCS3: suppressor of cytokine signaling 3; Ub: ubiquitin; V: V-set Ig-like domain. (Cowan et al., (2013) Frontiers in Bioscience 18:1311-1334).

The present disclosure relates to transgenic non-human animals whose genomes comprise two or more human genes selected from the group consisting of CD33, Siglec-5, Siglec-7, Siglec-9, Siglec-11, Siglec-14, and Siglec-16; to methods of screening candidate agents that bind to and/or modulate the function and/or activity of at least one of the human genes in the transgenic non-human animals; to methods of screening candidate agents to determine their effect on one or more activities and/or functions associated with expression of at least one of the human genes in the transgenic non-human animals; to methods of recapitulating a human Siglec immune system in a non-human animal; and to methods of generating a non-human animal disease model comprising a human Siglec repertoire.

The following description sets forth exemplary methods, parameters, and the like. It should be recognized, however, that such description is not intended as a limitation on the scope of the present disclosure but is instead provided as a description of exemplary embodiments.

GENERAL TECHNIQUES

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N. Y.; *Current Protocols in Molecular Biology* (F. M. Ausubel, et al. eds., (2003)); the series *Methods in Enzymology* (Academic Press, Inc.): PCR 2: A Practical Approach (M. J. MacPherson, B. D. Hames and G. R. Taylor eds. (1995)), Harlow and Lane, eds. (1988) Antibodies, *A Laboratory Manual*, and *Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

Definitions

As used herein, a "subject" or an "individual" refers to any animal, including non-human primates, domestic and farm animals, and zoo, sports, or pet animals, such as dogs, horses, cats, cows, as well as animals used in research, such as mice and rats.

As used herein, the term "animal" or "non-human animal" includes all vertebrate and invertebrate animals, except humans. Examples of animals include, but are not limited to, domesticated animals (e.g., cows, sheep, cats, dogs, and horses), primates (e.g., non-human primates such as monkeys), rabbits, and rodents (e.g., mice and rats). In some embodiments, the animal is a mouse. Additionally, the term refers to an individual animal in all stages of developments, including embryonic and fetal stages. As used herein, the term "transgenic animal" or "transgenic non-human animal" refers to an animal containing one or more cells bearing genetic information (e.g., DNA) received, directly or indirectly, by deliberate genetic manipulation at a subcellular level, such as by microinjection or infection with recombinant virus. This introduced DNA molecule mar be integrated within a chromosome, or it may be extra-chromosomally replicating DNA.

As used herein, the term "germ cell-line transgenic animal" refers to a transgenic animal in which the genetic information was introduced into a germ line cell, thereby conferring the ability to transfer the information to offspring. If such offspring in fact possess some or all of that information, then they too are transgenic animals.

As used herein, the term "wild-type" refers to a nucleic acid, polypeptide, and/or animal (e.g., a mouse or rat) when isolated from a naturally occurring source. A wild-type nucleic acid, polypeptide, and/or animal (e.g., a mouse or rat) is that which is most frequently observed in a population and is thus arbitrarily designated the "normal" or "wild-type" form of that nucleic acid, polypeptide, and/or animal. In contrast, the term "modified" or "mutant" refers to a nucleic acid, polypeptide, and/or animal (e.g., a mouse or rat) that displays modifications in sequence and/or functional properties (e.g., altered characteristics) when compared to the wild-type nucleic acid, polypeptide, and/or animal (e.g., a mouse or rat).

As used herein, the term "preventing" includes providing prophylaxis with respect to occurrence or recurrence of a particular disease, disorder, or condition in an individual. An individual may be predisposed to, susceptible to a particular disease, disorder, or condition, or at risk of developing such a disease, disorder, or condition, but has not yet been diagnosed with the disease, disorder, or condition.

As used herein, an individual "at risk" of developing a particular disease, disorder, or condition may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of a particular disease, disorder, or condition, as known in the art. An individual having one or more of these risk factors has a higher probability of developing a particular disease, disorder, or condition than an individual without one or more of these risk factors.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated", for example, if one or more symptoms associated with a particular disease, disorder, or condition are mitigated or eliminated.

An "effective amount" refers to at least an amount effective, at dosages and for periods of time necessary, to achieve the desired therapeutic or prophylactic result. An effective amount can be provided in one or more administrations. An effective amount herein may vary according to factors such as the disease state, age, sex, and weight of the individual, and the ability of the treatment to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

A "therapeutically effective amount" is at least the minimum concentration required to effect a measurable improvement of a particular disease, disorder, or condition. A therapeutically effective amount herein may vary according to factors such as the disease state, age, sex, and weight of the patient, and the ability to elicit a desired response in the individual. A therapeutically effective amount is also one in which any toxic or detrimental effects are outweighed by the therapeutically beneficial effects.

As used herein, administration "in conjunction" with another compound or composition includes simultaneous administration and/or administration at different times. Administration in conjunction also encompasses administration as a co-formulation or administration as separate compositions, including at different dosing frequencies or intervals, and using the same route of administration or different routes of administration.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR2 ("amidate"), P(O)R, P(O)OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As used herein, the terms "coordinately expressed" and "coordinate expression" refers to the co-regulated expression of two or more polynucleotides.

As used herein, the terms "polypeptide," "protein," and "peptide" are used interchangeably and may refer to a polymer of two or more amino acids.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

As used herein, the term "candidate agent" refers to a molecule that reduces (including significantly), decreases, blocks, inhibits, or interferes with a Siglec (mammalian, such as a human Siglec) biological activity in vitro, in situ, and/or in vivo. The term "agent" implies no specific mechanism of biological action whatsoever, and expressly includes and encompasses all possible pharmacological, physiological, and biochemical interactions with a Siglec whether direct or indirect, and whether interacting with a Siglec, one or more of its ligands, or through another mechanism, and its consequences which can be achieved by a variety of different, and chemically divergent, compositions. Exemplary agents include, without limitation, an antibody that specifically binds to a Siglec, a soluble Siglec receptor protein, a soluble Siglec-Fc fusion protein (e.g., Siglec immunoadhesins), a soluble Siglec receptor that binds to a Siglec ligand, a Siglec-Fc fusion protein (e.g., Siglec immunoadhesin) that binds to a Siglec ligand, an anti-sense molecule directed to a nucleic acid encoding a Siglec, a short interfering RNA ("siRNA") molecule directed to a nucleic acid encoding a Siglec, a Siglec inhibitory compound, an RNA or DNA aptamer that binds to a Siglec, and a Siglec structural analog. In some embodiments, a Siglec inhibitor (e.g., an antibody) binds (physically interacts with) an agent that decreases cellular levels of a Siglec, inhibits interaction between a Siglec and one or more Siglec ligands, or both, binds to a Siglec ligand, and/or inhibits (reduces) Siglec synthesis or production. In other embodiments, an agent of the present disclosure binds a Siglec and prevents its binding to one or more of its ligands. In still other embodiments, an agent of the present disclosure reduces or eliminates expression (i.e., transcription or translation) of a Siglec.

As used herein, the term "agent that binds or interacts with a Siglec" refers to a molecule that either directly or indirectly interacts with a Siglec protein. The term "agent" implies no specific mechanism of biological action whatsoever, and expressly includes and encompasses all possible pharmacological, physiological, and biochemical interactions with a Siglec whether direct or indirect, and whether interacting with a Siglec or through another mechanism, and its consequences which can be achieved by a variety of different, and chemically divergent, compositions.

As used herein, the term "RNA interference" or "RNAi" refers generally to a process in which a double-stranded RNA molecule or a short hairpin RNA molecule reducing or inhibiting the expression of a nucleic acid sequence with which the double-stranded or short hairpin RNA molecule shares substantial or total homology. The term "short interfering RNA" or "siRNA" or "RNAi agent" refers to an RNA sequence that elicits RNA interference. See Kreutzer et al., WO 00/44895; Zernicka-Goetz et al., WO 01/36646; Fire, WO 99/32619; Mello and Fire, WO 01/29058. As used herein, siRNA molecules include RNA molecules encompassing chemically modified nucleotides and non-nucleotides. The term "ddRNAi agent" refers to a DNA-directed RNAi agent that is transcribed from an exogenous vector. The terms "short hairpin RNA" or "shRNA" refer to an RNA structure having a duplex region and a loop region. In certain embodiments, ddRNAi agents are expressed initially as shRNAs.

As used herein, the term "aptamer" refers to a heterologous oligonucleotide capable of binding tightly and specifically to a desired molecular target, such as, for example, common metabolic cofactors (e.g., Coenzyme A, S-adenosyl methionine, and the like), proteins (e.g., complement protein C5, antibodies, and the like), or conserved structural elements in nucleic acid molecules (e.g., structures important for binding of transcription factors and the like). Aptamers typically comprise DNA or RNA nucleotide sequences ranging from about 10 to about 100 nucleotides in length, from about 10 to about 75 nucleotides in length, from about 10 to about 50 nucleotides in length, from about 10 to about 35 nucleotides in length, and from about 10 to about 25 nucleotides in length. Synthetic DNA or RNA oligonucleotides can be made using standard solid phase phosphoramidite methods and equipment, such as by using a 3900 High Throughput DNA Synthesizer™, available from Applied Biosystems (Foster City, CA.). Aptamers frequently incorporate derivatives or analogs of the commonly occurring nucleotides found in DNA and RNA (e.g., A, G, C, and T/U), including backbone or linkage modifications (e.g., peptide nucleic acid (PNA) or phosphothioate linkages) to increase resistance to nucleases, binding avidity, or to otherwise alter their pharmacokinetic properties. Exemplary modifications are set forth in U.S. Pat. Nos. 6,455,308; 4,469,863; 5,536,821; 5,541,306; 5,637,683; 5,637,684; 5,700,922; 5,717,083; 5,719,262; 5,739,308; 5,773,601; 5,886,165; 5,929,226; 5,977,296; 6,140,482; and in WIPO publications WO 00/56746 and WO 01/14398. Methods for synthesizing oligonucleotides comprising such analogs or derivatives are disclosed, for example, in the patent publications cited above, and in U.S. Pat. Nos. 6,455,308; 5,614,622; 5,739,314; 5,955,599; 5,962,674; 6,117,992; and in WO 00/75372.

The term "about" as used herein refers to the usual error range for the respective value readily known to the skilled person in this technical field. Reference to "about" a value or parameter herein includes (and describes) embodiments that are directed to that value or parameter per se.

As used herein and in the appended claims, the singular forms "a," "an," and "the" include plural reference unless the context clearly indicates otherwise. For example, reference to a "gene" is a reference to from one to many genes.

It is understood that aspect and embodiments of the present disclosure described herein include "comprising," "consisting," and "consisting essentially of" aspects and embodiments.

Transgenic Non-Human Animals

Certain aspects of the present disclosure relate to transgenic non-human animals whose genomes comprise two or more human genes selected from the group consisting of CD33, Siglec-5, Siglec-7, Siglec-9, Siglec-11, Siglec-14, and Siglec-16. In some embodiments, the two or more human genes are expressed (e.g., co-expressed) in one or more cells of the transgenic non-human animal. In some embodiments, the two or more human genes are coordinately expressed in one or more cells of the transgenic animal. In some embodiments, expression (e.g., co-expression, coordinate expression) of the two or more human genes in the transgenic non-human animal recapitulates the expression pattern of the two or more human genes in a corresponding human cell. In some embodiments, expression (e.g., co-expression, coordinate expression) of the two or more human genes humanizes the Siglec repertoire on the one or more cells of the transgenic non-human animal. In some embodiments, the one or more cells of the transgenic non-human animal are one or more of myeloid cells, natural killer (NK) cells, T cells, microglia, and any combinations thereof.

In some embodiments, the two or more human genes are expressed (e.g., co-expressed) in one or more myeloid cells of the transgenic non-human animal. In some embodiments, the two or more human genes are coordinately expressed in one or more myeloid cells of the transgenic non-human animal. In some embodiments, expression (e.g., co-expression, coordinate expression) of the two or more human genes in one or more myeloid cells of the transgenic non-human animal recapitulates the expression pattern of the two or more human genes in a corresponding human myeloid cell. In some embodiments, the one or more myeloid cells are one or more of myeloid-derived suppressor cells, granulocyte-like myeloid-derived suppressor cells, monocyte-like myeloid-derived suppressor cells, monocytes, macrophages, bone marrow-derived macrophages, M1 macrophages, activated M1 macrophages, M2 macrophages, neutrophils, M1 neutrophils, activated M1 neutrophils, M2 neutrophils, basophils, eosinophils, erythrocytes, dendritic cells, bone marrow-derived dendritic cells, megakaryocytes, and any combination thereof. In some embodiments, expression (e.g., co-expression, coordinate expression) of the two or more human genes on one or more myeloid cells humanizes the Siglec repertoire on the one or more myeloid cells.

In some embodiments, the two or more human genes are expressed (e.g., co-expressed) in one or more natural killer (NK) cells of the transgenic non-human animal. In some embodiments, the two or more human genes are coordinately expressed in one or more NK cells of the transgenic non-human animal. In some embodiments, expression (e.g., co-expression, coordinate expression) of the two or more human genes in one or more NK cells of the transgenic non-human animal recapitulates the expression pattern of the two or more human genes in a corresponding human NK cell. In some embodiments, the one or more NK cells are one or more of M1 NK cells, activated M1 NK cells, M2 NK cells, and any combination thereof. In some embodiments, expression (e.g., co-expression, coordinate expression) of the two or more human genes on one or NK cells humanizes the Siglec repertoire on the one or more NK cells.

In some embodiments, the two or more human genes are expressed (e.g., co-expressed) in one or more T cells of the transgenic non-human animal. In some embodiments, the two or more human genes are coordinately expressed in one or more T cells of the transgenic non-human animal. In some embodiments, expression (e.g., co-expression, coordinate expression) of the two or more human genes in one or more T cells of the transgenic non-human animal recapitulates the expression pattern of the two or more human genes in a corresponding human T cell. In some embodiments, the one or more T cells are one or more of T helper cells, cytotoxic T cells, regulatory T cells (Tregs), and any combination thereof. In some embodiments, expression (e.g., co-expression, coordinate expression) of the two or more human genes on one or more T cells humanizes the Siglec repertoire on the one or more T cells.

In some embodiments, the two or more human genes are expressed (e.g., co-expressed) in one or more microglial cells of the transgenic non-human animal. In some embodiments, the two or more human genes are coordinately expressed in one or more microglial cells of the transgenic non-human animal. In some embodiments, expression (e.g., co-expression, coordinate expression) of the two or more human genes in one or more microglial cells of the transgenic non-human animal recapitulates the expression pattern of the two or more human genes in a corresponding human microglial cell. In some embodiments, the one or more microglial cells are one or more of brain microglial cells, M1 microglial cells, activated M1 microglial cells, M2 microglial cells, and any combination thereof. In some embodiments, expression (e.g., co-expression, coordinate expression) of the two or more human genes on one or more microglial cells humanizes the Siglec repertoire on the one or more microglial cells.

In some embodiments, expression (e.g., co-expression, coordinate expression) of the two or more human genes in the transgenic non-human animals suppresses one or more myeloid immune cell functions in the transgenic non-human animal. In some embodiments, the one or more myeloid immune cell functions are one or more of phagocytosis; antigen presentation; immune cell recruitment, maturation, migration, proliferation, differentiation, and/or immune cell survival; modulation of adaptive immune cells (e.g., B cells and/or T cells); expression and/or secretion of one or more cytokines and/or chemokines (e.g., IL-1 alpha, IL-1beta, IL-1Ra, IL-4, IL-6, IL-8, IL-10, IL-11, IL-12, IL-13, IL-16, IL-17, IL-18, IL-20, IL-33, IL-35, CRP, LIF, MCP-1, MIP-1 beta, TNFalpha, IFN alpha, IFN, beta, IFN gamma, OSM, CNTF, G-CSF, GM-CSF, TGF beta, Osteopontin, CXCL9, CXCL10, etc.); tumor infiltration, tumor cell recognition, and/or tumor cell killing; releasing granules (degranulation) and/or neutrophil extracellular traps (NETs); anti-parasitic activities; bactericidal activities; clearance of cellular debris and/or protein aggregates; and any combinations thereof.

In some embodiments, expression (e.g., co-expression, coordinate expression) of the two or more human genes in the transgenic non-human animals suppresses one or more myeloid immune cell functions by about 5%, about 10%, about 15%, about 20%, about 25%, about 30%, about 35%, about 40%, about 45%, about 50%, about 55%, about 60%, about 70%, about 75%, about 80%, about 85%, about 90%, about 95%, or about 99% relative to a control non-human animal (e.g., an animal not expressing the two or more human genes). In some embodiments, expression (e.g., co-expression, coordinate expression) of the two or more human genes in the transgenic non-human animals suppresses one or more myeloid immune cell functions by about 1.5 fold, about 2 fold, about 2.5 fold, about 3 fold, about 3.5 fold, about 4 fold, about 4.5 fold, about 5 fold, about 5.5 fold, about 6 fold, about 6.5 fold, about 7 fold, about 7.5 fold, about 8 fold, about 8.5 fold, about 9 fold, about 10 fold, about 100 fold or about 1000 fold relative to a control non-human animal (e.g., an animal not expressing the two or more human genes).

Transgenic non-human animals of the present disclosure may be any non-human animal known in the art. Examples of non-human animals may include, without limitation, laboratory animals (e.g., mice, rats, hamsters, gerbils, guinea pigs, etc.), livestock (e.g., horses, cattle, pigs, sheep, goats, ducks, geese, chickens, etc.), non-human primates (e.g., apes, chimpanzees, orangutans, monkeys, etc.), fish, amphibians (e.g., frogs, salamanders, etc.), reptiles (e.g., snakes, lizards, etc.), and other animals (e.g., foxes, weasels, rabbits, mink, beavers, ermines, otters, sable, seals, coyotes, chinchillas, deer, muskrats, possums, etc.).

In some embodiments, the transgenic non-human animal is a rodent (e.g., a mouse, a rat, a hamster, a gerbil, or a guinea pig). Hamster strains useful for generating transgenic hamsters may include, but are not limited to, Syrian hamsters, Chinese hamsters, European hamsters, and Djungarian hamsters. Rat strains useful for generating transgenic rats may include, but are not limited to, Sprague Dawley® rats, Lewis rats, Fischer 344 rats, Long Evans rats, CD-IGS rats, and Wistar rats. In some embodiments, the transgenic non-human animal is a mouse. Mouse strains useful for generating transgenic mice may include, but are not limited to, CD-1® Nude mice, CD-1 mice, NU/NU mice, BALB/C Nude mice, NIH-III mice, SCID™ mice, outbred SCID™ mice, SCID Beige mice, C3H mice, C57BL/6 mice, DBA/2 mice, FVB mice, CB17 mice, 129 mice, SJL mice, B6C3F1 mice, BDF1 mice, CDF1 mice, CB6F1 mice, CF-1 mice, Swiss Webster mice, SKH1 mice, PGP mice, and B6SJL mice, and congenic mice. In some embodiments, mice useful for generating transgenic mice may further include, but are not limited to, hybrids of any of the aforementioned mouse strains, $F_1$ hybrids of any of the aforementioned mouse strains, $F_2$ hybrids of any of the aforementioned mouse strains, and outbred mice of any of the aforementioned mouse strains.

In some embodiments, the transgenic non-human animals of the present disclosure are chimeric transgenic non-human animals. In some embodiments, the transgenic non-human animals of the present disclosure are transgenic non-human animals with germ cells and somatic cells containing one or more (e.g., one or more, two or more, three or more, four or more, five or more, six or more, etc.) nucleotide sequences encoding two or more human genes selected from the group consisting of CD33, Siglec-5, Siglec-7, Siglec-9, Siglec-11, Siglec-14, and Siglec-16. In some embodiments, the one or more nucleotides sequences are stably integrated into the genome of the transgenic non-human animals. In some embodiments, the one or more nucleotides are bacterial artificial chromosomes stably integrated in to the genome of the transgenic non-human animal. In some embodiments, the one or more nucleotide sequences are extrachromosomal. In some embodiments, the extrachromosomal nucleotide sequence is provided as a minichromosome, a yeast artificial chromosome, or a bacterial artificial chromosome.

In some embodiments, the genomes of the transgenic non-human animals of the present disclosure comprise any of 1, 2, 3, 4, 5, 6, 7, 8, 9, 10, 11, 12, 13, 14, 15 or more copies of the two or more human genes selected from the group consisting of CD33, Siglec-5, Siglec-7, Siglec-9, Siglec-11, Siglec-14, and Siglec-16. In some embodiments, the copy number of the two or more human genes is the same in the genome of the transgenic non-human animal (e.g., the same number of copies of a first and second human gene, the same number of copies of a first, second, and third human gene, etc.). In some embodiments, the copy number of the two or more human genes is different in the genome of the transgenic non-human animal (e.g., a different number of copies of a first and second human gene, a different number of copies of a first, second, and third human gene, etc.). In some embodiments, the genome of the transgenic non-human animal comprises three or more human genes, and the copy number of at least two of the human genes is the same (e.g., the same number of copies of the first and second human gene, and a different number of copies of the third human gene; the same number of copies of the first and third human gene, and a different number of copies of the second human gene, etc.).

In some embodiments, a transgenic non-human animal of the present disclosure is pre-disposed to develop one or more diseases, disorders, and/or injuries. In some embodiments, the one or more diseases, disorders, and/or injuries is one or more of autoimmunity, susceptibility to infection, cancer, proliferative disorders, and/or neurodegenerative disorders. In some embodiments, the one or more diseases, disorders, and/or injuries is one or more of dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV infection, and *Haemophilus influenza* infection.

In some embodiments, the transgenic non-human animal is treated to generate one or more animal disease models (e.g., a transgenic non-human animal being implanted with a syngeneic tumor such as melanoma). In some embodiments, the transgenic non-human animal is interbred to generate one or more animal diseases models. In some embodiments, the transgenic non-human animal is bred with a disease model non-human animal. In some embodiments, the disease model non-human animal is a model of cancer (e.g., melanoma, acute myeloid leukemia, etc.), proliferative disorders, immune-related disease, infectious diseases (e.g., bacterial infections), and/or neurodegenerative diseases/disorders (e.g., Alzheimer's disease). In some embodiments, the neurodegenerative diseases/disorders are one or more of dementia, frontotemporal dementia (FTD), Alzheimer's disease, Parkinson's disease, amyotrophic lateral sclerosis (ALS), Huntington's disease, taupathy disease, and multiple sclerosis. In some embodiments, the disease model non-human animal is an Alzheimer's disease model non-human animal. In some embodiments, the genome of the disease model non-human animal comprises a polynucleotide comprising one or more mutations. In some embodiments, the one or more mutations are one or more inactivating mutations. Examples of inactivating mutations may include, but are not limited to, deletions, insertions, point mutations, and rearrangements. In some embodiments, the genome of the disease model non-human animal comprises a polynucleotide encoding a polypeptide comprising one or more mutations. In some embodiments, the polypeptide comprising one or more mutations is one or more of the polypeptides amyloid precursor protein (APP), presenilin 1 (PS1), presenilin 2 (PS2), alpha-synuclein, serine/threonine-protein kinase PINK1, parkin, leucine-rich repeat serine/threonine protein kinase 2 (LRRK2), protein deglycase (DJ-1), probable cation-transporting ATPase 13A2 (ATP13A2), superoxide dismutase (SOD1), TAR DNA-binding protein 43 (TARDBP), RNA-binding protein FUS, huntingtin (HTT), translation endoplasmic reticulum ATPase (VCP), microtubule-associated protein tau (MAPT), progranulin, protein C9orf72, charged multivesicular body protein 2b (CHMP2B), and clinical mutant forms thereof.

Dementia

Dementia is a non-specific syndrome (i.e., a set of signs and symptoms) that presents as a serious loss of global cognitive ability in a previously unimpaired person, beyond what might be expected from normal ageing. Dementia may be static as the result of a unique global brain injury. Alternatively, dementia may be progressive, resulting in long-term decline due to damage or disease in the body. While dementia is much more common in the geriatric population, it can also occur before the age of 65. Cognitive areas affected by dementia include, without limitation, memory, attention span, language, and problem solving. Generally, symptoms must be present for at least six months to before an individual is diagnosed with dementia.

Exemplary forms of dementia include, without limitation, frontotemporal dementia, Alzheimer's disease, vascular dementia, semantic dementia, and dementia with Lewy bodies.

Frontotemporal Dementia

Frontotemporal dementia (FTD) is a condition resulting from the progressive deterioration of the frontal lobe of the brain. Over time, the degeneration may advance to the temporal lobe. Second only to Alzheimer's disease (AD) in prevalence, FTD accounts for 20% of pre-senile dementia cases. The clinical features of FTD include memory deficits, behavioral abnormalities, personality changes, and language impairments (Cruts, M. & Van Broeckhoven, C., Trends Genet. 24:186-194 (2008); Neary, D., et al., Neurology 51:1546-1554 (1998); Ratnavalli, E., Brayne, C., Dawson, K. & Hodges, J. R., Neurology 58:1615-1621 (2002)).

A substantial portion of FTD cases are inherited in an autosomal dominant fashion, but even in one family, symptoms can span a spectrum from FTD with behavioral disturbances, to Primary Progressive Aphasia, to Cortico-Basal Ganglionic Degeneration. FTD, like most neurodegenerative diseases, can be characterized by the pathological presence of specific protein aggregates in the diseased brain. Historically, the first descriptions of FTD recognized the presence of intraneuronal accumulations of hyperphosphorylated Tau protein in neurofibrillary tangles or Pick bodies. A causal role for the microtubule associated protein Tau was supported by the identification of mutations in the gene encoding the Tau protein in several families (Hutton, M., et al., Nature 393:702-705 (1998). However, the majority of FTD brains show no accumulation of hyperphosphorylated Tau but do exhibit immunoreactivity to ubiquitin (Ub) and TAR DNA binding protein (TDP43) (Neumann, M., et al., Arch. Neurol. 64:1388-1394 (2007)). A majority of those FTD cases with Ub inclusions (FTD-U) were shown to carry mutations in the Progranulin gene.

Alzheimer's Disease

Alzheimer's disease (AD), is the most common form of dementia. There is no cure for the disease, which worsens as it progresses, and eventually leads to death. Most often, AD is diagnosed in people over 65 years of age. However, the less-prevalent early-onset Alzheimer's can occur much earlier.

Common symptoms of Alzheimer's disease include, behavioral symptoms, such as difficulty in remembering recent events; cognitive symptoms, confusion, irritability and aggression, mood swings, trouble with language, and long-term memory loss. As the disease progresses bodily functions are lost, ultimately leading to death. Alzheimer's disease develops for an unknown and variable amount of time before becoming fully apparent, and it can progress undiagnosed for years.

Taupathy Disease

Taupathy diseases, or Tauopathies, are a class of neurodegenerative disease caused by aggregation of the microtubule-associated protein tau within the brain. Alzheimer's disease (AD) is the most well-known taupathy disease, and involves an accumulation of tau protein within neurons in the form of insoluble neurofibrillary tangles (NFTs). Other taupathy diseases and disorders include progressive supranuclear palsy, dementia pugilistica (chromic traumatic encephalopathy), frontotemporal dementia and parkinsonism linked to chromosome 17, Lytico-Bodig disease (Parkinson-dementia complex of Guam), Tangle-predominant dementia, Ganglioglioma and gangliocytoma, Meningioangiomatosis, Subacute sclerosing panencephalitis, lead encephalopathy, tuberous sclerosis, Hallervorden-Spatz disease, lipofuscinosis, Pick's disease, corticobasal degeneration, Argyrophilic grain disease (AGD), Huntington's disease, and frontotemporal lobar degeneration.

Animal models have been developed to model various aspects of dementia, FTD, AD, and Taupathy diseases, including, for example, the accumulation of protein aggregation (e.g., plaques and neurofibrillary tangles) leading to lesions in the brain, the spreading of key histopathological markers (e.g., amyloid β plaques and neurofibrillary tangles) that lead to the definition of the Braak stages, and the formation of distinct clinical features (e.g., neuronal/synapse loss at specific predilection sites, early memory deficits, parkinsonism, memory loss in advanced stages) of FTD, AD, and Taupathy diseases. Examples of animal models useful for modeling one or more signs or symptoms of AD and/or FTD and/or Taupathy diseases may include, without limitation, the mouse strains PDAPP, J20, APP23, Tg2576, JNPL3, pR5, and 5XFAD, and the rat strains SHR72 and SHR318) (See e.g., Gotz, J. and Ittner, L. M. (2008) Nat. Rev. Nerurosci. 9:352-44; Koson, P. et al. (2008) Eur. J. Neurosci. 28(2): 239-46; and Götz, J. and Gotz, N. N. (2009) ASN Neuro. 1(4)).

Parkinson's Disease

Parkinson's disease, which may be referred to as idiopathic or primary parkinsonism, hypokinetic rigid syndrome (HRS), or paralysis agitans, is a neurodegenerative brain disorder that affects motor system control. The progressive death of dopamine-producing cells in the brain leads to the major symptoms of Parkinson's. Most often, Parkinson's disease is diagnosed in people over 50 years of age. Parkinson's disease is idiopathic (having no known cause) in most people. However, genetic factors also play a role in the disease.

Symptoms of Parkinson's disease include, without limitation, tremors of the hands, arms, legs, jaw, and face, muscle rigidity in the limbs and trunk, slowness of movement (bradykinesia), postural instability, difficulty walking, neuropsychiatric problems, changes in speech or behavior, depression, anxiety, pain, psychosis, dementia, hallucinations, and sleep problems.

Animal models have been developed to model various aspects of Parkinson's disease, including, for example, fragmented and dysfunctional mitochondria, altered mitophagy, ubiquitin proteasome dysfunction, altered reactive oxygen species production and calcium handling, alterations in motor function and behavior, and sensitivities to complex I toxins. Examples of animal models useful for modeling one or more signs or symptoms of Parkinson's disease may include, without limitation, toxin-based models (e.g., MPTP mice, MPTP monkeys, 6-OHDA rats, Rotenone, paraquat/maneb, MET/MDMA, etc.), genetic mutation models (e.g., mutations in α-synuclein, LRKK2, PINK1, PARKIN, DJ-1, ATP13A2, etc.), α-synuclein AAV virus injection model, α-synuclein preformed fibril injection model (See e.g., Luk, K C et al., *Science* 2012 Nov. 16; 338(6109): 949-953), and other models (SHH, Nurr1, Engrailed1, Pitx3, C-rel-NFKB, MitoPark, Atg7, VMAT2, etc.) (See e.g., Blesa, J. and Przedborski, J. (2014) *Front. Neuroanat.* 8: 155).

Amyotrophic Lateral Sclerosis (ALS)

As used herein, amyotrophic lateral sclerosis (ALS) or, motor neuron disease or, Lou Gehrig's disease are used interchangeably and refer to a debilitating disease with varied etiology characterized by rapidly progressive weakness, muscle atrophy and fasciculations, muscle spasticity, difficulty speaking (dysarthria), difficulty swallowing (dysphagia), and difficulty breathing (dyspnea).

It has been shown that Progranulin plays a role in ALS (Schymick, J C et al., (2007) J Neurol Neurosurg Psychiatry.; 78:754-6) and protects again the damage caused by ALS causing proteins such as TDP-43 (Laird, A S et al., (2010). PLoS ONE 5: e13368). It was also demonstrated that pro-NGF induces p75 mediated death of oligodendrocytes and corticospinal neurons following spinal cord injury (Beatty et al., Neuron (2002), 36, pp. 375-386; Giehl et al, Proc. Natl. Acad. Sci USA (2004), 101, pp 6226-30).

Animal models have been developed to model various aspects of ALS, including, for example, axonal and mitochondrial dysfunction, progressive neuromuscular dysfunction, gliosis, and motor neuron loss. Examples of animal models useful for modeling one or more signs or symptoms of ALS may include, without limitation, genetic mutation models (e.g., mutations in SOD1, TDP-43, FUS, VCP, etc.), and the mouse models SOD1$^{G37R}$, SOD1$^{H46R}$, SOD1$^{G93A}$, TDP-43$^{WT}$, TDP-43$^{G348C}$, and FUS$^{R521C}$ (See e.g., Philips, T. and Rothstein, J. (2016) *Curr. Protoc. Pharmacol.* 69: 1-21).

Huntington's Disease

Huntington's disease (HD) is an inherited neurodegenerative disease caused by an autosomal dominant mutation in the Huntingtin gene (HTT). Expansion of a cytokine-adenine-guanine (CAG) triplet repeat within the Huntingtin gene results in production of a mutant form of the Huntingtin protein (Htt) encoded by the gene. This mutant Huntingtin protein (mHtt) is toxic and contributes to neuronal death. Symptoms of Huntington's disease most commonly appear between the ages of 35 and 44, although they can appear at any age.

Symptoms of Huntington's disease, include, without limitation, motor control problems, jerky, random movements (chorea), abnormal eye movements, impaired balance, seizures, difficulty chewing, difficulty swallowing, cognitive problems, altered speech, memory deficits, thinking difficulties, insomnia, fatigue, dementia, changes in personality, depression, anxiety, and compulsive behavior.

Animal models have been developed to model various aspects of Huntington's disease, including, for example, production and aggregation of huningtin protein in striatal neurons as well as neurons in other regions (such as the cortex, thalamus, hypothalamus, and substantia nigra pars compacta), involuntary hyperkinetic (choreaform) movements of the arms, legs, and/or face, and severe cognitive changes. Examples of animal models useful for modeling one or more signs or symptoms of ALS may include, without limitation, toxin-based models (e.g., quinolinic acid, 3-nitroproprionic acid, etc.), genetic mutation models (e.g., mutations in mouse, rat, or primate HTT, etc.), and the mouse models R6/2, R6/1, N171-82Q, and YAC (See e.g., Ramaswamy, S. et al. (2007) *ILAR J.* 48(4): 356-73).

Human Genes

Certain aspects of the present disclosure relate to transgenic non-human animals whose genomes comprise two or more of the human CD33, Siglec-5, Siglec-7, Siglec-9, Siglec-11, Siglec-14, and/or Siglec-16 genes.

Human CD33 Gene

In some embodiments, the genome of a transgenic non-human animal of the present disclosure comprises a human CD33 gene. In some embodiments, the genome of the transgenic non-human animal comprises an inactivating mutation in the endogenous CD33 gene. In some embodiments, the transgenic non-human animal comprises a non-functional endogenous CD33 gene. In some embodiments, the genome of the transgenic non-human animal comprises a human CD33 gene and lacks an endogenous CD33 gene. In some embodiments, the genome of the transgenic non-human animal comprises a human CD33 gene and a non-functional endogenous CD33 gene. In some embodiments, the transgenic non-human animal is a mouse. In some embodiments, the genome of the mouse comprises an inactivating mutation in the endogenous murine CD33 gene. In some embodiments, the genome of the mouse comprises a non-functional murine CD33 gene. In some embodiments, the genome of the mouse comprises a human CD33 gene and lacks an endogenous murine CD33 gene. In some embodiments, the genome of the mouse comprises a human CD33 gene and a non-functional murine CD33 gene.

In some embodiments, the human CD33 gene comprises all intronic and exonic sequences of the CD33 gene encoded on chromosome 19 in the human genome. An exemplary polynucleotide comprising all intronic and exonic sequences of the CD33 gene encoded on chromosome 19 in the human genome is shown in SEQ ID NO: 15. In some embodiments, the human CD33 gene comprises the coding sequence for the human CD33 protein/polypeptide. In some embodiments, the human CD33 protein/polypeptide is encoded by a nucleic acid comprising the sequence of SEQ ID NO: 15. In some embodiments, the human CD33 protein/polypeptide is encoded by a nucleic acid comprising a sequence at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identical to the sequence of SEQ ID NO: 15.

In some embodiments, the human CD33 gene comprises a flanking sequence at the 5' end of the coding sequence for the human CD33 polypeptide. In some embodiments, the human CD33 gene comprises a flanking sequence at the 3' end of the coding sequence for the human CD33 polypeptide. In some embodiments, the human CD33 gene comprises a flanking sequence at the 5' end and 3' end of the coding sequence for the human CD33 polypeptide. In some embodiments, the flanking sequence is at least about 10,000, at least about 15,000, at least about 20,000, at least about 25,000, at least about 30,000, at least about 35,000, at least about 40,000, at least about 45,000, or at least about 50,000 base pairs in length. In some embodiments, the flanking sequence is at least about 10,000 base pairs in length.

In some embodiments, the flanking sequence comprises one or more (e.g., one or more, two or more, three or more, four or more, five or more, etc.) human transcriptional regulatory elements. In some embodiments, the one or more human transcriptional regulatory elements direct expression of the human CD33 gene in one or more cells of the transgenic non-human animal. In some embodiments, the one or more human transcriptional regulatory elements direct expression of the human CD33 gene and one or more additional genes in one or more cells of the transgenic non-human animal. In some embodiments, the one or more additional genes are one or more (e.g., one or more, two or more, three or more, four or more, five or more, or all six) of the human Siglec-5, Siglec-7, Siglec-9, Siglec-11, Siglec-14, and/or Siglec-16 genes. In some embodiments, the one or more human transcriptional regulatory elements direct coordinate expression of the human CD33 gene and the one or more additional genes in one or more cells of the transgenic non-human animal. In some embodiments, the one or more cells of the transgenic non-human animal are one or more of myeloid cells, natural killer (NK) cells, T cells, and/or microglia.

CD33 is variously referred to as a CD33 molecule, Siglec-3, Siglec-3, CD33 antigen (Gp67), P67, Gp67, sialic acid-binding-Ig-like lectin 3, myeloid cell surface antigen CD33, or FLJ00391.

CD33 is an immunoglobulin-like receptor primarily expressed on myeloid lineage cells, including without limitation, macrophages, dendritic cells, osteoclasts, monocytes, and microglia. In some embodiments, CD33 forms a receptor-signaling complex with CD64. In some embodiments, CD33 signaling results in the downstream inhibition of PI3K or other intracellular signals.

An exemplary amino acid sequence of human CD33 is set forth below as SEQ ID NO: 1:

```
          10         20         30         40
    MPLLLLLPLL WAGALAMDPN FWLQVQESVT VQEGLCVLVP 50         60         70         80
    CTFFHPIPYY DKNSPVHGYW FREGAIISRD SPVATNKLDQ 90        100        110        120
    EVQEETQGRF RLLGDPSRNN CSLSIVDARR RDNGSYFFRM 130        140        150        160
    ERGSTKYSYK SPQLSVHVTD LTHRPKILIP GTLEPGHSKN 170        180        190        200
    LTCSVSWACE QGTPPIFSWL SAAPTSLGPR TTHSSVLIIT 210        220        230        240
    PRPQDHGTNL TCQVKFAGAG VTTERTIQLN VTYVPQNPTT 250        260        270        280
    GIFPGDGSGK QETRAGVVHG AIGGAGVTAL LALCLCLIFF 290        300        310        320
    IVKTHRRKAA RTAVGRNDTH PTTGSASPKH QKKSKLHGPT 330        340        350        360
    ETSSCSGAAP TVEMDEELHY ASLNFHGMNP SKDTSTEYSE

VRTQ
```

In some embodiments, the CD33 is a preprotein that includes a signal sequence. In some embodiments, the CD33 is a mature protein. In some embodiments, the mature CD33 protein does not include a signal sequence. In some embodiments, the mature CD33 protein is expressed on a cell. In some embodiments, the mature CD33 protein is expressed on a cell, such as the surface of a cell.

Human CD33 proteins contain several domains, including without limitation, a signal sequence located at amino acid residues 1-17 of SEQ ID NO: 1, an extracellular immunoglobulin-like variable-type (IgV) domain located at amino acid residues 19-135 of SEQ ID NO: 1, an Ig-like C2-type domain located at amino acid residues 145-228 of SEQ ID NO: 1, a transmembrane domain located at amino acid residues 260-282 of SEQ ID NO: 1, an ITIM motif 1 located at amino acid residues 338-343 of SEQ ID NO: 1, and an ITIM motif 2 located at amino acid residues 356-361 of SEQ ID NO: 1. As one of skill in the art will appreciate, the beginning and ending residues of the domains of the present disclosure may vary depending upon the computer modeling program used or the method used for determining the domain.

In some embodiments, a human CD33 gene of the present disclosure encodes a polypeptide comprising the sequence of SEQ ID NO: 1. In some embodiments, a human CD33 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 1.

In some embodiments, a human CD33 gene of the present disclosure encodes an N-terminal truncation, a C-terminal truncation, or a fragment of a polypeptide comprising the sequence of SEQ ID NO: 1. N-terminal truncations, C-terminal truncations, or fragments may comprise least 10, at least 25, at least 50, at least 75, at least 100, at least 125, at least 150, at least 175, at least 200, at least 225, at least 250, at least 275, at least 300, at least 325, at least 350, but fewer than 364, consecutive amino acids of SEQ ID NO: 1.

In some embodiments, a human CD33 gene of the present disclosure encodes a polypeptide comprising the sequence of SEQ ID NO: 2. In some embodiments, a human CD33 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 2.

In some embodiments, a human CD33 gene of the present disclosure encodes an N-terminal truncation, a C-terminal truncation, or a fragment of a polypeptide comprising the sequence of SEQ ID NO: 2. N-terminal truncations, C-terminal truncations, or fragments may comprise least 10, at least 25, at least 50, at least 75, at least 100, at least 125, at least 150, at least 175, at least 200, at least 225, at least 250, at least 275, at least 300, but fewer than 310, consecutive amino acids of SEQ ID NO: 2.

In some embodiments, a human CD33 gene of the present disclosure encodes a polypeptide comprising the sequence of SEQ ID NO: 3. In some embodiments, a human CD33 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 3.

In some embodiments, a human CD33 gene of the present disclosure encodes an N-terminal truncation, a C-terminal truncation, or a fragment of a polypeptide comprising the sequence of SEQ ID NO: 3. N-terminal truncations, C-terminal truncations, or fragments may comprise least 10, at least 25, at least 50, at least 75, at least 100, at least 125, at least 150, at least 175, at least 200, at least 225, but fewer than 237, consecutive amino acids of SEQ ID NO: 3.

In some embodiments, a human CD33 gene of the present disclosure comprises one or more (e.g., one or more, two or more, three or more, four or more, five or more, etc.) single nucleotide polymorphisms (SNPs). In some embodiments, the one or more SNPs are one or more of SNP rs3865444$^{AC}$, SNP rs3865444$^{CC}$, SNP rs3865444$^{AA}$, SNP rs35112940$^{GG,\ AA,\ AG}$, SNP rs12459419$^{CC,\ CT\ or\ TT}$, and any combinations thereof.

In some embodiments, the human CD33 gene encodes a polypeptide comprising one or more (e.g., one or more, two or more, three or more, four or more, five or more, six or more, seven or more, eight or more, nine or more, 10 or more, or 11) mutations selected from: an alanine to valine mutation at a position corresponding to position 14 of SEQ ID NO: 1; a tryptophan to arginine mutation at a position corresponding to position 22 of SEQ ID NO: 1; an arginine to glycine mutation at a position corresponding to position 69 of SEQ ID NO: 1; a serine to asparagine mutation at a position corresponding to position 128 of SEQ ID NO: 1; an arginine to tryptophan mutation at a position corresponding to position 202 of SEQ ID NO: 1; an isoleucine to leucine mutation at a position corresponding to position 242 of SEQ ID NO: 1; a phenylalanine to leucine mutation at a position corresponding to position 243 of SEQ ID NO: 1; a valine to isoleucine mutation at a position corresponding to position 267 of SEQ ID NO: 1; a valine to leucine mutation at a position corresponding to position 294 of SEQ ID NO: 1; a glycine to arginine mutation at a position corresponding to position 304 of SEQ ID NO: 1; and a threonine to alanine mutation at a position corresponding to position 331 of SEQ ID NO: 1. In some embodiments, the human CD33 gene encodes a polypeptide comprising a glycine to arginine mutation at a position corresponding to position 304 of SEQ ID NO: 1. In some embodiments, the human CD33 gene encodes a polypeptide comprising an alanine to valine mutation at a position corresponding to position 14 of SEQ ID NO: 1. In some embodiments, the human CD33 gene encodes a polypeptide comprising a glycine to arginine mutation at a position corresponding to position 304 of SEQ ID NO: 1 and an alanine to valine mutation at a position corresponding to position 14 of SEQ ID NO: 1.

Human Siglec-5 Gene

In some embodiments, the genome of a transgenic non-human animal of the present disclosure comprises a human Siglec-5 gene. In some embodiments, the genome of the transgenic non-human animal comprises an inactivating mutation in the endogenous Siglec-5 gene. In some embodiments, the genome of the transgenic non-human animal comprises a non-functional endogenous Siglec-5 gene. In some embodiments, the genome of the transgenic non-human animal comprises a human Siglec-5 gene and lacks an endogenous Siglec-5 gene. In some embodiments, the genome of the transgenic non-human animal comprises a human Siglec-5 gene and a non-functional endogenous Siglec-5 gene. In some embodiments, the transgenic non-human animal is a mouse. In some embodiments, the genome of the mouse comprises an inactivating mutation in the endogenous murine Siglec-5 gene. In some embodiments, the genome of the mouse comprises a non-functional murine Siglec-5 gene. In some embodiments, the genome of the mouse comprises a human Siglec-5 gene and lacks an endogenous murine Siglec-5 gene. In some embodiments, the genome of the mouse comprises a human Siglec-5 gene and a non-functional murine Siglec-5 gene.

In some embodiments, the human Siglec-5 gene comprises all intronic and exonic sequences of the Siglec-5 gene encoded on chromosome 19 in the human genome. An exemplary polynucleotide comprising all intronic and exonic sequences of the Siglec-5 gene encoded on chromosome 19 in the human genome is shown in SEQ ID NO: 16. In some embodiments, the human Siglec-5 gene comprises the coding sequence for the human Siglec-5 protein/polypeptide. In some embodiments, the human Siglec-5 protein/polypeptide is encoded by a nucleic acid comprising the sequence of SEQ ID NO: 16. In some embodiments, the human Siglec-5 protein/polypeptide is encoded by a nucleic acid comprising a sequence at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identical to the sequence of SEQ ID NO: 16.

In some embodiments, the human Siglec-5 gene comprises a flanking sequence at the 5' end of the coding sequence for the human Siglec-5 polypeptide. In some embodiments, the human Siglec-5 gene comprises a flanking sequence at the 3' end of the coding sequence for the human Siglec-5 polypeptide. In some embodiments, the human Siglec-5 gene comprises a flanking sequence at the 5' end and 3' end of the coding sequence for the human Siglec-5 polypeptide. In some embodiments, the flanking sequence is at least about 10,000, at least about 15,000, at least about 20,000, at least about 25,000, at least about 30,000, at least about 35,000, at least about 40,000, at least about 45,000, or at least about 50,000 base pairs in length. In some embodiments, the flanking sequence is at least about 10,000 base pairs in length.

In some embodiments, the flanking sequence comprises one or more (e.g., one or more, two or more, three or more, four or more, five or more, etc.) human transcriptional regulatory elements. In some embodiments, the one or more human transcriptional regulatory elements direct expression of the human Siglec-5 gene in one or more cells of the transgenic non-human animal. In some embodiments, the one or more human transcriptional regulatory elements direct expression of the human Siglec-5 gene and one or more additional genes in one or more cells of the transgenic non-human animal. In some embodiments, the one or more additional genes are one or more (e.g., one or more, two or more, three or more, four or more, five or more, or all six) of the human CD33, Siglec-7, Siglec-9, Siglec-11, Siglec-14, and/or Siglec-16 genes. In some embodiments, the one or more human transcriptional regulatory elements direct coordinate expression of the human Siglec-5 gene and the one or more additional genes in one or more cells of the transgenic non-human animal. In some embodiments, the one or more cells of the transgenic non-human animal are one or more of myeloid cells, natural killer (NK) cells, T cells, and/or microglia.

An exemplary amino acid sequence of human Siglec-5 is set forth below as SEQ ID NO: 4:

```
          10         20         30         40
   MLPLLLLPLL WGGSLQEKPV YELQVQKSVT VQEGLCVLVP 50         60         70         80
   CSFSYPWRSW YSSPPLYVYW FRDGEIPYYA EVVATNNPDR 90        100        110        120
   RVKPETQGRF RLLGDVQKKN CSLSIGDARM EDTGSYFFRV 130        140        150        160
   ERGRDVKYSY QQNKLNLEVT ALIEKPDIHF LEPLESGRPT 170        180        190        200
   RLSCSLPGSCE AGPPLTFSW TGNALSPLDP ETTRSSELTL 210        220        230        240
   TPRPEDHGTN LTCQMKRQGA QVTTERTVQL NVSYAPQTIT 250        260        270        280
   IFRNGIALEI LQNTSYLPVL EGQALRLLCD APSNPPAHLS 290        300        310        320
   WFQGSPALNA TPISNTGILE LRRVRSAEEG GFTCRAQHPL 330        340        350        360
   GFLQIFLNLS VYSLPQLLGP SCSWEAEGLH CRCSFRARPA 370        380        390        400
   PSLCWRLEEK PLEGNSSQGS FKVNSSSAGP WANSSLILHG 410        420        430        440
   GLSSDLKVSC KAWNIYGSQS GSVLLLQGRS NLGTGVVPAA 450        460        470        480
   LGGAGVMALL CICLCLIFFL IVKARRKQAA GRPEKMDDED 490        500        510        520
   PIMGTITSGS RKKPWPDSPG DQASPPGDAP PLEEQKELHY 530        540        550
   ASLSFSEMKS REPKDQEAPS TTEYSEIKTSK
```

In some embodiments, a human Siglec-5 gene of the present disclosure encodes a polypeptide comprising the sequence of SEQ ID NO: 4. In some embodiments, a human Siglec-5 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 4.

In some embodiments, a human Siglec-5 gene of the present disclosure encodes an N-terminal truncation, a C-terminal truncation, or a fragment of a polypeptide comprising the sequence of SEQ ID NO: 4. N-terminal truncations, C-terminal truncations, or fragments may comprise least 10, at least 25, at least 50, at least 75, at least 100, at least 125, at least 150, at least 175, at least 200, at least 225, at least 250, at least 275, at least 300, at least 325, at least 350, at least 375, at least 400, at least 425, at least 450, at least 475, at least 500, but fewer than 501, consecutive amino acids of SEQ ID NO: 4.

In some embodiments, the human Siglec-5 gene encodes a polypeptide comprising one or more (e.g., one or more, two or more, three or more, four or more, or five) mutations selected from: a valine to alanine mutation at a position corresponding to position 72 of SEQ ID NO: 4; a methionine to valine mutation at a position corresponding to position 215 of SEQ ID NO: 4; a phenylalanine to serine mutation at a position corresponding to position 322 of SEQ ID NO: 4; an arginine to tryptophan mutation at a position corresponding to position 358 of SEQ ID NO: 4; and a proline to alanine mutation at a position corresponding to position 499 of SEQ ID NO: 4.

Human Siglec-7 Gene

In some embodiments, the genome of a transgenic non-human animal of the present disclosure comprises a human Siglec-7 gene. In some embodiments, the genome of the transgenic non-human animal comprises an inactivating mutation in the endogenous Siglec-7 gene. In some embodiments, the genome of the transgenic non-human animal comprises a non-functional endogenous Siglec-7 gene. In some embodiments, the genome of the transgenic non-human animal comprises a human Siglec-7 gene and lacks an endogenous Siglec-7 gene. In some embodiments, the genome of the transgenic non-human animal comprises a human Siglec-7 gene and a non-functional endogenous Siglec-7 gene. In some embodiments, the transgenic non-human animal is a mouse. In some embodiments, the genome of the mouse comprises an inactivating mutation in the endogenous murine Siglec-7 gene. In some embodiments, the genome of the mouse comprises a non-functional murine Siglec-7 gene. In some embodiments, the genome of the mouse comprises a human Siglec-7 gene and lacks an endogenous murine Siglec-7 gene. In some embodiments, the genome of the mouse comprises a human Siglec-7 gene and a non-functional murine Siglec-7 gene.

In some embodiments, the human Siglec-7 gene comprises all intronic and exonic sequences of the Siglec-7 gene encoded on chromosome 19 in the human genome. An exemplary polynucleotide comprising all intronic and exonic sequences of the Siglec-7 gene encoded on chromosome 19 in the human genome is shown in SEQ ID NO: 17. In some embodiments, the human Siglec-7 gene comprises the coding sequence for the human Siglec-7 protein/polypeptide. In some embodiments, the human Siglec-7 protein/polypeptide is encoded by a nucleic acid comprising the sequence of SEQ ID NO: 17. In some embodiments, the human Siglec-7 protein/polypeptide is encoded by a nucleic acid comprising a sequence at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identical to the sequence of SEQ ID NO: 17.

In some embodiments, the human Siglec-7 gene comprises a flanking sequence at the 5' end of the coding sequence for the human Siglec-7 polypeptide. In some embodiments, the human Siglec-7 gene comprises a flanking sequence at the 3' end of the coding sequence for the human Siglec-7 polypeptide. In some embodiments, the human Siglec-7 gene comprises a flanking sequence at the 5' end and 3' end of the coding sequence for the human Siglec-7 polypeptide. In some embodiments, the flanking sequence is at least about 10,000, at least about 15,000, at least about 20,000, at least about 25,000, at least about 30,000, at least about 35,000, at least about 40,000, at least about 45,000, or at least about 50,000 base pairs in length. In some embodiments, the flanking sequence is at least about 10,000 base pairs in length.

In some embodiments, the flanking sequence comprises one or more (e.g., one or more, two or more, three or more, four or more, five or more, etc.) human transcriptional regulatory elements. In some embodiments, the one or more human transcriptional regulatory elements direct expression of the human Siglec-7 gene in one or more cells of the transgenic non-human animal. In some embodiments, the one or more human transcriptional regulatory elements direct expression of the human Siglec-7 gene and one or more additional genes in one or more cells of the transgenic non-human animal. In some embodiments, the one or more additional genes are one or more (e.g., one or more, two or more, three or more, four or more, five or more, or all six) of the human CD33, Siglec-5, Siglec-9, Siglec-11, Siglec-14, and/or Siglec-16 genes. In some embodiments, the one or more human transcriptional regulatory elements direct coordinate expression of the human Siglec-7 gene and the one or more additional genes in one or more cells of the transgenic non-human animal. In some embodiments, the one or more cells of the transgenic non-human animal are one or more of myeloid cells, natural killer (NK) cells, T cells, and/or microglia.

Siglec-7 is variously referred to as a Siglec-7 molecule, Sialic acid-binding Ig-like lectin 7, AIRM1, CD328, CDw328, D-Siglec, QA79, SIGLEC19P, SIGLECP2, p75, and p75/AIRM1.

An exemplary amino acid sequence of human Siglec-7 is set forth below as SEQ ID NO: 5:

```
             10          20          30          40
     MLLLLLLPLL  WGRERVEGQK  SNRKDYSLTM  QSSVTVQEGM 50          60          70          80
     CVHVRCSFSY  PVDSQTDSDP  VHGYWFRAGN  DISWKAPVAT 90         100         110         120
     NNPAWAVQEE  TRDRFHLLGD  PQTKNCTLSI  RDARMSDAGR 130         140         150         160
     YFFRMEKGNI  KWNYKYDQLS  VNVTALTHRP  NILIPGTLES 170         180         190         200
     GCFQNLTCSV  PWACEQGTPP  MISWMGTSVS  PLHPSTTRSS 210         220         230         240
     VLTLIPQPQH  HGTSLTCQVT  LPGAGVTTNR  TIQLNVSYPP 250         260         270         280
     QNLTVTVFQG  EGTASTALGN  SSSLSVLEGQ  SLRLVCAVDS 290         300         310         320
     NPPARLSWTW  RSLTLYPSQP  SNPLVLELQV  HLGDEGEFTC 330         340         350         360
     RAQNSLGSQH  VSLNLSLQQE  YTGKMRPVSG  VLLGAVGGAG 370         380         390         400
     ATALVFLSFC  VIFIVVRSCR  KKSARPAADV  GDIGMKDANT 410         420         430         440
     IRGSASQGNL  TESWADDNPR  HHGLAAHSSG  EEREIQYAPL 450         460
     SFHKGEPQDL  SGQEATNNEY  SEIKIPK
```

In some embodiments, the Siglec-7 is a preprotein that includes a signal sequence. In some embodiments, the Siglec-7 is a mature protein. In some embodiments, the mature Siglec-7 protein does not include a signal sequence. In some embodiments, the mature Siglec-7 protein is expressed on a cell. In some embodiments, the mature Siglec-7 protein is expressed on a cell, such as the surface of a cell.

Human Siglec-7 proteins, contain several domains, including without limitation, a signal sequence located at amino acid residues 1-18 of SEQ ID NO: 5, an extracellular immunoglobulin-like variable-type (IgV) domain located at amino acid residues 39-122 of SEQ ID NO: 5, two Ig-like C2-type domains located at amino acid residues 150-233 and 240-336 of SEQ ID NO: 5, a transmembrane domain located at amino acid residues 354-376 of SEQ ID NO: 5, an ITIM motif 1 located at amino acid residues 435-440 of SEQ ID NO: 5, and an ITIM motif 2 located at amino acid residues 459-463 of SEQ ID NO: 5. As one of skill in the art will appreciate, the beginning and ending residues of the domains of the present disclosure may vary depending upon the computer modeling program used or the method used for determining the domain.

In some embodiments, a human Siglec-7 gene of the present disclosure encodes a polypeptide comprising the sequence of SEQ ID NO: 5. In some embodiments, a human Siglec-7 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 5.

In some embodiments, a human Siglec-7 gene of the present disclosure encodes an N-terminal truncation, a C-terminal truncation, or a fragment of a polypeptide comprising the sequence of SEQ ID NO: 5. N-terminal truncations, C-terminal truncations, or fragments may comprise least 10, at least 25, at least 50, at least 75, at least 100, at least 125, at least 150, at least 175, at least 200, at least 225, at least 250, at least 275, at least 300, at least 325, at least 350, at least 375, at least 400, at least 425, at least 450, but fewer than 467, consecutive amino acids of SEQ ID NO: 5.

In some embodiments, a human Siglec-7 gene of the present disclosure encodes a polypeptide comprising the sequence of SEQ ID NO: 6. In some embodiments, a human Siglec-7 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 6.

In some embodiments, a human Siglec-7 gene of the present disclosure encodes an N-terminal truncation, a C-terminal truncation, or a fragment of a polypeptide comprising the sequence of SEQ ID NO: 6. N-terminal truncations, C-terminal truncations, or fragments may comprise least 10, at least 25, at least 50, at least 75, at least 100, at least 125, at least 150, at least 175, at least 200, at least 225, at least 250, at least 275, at least 300, at least 325, at least 350, but fewer than 374, consecutive amino acids of SEQ ID NO: 6.

In some embodiments, a human Siglec-7 gene of the present disclosure encodes a polypeptide comprising the sequence of SEQ ID NO: 7. In some embodiments, a human Siglec-7 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 7.

In some embodiments, a human Siglec-7 gene of the present disclosure encodes an N-terminal truncation, a C-terminal truncation, or a fragment of a polypeptide comprising the sequence of SEQ ID NO: 7. N-terminal truncations, C-terminal truncations, or fragments may comprise least 10, at least 25, at least 50, at least 75, at least 100, at least 125, but fewer than 145, consecutive amino acids of SEQ ID NO: 7.

In some embodiments, a human Siglec-7 gene of the present disclosure encodes a polypeptide comprising the sequence of SEQ ID NO: 8. In some embodiments, a human Siglec-7 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 8.

In some embodiments, a human Siglec-7 gene of the present disclosure encodes an N-terminal truncation, a C-terminal truncation, or a fragment of a polypeptide comprising the sequence of SEQ ID NO: 8. N-terminal truncations, C-terminal truncations, or fragments may comprise least 10, at least 25, at least 50, at least 75, at least 100, at least 125, but fewer than 145, consecutive amino acids of SEQ ID NO: 8.

In some embodiments, the human Siglec-7 gene encodes a polypeptide comprising a leucine to proline mutation at a position corresponding to position 215 of SEQ ID NO: 5.

Human Siglec-9 Gene

In some embodiments, the genome of a transgenic non-human animal of the present disclosure comprises a human Siglec-9 gene. In some embodiments, the genome of the transgenic non-human animal comprises an inactivating mutation in the endogenous Siglec-9 gene. In some embodiments, the genome of the transgenic non-human animal comprises a non-functional endogenous Siglec-9 gene. In some embodiments, the genome of the transgenic non-human animal comprises a human Siglec-9 gene and lacks an endogenous Siglec-9 gene. In some embodiments, the genome of the transgenic non-human animal comprises a human Siglec-9 gene and a non-functional endogenous Siglec-9 gene. In some embodiments, the transgenic non-human animal is a mouse. In some embodiments, the genome of the mouse comprises an inactivating mutation in the endogenous murine Siglec-9 gene. In some embodiments, the genome of the mouse comprises a non-functional murine Siglec-9 gene. In some embodiments, the genome of the mouse comprises a human Siglec-9 gene and lacks an endogenous murine Siglec-9 gene. In some embodiments, the genome of the mouse comprises a human Siglec-9 gene and a non-functional murine Siglec-9 gene.

In some embodiments, the human Siglec-9 gene comprises all intronic and exonic sequences of the Siglec-9 gene encoded on chromosome 19 in the human genome. An exemplary polynucleotide comprising all intronic and exonic sequences of the Siglec-9 gene encoded on chromosome 19 in the human genome is shown in SEQ ID NO: 18. In some embodiments, the human Siglec-9 gene comprises the coding sequence for the human Siglec-9 protein/polypeptide. In some embodiments, the human Siglec-9 protein/polypeptide is encoded by a nucleic acid comprising the sequence of SEQ ID NO: 18. In some embodiments, the human Siglec-9 protein/polypeptide is encoded by a nucleic acid comprising a sequence at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identical to the sequence of SEQ ID NO: 18.

In some embodiments, the human Siglec-9 gene comprises a flanking sequence at the 5' end of the coding sequence for the human Siglec-9 polypeptide. In some embodiments, the human Siglec-9 gene comprises a flanking sequence at the 3' end of the coding sequence for the human Siglec-9 polypeptide. In some embodiments, the human Siglec-9 gene comprises a flanking sequence at the 5' end and 3' end of the coding sequence for the human Siglec-9 polypeptide. In some embodiments, the flanking sequence is at least about 10,000, at least about 15,000, at least about 20,000, at least about 25,000, at least about 30,000, at least about 35,000, at least about 40,000, at least about 45,000, or at least about 50,000 base pairs in length. In some embodiments, the flanking sequence is at least about 10,000 base pairs in length.

In some embodiments, the flanking sequence comprises one or more (e.g., one or more, two or more, three or more, four or more, five or more, etc.) human transcriptional regulatory elements. In some embodiments, the one or more human transcriptional regulatory elements direct expression of the human Siglec-9 gene in one or more cells of the transgenic non-human animal. In some embodiments, the one or more human transcriptional regulatory elements direct expression of the human Siglec-9 gene and one or more additional genes in one or more cells of the transgenic non-human animal. In some embodiments, the one or more additional genes are one or more (e.g., one or more, two or more, three or more, four or more, five or more, or all six) of the human CD33, Siglec-5, Siglec-7, Siglec-11, Siglec-14, and/or Siglec-16 genes. In some embodiments, the one or more human transcriptional regulatory elements direct coordinate expression of the human Siglec-9 gene and the one or more additional genes in one or more cells of the transgenic non-human animal. In some embodiments, the one or more cells of the transgenic non-human animal are one or more of myeloid cells, natural killer (NK) cells, T cells, and/or microglia.

Siglec-9 is variously referred to as a Siglec-9 molecule, Sialic acid-binding Ig-like lectin 9, CD329 antigen, CD329; CDw329, FOAP-9, and OBBP-LIKE.

Siglec-9 is an immunoglobulin-like receptor primarily expressed on myeloid lineage cells, including without limitation, macrophages, neutrophils, NK cells, dendritic cells, osteoclasts, monocytes, and microglia. In some embodiments, Siglec-9 forms a receptor-signaling complex with CD64. In some embodiments, Siglec-9 signaling results in the downstream inhibition of PI3K or other intracellular signals.

An exemplary amino acid sequence of human Siglec-9 is set forth below as SEQ ID NO: 9:

```
         10         20         30         40
MLLLLLPLLW GRERAEGQTS KLLTMQSSVT VQEGLCVHVP 50         60         70         80
CSFSYPSHGW IYPGVVHGY WFREGANTDQ DAPVATNNPA 90        100        110        120
RAVWEETRDR FHLLGDPHTK NCTLSIRDAR RSDAGRYFFR 130        140        150        160
MEKGSIKWNY KHHRLSVNVT ALTHRPNILI PGTLESGCPQ 170        180        190        200
NLTCSVPWAC EQGTPPMISW IGTSVSPLDP STTRSSVLTL 210        220        230        240
IPQPQDHGTS LTCQVTFPGA SVTTNKTVHL NVSYPPQNLT
```

```
         250        260        270        280
MTVFQGDGTV STVLGNGSSL SLPEGQSLRL VCAVDAVDSN 290        300        310        320
PPARLSLSWR GLTLCPSQPS NPGVLELPWV HLRDAAEFTC 330        340        350        360
RAQNPLGSQQ VYLNVSLQSK ATSGVTQGVV GGAGATALVF 370        380        390        400
LSFCVIFVVV RSCRKKSARP AAGVGDTGIE DANAVRGSAS 410        420        430        440
QGPLTEPWAE DSPPDQPPPA SARSSVGEGE LQYASLSFQM 450        460
VKPWDSRGQE ATDTEYSEIK IHR
```

In some embodiments, the Siglec-9 is a preprotein that includes a signal sequence. In some embodiments, the Siglec-9 is a mature protein. In some embodiments, the mature Siglec-9 protein does not include a signal sequence. In some embodiments, the mature Siglec-9 protein is expressed on a cell. In some embodiments, the mature Siglec-9 protein is expressed on a cell, such as the surface of a cell.

Human Siglec-9 proteins contain several domains, including without limitation, a signal sequence located at amino acid residues 1-17 SEQ ID NO: 9, an extracellular immunoglobulin-like variable-type (IgV) domain located at amino acid residues 20-140 of SEQ ID NO: 9, two Ig-like C2-type domains located at amino acid residues 146-229 and 236-336 of SEQ ID NO: 9, a transmembrane domain located at amino acid residues 348-370 of SEQ ID NO: 9, an ITIM motif located at amino acid residues 431-436 of SEQ ID NO: 9, and SLAM-like motif located at amino acid residues 454-459 of SEQ ID NO: 9. As one of skill in the art will appreciate, the beginning and ending residues of the domains of the present disclosure may vary depending upon the computer modeling program used or the method used for determining the domain.

In some embodiments, a human Siglec-9 gene of the present disclosure encodes a polypeptide comprising the sequence of SEQ ID NO: 9. In some embodiments, a human Siglec-9 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 9.

In some embodiments, a human Siglec-9 gene of the present disclosure encodes an N-terminal truncation, a C-terminal truncation, or a fragment of a polypeptide comprising the sequence of SEQ ID NO: 9. N-terminal truncations, C-terminal truncations, or fragments may comprise least 10, at least 25, at least 50, at least 75, at least 100, at least 125, at least 150, at least 175, at least 200, at least 225, at least 250, at least 275, at least 300, at least 325, at least 350, at least 375, at least 400, at least 425, at least 450, but fewer than 463, consecutive amino acids of SEQ ID NO: 9.

In some embodiments, a human Siglec-9 gene of the present disclosure encodes a polypeptide comprising the sequence of SEQ ID NO: 10. In some embodiments, a human Siglec-9 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 10.

In some embodiments, a human Siglec-9 gene of the present disclosure encodes an N-terminal truncation, a C-terminal truncation, or a fragment of a polypeptide comprising the sequence of SEQ ID NO: 10. N-terminal truncations, C-terminal truncations, or fragments may comprise least 10, at least 25, at least 50, at least 75, at least 100, at least 125, at least 150, at least 175, at least 200, at least 225, at least 250, at least 275, at least 300, at least 325, at least 350, at least 375, at least 400, at least 425, at least 450, at least 475, but fewer than 479, consecutive amino acids of SEQ ID NO: 10.

In some embodiments, the human Siglec-9 gene encodes a polypeptide comprising one or more (e.g., one or more, two or more, three or more, four or more, five or more, six or more, or seven) mutations selected from: a lysine to glutamate mutation at a position corresponding to position 100 of SEQ ID NO: 9; a serine to asparagine mutation at a position corresponding to position 125 of SEQ ID NO: 9; a lysine to glutamine mutation at a position corresponding to position 131 of SEQ ID NO: 9; an asparagine to lysine mutation at a position corresponding to position 147 of SEQ ID NO: 9; an alanine to glutamate mutation at a position corresponding to position 315 of SEQ ID NO: 9; an alanine to aspartate mutation at a position corresponding to position 316 of SEQ ID NO: 9; and a valine to alanine mutation at a position corresponding to position 349 of SEQ ID NO: 9.

Human Siglec-11 Gene

In some embodiments, the genome of a transgenic non-human animal of the present disclosure comprises a human Siglec-11 gene. In some embodiments, the genome of the transgenic non-human animal comprises an inactivating mutation in the endogenous Siglec-11 gene. In some embodiments, the genome of the transgenic non-human animal comprises a non-functional endogenous Siglec-11 gene. In some embodiments, the genome of the transgenic non-human animal comprises a human Siglec-11 gene and lacks an endogenous Siglec-11 gene. In some embodiments, the genome of the transgenic non-human animal comprises a human Siglec-11 gene and a non-functional endogenous Siglec-11 gene. In some embodiments, the transgenic non-human animal is a mouse. In some embodiments, the genome of the mouse comprises an inactivating mutation in the endogenous murine Siglec-11 gene. In some embodiments, the genome of the mouse comprises a non-functional murine Siglec-11 gene. In some embodiments, the genome of the mouse comprises a human Siglec-11 gene and lacks an endogenous murine Siglec-11 gene. In some embodiments, the genome of the mouse comprises a human Siglec-11 gene and a non-functional murine Siglec-11 gene.

In some embodiments, the human Siglec-11 gene comprises all intronic and exonic sequences of the Siglec-11 gene encoded on chromosome 19 in the human genome. An exemplary polynucleotide comprising all intronic and exonic sequences of the Siglec-11 gene encoded on chromosome 19 in the human genome is shown in SEQ ID NO: 19. In some embodiments, the human Siglec-11 gene comprises the coding sequence for the human Siglec-11 polypeptide. In some embodiments, the human Siglec-11 protein/polypeptide is encoded by a nucleic acid comprising the sequence of SEQ ID NO: 19. In some embodiments, the human Siglec-11 protein/polypeptide is encoded by a nucleic acid comprising a sequence at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identical to the sequence of SEQ ID NO: 19.

In some embodiments, the human Siglec-11 gene comprises a flanking sequence at the 5' end of the coding sequence for the human Siglec-11 polypeptide. In some embodiments, the human Siglec-11 gene comprises a flanking sequence at the 3' end of the coding sequence for the human Siglec-11 polypeptide. In some embodiments, the human Siglec-11 gene comprises a flanking sequence at the 5' end and 3' end of the coding sequence for the human Siglec-11 polypeptide. In some embodiments, the flanking sequence is at least about 10,000, at least about 15,000, at least about 20,000, at least about 25,000, at least about 30,000, at least about 35,000, at least about 40,000, at least about 45,000, or at least about 50,000 base pairs in length. In some embodiments, the flanking sequence is at least about 10,000 base pairs in length.

In some embodiments, the flanking sequence comprises one or more (e.g., one or more, two or more, three or more, four or more, five or more, etc.) human transcriptional regulatory elements. In some embodiments, the one or more human transcriptional regulatory elements direct expression of the human Siglec-11 gene in one or more cells of the transgenic non-human animal. In some embodiments, the one or more human transcriptional regulatory elements direct expression of the human Siglec-11 gene and one or more additional genes in one or more cells of the transgenic non-human animal. In some embodiments, the one or more additional genes are one or more (e.g., one or more, two or more, three or more, four or more, five or more, or all six) of the human CD33, Siglec-5, Siglec-7, Siglec-9, Siglec-14, and/or Siglec-16 genes. In some embodiments, the one or more human transcriptional regulatory elements direct coordinate expression of the human Siglec-11 gene and the one or more additional genes in one or more cells of the transgenic non-human animal. In some embodiments, the one or more cells of the transgenic non-human animal are one or more of myeloid cells, natural killer (NK) cells, T cells, and/or microglia.

An exemplary amino acid sequence of human Siglec-11 is set forth below as SEQ ID NO: 11:

```
         10         20         30         40
MVPGQAPQS  PEMLLLPLLL PVLGAGSLNK DPSYSLQVQR 50         60         70         80
QVPVPEGLCV IVSCNLSYPR DGWDESTAAY GYWFKGRTSP 90        100        110        120
KTGAPVATNN QSREVEMSTR DRFQLTGDPG KGSCSLVIRD 130        140        150        160
AQREDEAWYF FRVERGSRVR HSFLSNAFFL KVTALTKKPD 170        180        190        200
VYIPETLEPG QPVTVICVFN WAFKKCPAPS FSWTGAALSP 210        220        230        240
RRTRPSTSHF SVLSFTPSPQ DHDTDLTCHV DFSRKGVSAQ 250        260        270        280
RTVRLRVAYA PKDLIISISH DNTSALELQG NVIYLEVQKG 290        300        310        320
QFLRLLCAAD SQPPATLSWV LQDRVLSSSH PWGPRTLGLE
```

```
        330        340        350        360
LRGVRAGDSG RYTCRAENRL GSQQQALDLS VQYPPENLRV 370        380        390        400
MVSQANRTVL ENLGNGTSLP VLEGQSLRLV CVTHSSPPAR 410        420        430        440
LSWTRWGQTV GPSQPSDPGV LELPPIQMEH EGEFTCHAQH 450        460        470        480
PLGSQHVSLS LSVHYPPQLL GPSCSWEAEG LHCSCSSQAS 490        500        510        520
PAPSLRWWLG EELLEGNSSQ GSFEVTPSSA GPWANSSLSL 530        540        550        560
HGGLSSGLRL RCKAWNVHGA QSGSVFQLLP GKLEHGGGLG 570        580        590        600
LGAALGAGVA ALLAFCSCLV VFRVKICRKE ARKRAAAEQD 610        620        630        640
VPSTLGPISQ GHQHECSAGS SQDHPPPGAA TYTPGKGEEQ 650        660        670        680
ELHYASLSFQ GLRLWEPADQ EAPSTTEYSE IKIHTGQPLR

690
GPGFGLQLER EMSGMVPK
```

In some embodiments, a human Siglec-11 gene of the present disclosure encodes a polypeptide comprising the sequence of SEQ ID NO: 11. In some embodiments, a human Siglec-11 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 11.

In some embodiments, a human Siglec-11 gene of the present disclosure encodes an N-terminal truncation, a C-terminal truncation, or a fragment of a polypeptide comprising the sequence of SEQ ID NO: 11. N-terminal truncations, C-terminal truncations, or fragments may comprise least 10, at least 25, at least 50, at least 75, at least 100, at least 125, at least 150, at least 175, at least 200, at least 225, at least 250, at least 275, at least 300, at least 325, at least 350, at least 375, at least 400, at least 425, at least 450, at least 475, at least 500, at least 525, at least 550, at least 575, at least 600, at least 625, at least 650, at least 675, but fewer than 698, consecutive amino acids of SEQ ID NO: 11.

In some embodiments, a human Siglec-11 gene of the present disclosure encodes a polypeptide comprising the sequence of SEQ ID NO: 12. In some embodiments, a human Siglec-11 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 12.

In some embodiments, a human Siglec-11 gene of the present disclosure encodes an N-terminal truncation, a C-terminal truncation, or a fragment of a polypeptide comprising the sequence of SEQ ID NO: 12. N-terminal truncations, C-terminal truncations, or fragments may comprise least 10, at least 25, at least 50, at least 75, at least 100, at least 125, at least 150, at least 175, at least 200, at least 225, at least 250, at least 275, at least 300, at least 325, at least 350, at least 375, at least 400, at least 425, at least 450, at least 475, at least 500, at least 525, at least 550, at least 575, at least 600, but fewer than 602, consecutive amino acids of SEQ ID NO: 12.

Human Siglec-14 Gene

In some embodiments, the genome of a transgenic non-human animal of the present disclosure comprises a human Siglec-14 gene. In some embodiments, the genome of the transgenic non-human animal comprises an inactivating mutation in the endogenous Siglec-14 gene. In some embodiments, the genome of the transgenic non-human animal comprises a non-functional endogenous Siglec-14 gene. In some embodiments, the genome of the transgenic non-human animal comprises a human Siglec-14 gene and lacks an endogenous Siglec-14 gene. In some embodiments, the genome of the transgenic non-human animal comprises a human Siglec-14 gene and a non-functional endogenous Siglec-14 gene.

In some embodiments, the human Siglec-14 gene comprises all intronic and exonic sequences of the Siglec-14 gene encoded on chromosome 19 in the human genome. An exemplary polynucleotide comprising all intronic and exonic sequences of the Siglec-14 gene encoded on chromosome 19 in the human genome is shown in SEQ ID NO: 20. In some embodiments, the human Siglec-14 gene comprises the coding sequence for the human Siglec-14 polypeptide. In some embodiments, the human Siglec-14 protein/polypeptide is encoded by a nucleic acid comprising the sequence of SEQ ID NO: 20. In some embodiments, the human Siglec-14 protein/polypeptide is encoded by a nucleic acid comprising a sequence at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identical to the sequence of SEQ ID NO: 20.

In some embodiments, the human Siglec-14 gene comprises a flanking sequence at the 5' end of the coding sequence for the human Siglec-14 polypeptide. In some embodiments, the human Siglec-14 gene comprises a flanking sequence at the 3' end of the coding sequence for the human Siglec-14 polypeptide. In some embodiments, the human Siglec-14 gene comprises a flanking sequence at the 5' end and 3' end of the coding sequence for the human Siglec-14 polypeptide. In some embodiments, the flanking sequence is at least about 10,000, at least about 15,000, at least about 20,000, at least about 25,000, at least about 30,000, at least about 35,000, at least about 40,000, at least about 45,000, or at least about 50,000 base pairs in length. In some embodiments, the flanking sequence is at least about 10,000 base pairs in length.

In some embodiments, the flanking sequence comprises one or more (e.g., one or more, two or more, three or more, four or more, five or more, etc.) human transcriptional regulatory elements. In some embodiments, the one or more human transcriptional regulatory elements direct expression of the human Siglec-14 gene in one or more cells of the transgenic non-human animal. In some embodiments, the one or more human transcriptional regulatory elements direct expression of the human Siglec-14 gene and one or more additional genes in one or more cells of the transgenic non-human animal. In some embodiments, the one or more additional genes are one or more (e.g., one or more, two or more, three or more, four or more, five or more, or all six) of the human CD33, Siglec-5, Siglec-7, Siglec-9, Siglec-11, and/or Siglec-16 genes. In some embodiments, the one or more human transcriptional regulatory elements direct coordinate expression of the human Siglec-14 gene and the one or more additional genes in one or more cells of the transgenic non-human animal. In some embodiments, the one or more cells of the transgenic non-human animal are one or more of myeloid cells, natural killer (NK) cells, T cells, and/or microglia.

An exemplary amino acid sequence of human Siglec-14 is set forth below as SEQ ID NO: 13:

```
            10         20         30         40
     MLPLLLLPLL WGGSLQEKPV YELQVQKSVT VQEGLCVLVP 50         60         70         80
     CSFSYPWRSW YSSPPLYVYW FRDGEIPYYA EVVATNNPDR 90        100        110        120
     RVKPETQGRF RLLGDVQKKN CSLSIGDARM EDTGSYFFRV 130        140        150        160
     ERGRDVKYSY QQNKLNLEVT ALIEKPDIHF LEPLESGRPT 170        180        190        200
     RLSCSLPGSC EAGPPLTFSW TGNALSPLDP ETTRSSELTL 210        220        230        240
     TPRPEDHGTN LTCQVKRQGA QVTTERTVQL NVSYAPQNLA 250        260        270        280
     ISIFFRNGTG TALRILSNGM SVPIQEGQSL FLACTVDSNP 290        300        310        320
     PASLSWFREG KALNPSQTSM SGTLELPNIG AREGGEFTCR 330        340        350        360
     VQHPLGSQHL SFILSVQRSS SSCICVTEKQ QGSWPLVLTL 370        380        390
     IRGALMGAGF LLTYGLTWIY YTRCGGPQQS RAERPG
```

In some embodiments, a human Siglec-14 gene of the present disclosure encodes a polypeptide comprising the sequence of SEQ ID NO: 13. In some embodiments, a human Siglec-14 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 13.

In some embodiments, a human Siglec-14 gene of the present disclosure encodes an N-terminal truncation, a C-terminal truncation, or a fragment of a polypeptide comprising the sequence of SEQ ID NO: 13. N-terminal truncations, C-terminal truncations, or fragments may comprise least 10, at least 25, at least 50, at least 75, at least 100, at least 125, at least 150, at least 175, at least 200, at least 225, at least 250, at least 275, at least 300, at least 325, at least 350, at least 375, but fewer than 396, consecutive amino acids of SEQ ID NO: 13.

Human Siglec-16 Gene

In some embodiments, the genome of a transgenic non-human animal of the present disclosure comprises a human Siglec-16 gene. In some embodiments, the genome of the transgenic non-human animal comprises an inactivating mutation in the endogenous Siglec-16 gene. In some embodiments, the genome of the transgenic non-human animal comprises a non-functional endogenous Siglec-16 gene. In some embodiments, the genome of the transgenic non-human animal comprises a human Siglec-16 gene and lacks an endogenous Siglec-16 gene. In some embodiments, the genome of the transgenic non-human animal comprises a human Siglec-16 gene and a non-functional endogenous Siglec-16 gene.

In some embodiments, the human Siglec-16 gene comprises all intronic and exonic sequences of the Siglec-16 gene encoded on chromosome 19 in the human genome. An exemplary polynucleotide comprising all intronic and exonic sequences of the Siglec-16 gene encoded on chromosome 19 in the human genome is shown in SEQ ID NO: 21. In some embodiments, the human Siglec-16 gene comprises the coding sequence for the human Siglec-16 polypeptide. In some embodiments, the human Siglec-16 protein/polypeptide is encoded by a nucleic acid comprising the sequence of SEQ ID NO: 21. In some embodiments, the human Siglec-16 protein/polypeptide is encoded by a nucleic acid comprising a sequence at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identical to the sequence of SEQ ID NO: 21.

In some embodiments, the human Siglec-16 gene comprises a flanking sequence at the 5' end of the coding sequence for the human Siglec-16 polypeptide. In some embodiments, the human Siglec-16 gene comprises a flanking sequence at the 3' end of the coding sequence for the human Siglec-16 polypeptide. In some embodiments, the human Siglec-16 gene comprises a flanking sequence at the 5' end and 3' end of the coding sequence for the human Siglec-16 polypeptide. In some embodiments, the flanking sequence is at least about 10,000, at least about 15,000, at least about 20,000, at least about 25,000, at least about 30,000, at least about 35,000, at least about 40,000, at least about 45,000, or at least about 50,000 base pairs in length. In some embodiments, the flanking sequence is at least about 10,000 base pairs in length.

In some embodiments, the flanking sequence comprises one or more (e.g., one or more, two or more, three or more, four or more, five or more, etc.) human transcriptional regulatory elements. In some embodiments, the one or more human transcriptional regulatory elements direct expression of the human Siglec-16 gene in one or more cells of the transgenic non-human animal. In some embodiments, the one or more human transcriptional regulatory elements direct expression of the human Siglec-16 gene and one or more additional genes in one or more cells of the transgenic non-human animal. In some embodiments, the one or more additional genes are one or more (e.g., one or more, two or more, three or more, four or more, five or more, or all six) of the human CD33, Siglec-5, Siglec-7, Siglec-9, Siglec-11, and/or Siglec-14 genes. In some embodiments, the one or more human transcriptional regulatory elements direct coordinate expression of the human Siglec-16 gene and the one or more additional genes in one or more cells of the transgenic non-human animal. In some embodiments, the one or more cells of the transgenic non-human animal are one or more of myeloid cells, natural killer (NK) cells, T cells, and/or microglia.

An exemplary amino acid sequence of human Siglec-16 is set forth below as SEQ ID NO: 14:

```
         10         20         30         40
  MLLLPLLLPV LGAGSLNKDP SYSLQVQRQV PVPEGLCVIV 50         60         70         80
  SCNLSYPRDG WDESTAAYGY WFKGRTSPKT GAPVATNNQS
```

-continued
```
         90        100        110        120
  REVAMSTRDR FQLTGDPGKG SCSLVIRDAQ REDEAWYFFR 130        140        150        160
  VERGSRVRHS FLSNAFFLKV TALTQKPDVY IPETLEPGQP 170        180        190        200
  VTVICVFNWA FKKCPAPSFS WTGAALSPRR TRPSTSHFSV 210        220        230        240
  LSFTPSPQDH DTDLTCHVDF SRKGVSAQRT VRLRVASLEL 250        260        270        280
  QGNVIYLEVQ KGQFLRLLCA ADSQPPATLS WVLQDRVLSS 290        300        310        320
  SHPWGPRTLG LELPGVKAGD SGRYTCRAEN RLGSQQRALD 330        340        350        360
  LSVQYPPENL RVMVSQANRT VLENLRNGTS LRVLEGQSLR 370        380        390        400
  LVCVTHSSPP ARLSWTWGEQ TVGPSQPSDP GVLQLPRVQM 410        420        430        440
  EHEGEFTCHA RHPLGSQRVS LSFSVHCKSG PMTGVVLVAV 450        460        470        480
  GEVAMKILLL CLCLILLRVR SCRRKAARAA LGMEAADAVT
```
D In some embodiments, a human Siglec-16 gene of the present disclosure encodes a polypeptide comprising the sequence of SEQ ID NO: 14. In some embodiments, a human Siglec-16 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 14.

In some embodiments, a human Siglec-16 gene of the present disclosure encodes an N-terminal truncation, a C-terminal truncation, or a fragment of a polypeptide comprising the sequence of SEQ ID NO: 14. N-terminal truncations, C-terminal truncations, or fragments may comprise least 10, at least 25, at least 50, at least 75, at least 100, at least 125, at least 150, at least 175, at least 200, at least 225, at least 250, at least 275, at least 300, at least 325, at least 350, at least 375, at least 400, at least 425, at least 450, at least 475, but fewer than 481, consecutive amino acids of SEQ ID NO: 14.

Gene Combinations

In some embodiments, the genome of a transgenic non-human animal of the present disclosure comprises two or more, three or more, four or more, five or more, six or more, or all seven of the human CD33, Siglec-5, Siglec-7, Siglec-9, Siglec-11, Siglec-14, and/or Siglec-16 genes.

In some embodiments, the genome of transgenic non-human animal comprises one or more polynucleotides encoding two or more human genes. In some embodiments, the two or more human genes are encoded on separate polynucleotides. In some embodiments, the two or more human genes are encoded on a single polynucleotide. In some embodiments, the one or more polynucleotides are bacterial artificial chromosomes (BACs).

In some embodiments, the genome of the transgenic non-human animal comprises two of the human CD33, Siglec-5, Siglec-7, Siglec-9, Siglec-11, Siglec-14, and Siglec-16 genes. In some embodiments, the genome of the transgenic non-human animal comprises the human CD33 and Siglec-5 genes; the human CD33 and Siglec-7 genes; the human CD33 and Siglec-9 genes; the human CD33 and Siglec-11 genes; the human CD33 and Siglec-14 genes; the human CD33 and Siglec-16 genes; the human Siglec-5 and Siglec-7 genes; the human Siglec-5 and Siglec-9 genes; the human Siglec-5 and Siglec-11 genes; the human Siglec-5 and Siglec-14 genes; the human Siglec-5 and Siglec-16 genes; the human Siglec-7 and Siglec-9 genes; the human Siglec-7 and Siglec-11 genes; the human Siglec-7 and Siglec-14 genes; the human Siglec-7 and Siglec-16 genes; the human Siglec-9 and Siglec-11 genes; the human Siglec-9 and Siglec-14 genes; the human Siglec-9 and Siglec-16 genes; the human Siglec-11 and Siglec-14 genes; the human Siglec-11 and Siglec-16 genes; or the human Siglec-14 and Siglec 16 genes. In some embodiments, the two human genes are encoded on one or more BACs. In some embodiments, the two human genes are encoded on a single BAC. In some embodiments, the genome of the transgenic non-human animal comprises the human Siglec-5 and Siglec-14 genes. In some embodiments, the genome of the transgenic non-human animal comprises the human Siglec-11 and Siglec-16 genes.

In some embodiments, the genome of the transgenic non-human animal comprises three of the human CD33, Siglec-5, Siglec-7, Siglec-9, Siglec-11, Siglec-14, and Siglec-16 genes. In some embodiments, the genome of the transgenic non-human animal comprises the human CD33, Siglec-5, and Siglec-7 genes; the human CD33, Siglec-5, and Siglec-9 genes; the human CD33, Siglec-5, and Siglec-11 genes; the human CD33, Siglec-5, and Siglec-14 genes; the human CD33, Siglec-5, and Siglec-16 genes; the human CD33, Siglec-7, and Siglec-9 genes; the human CD33, Siglec-7, and Siglec-11 genes; the human CD33, Siglec-7, and Siglec-14 genes; the human CD33, Siglec-7, and Siglec-16 genes; the human CD33, Siglec-9, and Siglec-11 genes; the human CD33, Siglec-9, and Siglec-14 genes; the human CD33, Siglec-9, and Siglec-16 genes; the human CD33, Siglec-11, and Siglec-14 genes; the human CD33, Siglec-11, and Siglec-16 genes; the human CD33, Siglec-14, and Siglec-16 genes; the human Siglec-5, Siglec-7, and Siglec-9 genes; the human Siglec-5, Siglec-7, and Siglec-11 genes; the human Siglec-5, Siglec-7, and Siglec-14 genes; the human Siglec-5, Siglec-7, and Siglec-16 genes; the human Siglec-5, Siglec-9, and Siglec-11 genes; the human Siglec-5, Siglec-9, and Siglec-14 genes; the human Siglec-5, Siglec-9, and Siglec-16 genes; the human Siglec-5, Siglec-11, and Siglec-14 genes; the human Siglec-5, Siglec-11, and Siglec-16 genes; the human Siglec-5, Siglec-14, and Siglec-16 genes; the human Siglec-7, Siglec-9, and Siglec-11 genes; the human Siglec-7, Siglec-9, and Siglec-14 genes; the human Siglec-7, Siglec-9, and Siglec-16 genes; the human Siglec-7, Siglec-11, and Siglec-14 genes; the human Siglec-7, Siglec-11, and Siglec-16 genes; the human Siglec-7, Siglec-14, and Siglec-16 genes; the human Siglec-9, Siglec-11, and Siglec-14 genes; the human Siglec-9, Siglec-11, and Siglec-16 genes; the human Siglec-9, Siglec-14, and Siglec-16 genes; or the human Siglec-11, Siglec-14, and Siglec-16 genes. In some embodiments, the three human genes are encoded on one or more BACs. In some embodiments, the three human genes are encoded on a single BAC. In some embodiments, the genome of the transgenic non-human animal comprises the human CD33, Siglec-7, and Siglec-9 genes.

In some embodiments, the genome of the transgenic non-human animal comprises four of the human CD33, Siglec-5, Siglec-7, Siglec-9, Siglec-11, Siglec-14, and Siglec-16 genes. In some embodiments, the genome of the transgenic non-human animal comprises the human CD33, Siglec-5, Siglec-7, and Siglec-9 genes; the human CD33, Siglec-5, Siglec-7, and Siglec-11 genes; the human CD33, Siglec-5, Siglec-7, and Siglec-14 genes; the human CD33, Siglec-5, Siglec-7, and Siglec-16 genes; the human CD33, Siglec-5, Siglec-9, and Siglec-11 genes; the human CD33, Siglec-5, Siglec-9, and Siglec-14 genes; the human CD33, Siglec-5, Siglec-9, and Siglec-16 genes; the human CD33, Siglec-5, Siglec-11, and Siglec-14 genes; the human CD33, Siglec-5, Siglec-11, and Siglec-16 genes; the human CD33, Siglec-5, Siglec-14, and Siglec-16 genes; the human CD33, Siglec-7, Siglec-9, and Siglec-11 genes; the human CD33, Siglec-7, Siglec-9, and Siglec-14 genes; the human CD33, Siglec-7, Siglec-9, and Siglec-16 genes; the human CD33, Siglec-7, Siglec-11, and Siglec-14 genes; the human CD33, Siglec-7, Siglec-11, and Siglec-16 genes; the human CD33, Siglec-7, Siglec-14, and Siglec-16 genes; the human CD33, Siglec-9, Siglec-11, and Siglec-14 genes; the human CD33, Siglec-9, Siglec-11, and Siglec-16 genes; the human CD33, Siglec-9, Siglec-14, and Siglec-16 genes; the human CD33, Siglec-11, Siglec-14, and Siglec-16 genes; the human Siglec-5, Siglec-7, Siglec-9, and Siglec-11 genes; the human Siglec-5, Siglec-7, Siglec-9, and Siglec-14 genes; the human Siglec-5, Siglec-7, Siglec-9, and Siglec-16 genes; the human Siglec-5, Siglec-7, Siglec-11, and Siglec-14 genes; the human Siglec-5, Siglec-7, Siglec-11, and Siglec-16 genes; the human Siglec-5, Siglec-7, Siglec-14, and Siglec-16 genes; the human Siglec-5, Siglec-9, Siglec-11, and Siglec-14 genes; the human Siglec-5, Siglec-9, Siglec-11, and Siglec-16 genes; the human Siglec-5, Siglec-9, Siglec-14, and Siglec-16 genes; the human Siglec-5, Siglec-11, Siglec-14, and Siglec-16 genes; the human Siglec-7, Siglec-9, Siglec-11, and Siglec-14 genes; the human Siglec-7, Siglec-9, Siglec-11, and Siglec-16 genes; the human Siglec-7, Siglec-9, Siglec-14, and Siglec-16 genes; the human Siglec-7, Siglec-11, Siglec-14, and Siglec-16 genes; or the human Siglec-9, Siglec-11, Siglec-14, and Siglec-16 genes. In some embodiments, the four human genes are encoded on one or more BACs. In some embodiments, the four human genes are encoded on two BACs. In some embodiments, the four human genes are encoded on a single BAC.

In some embodiments, the genome of the transgenic non-human animal comprises five of the human CD33, Siglec-5, Siglec-7, Siglec-9, Siglec-11, Siglec-14, and Siglec-16 genes. In some embodiments, the genome of the transgenic non-human animal comprises the human CD33, Siglec-5, Siglec-7, Siglec-9, and Siglec-11 genes; the human CD33, Siglec-5, Siglec-7, Siglec-9, and Siglec-14 genes; the human CD33, Siglec-5, Siglec-7, Siglec-9, and Siglec-16 genes; the human CD33, Siglec-5, Siglec-7, Siglec-11, and Siglec-14 genes; the human CD33, Siglec-5, Siglec-7, Siglec-11, and Siglec-16 genes; the human CD33, Siglec-5, Siglec-7, Siglec-14, and Siglec-16 genes; the human CD33, Siglec-5, Siglec-9, Siglec-11, and Siglec-14 genes; the human CD33, Siglec-5, Siglec-9, Siglec-11, and Siglec-16 genes; the human CD33, Siglec-5, Siglec-9, Siglec-14, and Siglec-16 genes; the human CD33, Siglec-5, Siglec-11, Siglec-14, and Siglec-16 genes; the human CD33, Siglec-7, Siglec-9, Siglec-11, and Siglec-14 genes; the human CD33, Siglec-7, Siglec-9, Siglec-11, and Siglec-16 genes; the human CD33, Siglec-7, Siglec-9, Siglec-14, and Siglec-16 genes; the human CD33, Siglec-7, Siglec-11, Siglec-14, and Siglec-16 genes; the human CD33, Siglec-9, Siglec-11, Siglec-14, and Siglec-16 genes; the human Siglec-5, Siglec-7, Siglec-9, Siglec-11, and Siglec-14 genes; the human Siglec-5, Siglec-7, Siglec-9, Siglec-11, and Siglec-16 genes; the human Siglec-5, Siglec-7, Siglec-9, Siglec-14, and Siglec-16 genes; the human Siglec-5, Siglec-7, Siglec-11, Siglec-14, and Siglec-16 genes; the human Siglec-5, Siglec-9, Siglec-11, Siglec-14, and Siglec-16 genes; or the human Siglec-7, Siglec-9, Siglec-11, Siglec-14, and Siglec-16 genes. In some embodiments, the five human genes are encoded on one or more BACs. In some embodiments, the five human genes are encoded on two BACs. In some embodiments, the five human genes are encoded on a single BAC.

In some embodiments, the genome of the transgenic non-human animal comprises six of the human CD33, Siglec-5, Siglec-7, Siglec-9, Siglec-11, Siglec-14, and Siglec-16 genes. In some embodiments, the genome of the transgenic non-human animal comprises the human CD33, Siglec-5, Siglec-7, Siglec-9, Siglec-11, and Siglec-14 genes; the human Siglec-5, Siglec-7, Siglec-9, Siglec-11, Siglec-14, and Siglec-16 genes; the human CD33, Siglec-7, Siglec-9, Siglec-11, Siglec-14, and Siglec-16 genes; the human CD33, Siglec-5, Siglec-9, Siglec-11, Siglec-14, and Siglec-16 genes; the human CD33, Siglec-5, Siglec-7, Siglec-11, Siglec-14, and Siglec-16 genes; the human CD33, Siglec-5, Siglec-7, Siglec-9, Siglec-14, and Siglec-16 genes; or the human CD33, Siglec-5, Siglec-7, Siglec-9, Siglec-11, and Siglec-16 genes. In some embodiments, the six human genes are encoded on one or more BACs. In some embodiments, the six human genes are encoded on a single BAC.

In some embodiments, the genome of the transgenic non-human animal comprises the human CD33, Siglec-5, Siglec-7, Siglec-9, Siglec-11, Siglec-14, and Siglec-16 genes. In some embodiments, the seven human genes are encoded on one or more BACs. In some embodiments, the seven human genes are encoded on three BACs. In some embodiments, the seven human genes are encoded on a single BAC.

In some embodiments, the transgenic non-human animal is a rodent (e.g., a mouse or rat). In some embodiments, the transgenic non-human animal is a mouse. In some embodiments, the genome of the transgenic mouse comprises one or more (e.g., one or more, two or more, three or more, four or more, etc.) non-functional murine genes. In some embodiments, the one or more non-functional murine genes are one or more of the murine CD33 gene, the murine Siglec-5 gene, the murine Siglec-7 gene, the murine Siglec-9 gene, the murine Siglec-11 gene, and any combination thereof. In some embodiments, the genome of the transgenic mouse comprises a non-functional murine CD33 gene, a non-functional murine Siglec-5 gene, a non-functional murine Siglec-7 gene, a non-functional murine Siglec-9 gene, and a non-functional murine Siglec-11 gene.

Methods

Certain aspects of the present disclosure relate to methods of screening candidate agents that bind to and/or modulate the function and/or activity of at least one of the human genes in the transgenic non-human animals; to methods of screening candidate agents to determine their effect on one or more activities and/or functions associated with expression of at least one of the human genes in the transgenic non-human animals; to methods of recapitulating a human Siglec immune system in a non-human animal; and to methods of generating a non-human animal disease model comprising a human Siglec repertoire.

Transgenic non-human animals of the present disclosure may be generated by any method known in the art. In some embodiments, the method comprises introducing one or more polynucleotides encoding two or more of the human CD33, Siglec-5, Siglec-7, Siglec-9, Siglec-11, Siglec-14, and Siglec-16 genes into one or more cells of an animal (e.g., by pronuclear injection of purified polynucleotides into the zygote of an animal) to generate a founder transgenic non-human animal. In some embodiments, the one or more polynucleotides are one or more bacterial artificial chromosomes (BACs). Once founder transgenic non-human animals are produced whose genome comprises two or more of the human CD33, Siglec-5, Siglec-7, Siglec-9, Siglec-11, Siglec-14, and Siglec-16 genes, the founder animals may be bred, inbred, outbred, or crossbred to produce progeny (colonies) of the particular non-human animal Examples of such breeding strategies may include, but are not limited to, outbreeding of the founder animals with more than one integration site in order to establish separate lines; inbreeding of separate lines in order to produce compound transgenic that express the transgenes at higher levels due to the effects of additive expression of each transgene; crossing of heterozygous transgenic animals to produce transgenic animals homozygous for a given integration site in order to both augment expression and eliminate the need for screening of animals by DNA analysis; crossing of separate homozygous lines to produce compound heterozygous or homozygous lines; and breeding animals to different inbred genetic backgrounds so as to examine effects of modifying alleles on expression of the transgenes and the physiological effects of expression.

Transgenic non-human animals are produced by introducing one or more transgenes into the germline of the transgenic animal. Methods of introducing DNA into cells are generally available and well-known in the art, and different methods of introducing transgenes may be used (See e.g., Hogan et al. *Manipulating the Mouse Embryo: A Laboratory Manual Cold Spring Harbor Laboratory*, $2^{nd}$ edition, Cold Spring Harbor Laboratory (1994); U.S. Pat. Nos. 5,602,229; 5,175,384; 6,066,778; and 6,037,521). Technology used in developing transgenic animals include pronuclear microinjection (See e.g., Gordon, J. W. (1980) PNAS 77, 7380-7384; U.S. Pat. No. 4,873,191), homologous recombination (targeted transgenesis by transferring embryonic stem cells into blastocysts; Thompson et al. (1989) *Cell* 56: 313-321), RNA interference (RNAi)/CRISPR-Cas/TALENs for silencing of specific gene function, retrovirus gene transfer into germ lines (See e.g., Van der Putten et al. (1985) *PNAS* 82: 6148-6152), electroporation of embryos (See e.g., Lo. (1983) *Mol. Cell. Biol.* 3: 1803-1814), and sperm-mediated gene transfer (See e.g., Lavitrano et al. (1989) *Cell* 57: 717-723).

Generally, the zygote is the best target for microinjection. In mice, for example, the male pronucleus reaches the size of approximately 20 μm in diameter, which allows reproducible injection of 1-2 pL of DNA solution. The use of zygotes as a target for gene transfer has a major advantage because, in most cases, the injected DNA will be incorporated into the host genome before the first cleavage. Consequently, nearly all cells of the transgenic non-human animal will carry the incorporated transgene(s). Generally, this will result in the efficient transmission of the transgene to offspring of the founder since 50% of the germ cells will harbor the transgene. The pronuclear microinjection method of producing a transgenic animal results in the introduction of linear DNA sequences into the chromosomes of the fertilized eggs. Bacterial artificial chromosome (BAC) containing the genes of interest, or an alternative plasmid construct containing the genes of interest, is injected into pronuclei (i.e., fertilized eggs at a pronuclear state). The manipulated pronuclei are subsequently injected into the uterus of a pseudopregnant female. Mice generated using this method can have on or multiple copies of the transgenes, which can be assayed by any method known in the art (e.g., by southern blot technology).

The transgenic non-human animals of the present disclosure may also be generated by introducing one or more targeting vectors into embryonic stem (ES) cells. ES cells may be obtained by culturing pre-implantation embryos in vitro under appropriate conditions (See e.g., Evans et al. (1981) *Nature* 292: 154-6; Bradley et al. (1984) *Nature* 309: 255-8; Gossler et al. (1986) *PNAS* 83: 9065-9; Robertson et al. (1986) *Nature* 322: 445-8). Transgenes may be efficiently introduced into ES cells by DNA transfection using a variety of methods known in the art, including, without limitation, electroporation, calcium phosphate co-precipitation, protoplast or spheroplast fusion, lipofection, polymer-based transfections, and DEAE-dextran-mediated transfection. Transgenes may also be introduced into ES cells by retrovirus-mediated transduction of by micro-injection. Such transfected ES cells may thereafter colonize an embryo following their introduction into the blastocoel of a blastocyst-stage embryo and contribute to the germ line of the resulting chimeric animals (See e.g., Jaenisch, (1988) *Science* 240: 1468-74). Prior to the introduction of transfected ES cells in the blastocoel, the transfected ES cells may be subjected to various selection protocols to enrich for ES cells that have integrated the transgenes if the transgenes provide a means for such a selection. Alternatively, PCR amplification may be used to screen for ES cells that have integrated the transgenes. This technique obviates the need for growth of the transfected ES cells under appropriate selective conditions prior to transfer in to the blastocoel.

Retroviral infection may also be used to introduce transgenes into a non-human animal Examples of suitable retroviruses may include, but are not limited to, human immunodeficiency virus (HIV), murine Moloney leukemia virus (MoMuLV), murine Moloney sarcoma virus (MSV), Harvey sarcoma virus (HaSV), spleen necrosis virus (SNV), Rous sarcoma virus (RSV) and Friend virus (See also, WO95/02697). The developing non-human embryo may be cultured in vitro to the blastocyst stage. During this time, blastomeres may be targets for retroviral infection. Efficient infection of the blastomeres may be obtained by enzymatic treatment to remove the zona pellucida. The viral vector system used to introduce the transgenes is typically a replication-defective retrovirus carrying the transgenes. Transfection is easily and efficiently obtained by culturing the blastomeres on a monolayer of virus-producing cells. Alternatively, infection can be performed at a later stage. Virus or virus-producing cells may be injected into the blastocoel. Most of the founder animals will be mosaic for the transgenes since incorporation occurs only in a subset of the cells which formed the transgenic non-human animal. Furthermore, the founder animal may contain retroviral insertion of the transgenes at a variety of positions in the genome; these generally segregate in the offspring. In addition, it is also possible to introduce transgenes into the germ line by intrauterine retroviral infection of the midgestation embryo.

Viral vectors may be used to produce a transgenic animal. In some embodiments, the viral vectors are replication-defective viral vectors (i.e., they are unable to replicate autonomously in the target cell). Generally, the genome of the replication defective viral vectors which are used lack at least one region which is necessary for the replication of the virus in the infected cell. These regions may either be eliminated (in whole or in part) or be rendered non-functional by any technique known in the art. These may include, for example, the total removal, substitution, partial deletion, or addition of one or more bases to an essential (for replication) region. Such techniques may be performed in vitro or in situ, using the techniques of genetic manipulation or by treatment with one or more mutagenic agents. In some embodiments, the replication-defective virus retain the sequences of its genome which are necessary for encapsidating the viral particles. Methods of producing viral vectors comprising one or more transgenes are known in the art.

Methods of Screening Candidate Agents

Certain aspects of the present disclosure relate to methods of screening candidate agents in any of the transgenic non-human animals described herein.

In some embodiments, the method comprises administering one or more candidate agents to a transgenic non-human animal of the present disclosure, and determining whether the one or more candidate agents bind to and/or modulates the function and/or activity of at least one of the two or more human CD33, Siglec-5, Siglec-7, Siglec-9, Siglec-11, Siglec-14, and/or Siglec-16 genes in the transgenic non-human animal.

In some embodiments, the method comprises administering one or more candidate agents to a transgenic non-human animal of the present disclosure, and determining the effect of the one or more candidate agents on one or more activities and/or functions associated with expression of at least one of the two or more human genes in the transgenic non-human animal. In some embodiments, the one or more candidate agents inhibits one or more activities and/or functions associated with expression of two or more (e.g., two or more, three or more, four or more, five or more, six or more, etc.) of the human CD33, Siglec-5, Siglec-7, Siglec-9, Siglec-11, Siglec-14, and/or siglec-16 genes in the transgenic non-human animal.

In some embodiments, the one or more candidate agents are any of 1 or more, 2 or more, 3 or more, 4 or more, 5 or more, 6 or more, 7 or more, 8 or more, 9 or more, or 10 or more candidate agents. In some embodiments, the one or more candidate agents are administered once to the transgenic non-human animal. In some embodiments, the candidate agents are administered two or more (e.g., two or more, three or more, four or more, five or more, six or more, seven or more, eight or more, nine or more, or ten or more) times to the transgenic non-human animal. In some embodiments, the one or more candidate agents are administered at the same dose two or more times in the transgenic non-human animal. In some embodiments, the one or more candidate agents are administered at two or more different doses two or more times in the transgenic non-human animal.

In some embodiments, the one or more candidate agents are two or more candidate agents. In some embodiments, the two or more candidate agents are administered at the same time to the transgenic non-human animal. In some embodiments, the two or more candidate agents are administered sequentially to the transgenic non-human animal. In some embodiments, the two or more candidate agents target one or more of the human CD33, Siglec-5, Siglec-7, Siglec-9, Siglec-11, Siglec-14, and/or Siglec-16 genes. In some embodiments, the two or more candidate agents target the same human gene (e.g., a first and second candidate agent target a single human gene; a first, second, and third candidate agent target a single human gene, etc.) In some embodiments, the two or more candidate agents target two or more of the human genes (e.g., the first candidate agent targets a first human gene, the second candidate agent targets a second human gene; the first candidate agent targets a first human gene, the second candidate agent targets a second human gene, the third candidate agent targets a third human gene, etc.). In some embodiments, the one or more candidate agents are three or more candidates agents, and at least two of the three or more candidate agents target the same human gene (e.g., a first and second candidate agent target a first human gene, a third candidate agent targets a second human gene, etc.).

Examples of candidate agents may include, but are not limited to, compounds that specifically inhibit Siglec synthesis and/or release, antisense molecules directed to one or more Siglecs, short interfering RNA (siRNA) molecules directed to one or more nucleic acids encoding one or more Siglecs, antibodies (e.g., monospecific antibodies, bispecific antibodies) that bind to one or more Siglecs, soluble Siglec receptors (e.g., soluble Siglec receptors that bind one or more Siglec ligands), Siglec-Fc fusion proteins, Siglec immunoadhesins, compounds that specifically inhibit one or more Siglec activities such as small molecule inhibitors and/or peptide inhibitors, compounds that specifically inhibit one or more Siglecs from binding to one or more ligands, Siglec structural analogs, RNA or DNA aptamers that binds one or more Siglecs, compounds that inhibit the synthesis of one or more Siglec ligands (e.g., sialic acid-containing glycans present on proteins or other molecules), compounds that promote Siglec ligand degradation, and compounds that directly degrade one or more Siglec ligands. In some embodiments, the one or more candidate agents are one or more antibodies.

In some embodiments, the effect of the one or more candidate agents is one or more of reducing cell surface levels of one or more polypeptides encoded by the human CD33, Siglec-5, Siglec-7, Siglec-9, Siglec-11, Siglec-14, or Siglec-16 genes; competing for binding with a natural ligand of one or more polypeptides encoded by the human CD33, Siglec-5, Siglec-7, Siglec-9, Siglec-11, Siglec-14, or Siglec-16 genes; reducing T cell proliferation and/or phagocytosis; increasing the survival of macrophages, neutrophils, NK cells, and/or dendritic cells; inducing CCR7 and/or F-actin in microglia, macrophages, neutrophils, NK cells, and/or dendritic cells; increasing expression of one or more inflammatory cell surface markers on macrophages, neutrophils, and/or NK cells; suppressing myeloid-derived suppressor cell (MDSC) proliferation, activation, and/or function; reducing IL-10 secretion from one or more myeloid cells; inducing SYK and/or ERK activation and/or phosphorylation; and any combination thereof.

In some embodiments, the one or more candidate agents inhibits one or more activities and/or functions associated with expression of two or more (e.g., two or more, three or more, four or more, five or more, six or more, etc.) of the human CD33, Siglec-5, Siglec-7, Siglec-9, Siglec-11, Siglec-14, and/or siglec-16 genes in the transgenic non-human animal. In some embodiments, the one or more activities and/or functions are one or more of immune cell suppression; decreased expression of one or more pro-inflammatory cytokines, optionally wherein the one or more pro-inflammatory cytokines are selected from a group consisting IFN-α4, IFN-beta, IL-1I3, IL-1alpha, TNF-α, IL-6, IL-8, CRP, IL-20 family members, LIF, IFN-gamma, OSM, CNTF, GM-CSF, IL-11, IL-12, IL-17, IL-18, CRP, MCP-1, and MIP-1-beta; decreased expression of one or more pro-inflammatory cytokines in one or more cells selected from the group consisting of macrophages, neutrophils, NK cells, dendritic cells, bone marrow-derived dendritic cells, monocytes, osteoclasts, T cells, T helper cells, cytotoxic T cells, granulocytes, and microglial cells; increased expression of one or more anti-inflammatory cytokines, optionally wherein the one or more anti-inflammatory cytokines are selected from the group consisting of IL4, IL10, IL13, IL35, IL16, TGF-beta, IL1ra, G-CSF, and soluble receptors for TNF, IFN-beta1a, IFN-beta1b, and IL6; increased expression of one or more anti-inflammatory cytokines in one or more cells selected from the group consisting of macrophages, neutrophils, NK cells, dendritic cells, bone marrow-derived dendritic cells, monocytes, osteoclasts, T cells, T helper cells, cytotoxic T cells, granulocytes, and microglial cells; inhibition of extracellular signal-regulated kinase (ERK) phosphorylation; decreasing tyrosine phosphorylation on one or more cellular proteins, optionally, wherein the one or more cellular proteins comprise ZAP-70 and the tyrosine phosphorylation occurs on Tyr-319 of ZAP-70; decreased expression of C—C chemokine receptor 7 (CCR7); inhibition of microglial cell chemotaxis toward CCL19-expressing and CCL21-expressing cells; decreasing T cell proliferation induced by one or more cells selected from the group consisting of dendritic cells, bone marrow-derived dendritic cells, monocytes, microglia, M1 microglia, activated M1 microglia, M2 microglia, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, and M2 NK cells; inhibition of osteoclast production, decreased rate of osteoclastogenesis, or both; decreasing survival of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; decreasing proliferation of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; inhibiting migration of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; inhibiting one or more functions of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; inhibiting maturation of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; inhibition of one or more types of clearance selected from the group consisting of apoptotic neuron clearance, nerve tissue debris clearance, non-nerve tissue debris clearance, bacteria clearance, other foreign body clearance, disease-causing protein clearance, disease-causing peptide clearance, and tumor cell clearance; optionally wherein the disease-causing protein is selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides and the tumor cell is from a cancer selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer; inhibition of phagocytosis of one or more of apoptotic neurons, nerve tissue debris, non-nerve tissue debris, bacteria, other foreign bodies, disease-causing proteins, disease-causing peptides, disease-causing nucleic acids, or tumor cells; optionally wherein the disease-causing nucleic acids are antisense GGCCCC (G2C4) repeat-expansion RNA, the disease-causing proteins are selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and the tumor cells are from a cancer selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, or thyroid cancer; inhibition of tumor cell killing by one or more of microglia, macrophages, neutrophils, NK cells, dendritic cells, bone marrow-derived dendritic cells, neutrophils, T cells, T helper cells, or cytotoxic T cells; inhibiting anti-tumor cell proliferation activity of one or more of microglia, macrophages, neutrophils, NK cells, dendritic cells, bone marrow-derived dendritic cells, neutrophils, T cells, T helper cells, or cytotoxic T cells; inhibition of anti-tumor cell metastasis activity of one or more of microglia, macrophages, neutrophils, NK cells, dendritic cells, bone marrow-derived dendritic cells, neutrophils, T cells, T helper cells, or cytotoxic T cells; inhibition of one or more ITAM motif containing receptors, optionally wherein the one or more ITAM motif containing receptors are selected from the group consisting of TREM1, TREM2, Sirp beta, FcgR, DAP10, and DAP12; inhibition of signaling by one or more pattern recognition receptors (PRRs), optionally wherein the one or more PRRs are selected from the group consisting of receptors that identify pathogen-associated molecular patterns (PAMPs), receptors that identify damage-associated molecular patterns (DAMPs), and any combination thereof; inhibition of one or more receptors comprising the motif D/Ex0-2YxxL/IX6-8YxxL/I (SEQ ID NO: 22); inhibition of signaling by one or more Toll-like receptors; inhibition of the JAK-STAT signaling pathway; inhibition of nuclear factor kappa-light-chain-enhancer of activated B cells (NFκB); de-phosphorylation of an ITAM motif containing receptor; decreased expression of one or more inflammatory receptors, optionally wherein the one or more inflammatory receptors comprise CD86 and the one or more inflammatory receptors are expressed on one or more of microglia, macrophages, neutrophils, NK cells, dendritic cells, bone marrow-derived dendritic cells, neutrophils, T cells, T helper cells, or cytotoxic T cells; decreasing expression of one or more ITAM-dependent genes, optionally wherein the one more ITAM-dependent genes are activated by nuclear factor of activated T cells (NFAT) transcription factors; promoting differentiation of one or more of immunosuppressor dendritic cells, immunosuppressor macrophages, immunosuppressor neutrophils, immunosuppressor NK cells, myeloid derived suppressor cells, tumor-associated macrophages, tumor-associated neutrophils, tumor-associated NK cells, and regulatory T cells; rescuing functionality of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells; increasing infiltration of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells into tumors; increasing the number of tumor-promoting myeloid/granulocytic immune-suppressive cells in a tumor, in peripheral blood, or other lymphoid organ; enhancing tumor-promoting activity of myeloid-derived suppressor cells; increasing expression of tumor-promoting cytokines in a tumor or in peripheral blood, optionally wherein the tumor-promoting cytokines are TGF-beta or IL-10; increasing tumor infiltration of tumor-promoting FoxP3+ regulatory T lymphocytes; enhancing tumor-promoting activity of myeloid-derived suppressor cells (MDSC); decreasing activation of tumor-specific T lymphocytes with tumor killing potential; decreasing infiltration of tumor-specific NK cells with tumor killing potential; decreasing the tumor killing potential of NK cells; decreasing infiltration of tumor-specific B lymphocytes with potential to enhance immune response; decreasing infiltration of tumor-specific T lymphocytes with tumor killing potential; increasing tumor volume; increasing tumor growth rate; increasing metastasis; increasing rate of tumor recurrence; decreasing efficacy of one or more immune-therapies that modulate anti-tumor T cell responses, optionally wherein the one or more immune-therapies are immune-therapies that target one or more target proteins selected from the group consisting of PD1/PDLL, CTLA4, CD40, OX40, ICOS, CD28, CD137/4-1BB, CD27, GITR, PD-L1, CTLA4, PD-L2, PD-1, B7-H3, B7-H4, HVEM, BTLA, KIR, GALS, TIM3, A2AR, LAG, DR-5, and any combination thereof, or cancer vaccines; inhibition of PLCγ/PKC/calcium mobilization; inhibition of PI3K/Akt, Ras/MAPK signaling; and any combination thereof.

In some embodiments, the transgenic non-human animal suffers from a disease, disorder, and/or injury. In some embodiments, administering the one or more candidate agents reduced or eliminates one or more signs and/or symptoms of the disease, disorder, and/or injury. In some embodiments, the disease, disorder, and/or injury is one or more of autoimmunity, susceptibility to infection, cancer, proliferative disorders, and/or neurodegenerative disorders.

In some embodiments, the disease, disorder, and/or injury is one or more of dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV infection, and *Haemophilus influenza* infection.

Methods of Recapitulating a Human Siglec Immune System

Certain aspects of the present disclosure relate to a method of recapitulating a human Siglec immune system in a non-human animal. In some embodiments, the method comprises generating a transgenic non-human animal whose genome comprises two or more of the human CD33, Siglec-5, Siglec-7, Siglec-9, Siglec-11, Siglec-14, and/or Siglec-16 genes. In some embodiments, the two or more human genes are coordinately expressed in one or more cells of the transgenic non-human animal. In some embodiments, the one or more cells of the transgenic non-human animal are one or more of myeloid cells, natural killer (NK) cells, T cells, microglia, and any combinations thereof. In some embodiments, the transgenic non-human animal comprising a recapitulated human Siglec immune system is any of the transgenic non-human animals described herein. Methods of generating transgenic non-human animals are known in the art (e.g., by any of the methods described herein).

Without wishing to be bound by theory, it is thought that recapitulating a human Siglec immune system in a non-human animal comprises the coordinate expression of multiple (i.e., two or more) human Siglec genes in the non-human animal that mimics the cell-type specificity (e.g., myeloid lineages: monocytes, macrophages dendritic cells, microglia, etc.) and gene expression (e.g., expression levels, cellular localization of the proteins at the cell surface, etc.) observed in the corresponding human cells. Furthermore, without wishing to be bound by theory, it is thought coordinate expression of multiple human Siglec proteins in non-human animals would allow these proteins to form heteromers (e.g., heterodimers, etc.) in the myeloid cells of the non-human animals, and that the myeloid cells expressing the human Siglec genes would respond to the ligands of the human Siglec proteins equivalently to human cells with respect to ITIM signaling, as well as the suppressive/activating functions of the human Siglec proteins, thus recapitulating the human Siglec immune system in a non-human animal.

Methods of Generating Non-Human Animal Disease Models with a Human Siglec Repertoire Certain aspects of the present disclosure relate to methods of generating non-human disease models comprising a human Siglec repertoire. In some embodiments, the method comprises introducing one or more genetic determinants of a disease into the genome of any of the transgenic non-human animals described herein.

In some embodiments, the disease is one or more of cancer (e.g., melanoma, acute myeloid leukemia, etc.), proliferative disorders, infectious diseases (e.g., bacterial infections), and/or neurodegenerative diseases. In some embodiments, the neurodegenerative diseases are one or more of dementia, frontotemporal dementia (FTD), Alzheimer's disease, Parkinson's disease, amyotrophic lateral sclerosis (ALS), Huntington's disease, taupathy disease, and/or multiple sclerosis. In some embodiments, the disease is Alzheimer's disease.

In some embodiments, the one or more genetic determinants are introduced into the genome of the transgenic non-human animal by genetic manipulation. Methods of genetically manipulating animals are known in the art, including, for example, by the introduction of plasmids/cosmids, knock in/knock out technology, through the use of transposons/retrotransposons, the use of viruses (e.g., adenovirus, adeno-associated virus, herpes virus, Rous sarcoma virus, HIV, etc.), the use of the CRISPR/Cas system, the use of TALENs, the use of Zinc finger nucleases, etc.

In some embodiments, the one or more genetic determinants are introduced into the genome of the transgenic non-human animal by mating. In some embodiments, the transgenic non-human animal is mated with an animal that is heterozygous or homozygous for the one or more genetic determinants. In some embodiments, progeny from this mating are screened to identify animals comprising the one or more genetic determinants as well as two or more of the human CD33, Siglec-5, Siglec-7, Siglec-9, Siglec-11, Siglec-14 and/or Siglec-16 genes. Methods of screening animals to identify animals comprising the one or more genetic determinants and the two or more human genes are known in the art (e.g., by PCR analysis, southern blot analysis, western blot analysis, FACS analysis, etc.).

In some embodiments, the one or more genetic determinants are one or more polynucleotides comprising a mutation. In some embodiments, the one or more mutations are one or more inactivating mutations. Examples of inactivating mutations may include, but are not limited to, deletions, insertions, point mutations, and rearrangements. In some embodiments, the one or more genetic determinants are one or more polynucleotides encoding one or more polypeptides comprising a mutation. In some embodiments, the one or more polypeptides comprising a mutation are one or more of amyloid precursor protein (APP), presenilin 1 (PS1), presenilin 2 (PS2), alpha-synuclein, serine/threonine-protein kinase PINK1, parkin, leucine-rich repeat serine/threonine protein kinase 2 (LRRK2), protein deglycase (DJ-1), probable cation-transporting ATPase 13A2 (ATP13A2), superoxide dismutase (SOD1), TAR DNA-binding protein 43 (TARDBP), RNA-binding protein FUS, translation endoplasmic reticulum ATPase (VCP), microtubule-associated protein tau, progranulin, protein C9orf72, charged multivesicular body protein 2b (CHMP2B), and any combinations thereof. In some embodiments, the polypeptide comprising a mutation is amyloid precursor protein (APP).

The present disclosure will be more fully understood by reference to the following Examples. They should not, however, be construed as limiting the scope of the present disclosure. It is understood that the examples and embodiments described herein are for illustrative purposes only and that various modifications or changes in light thereof will be suggested to persons skilled in the art and are to be included within the spirit and purview of this disclosure and scope of the appended claims.

EXAMPLES

Example 1: Generation of Transgenic Mice Harboring Human CD33, Siglec-7, and Siglec-9

The amino acid sequence of human CD33 is set forth below in SEQ ID NO: 1. Human CD33 contains a signal sequence located at amino acid residues 1-17 of SEQ ID NO: 1, an extracellular immunoglobulin-like variable-type (IgV) domain located at amino acid residues 19-135 of SEQ ID NO: 1, an Ig-like C2-type domain located at amino acid residues 145-228 of SEQ ID NO: 1, a transmembrane domain located at amino acid residues 260-282 of SEQ ID NO: 1, an ITIM motif 1 located at amino acid residues 338-343 of SEQ ID NO: 1, and an ITIM motif 2 located at amino acid residues 356-361 of SEQ ID NO: 1. The structure of CD33 is depicted in FIG. 1.

CD33 Amino Acid Sequence (SEQ ID NO: 1):

```
        10         20         30         40
MPLLLLLPLL WAGALAMDPN FWLQVQESVT VQEGLCVLVP 50         60         70         80
CTFFHPIPYY DKNSPVHGYW FREGAIISRD SPVATNKLDQ 90        100        110        120
EVQEETQGRF RLLGDPSRNN CSLSIVDARR RDNGSYFFRM 130        140        150        160
ERGSTKYSYK SPQLSVHVTD LTHRPKILIP GTLEPGHSKN 170        180        190        200
LTCSVSWACE QGTPPIFSWL SAAPTSLGPR TTHSSVLIIT 210        220        230        240
PRPQDHGTNL TCQVKFAGAG VTTERTIQLN VTYVPQNPTT 250        260        270        280
GIFPGDGSGK QETRAGVVHG AIGGAGVTAL LALCLCLIFF 290        300        310        320
IVKTHRRKAA RTAVGRNDTH PTTGSASPKH QKKSKLHGPT 330        340        350        360
ETSSCSGAAP TVEMDEELHY ASLNFHGMNP SKDTSTEYSE

VRTQ
```

The amino acid sequence of human Siglec-7 is set forth below in SEQ ID NO: 5. Human Siglec-7 contains a signal sequence located at amino acid residues 1-18 SEQ ID NO: 5, an extracellular immunoglobulin-like variable-type (IgV) domain located at amino acid residues 39-122 of SEQ ID NO: 5, two Ig-like C2-type domains located at amino acid residues 150-233 and 240-336 of SEQ ID NO: 5, a transmembrane domain located at amino acid residues 354-376 of SEQ ID NO: 5, an ITIM motif 1 located at amino acid residues 435-440 of SEQ ID NO: 5, and an ITIM motif 2 located at amino acid residues 459-463 of SEQ ID NO: 5.

Siglec-7 Amino Acid Sequence (SEQ ID NO: 5):

```
        10         20         30         40
MLLLLLLPLL WGRERVEGQK SNRKDYSLTM QSSVTVQEGM 50         60         70         80
CVHVRCSFSY PVDSQTDSDP VHGYWFRAGN DISWKAPVAT 90        100        110        120
NNPAWAVQEE TRDRFHLLGD PQTKNCTLSI RDARMSDAGR 130        140        150        160
YFFRMEKGNI KWNYKYDQLS VNVTALTHRP NILIPGTLES 170        180        190        200
GCFQNLTCSV PWACEQGTPP MISWMGTSVS PLHPSTTRSS 210        220        230        240
VLTLIPQPQH HGTSLTCQVT LPGAGVTTNR TIQLNVSYPP 250        260        270        280
QNLTVTVFQG EGTASTALGN SSSLSVLEGQ SLRLVCAVDS 290        300        310        320
NPPARLSWTW RSLTLYPSQP SNPLVLELQV HLGDEGEFTC 330        340        350        360
RAQNSLGSQH VSLNLSLQQE YTGKMRPVSG VLLGAVGGAG 370        380        390        400
ATALVFLSFC VIFIVVRSCR KKSARPAADV GDIGMKDANT 410        420        430        440
IRGSASQGNL TESWADDNPR HHGLAAHSSG EEREIQYAPL 450        460
SFHKGEPQDL SGQEATNNEY SEIKIPK
```

Figure 2:
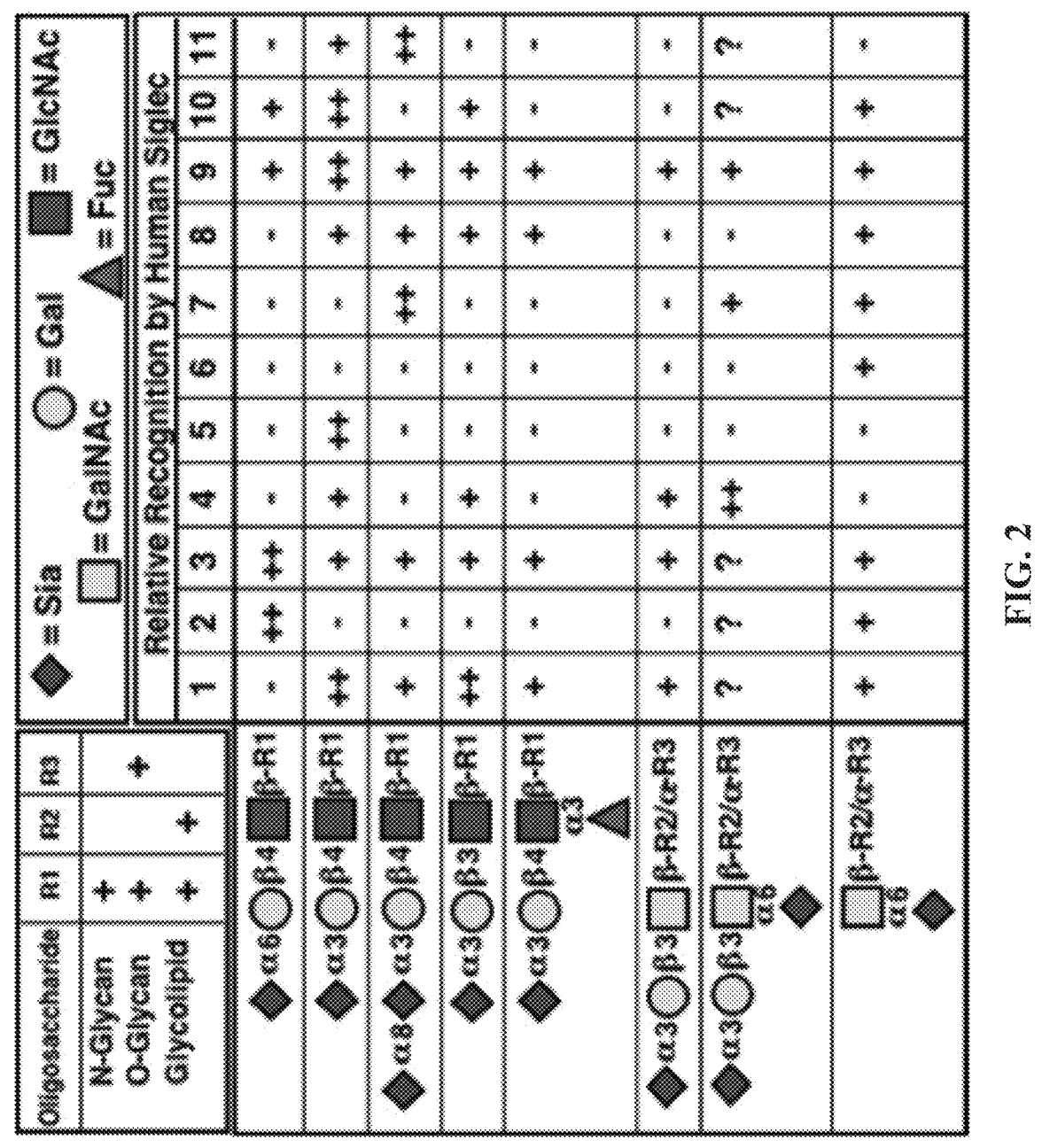
Figure 3:
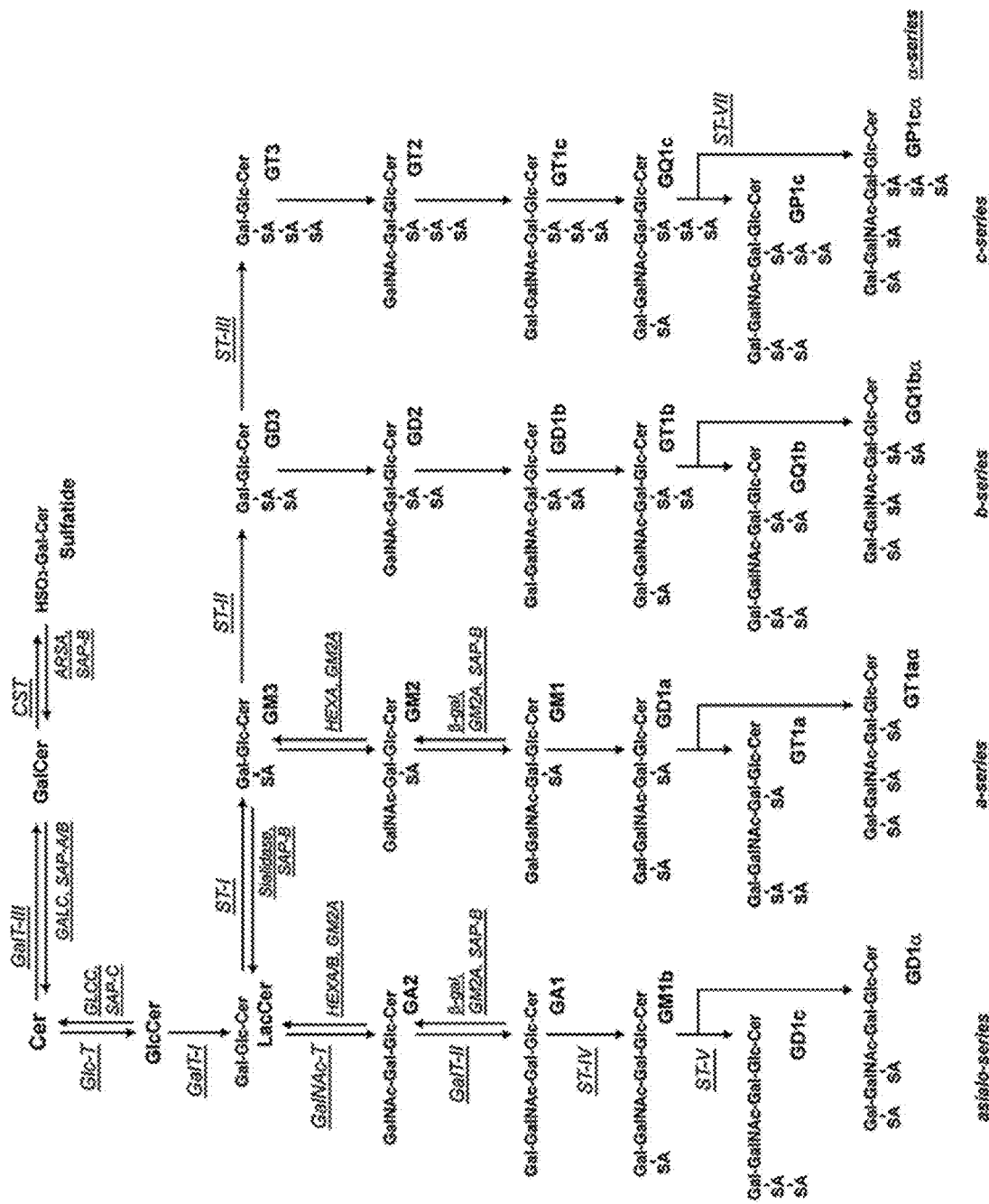
FIG. 3 shows the structure and metabolism of gangliosides in mammalian brain. The nomenclature of gangliosides in the figure follows the system of Svennerholm (1964) J. Lipid Res. 5:145-155 (Ariga T et al. (2008) J. Lipid Res. 49:1157-1175).

The purpose of the following example was to generate transgenic mice that coordinately express multiple human Siglec proteins. The genomes of the mice were engineered to contain multiple human Siglec transgenes under the control of their native human gene regulatory elements by introducing into the mouse genome Bacterial Artificial Chromosomes (BACs) encompassing the human locus containing the indicated Siglec genes and their regulatory network. Exemplary ligands bound by human Siglec proteins are depicted in FIG. 2 and FIG. 3. Without wishing to be bound by theory, it was believed that such mice would express the Siglec genes in a human pattern of gene expression, the expressed proteins would function appropriately, and the transgenic mice would allow for the development of therapeutics targeting the human proteins.

Methodologies

Identifying BACs of interest: Bacterial Artificial Chromosomes (BACs) harboring the human Siglec genes CD33, Siglec-7, and Siglec-9 with all intronic and exonic sequences were identified using the UCSC genome browser and the CloneDB from NCBI. BAC clones were further selected to identify those clones harboring a minimum of at least 10 kilobases of 5' and 3' flanking sequences in addition to the indicated Siglec genes to maximize the likelihood of identifying BAC clones that include the relevant human gene regulatory sequences in addition to human CD33, Siglec-7, and Siglec-9.

Isolating and purifying BAC clones: BAC clones meeting all of the selection requirements were obtained from Invitrogen/Life Technologies/Fisher Scientific as bacterial stab cultures. The cultures were grown, and BAC DNA was isolated and purified using standard techniques. Agarose gel electrophoresis after restriction digestion was used to confirm size and intactness of the inserts.

Generating transgenic animals: Mice harboring BAC clones of interest were generated by injecting the purified BAC DNA into mouse C57BL6/j zygotes by standard pronuclear injection techniques. Zygotes were returned to females, and the resulting pups were genotyped for the presence of the transgenes. Founder animals harboring the transgenes were then bred to non-transgenic animals, and progeny were screened for expression of the transgenes using standard techniques.

Generating murine CD33 knockout transgenic animals: Transgenic mice carrying the human CD33, Siglec-7, and Siglec-9 transgenes were bred with murine CD33-deficient mice that harbored a deletion within the mouse CD33 gene to obtain mice that carried the human CD33 transgene (as well as the human Siglec-7 and Siglec-9 transgenes), and were heterozygous for the murine CD33 knockout allele. The resulting mice were then bred with the same murine CD33-deficient mice to obtain mice carrying the human CD33 transgene (as well as the human Siglec-7 and Siglec-9 transgenes), but lacked the mouse CD33 gene (the mice were homozygous for the murine CD33 knockout allele). Mouse breeding and genotyping were carried out using standard techniques.

FACS analysis: Mice carrying the human CD33, Siglec-7, and Siglec-9 transgenes were analyzed by FACS analysis using standard techniques. Briefly, peripheral blood was obtained from 4-8 week old transgenic animals, and peripheral blood cells were subjected to multi-color flow cytometry panel staining Cells were incubated with the cell viability dye and indicated antibodies for 30 minutes on ice, washed twice with cold FACS buffer, and fixed with 4% PFA. The stained and fixed cells were then applied to a BD FACS CANTO II cytometer, data were acquired, and the resulting data was analyzed with FlowJo software.

For experiments testing the expression of human CD33 and Siglec-9, peripheral blood cells were stained with a cell viability dye and the following antibodies: anti-mouse CD11b (BD Biosciences, M1/70, 1:100), anti-mouse NK1.1 (Affymetrix, PK136, 1:100), anti-human Siglec-9 (Biolegend, K8, 1:20), and anti-human CD33 (Affymetrix, HIM3-4, 1:20).

For experiments testing the expression of human CD33, Siglec-7, and Siglec-9, peripheral blood cells were stained with a cell viability dye (Aqua dye) and the following antibodies: anti-mouse CD3, anti-mouse CD11b, anti-mouse NK1.1, anti-mouse Ly6G, anti-mouse Ly6C, anti-human CD33, and anti-human Siglec-7 or anti-human Siglec 9. Peripheral blood mononuclear cells (PBMCs) were FACS sorted to obtain T cells (CD-3 positive, NK1.1-negative), NK cells (CD3-negative, NK1.1-positive), myeloid cells (CD3-negative, NK1.1-negative), CD11b+ cells (CD11b-positive), monocytic myeloid-derived suppressor cells (Mo-MDSCs; CD11b-positive, Ly6G-negative, Ly6C-positive), or granulocytic MDSCs/neutrophils (G-MDSCs/neutrophils; CD11b-positive, Ly6G-positive, Ly6C-positive).

Results

To obtain mice coordinately expressing multiple human Siglec genes, Bacterial Artificial Chromosomes (BACs) harboring key human Siglec genes with sufficient flanking sequences were identified using the UCSC genome browser and the CloneDB from NCBI. Three BAC clones (BACRP11-891J20, CTD-3187F8, and BACRP11-795H8) were identified that were predicted to contain the coding sequences for the human genes CD33, Siglec-7, and Siglec-9. Each BAC was tested by PCR analysis to confirm the proper human sequences of interest; however, BAC clone CTD-3187F8 failed to show a signal corresponding to the presence of the correct 5' end of the BAC, while BAC clone BACRP11-795H8 failed to show the presence of the appropriate human CD33 sequence.

Figure 4:
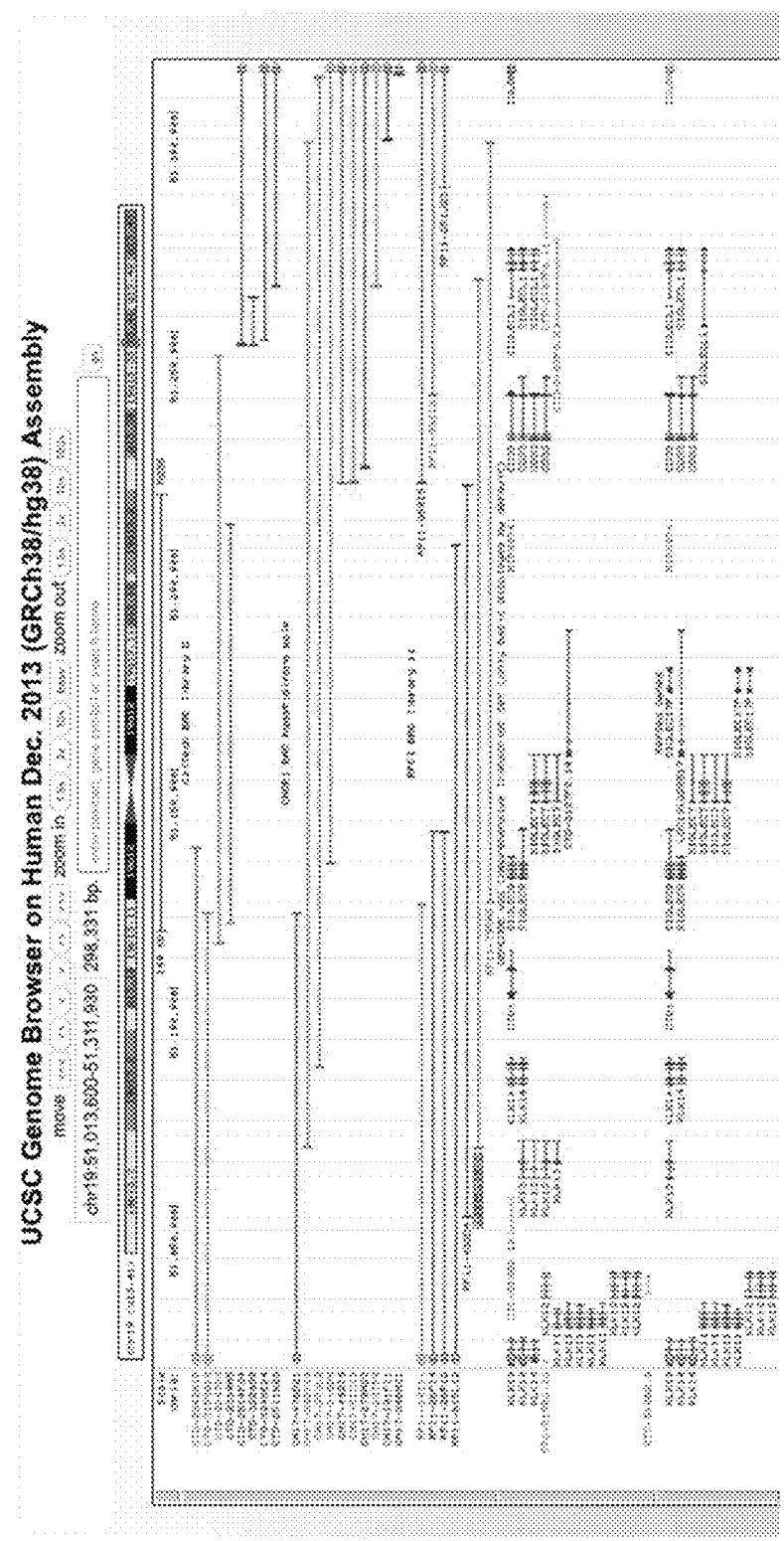
FIG. 4 shows a UCSC genome browser map of the genes, including CD33, Siglec-7, and Siglec-9, on a region of human Chromosome 19 that are included in the bacterial artificial chromosome (BAC) BACRP11-891J20, as labelled.
Figure 5:
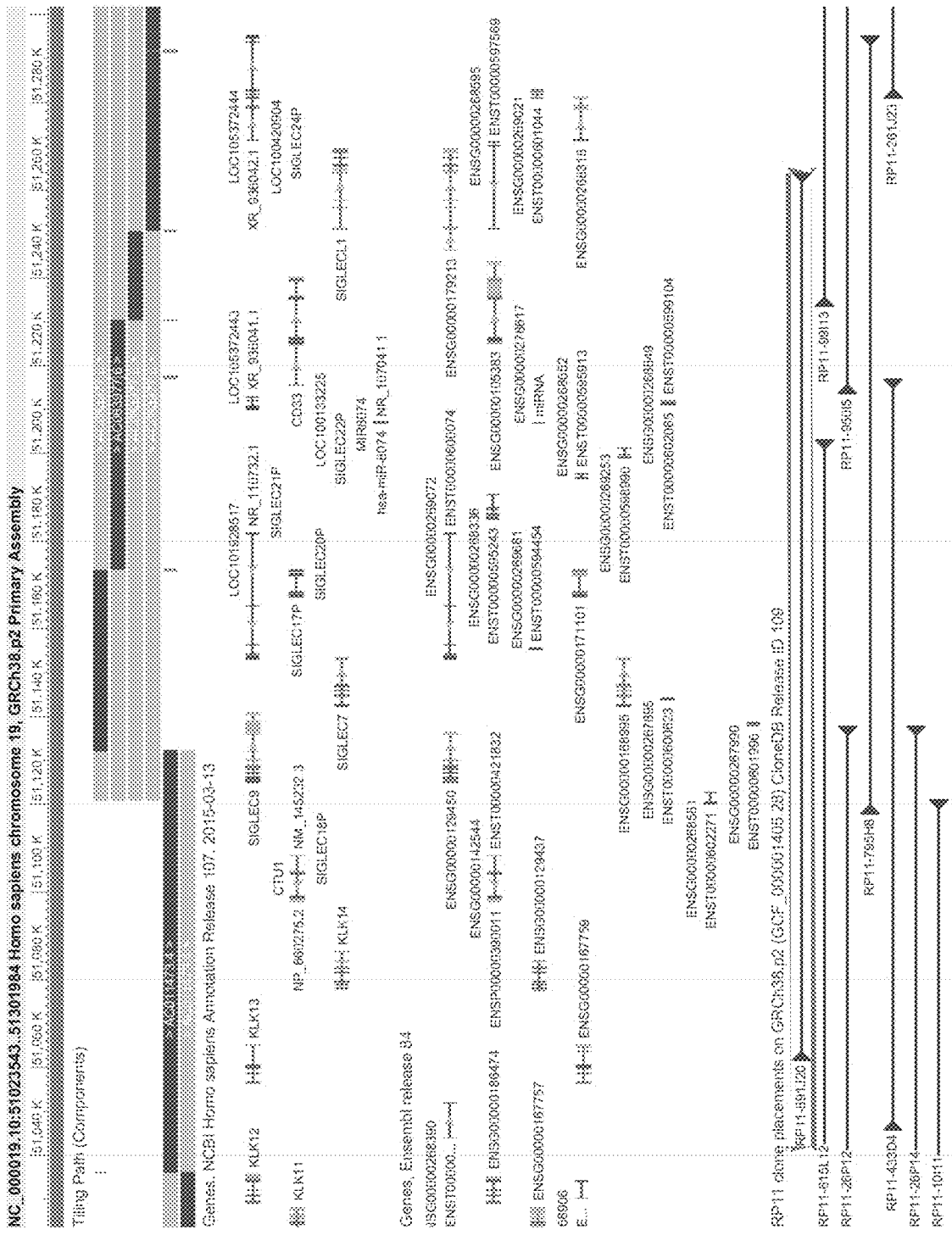
FIG. 5 shows a CloneDB map of the genes, including CD33, Siglec-7, and Siglec-9, on a region of human Chromosome 19 that are included in the bacterial artificial chromosome (BAC) BACRP11-891J20, as labelled.
Figure 6:
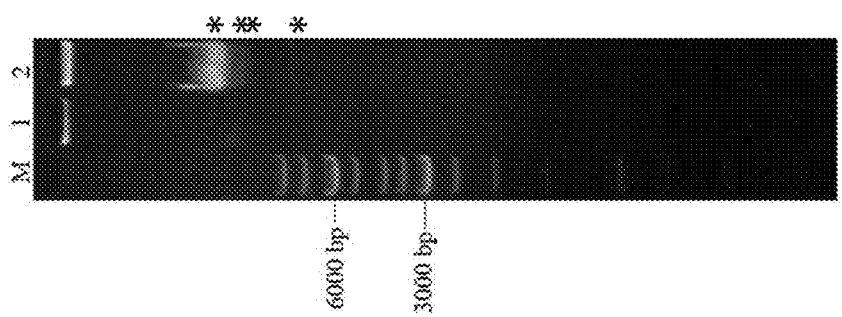
FIG. 6 shows the NotI restriction enzyme digestion of BACRP11-891J20. Asterisks indicate DNA fragments corresponding to the restriction fragments predicted for digestion of chromosomal DNA carrying human CD33, human Siglec-7, and human Siglec-9.

Maps of the human chromosomal region of interest encompassed by BACRP11-891J20 are shown in FIG. 4 (from the UCSC genome browser) and FIG. 5 (from the CLONEDB NCBI browser). The chromosomal DNA within BACRP11-891J20 spanned 196,887 nucleotides of the human genome, covering nucleotide positions 51,063,322-51,262,208 on human chromosome 19, based on the hg38 build of the UCSC genome browser (the human Siglec genes are found within a cluster on chromosome 19). Clone BACRP11-891J20 was tested via restriction digest/gel electrophoresis, the intactness and expected size of the human DNA insert was confirmed (FIG. 6).

Figure 7A:
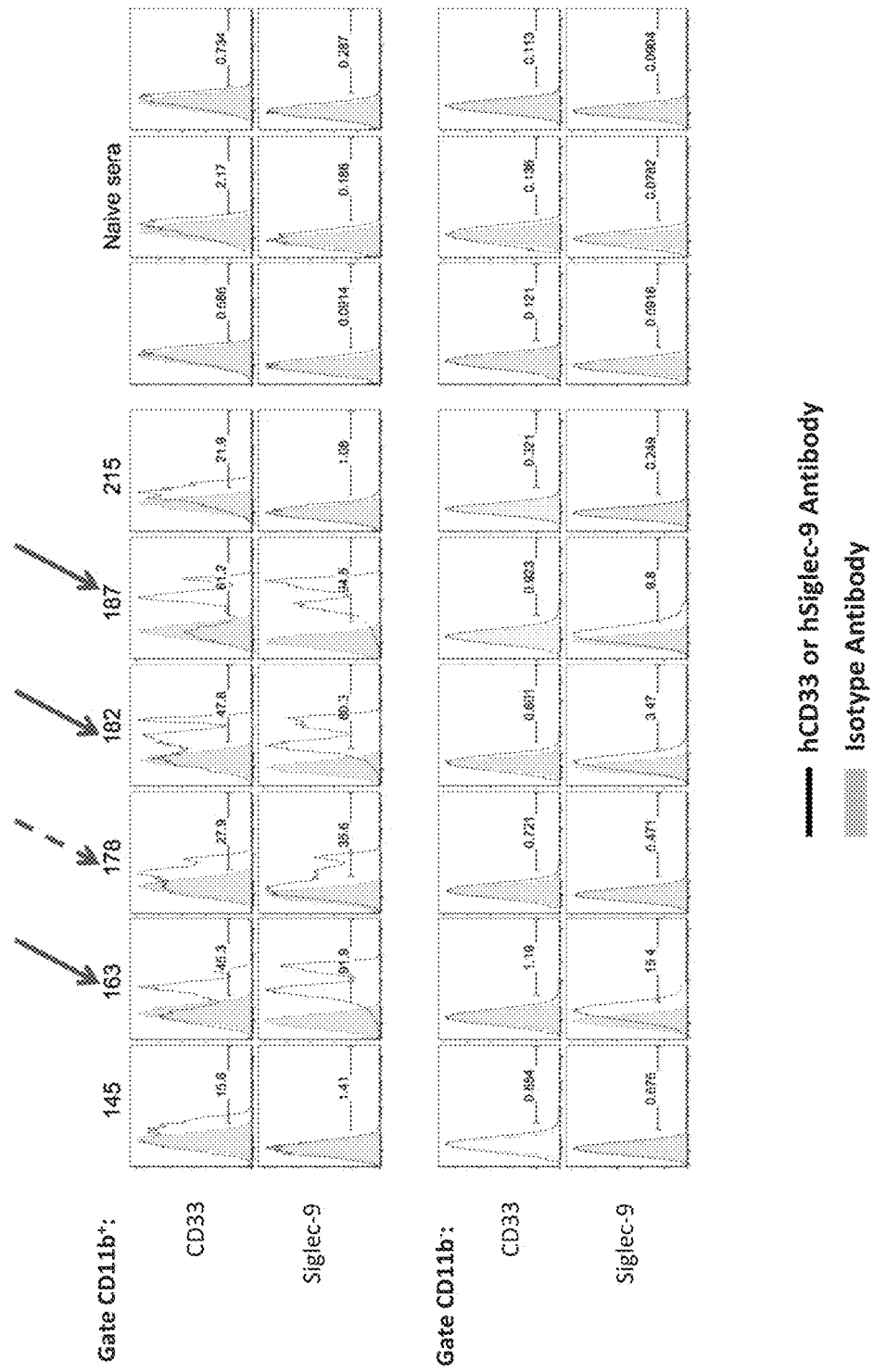
FIG. 7A-7B show human CD33 and human Siglec-9 expression on cells isolated from BACRP11-891J20 transgenic mice.
Figure 7B:
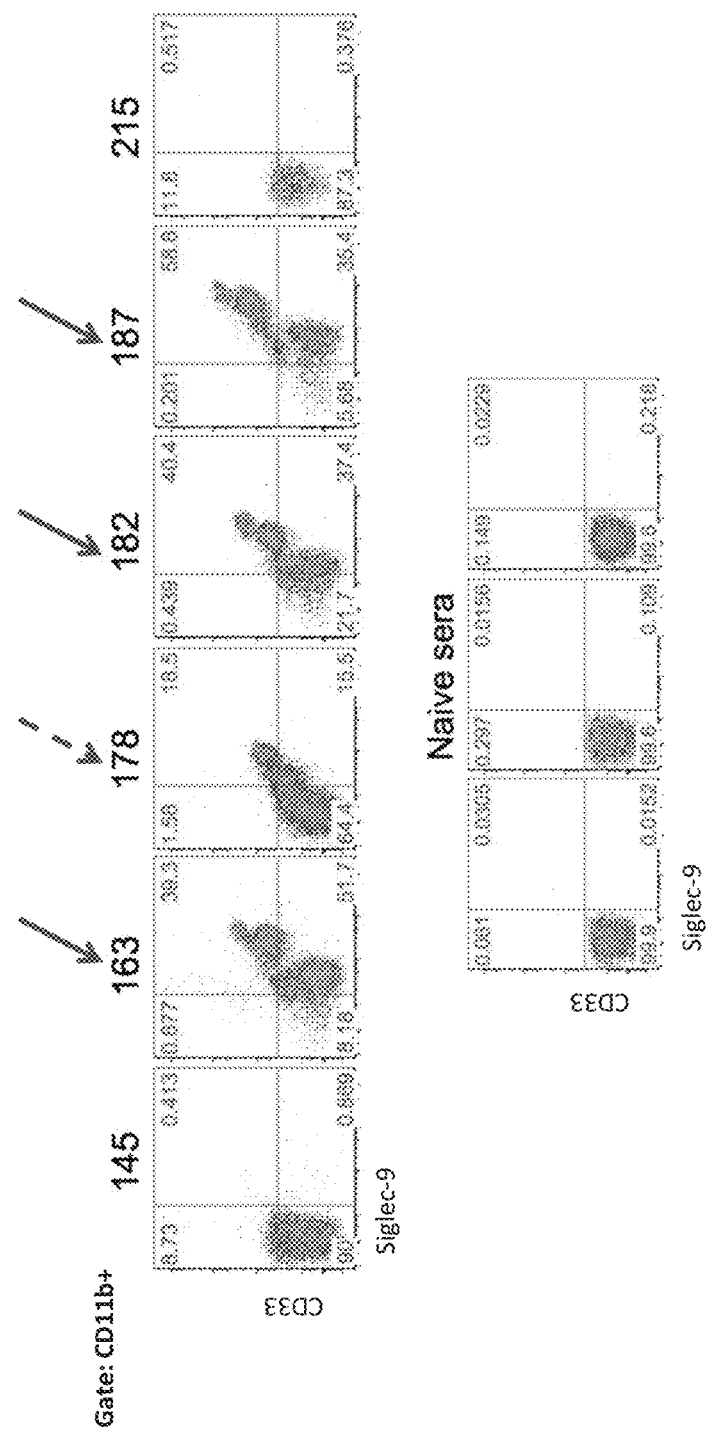

Transgenic mice harboring BACRP11-891J20 were generated by pronuclear injection of the BAC DNA into C57BL6/j zygotes. The resulting pups were genotyped to identify founder animals harboring the human transgenes (mouse #s 145, 163, 178, 182, 187, and 215). These animals were then analyzed by FACS analysis to monitor human CD33 and Siglec-9 protein expression on CD11b-positive and CD11b-negative cells (FIG. 7A). Expression of both human CD33 and Siglec-9 was observed on CD11b-positive cells from founder animals 163, 178, 182, and 187 (FIGS. 7A and 7B). Little to no expression of human CD33 and Siglec-9 were observed on CD11b-negative cells from these animals. Expression of human CD33 (but little to no expression of Siglec-9) was observed on CD11b-positive cells from founder animals 145 and 215. Expression levels of human CD33 and Siglec-9 varied across founder animals, with some animals showing high, medium, or low levels of human CD33 and Siglec-9 expression.

Taken together, this data suggested that transgenic animals were successfully generated that both carried human genes from the Siglec locus and were capable of coordinately expressing genes from this locus.

Example 2: Analysis of Human CD33, Siglec-7, and Siglec-9 Transgene Expression in Select Murine Cell Types Methodologies FACS analysis: Mice carrying the human CD33, Siglec-7, and Siglec-9 transgenes were analyzed by FACS analysis using standard techniques. Briefly, peripheral blood was obtained from 4-8 week old transgenic animals, and peripheral blood cells were subjected to multi-color flow cytometry panel staining Cells were incubated with the cell viability dye and indicated antibodies for 30 minutes on ice, washed twice with cold FACS buffer, and fixed with 4% PFA. The stained and fixed cells were then applied to a BD FACS CANTO II cytometer, data were acquired, and the resulting data was analyzed with FlowJo software.

For experiments testing the expression of human CD33, Siglec-7, and Siglec-9, peripheral blood cells were stained with a cell viability dye (Aqua dye) and the following antibodies: anti-mouse CD3, anti-mouse CD11b, anti-mouse NK1.1, anti-mouse Ly6G, anti-mouse Ly6C, anti-human CD33, and anti-human Siglec-7 or anti-human Siglec 9. Peripheral blood mononuclear cells (PBMCs) were FACS sorted to obtain T cells (CD-3 positive, NK1.1-negative), NK cells (CD3-negative, NK1.1-positive), myeloid cells (CD3-negative, NK1.1-negative), CD11b+ cells (CD11b-positive), monocytic myeloid-derived suppressor cells (Mo-MDSCs; CD11b-positive, Ly6G-negative, Ly6C-positive), or granulocytic MDSCs/neutrophils (G-MDSCs/neutrophils; CD11b-positive, Ly6G-positive, Ly6C-positive).

BMDMs: Bone marrow-derived macrophages (BMDMs) were generated in vitro using standard techniques. Briefly, total bone marrow was cultured in DMEM supplemented with 10% bovine calf serum, 5% horse serum, and 6 ng/mL recombinant human CSF-1 (R&D Systems). Cells were cultured for 5-6 days, and adherent cells were detached with 1 mM EDTA in PBS. Cells were stained with the following antibodies: anti-mouse CD11b, anti-mouse CD40, anti-mouse GR1 (BD Pharmingen), anti-mouse F4/80 (Caltag Laboratories), anti-human CD33, and anti-human Siglec-7 or anti-human Siglec-9, and analyzed by FACS analysis as described above.

BMDCs: Bone marrow-derived dendritic cells (BMDCs) were generated in vitro using standard techniques. Briefly, total bone marrow was cultured in DMEM supplemented with 10% bovine calf serum, 5% horse serum, and 6 ng/mL GM-CSF (R&D Systems). Cells were cultured for 5-6 days, and adherent cells were detached with 1 mM EDTA in PBS. Cells were stained with the following antibodies: anti-mouse CD11b, anti-mouse CD40, anti-mouse GR1 (BD Pharmingen), anti-mouse F4/80 (Caltag Laboratories), anti-human CD33, and anti-human Siglec-7 or anti-human Siglec-9, and analyzed by FACS analysis as described above.

Brain microglia: Brain microglia were isolated from the transgenic animals using standard techniques (e.g., Bennett et al. (2016) PNAS 113(12): e1738-46). Cells were stained with a cell viability dye (Aqua dye) and the following antibodies: anti-mouse CD11b, anti-mouse CD45, anti-mouse F4/80 (Caltag Laboratories), and anti-human CD33, and analyzed by FACS analysis as described above.

Human NK and myeloid cells: Human NK and myeloid cells were isolated from the peripheral blood of an anonymous donor according to standard techniques.

Results

Figure 9:
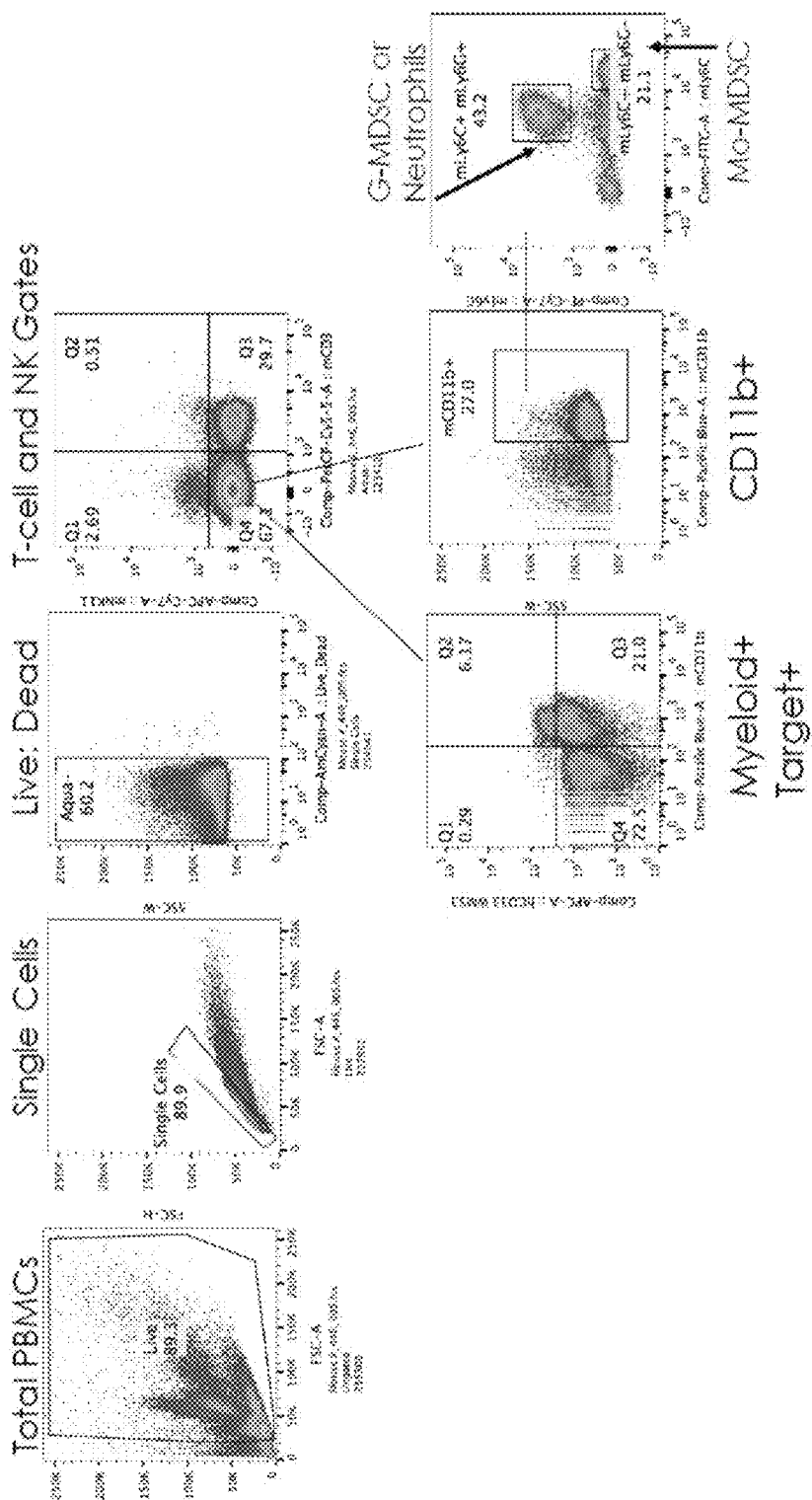
FIG. 9 shows the FACS gating strategy for the analysis of peripheral blood cells.

The transgenic founder animals from Example 1 were then crossed to non-transgenic mice. Pups resulting from this breeding scheme were genotyped to identify progeny animals harboring the human transgenes, and cells isolated from these animals were tested for protein expression of human CD33, Siglec-7 and Siglec-9 by FACS analysis. To characterize mouse cell subpopulations that expressed the human transgenes, cells isolated from these mice were also stained with antibodies to specifically identify particular immune cell subpopulations. The panel of antibodies used to sort for particular mouse cell subpopulations is summarized in FIG. 8. The cell isolation strategy used in these experiments is summarized in FIG. 9.

Figure 10:
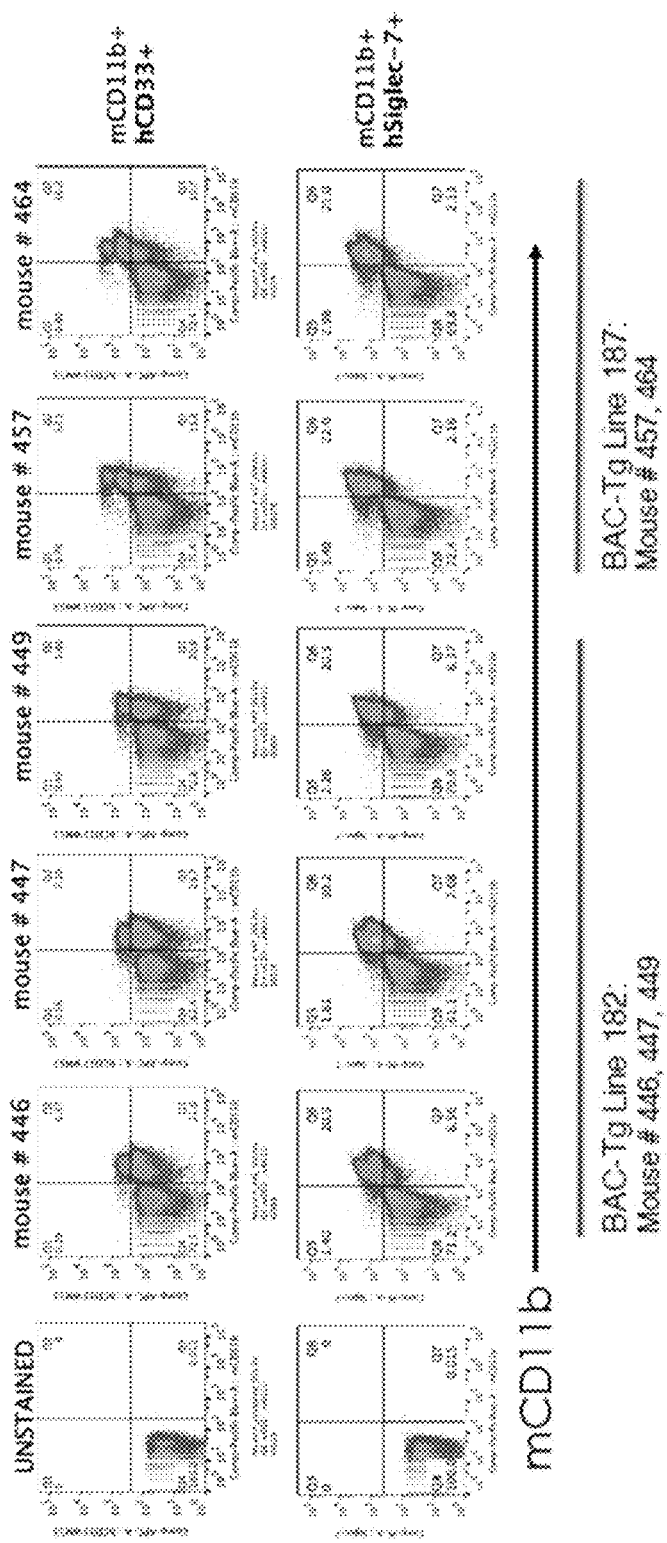
FIG. 10 shows results of FACS analysis demonstrating the expression pattern of human CD33 and human Siglec-7 on CD11b-positive primary myeloid cells from peripheral blood of BACRP11-891J20 transgenic mice.

Human CD33 expression was positive on up to 50% of CD11b-positive myeloid cells in mice from the higher expression mouse #187 founder line (mouse #457 and #464), while CD33 was expressed on only a minority of the CD11-b-positive myeloid cells in mice from the lower expression mouse #182 founder line (mouse #446, #447, and #449) (FIG. 10). Human Siglec-7 expression was positive on all CD11b-positive myeloid cells in mice from the higher expression mouse #187 founder line (mouse #457 and #464), and was expressed in a majority of such cells in mice from the lower expression mouse #182 founder line (mouse #446, #447, and #449) (FIG. 10).

Figure 11:
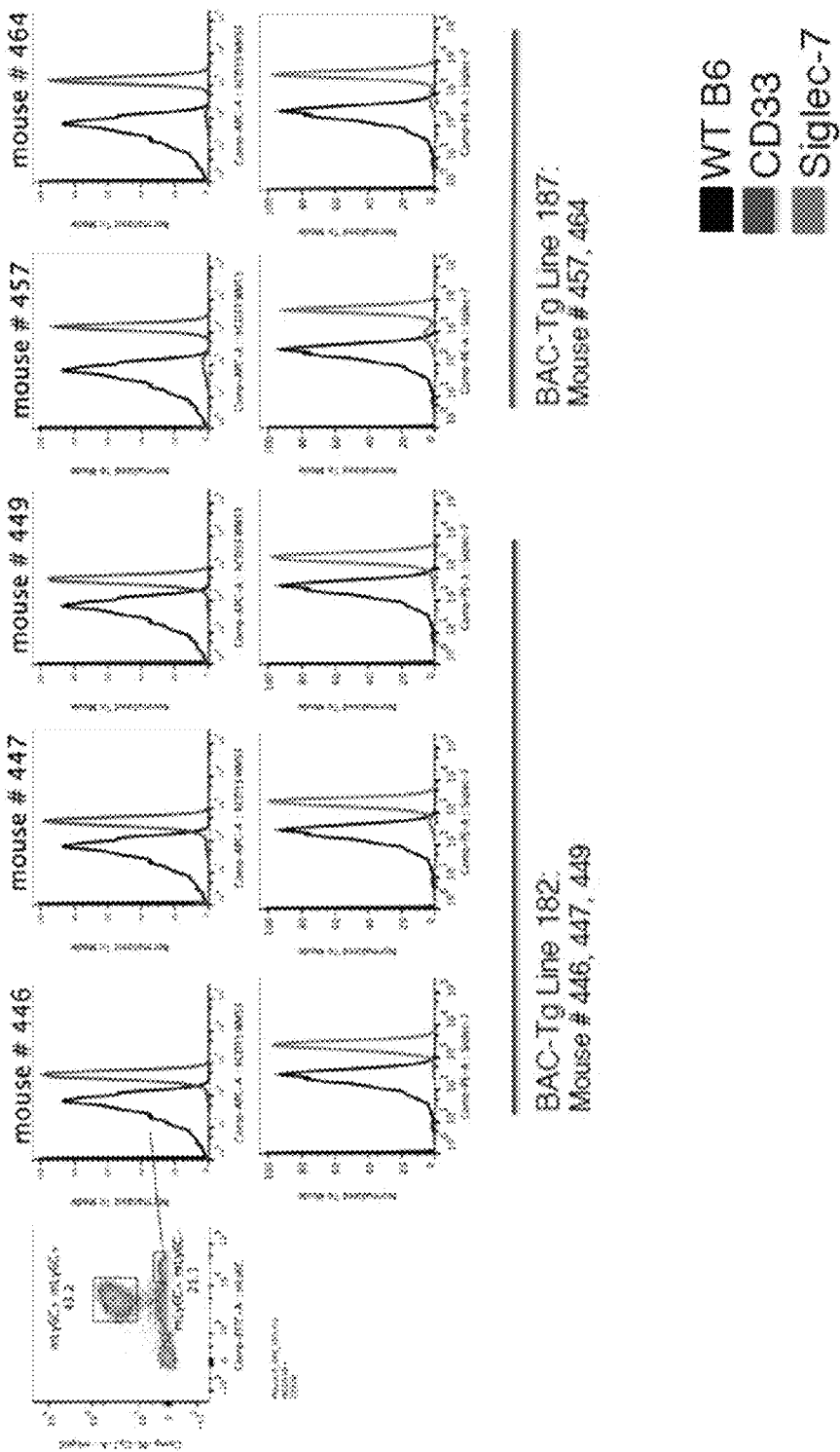
FIG. 11 shows results of FACS analysis demonstrating the expression pattern of human CD33 (purple line) and human Siglec-7 (green line) on primary monocyte-myeloid-derived suppressor cells (Mo-MDSCs) from peripheral blood of non-transgenic and BACRP11-891J20 transgenic mice. The black line indicates wild-type (WT) B6 non-transgenic mice.

Human CD33 expression was positive on most monocytic myeloid-derived suppressor cells (Mo-MDSCs) in mice from the higher expression mouse #187 founder line (mouse #457 and #464), and all such cells in mice from the lower expression mouse #182 founder line (mouse #446, #447, and #449) (FIG. 11). Human Siglec-7 expression was also positive on most Mo-MDSCs in mice from the higher expression mouse #187 founder line (mouse #457 and #464), and all such cells in mice from the lower expression mouse #182 founder line (mouse #446, #447, and #449) (FIG. 11).

Figure 12:
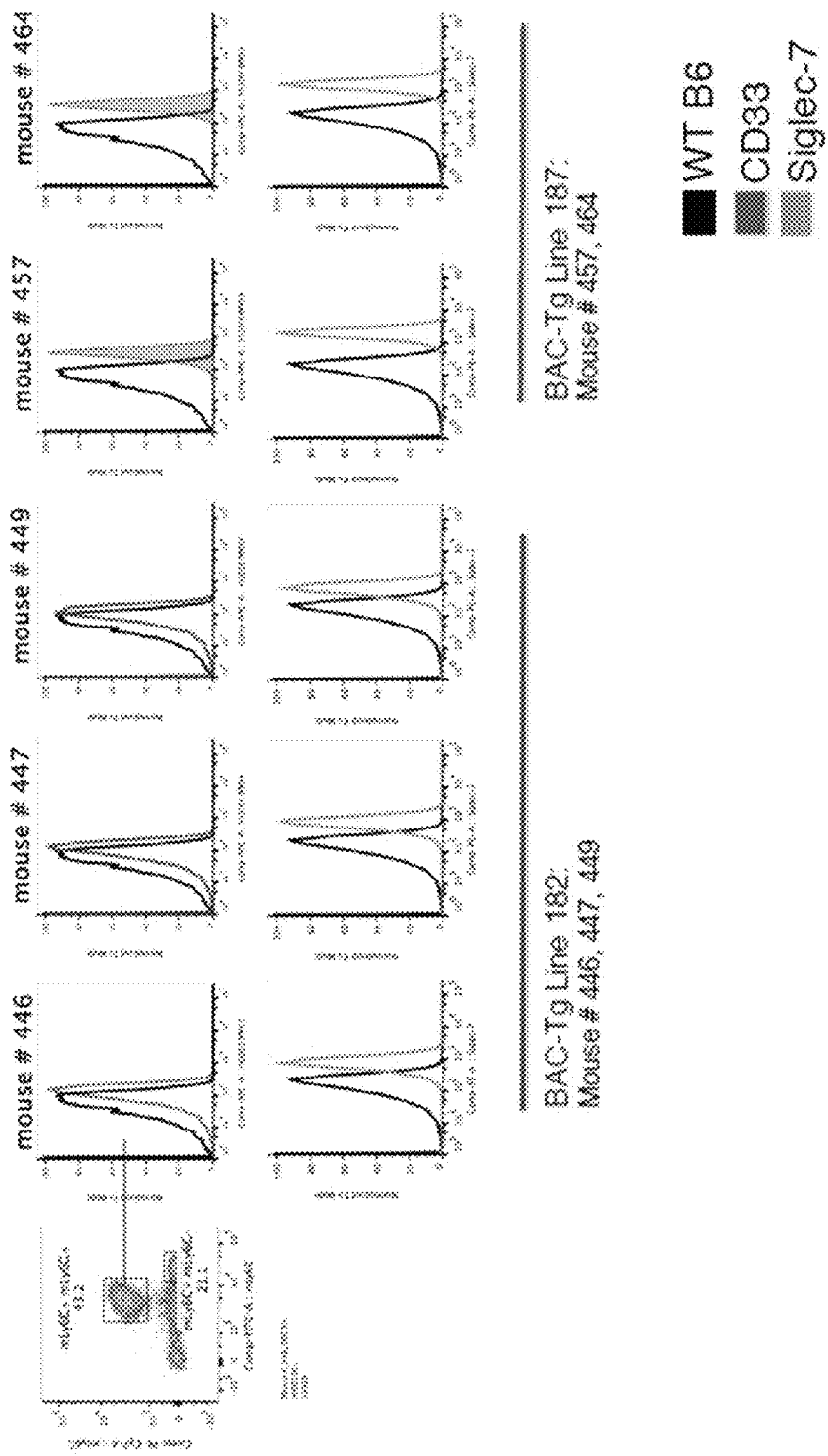
FIG. 12 shows results of FACS analysis demonstrating the expression pattern of human CD33 (red line) and human Siglec-7 (blue line) on primary granulocyte-myeloid-derived suppressor cells/neutrophils (G-MDSCs/neutrophils) from peripheral blood of non-transgenic and BACRP11-891J20 transgenic mice. The black line indicates wild-type (WT) B6 non-transgenic mice.

Human CD33 expression was very low on most granulocytic MDSCs/neutrophils (G-MDSCs) in mice from both the higher expression mouse #187 founder line (mouse #457 and #464) and lower expression mouse #182 founder line (mouse #446, #447, and #449) (FIG. 12). Human Siglec-7 expression was high on most G-MDSCs/neutrophils in mice from the higher expression mouse #187 founder line (mouse #457 and #464), and moderately expressed on such cells in mice from the lower expression mouse #182 founder line (mouse #446, #447, and #449) (FIG. 12).

Figure 13:
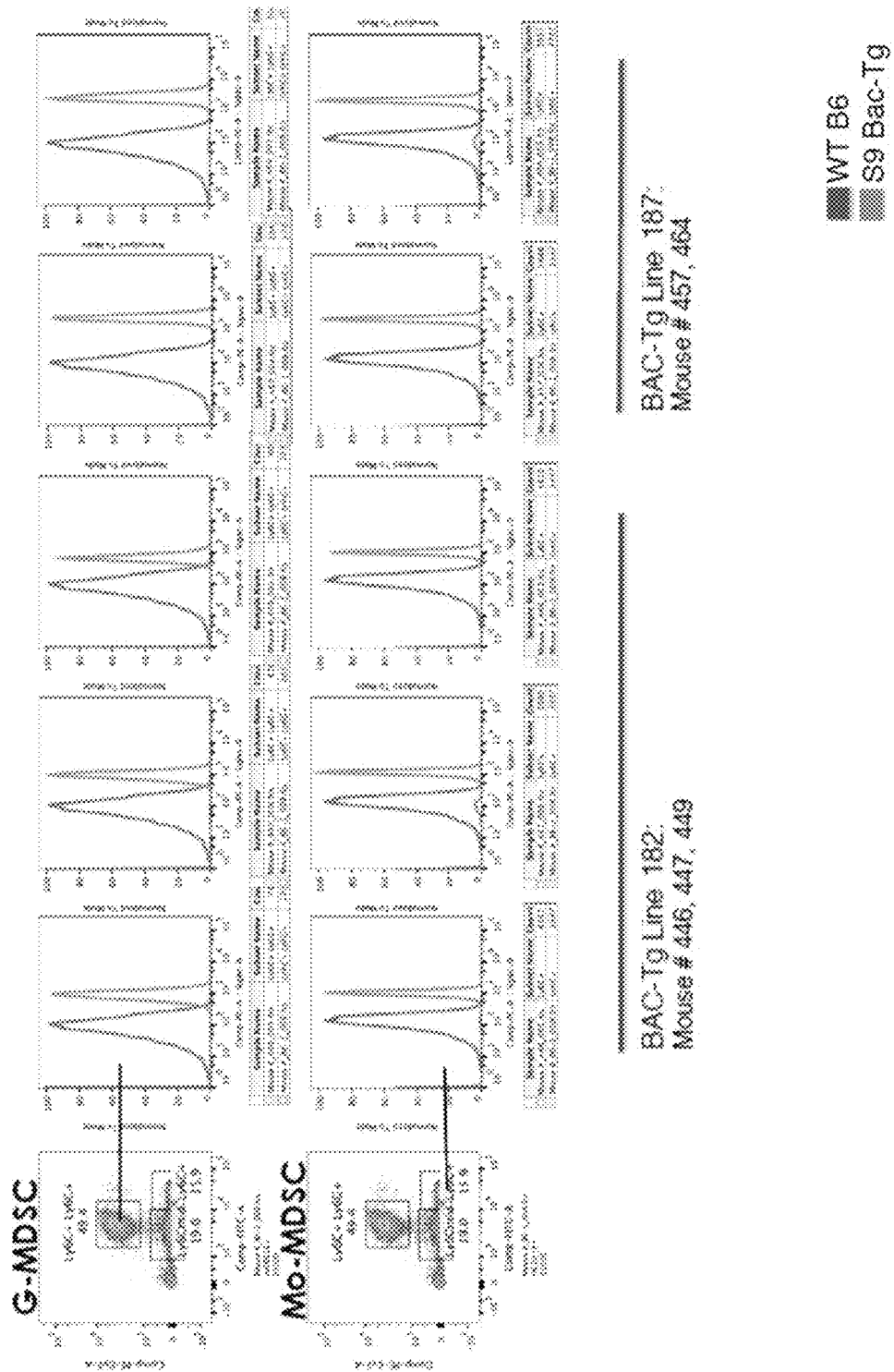
FIG. 13 shows results of FACS analysis demonstrating the expression pattern of human Siglec-9 on primary monocyte-myeloid-derived suppressor cells (MDSCs) and primary granulocyte-myeloid-derived suppressor cells/neutrophils (G-MDSCs/neutrophils) from peripheral blood of control non-transgenic mice (red line) and BACRP11-891J20 transgenic mice (blue line).

Human Siglec-9 expression was high on CD11b-positive myeloid cells in mice from the higher expression mouse #187 founder line (mouse #457 and #464), but moderate in mice from the lower expression mouse #182 founder line (mouse #446, #447, and #449). Similar results were observed for human Siglec-9 expression on Mo-MDSCs and G-MDSCs/neutrophils (FIG. 13).

Figure 14A:
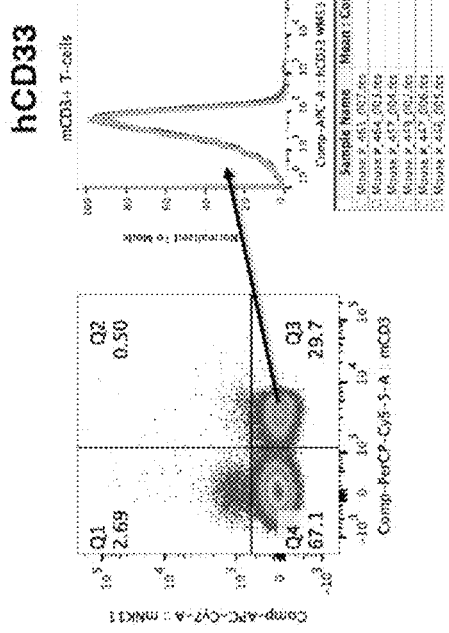
FIG. 14A-14C show results of FACS analysis demonstrating the expression pattern of human CD33 (FIG. 14A), human Siglec-7 (FIG. 14B), and human Siglec-9 (FIG. 14C) on primary T cells from peripheral blood of BACRP11-891J20 transgenic mice.
Figure 14B:
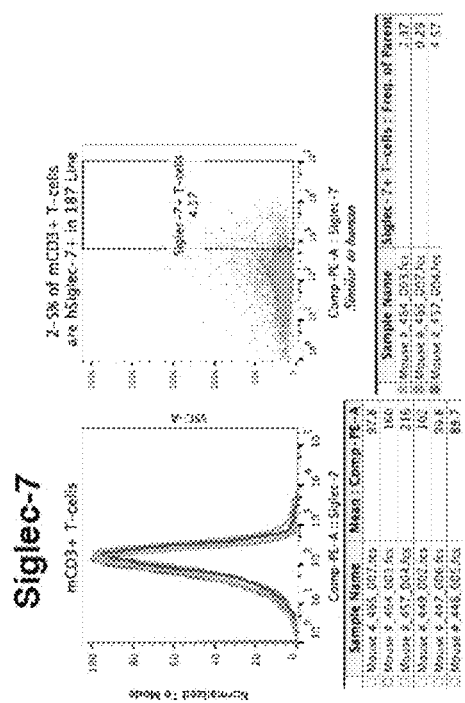
Figure 14C:
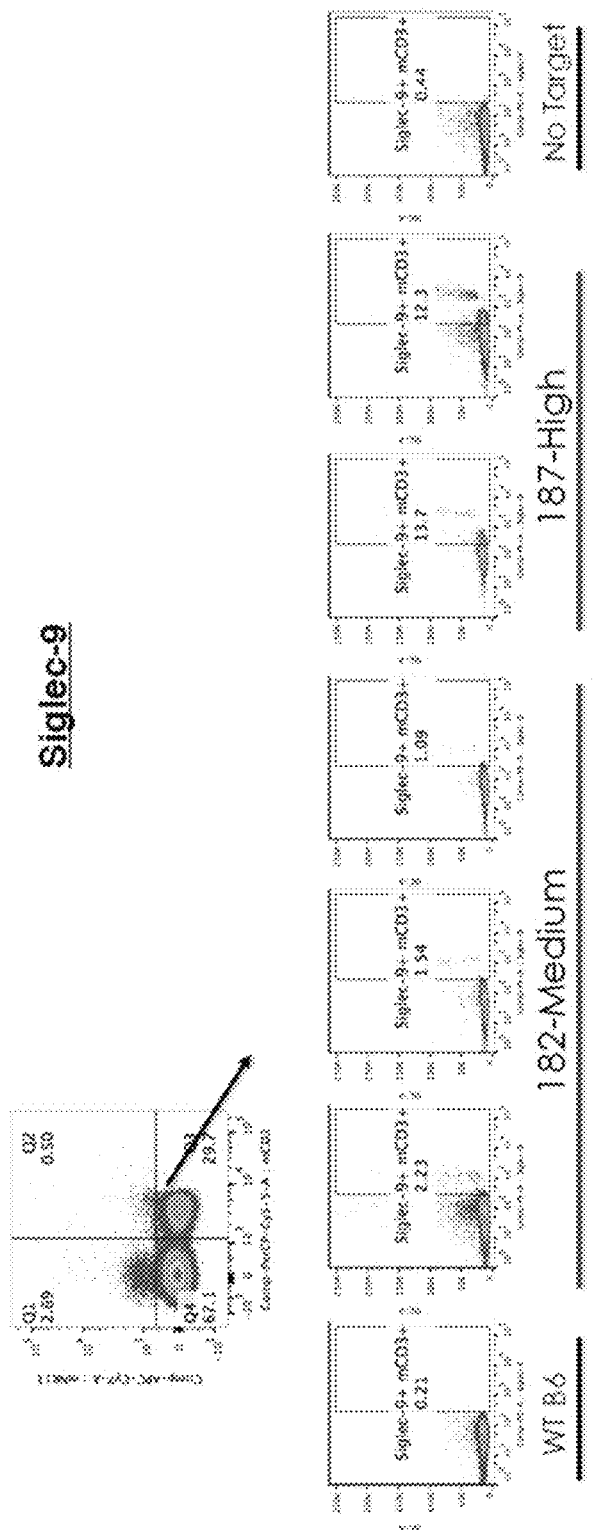

Human CD33 expression was negative on T cells in mice from both the higher expression mouse #187 founder line and lower expression mouse #182 founder line (FIG. 14A). Human Siglec-7 expression was observed on approximately 5% of T cells in mice from the higher expression mouse #187 founder line, while no human Siglec-7 expression was observed on T cells in mice from the lower expression mouse #182 founder line (FIG. 14B). Surprisingly, the expression pattern of human CD33 and Siglec-7 on T cells in mice from the higher expression mouse #187 founder line recapitulated the pattern of human expression of these proteins in T cells. Human Siglec-9 expression was observed on 10-15% of T cells in mice from the higher expression mouse #187 founder line, and minimal human Siglec-7 expression was observed on T cells in mice from the lower expression mouse #182 founder line (FIG. 14C).

Figure 15A:
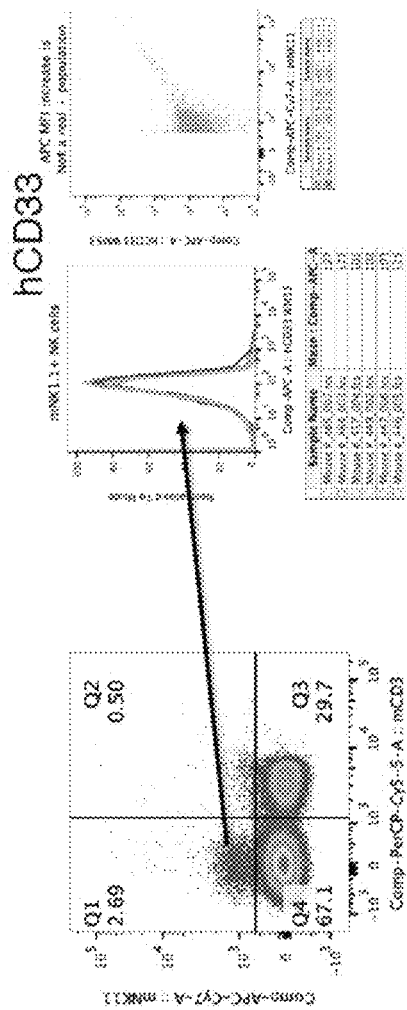
FIG. 15A-15C show results of FACS analysis demonstrating the expression pattern of human CD33 (FIG. 15A) on primary natural killer (NK) cells from peripheral blood of BACRP11-891J20 transgenic mice, the expression pattern of human Siglec-7 (FIG. 15B) on primary natural killer (NK) cells from peripheral blood of control non-transgenic mice (blue line) and BACRP11-891J20 transgenic mice (red line), and the expression pattern of human Siglec-9 (FIG. 15C) on primary natural killer (NK) cells from peripheral blood of control non-transgenic mice (red line) and BACRP11-891J20 transgenic mice (blue line).
Figure 15B:
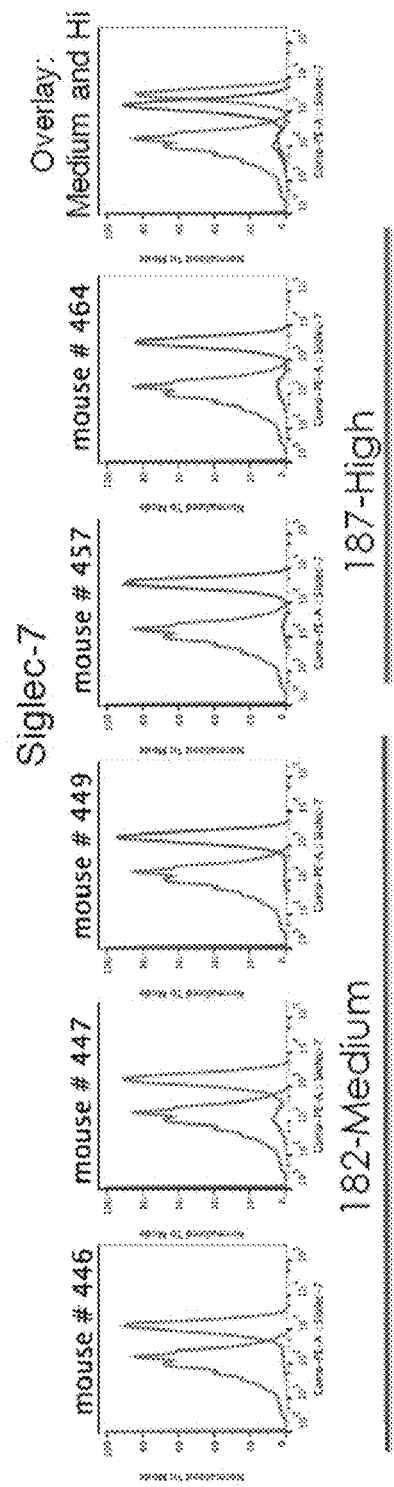
Figure 15C:
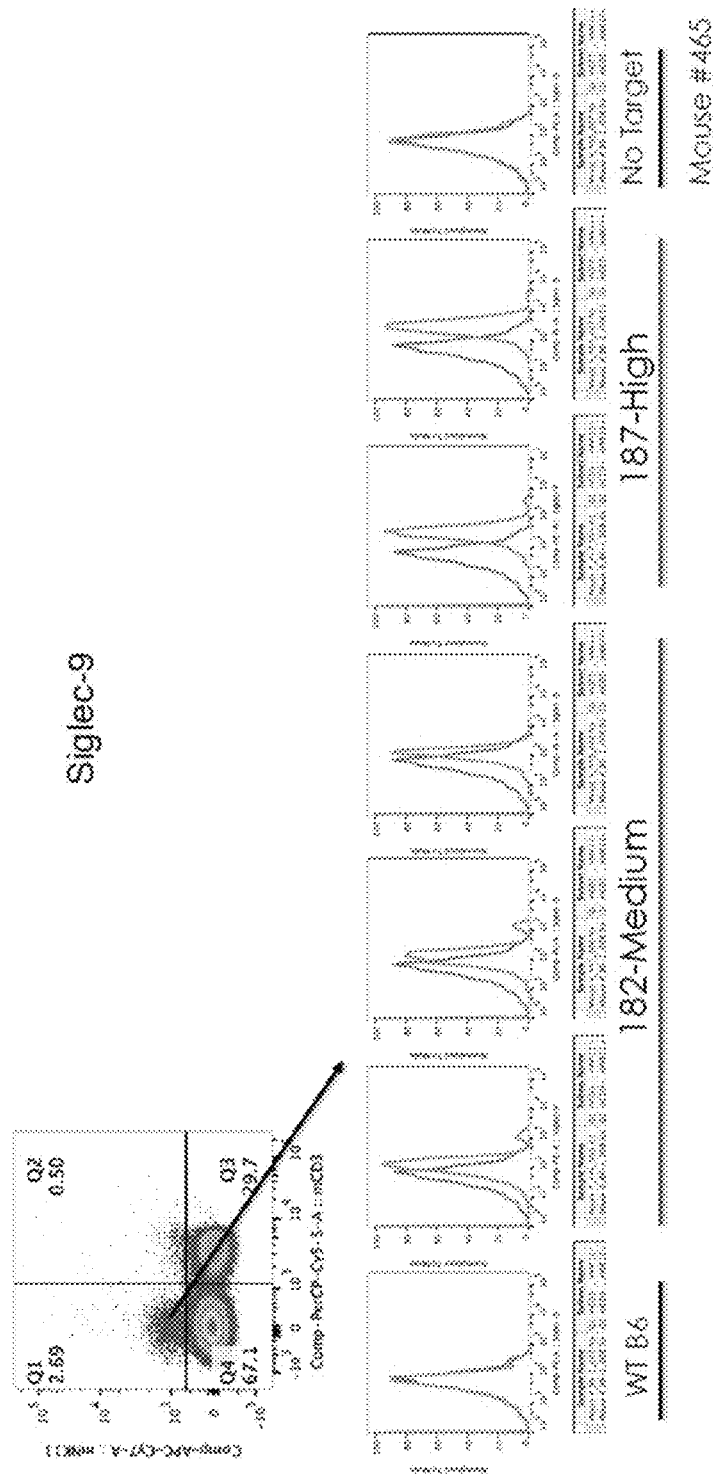

Human CD33 expression was negative on NK cells in mice from both the higher expression mouse #187 founder line, and the lower expression mouse #182 founder line (FIG. 15A). Human Siglec-7 (FIG. 15B) and Siglec-9 (FIG. 15C) were highly expressed on NK cells in mice from the higher expression mouse #187 founder line, and were moderately expressed in mice from the lower expression mouse #182 founder line. Surprisingly, the expression pattern of all three human transgenes recapitulated the pattern of human expression of these genes on NK cells.

A summary of the results of human CD33, Siglec-7, and Siglec-9 expression in the various subpopulations of peripheral blood cells is provided in Table A below.

TABLE A summary of expression results from peripheral blood cells

| | Mice from higher expression founder line (187) | | | Mice from lower expression founder line (182) | | |
|---|---|---|---|---|---|---|
| | hCD33 | hSiglec-7 | hSiglec-9 | hCD33 | hSiglec-7 | hSiglec-9 |
| Myeloid cells | >50% of cells | All cells | High | Small subset of cells | Majority of cells | Medium |
| Mo-MDSCs | High on most cells | High on most cells | High | Medium on all cells | Medium on all cells | Medium |
| G-MDSCs/ neutrophils | High | High on most cells | High | Very low | Medium | Medium |
| T cells | Negative | ~5% of cells | 10-15% of cells | Negative | Negative | Minimal |
| NK cells | Negative | High | High | Negative | Moderate | Moderate |

Figure 16:
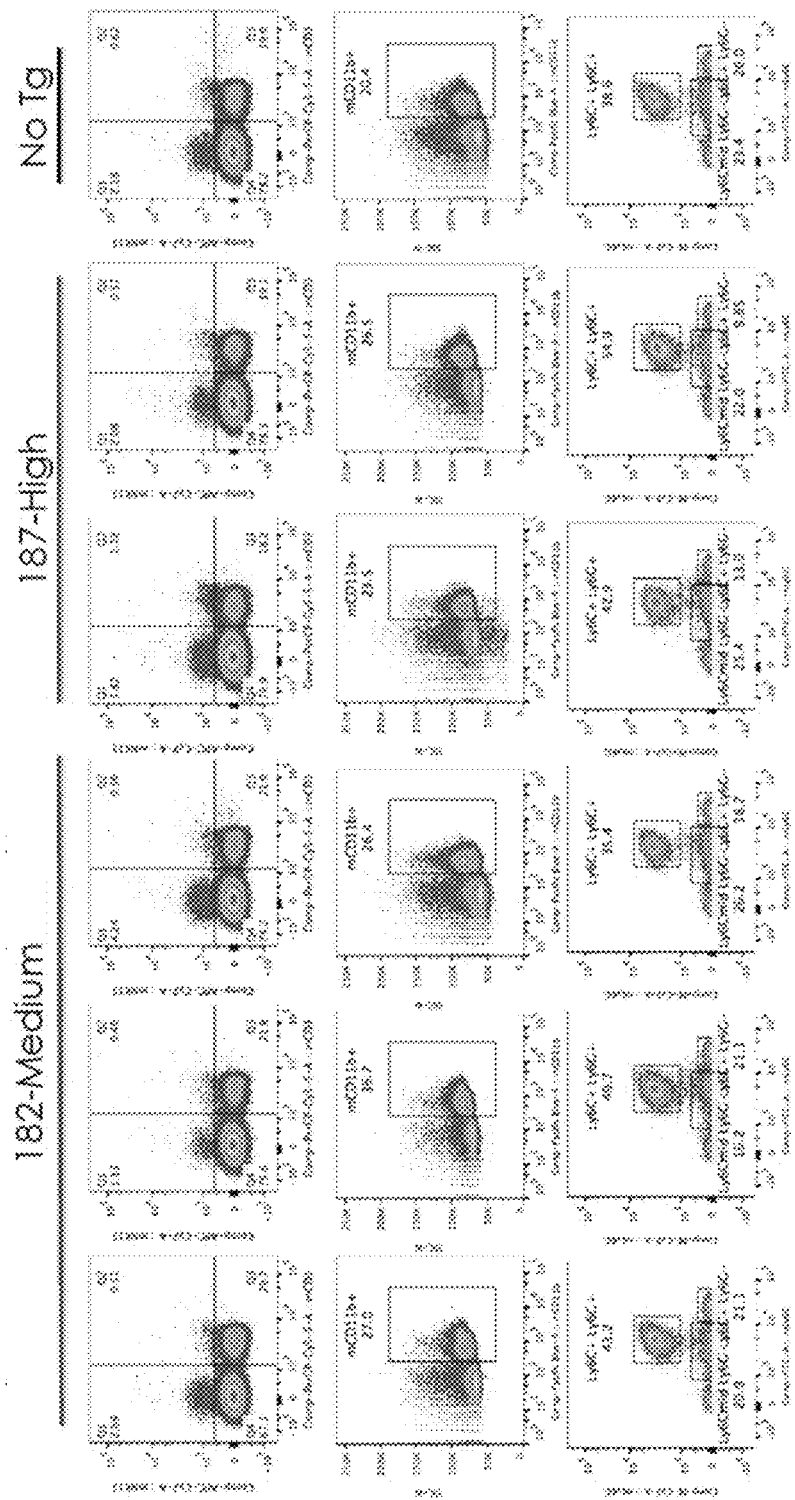
FIG. 16 shows results of FACS analysis comparing the immune cell populations in the periphery of control non-transgenic and BACRP11-891J20 transgenic mice.

The overall percentages of peripheral blood cells did not appear to be altered in the transgenic 187 or 182 founder mouse lines relative to a non-transgenic mouse (FIG. 16). Specifically, no gross alterations in the number of T cells, NK cells, myeloid cells, CD11b-positive cells, Mo-MDSCs, or G-MDSCs/neutrophils were observed in peripheral blood tested from the higher expression mouse #187 founder line or the lower expression mouse #182 founder line (FIG. 16).

Figure 17:
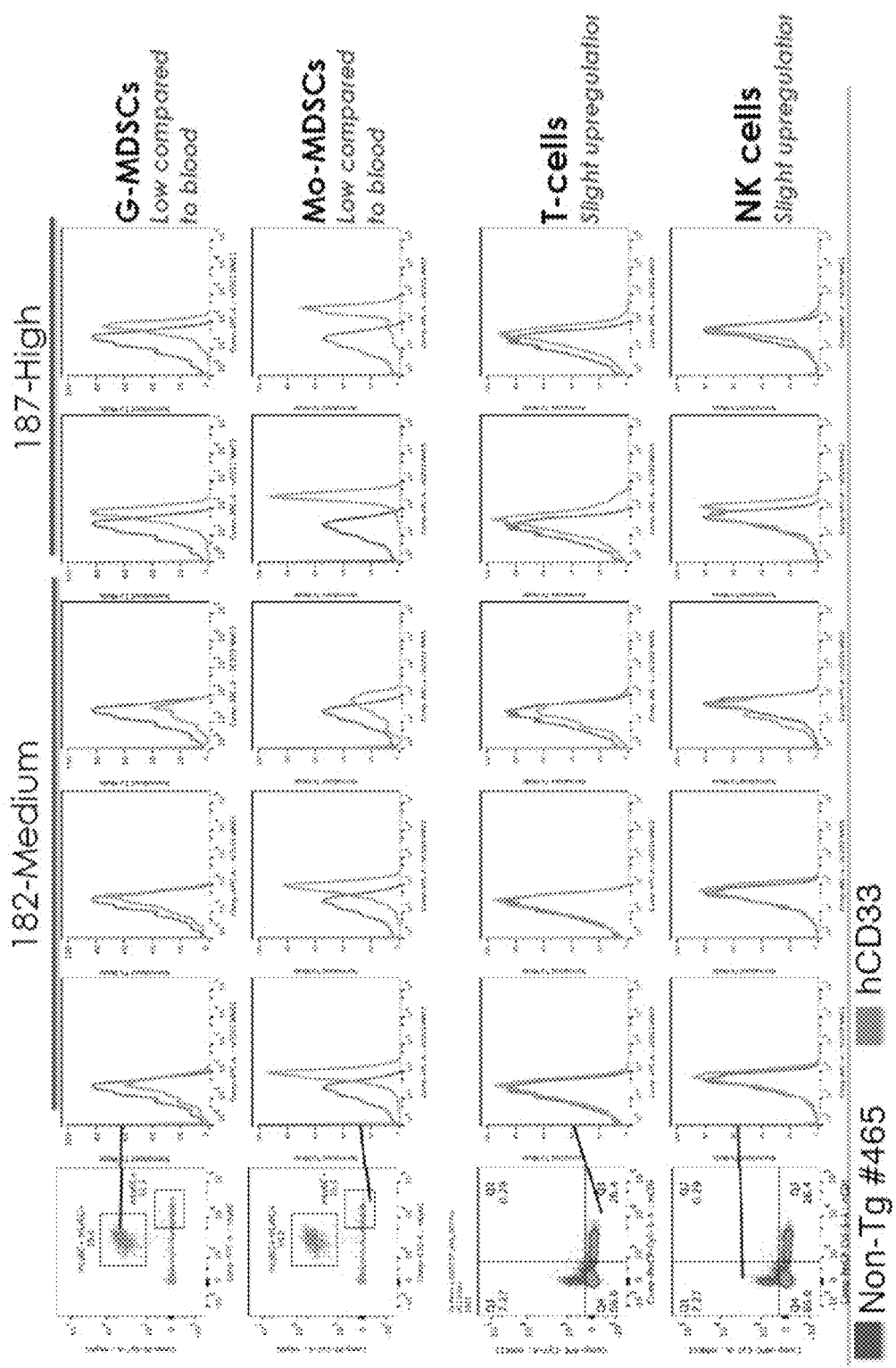
FIG. 17 shows results of FACS analysis demonstrating the expression pattern of human CD33 on primary G-MDSCs, primary Mo-MDSCs, primary T cells and primary NK cells from the spleens of control non-transgenic mice (red line) and BACRP11-891J20 transgenic mice (blue line).
Figure 18:
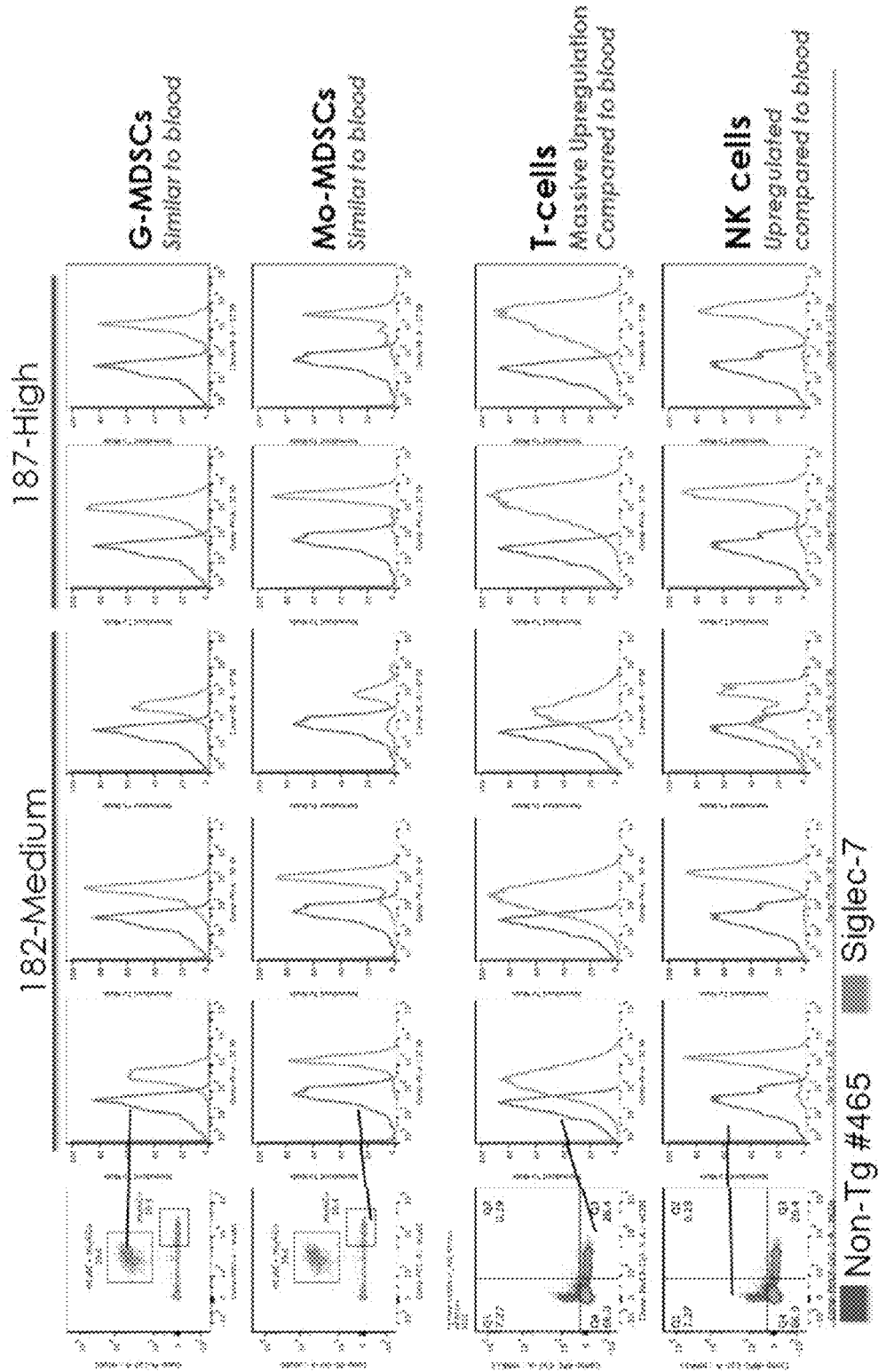
FIG. 18 shows results of FACS analysis demonstrating the expression pattern of human Siglec-7 on primary G-MDSCs, primary Mo-MDSCs, primary T cells and primary NK cells from the spleens of control non-transgenic mice (red line) and BACRP11-891J20 transgenic mice (blue line).
Figure 19:
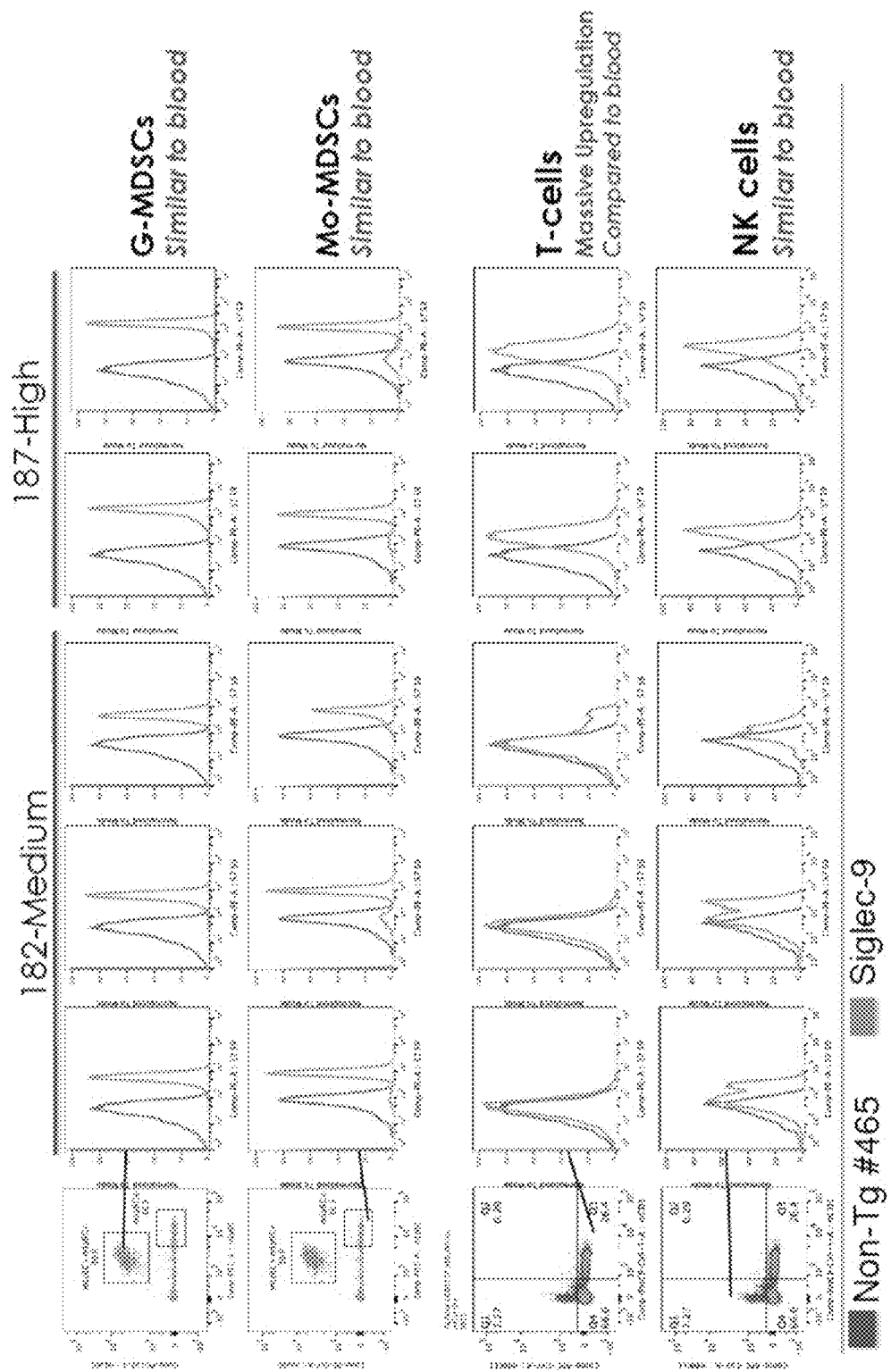
FIG. 19 shows results of FACS analysis demonstrating the expression pattern of human Siglec-9 on primary G-MDSCs, primary Mo-MDSCs, primary T cells and primary NK cells from the spleens of control non-transgenic mice (red line) and BACRP11-891J20 transgenic mice (blue line).

Human CD33 expression levels on splenic immune cells were comparable to those of their counterparts in peripheral blood (FIG. 17). Human CD33 levels were mildly reduced on splenic MDSCs relative to peripheral blood MDSCs, and CD33 remained low or absent on T and NK cells (FIG. 17). Human Siglec-7 expression levels on MDSCs isolated from the spleen were similar to that observed on MDSCs from peripheral blood, but expression of Siglec-7 was greatly increased on splenic T cells, and to a lesser extent splenic NK cells, than their counterparts in peripheral blood (FIG. 18). Human Siglec-9 expression on splenic MDSCs and NK cells was similar to the expression observed on their counterparts in peripheral blood, but Siglec-9 expression was greatly increased on splenic T cells relative to peripheral blood T cells (FIG. 19). A summary of the relative expression of human CD33, Siglec-7, and Siglec-9 on splenic vs. peripheral blood cells is provided in Table B below.

TABLE B

Relative transgene expression in splenic cells

| | hCD33 | hSiglec-7 | hSiglec-9 |
|---|---|---|---|
| Mo-MDSCs | Low compared to blood | Similar to blood | Similar to blood |
| G-MDSCs/ neutrophils | Low compared to blood | Similar to blood | Similar to blood |
| T cells | Slightly upregulated compared to blood | Massively upregulated compared to blood | Massively upregulated compared to blood |
| NK cells | Slightly upregulated compared to blood | Upregulated compared to blood | Similar to blood |

Figure 20:
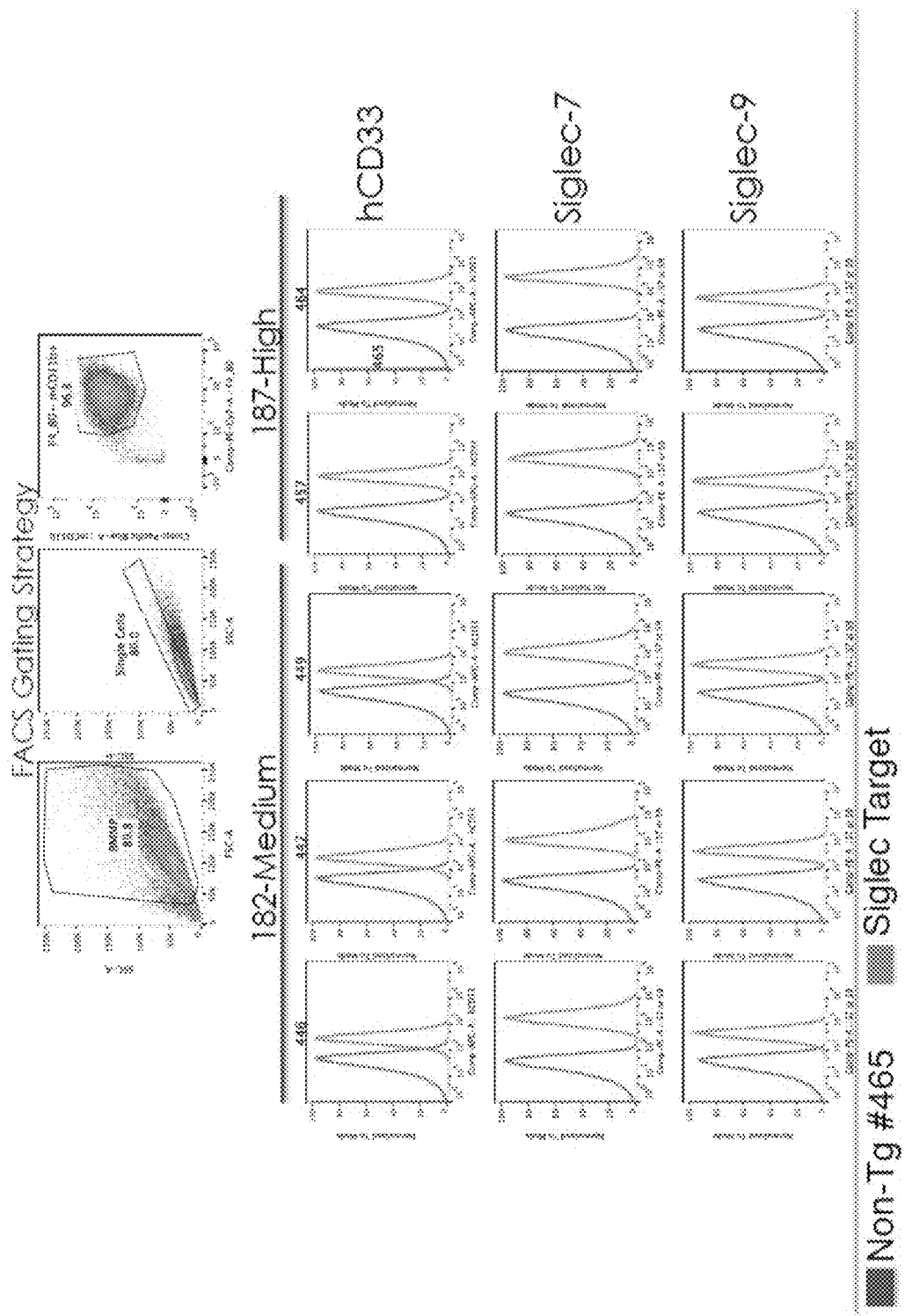
FIG. 20 shows results of FACS analysis demonstrating the expression pattern of human CD33, human Siglec-7, and human Siglec-9 on primary bone marrow-derived macrophages (BMDMs) from control non-transgenic mice (red line) and BACRP11-891J20 transgenic mice (blue line).
Figure 21:
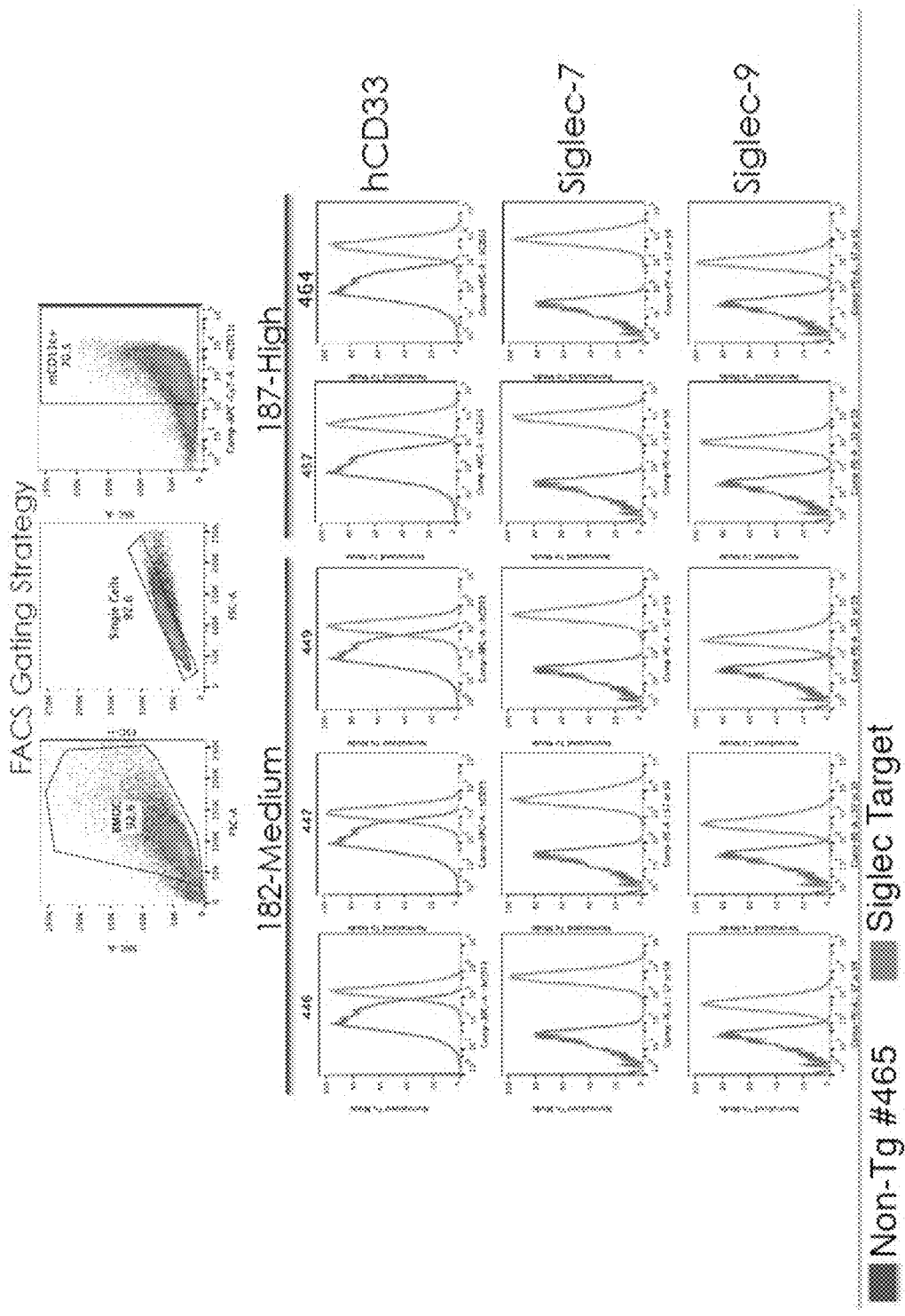
FIG. 21 shows results of FACS analysis demonstrating the expression pattern of human CD33, Siglec-7, and Siglec-9 on primary bone marrow-derived dendritic cells (BMDCs) from control non-transgenic mice (red line) and BACRP11-891J20 transgenic mice (blue line).

Transgenic mouse BMDMs (FIG. 20) and BMDCs (FIG. 21) from either the higher expression mouse #187 founder line or the lower expression mouse #182 founder line expressed high levels of human CD33, human Siglec-7, and human Siglec-9.

Figure 23:
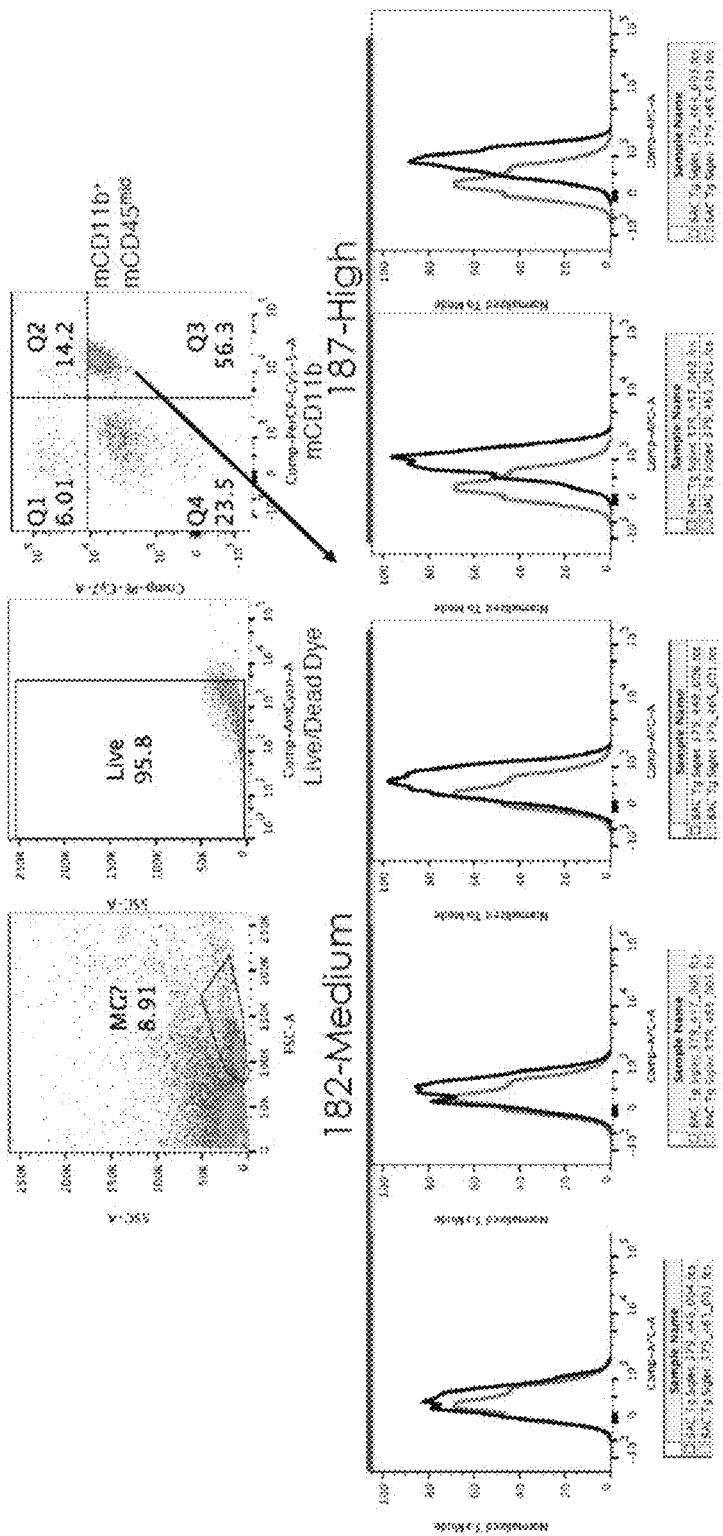
FIG. 23 shows results of FACS analysis demonstrating the expression pattern of human CD33 on primary brain microglia from BACRP11-891J20 transgenic mice.

Next, experiments were conducted to determine the expression of human CD33 on brain microglia isolated from rederived transgenic animals from the higher expression mouse #187 founder line or the lower expression mouse #182 founder line. The FACS panel design used to stain mouse brain microglia is summarized in FIG. 22. Brain microglia isolated from mice derived from the lower expression mouse #182 founder line showed little to no human CD33 expression, while human CD33 expression was apparent in brain microglia isolated from mice derived from the higher expression mouse #187 founder line (FIG. 23).

Figure 24A:
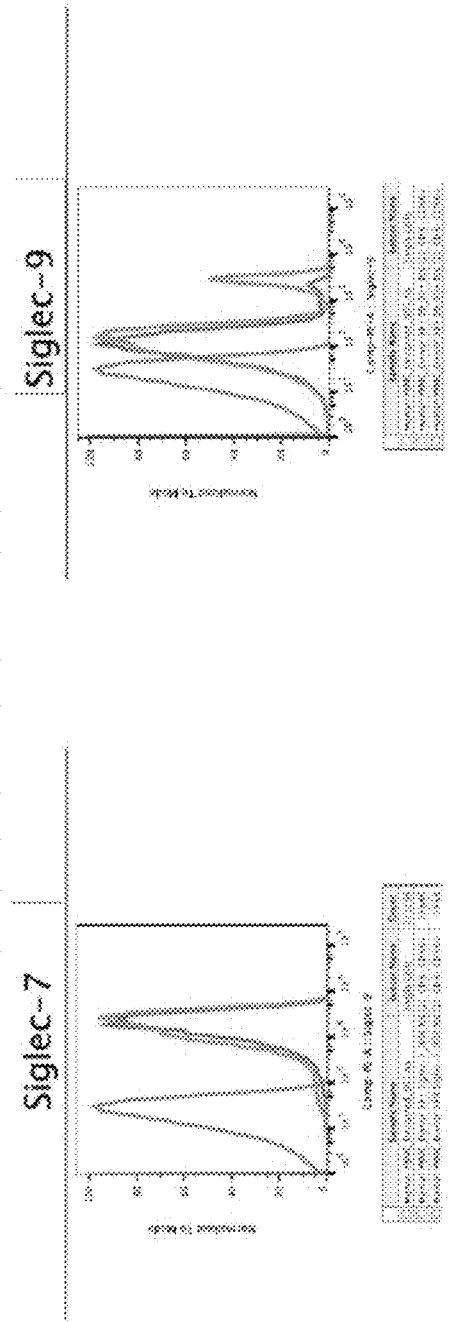
FIG. 24A-24B show results of FACS analysis demonstrating the expression pattern of human Siglec-7 and human Siglec-9 on primary NK cells from peripheral blood of either a human patient (FIG. 24A) or BACRP11-891J20 transgenic mice (FIG. 24B).
Figure 24B:
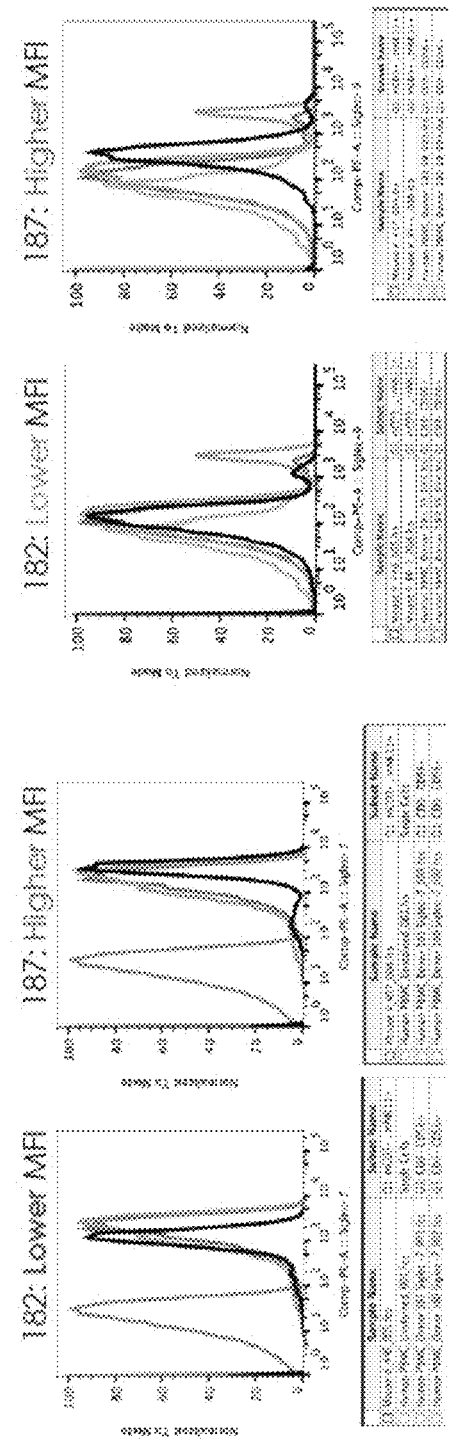
Figure 25A:
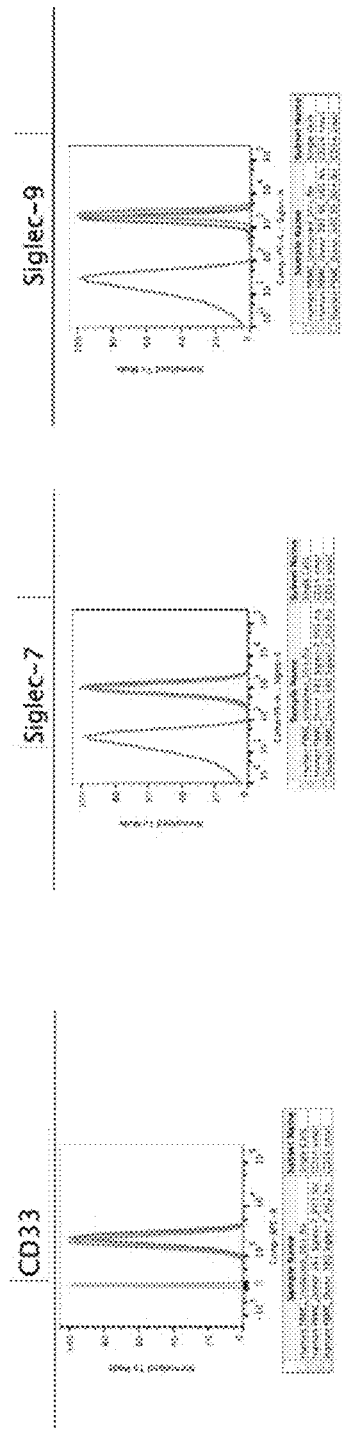
FIG. 25A-25B show results of FACS analysis demonstrating the expression pattern of human CD33, human Siglec-7, and human Siglec-9 on primary myeloid cells from peripheral blood of either a human patient (FIG. 25A) or BACRP11-891J20 transgenic mice (FIG. 25B).
Figure 25B:
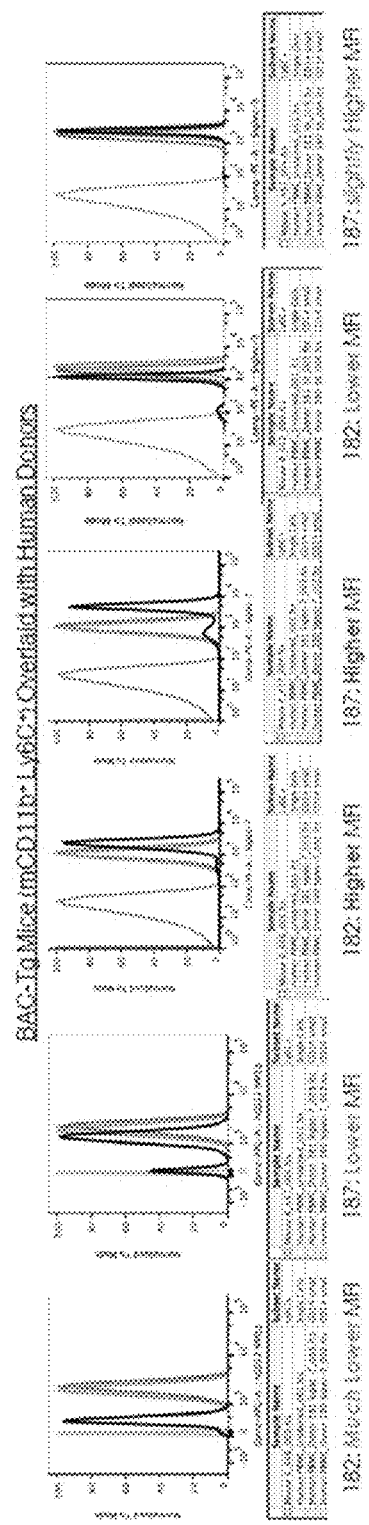

Finally, expression levels of human CD33, human Siglec-7, and human Siglec-9 were directly compared between human primary cells and primary cells isolated from the higher expression mouse #187 founder line or the lower expression mouse #182 founder line. Surprisingly, expression levels of human Siglec-7 and human Siglec-9 were comparable between NK cells isolated from the human donor (FIG. 24A) and NK cells isolated from either the higher expression mouse #187 founder line or the lower expression mouse #182 founder line (FIG. 24B) Similarly, expression levels of human CD33, human Siglec-7, and human Siglec-9 were comparable between myeloid cells isolated from the human donor (FIG. 25A) and myeloid cells isolated from either the higher expression mouse #187 founder line or the lower expression mouse #182 founder line (FIG. 25B).

Taken together, this data suggested that transgenic animals had been generated which coordinately expressed the human CD33, human Siglec-7, and human Siglec-9 genes. Moreover, this data suggested that these transgenic animals not only coordinately expressed the human genes, but expressed them at or near the same levels, and on the same cell types, as was observed in primary cells isolated from a human donor. The data provided herein suggested that, for the first time, transgenic animals had been developed which had been "humanized for the Siglec locus. Without wishing to be bound by theory, these transgenic animals harboring a "humanized" Siglec system will allow for the study and development of novel therapeutics that interact with and target human Siglec proteins, opening the door for the improvement of treatment strategies for diseases in which the human Siglecs may be involved (e.g., neurodegenerative diseases, proliferative diseases, etc.)

Example 3: Generation of Transgenic Mice Harboring Human Siglec-5 and Siglec-14

Methodologies

Identifying BACs of interest: Bacterial Artificial Chromosomes (BACs) harboring the human Siglec genes Siglec-5 and Siglec-14 with all intronic and exonic sequences were identified using the UCSC genome browser and the CloneDB from NCBI. BAC clones were further selected to identify those clones harboring a minimum of at least 10 kilobases of 5' and 3' flanking sequences in addition to the indicated Siglec genes to maximize the likelihood of identifying BAC clones that include the relevant human gene regulatory sequences in addition to human Siglec-5 and Siglec-14.

Isolating and purifying BAC clones: BAC clones meeting all of the selection requirements were isolated and purified as described in Example 1.

Generating transgenic animals: Mice harboring BAC clones of interest were generated as described in Example 1.

Isolating primary cells: Primary cells from mice and humans were isolated as described in Examples 1 and 2. Bone marrow cells were cultured to differentiate dendritic cells for 7 days.

FACS analysis: Mice carrying the human Siglec-5 and Siglec-14 transgenes were analyzed by FACS analysis using standard techniques. Briefly, peripheral blood was obtained from 4-8 week old transgenic animals, and peripheral blood cells were subjected to multi-color flow cytometry panel staining. Cells were incubated with the cell viability dye and the following antibodies: anti-mouse cD11b (BD Biosciences, M1/70, 1:100), anti-mouse CD3, anti-mouse NK1.1, and anti-human Siglec-5 (Biolegend, 1A5, 1:20). Alternatively, peripheral blood, spleen, and bone marrow-derived cells were subjected to multi-color flow cytometry panel staining. Cells were incubated with the cell viability dye and the following antibodies: anti-mouse cD11b (BD Biosciences, M1/70, 1:100), anti-mouse CD3 (Affymetrix, 145-2C11, 1:100), anti-mouse CD11b (Biolegend, 1A8, 1:200), and anti-human Siglec-5 (Biolegend, 1A5, 1:20). Bone marrow-derived cells were additionally stained with anti-human Siglec-7. The cells were stained for 30 minutes on ice, washed twice with cold FACS buffer, and fixed with 4% PFA. The stained and fixed cells were then applied to a BD FACS CANTO II cytometer, data were acquired, and the resulting data was analyzed with FlowJo software.

Results

To obtain mice coordinately expressing multiple human Siglec genes, Bacterial Artificial Chromosomes (BACs) harboring key human Siglec genes with sufficient flanking sequences were identified using the UCSC genome browser and the CloneDB from NCBI. Three BAC clones (BACCTD-2026P14, BACRP11-145E6, and BACRP11-105H4) were identified that were predicted to contain the coding sequences for the human genes Siglec-5 and Siglec-14. Each BAC was tested by PCR analysis to confirm the proper human sequences of interest; however, BAC clone BACRP11-145E6 failed to show a signal corresponding to the presence of Siglec-14, while BAC clone BACRP11-105H4 could not be successfully isolated.

Figure 26:
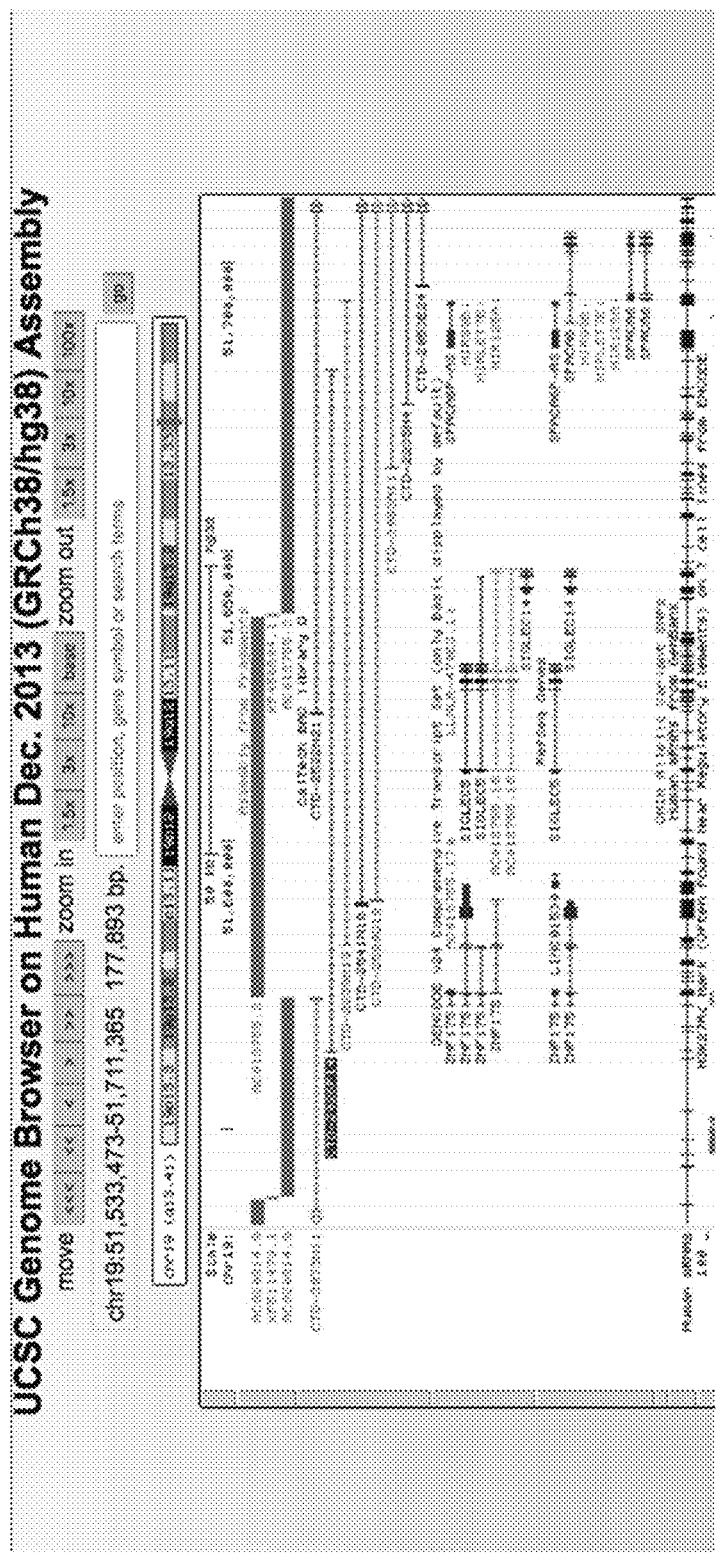
FIG. 26 shows a UCSC genome browser map of the genes, including Siglec-5 and Siglec-14, on a region of human Chromosome 19 included in the bacterial artificial chromosome (BAC) BACCTD-2026P14.
Figure 27:
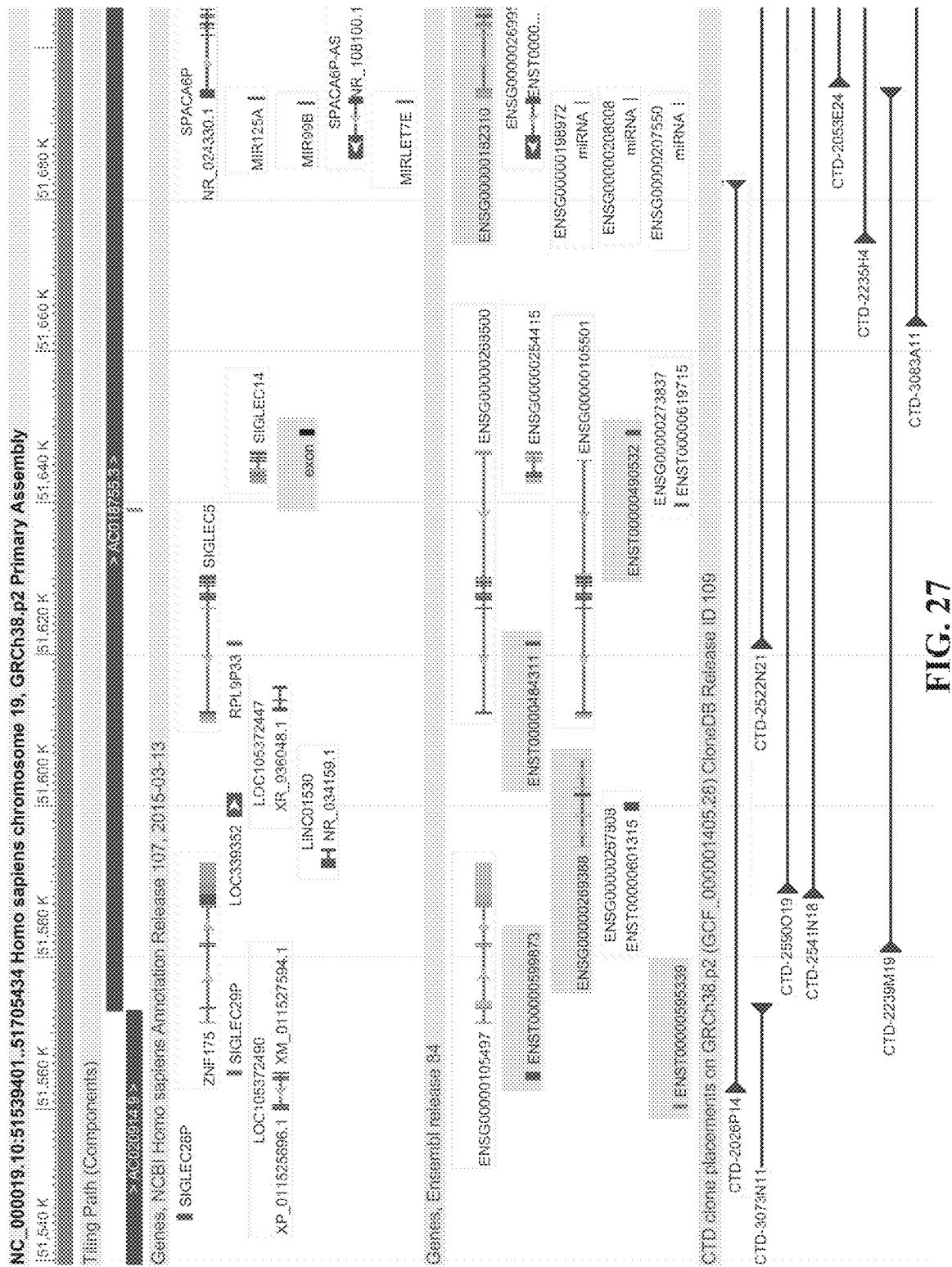
FIG. 27 shows a CloneDB map of the genes, including Siglec-5 and Siglec-14, on a region of human Chromosome 19 included in the bacterial artificial chromosome (BAC) BACCTD-2026P14.

Maps of the human chromosomal region of interest encompassed by BACCTD-2026P14 are shown in FIG. 26 (from the UCSC genome browser) and FIG. 27 (from the CLONEDB NCBI browser). The chromosomal DNA within BACCTD-2026P14 spanned 118,595 nucleotides of the human genome, covering nucleotide positions 51,563,112-51,681,716 on human chromosome 19, based on the hg38 build of the UCSC genome browser (the human Siglec genes are found within a cluster on chromosome 19). Sequences within the Siglec-5 gene were amplified by PCR and sequenced by the Sanger method to confirm the presence of the gene in BACCTD-2026P14.

Figure 28:
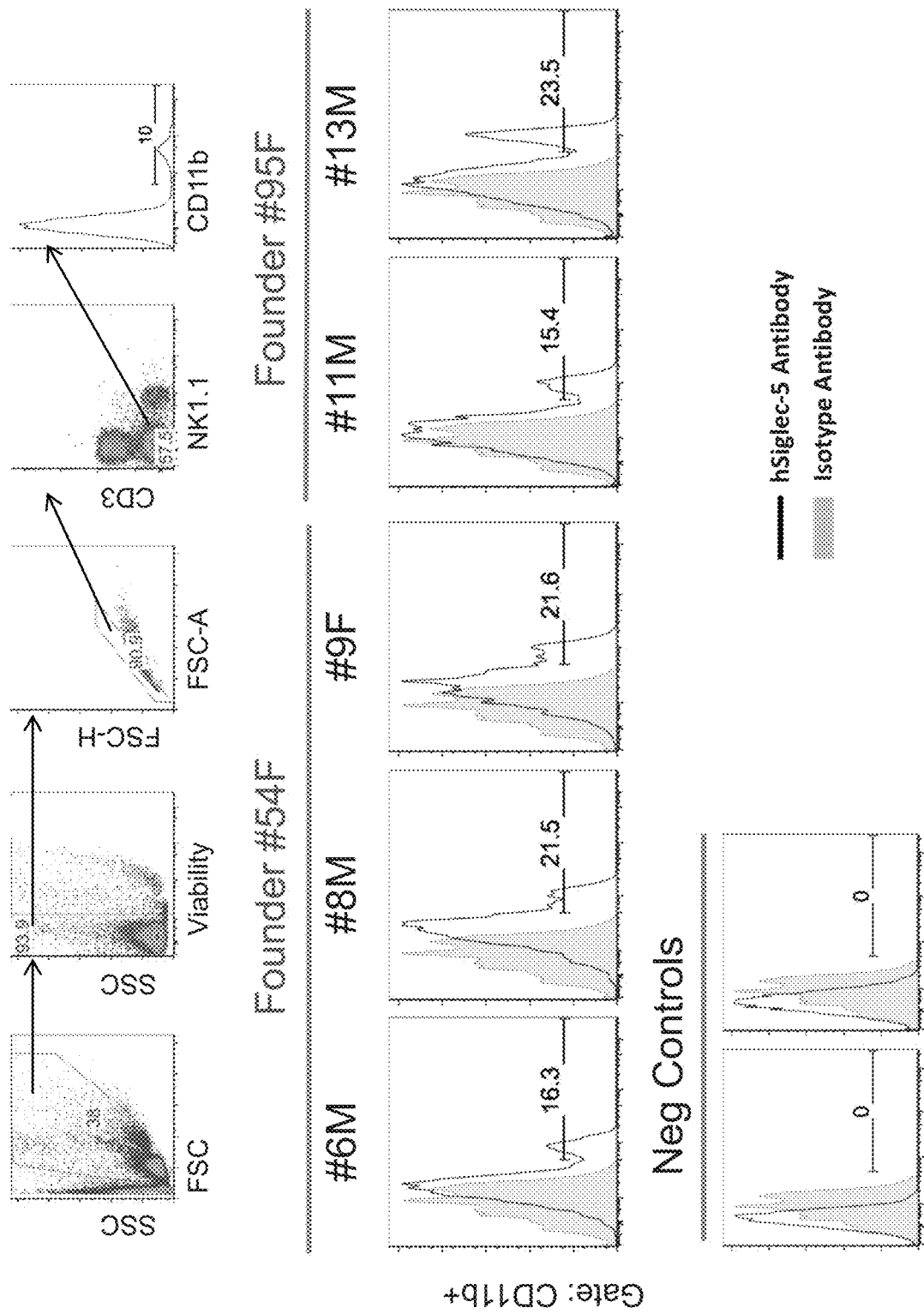
FIG. 28 shows results of FACS analysis demonstrating the expression pattern of human Siglec-5 on CD11b-positive primary cells from peripheral blood of BACCTD-2026P14 transgenic mice (#6M, #8M, #9F, #11M, and #13m) and control non-transgenic mice (Neg Controls).

Transgenic mice harboring BACCTD-2026P14 were generated by pronuclear injection of the BAC DNA into C57BL6/j zygotes. The resulting pups were genotyped to identify founder animals harboring the human transgenes (mouse #s 54 and 95). These founder animals were then bred to non-transgenic animals, and progeny animals (mouse #s 6, 8, 9, 11, and 13) were then analyzed by FACS analysis to monitor human Siglec-5 protein expression on CD11b-positive cells (FIG. 28). Expression of human Siglec-5 was observed on 10-20% of the CD11b-positive cells from mice derived from both of the founder animals, whereas control non-transgenic animals were negative for human Siglec-5 (FIG. 28).

Figure 29:
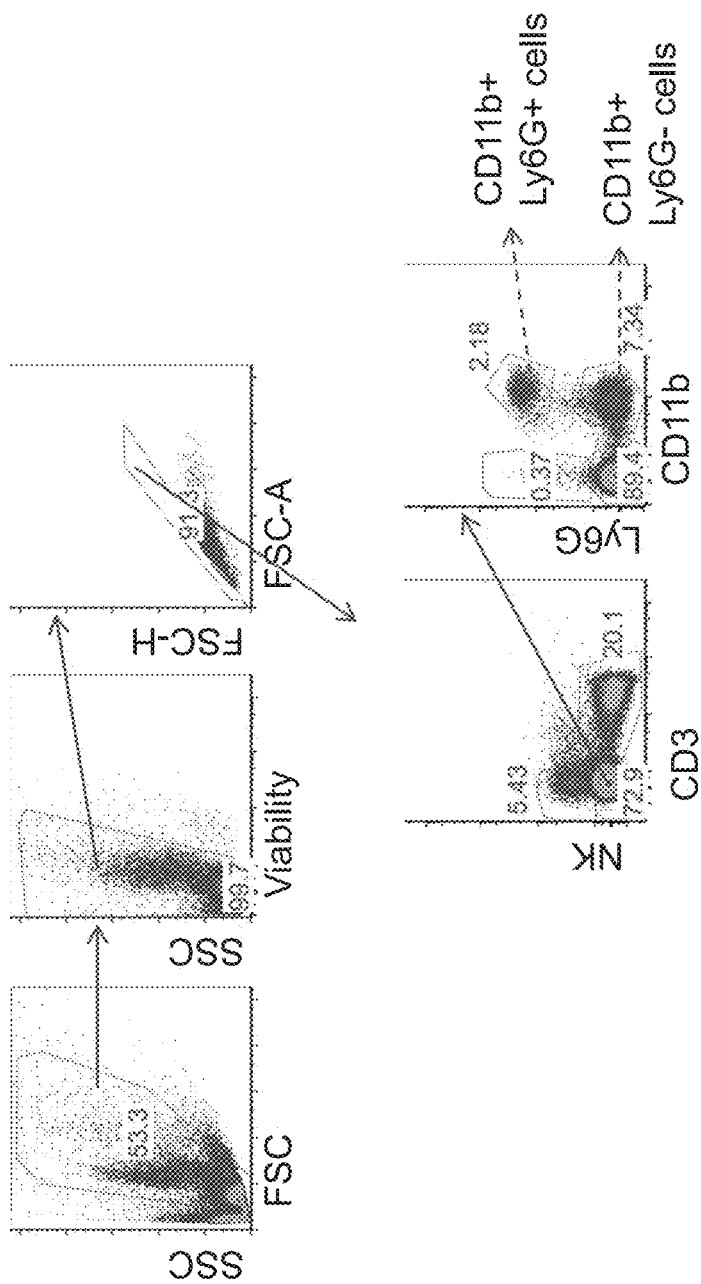
FIG. 29 shows the FACS gating strategy for the analysis of peripheral blood and spleen cells.

Transgenic mouse #13 (from founder animal #95) was then bred to generate progeny animals. Pups resulting from this breeding scheme were genotyped to identify progeny animals harboring the human transgenes, and cells isolated from these animals were tested for protein expression of human Siglec-5 by FACS analysis. To characterize mouse cell subpopulations that expressed the human Siglec-5, cells isolated from these mice were also stained with antibodies to specifically identify particular immune cell subpopulations. The cell isolation strategy used in these experiments is summarized in FIG. 29.

Figure 30:
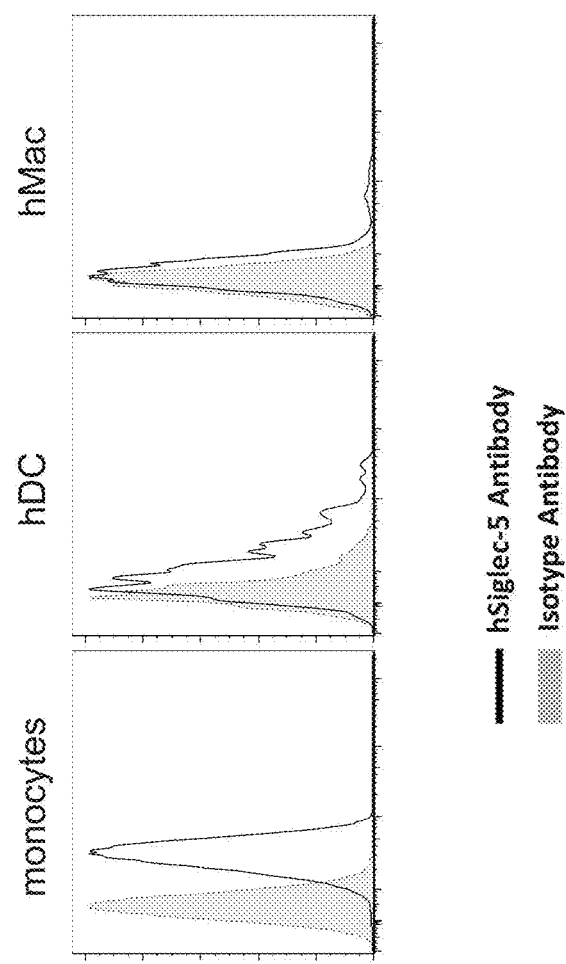
FIG. 30 shows results of FACS analysis demonstrating the expression pattern of human Siglec-5 on primary monocytes, dendritic cells (hDC), and macrophages (hMac) from peripheral blood of a human patient stained with an isotype control antibody (grey) or an anti-human Siglec-5 antibody (black line).
Figure 31:
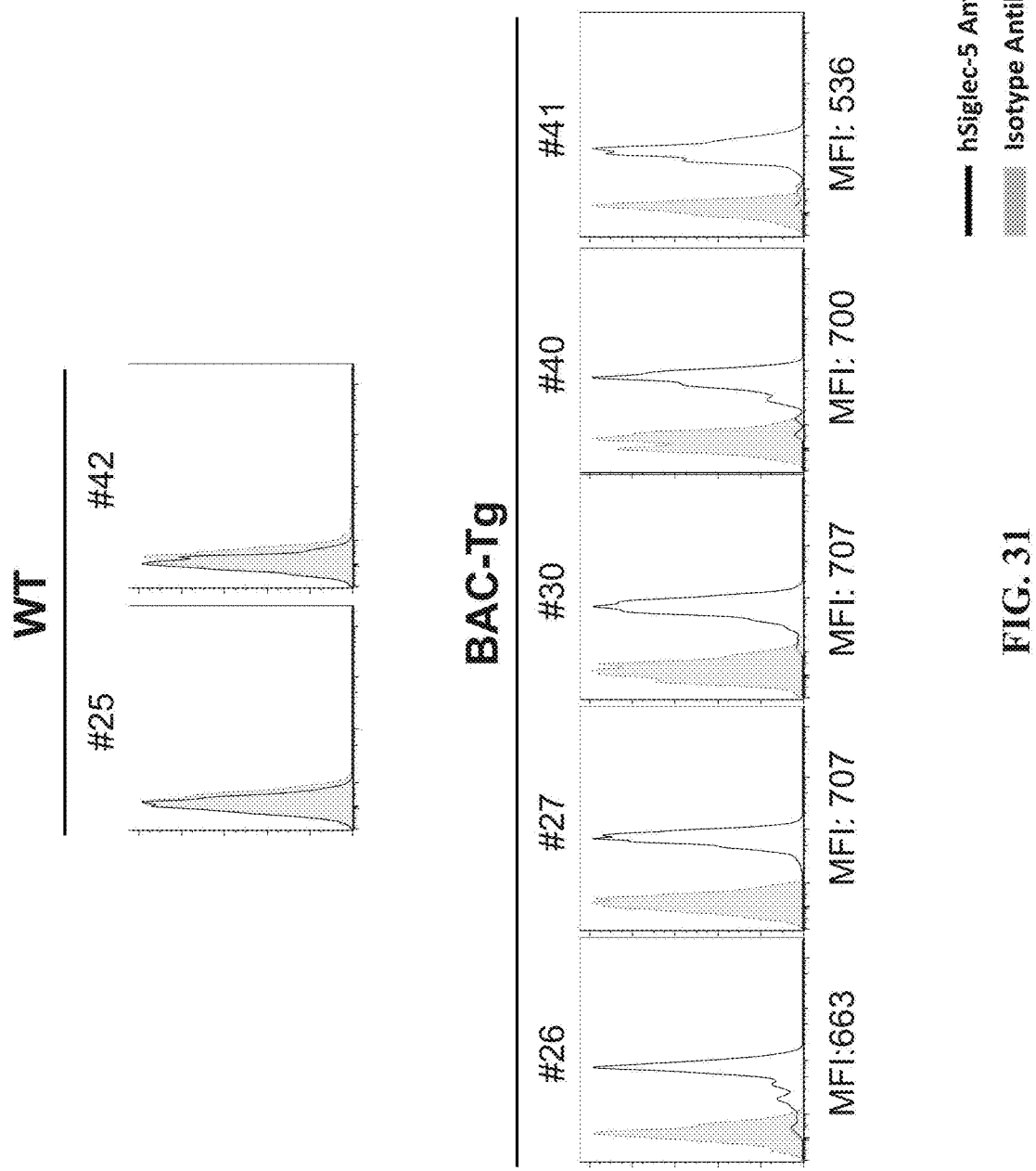
FIG. 31 shows results of FACS analysis demonstrating the expression pattern of human Siglec-5 on CD11b$^+$/Ly6G$^+$ primary cells from peripheral blood of control non-transgenic mice (#25 and #42) and BACCTD-2026P14 transgenic mice (#26, #27, #30, #40, and #41) stained with an isotype control antibody (grey) or an anti-human Siglec-5 antibody (black line).
Figure 32:
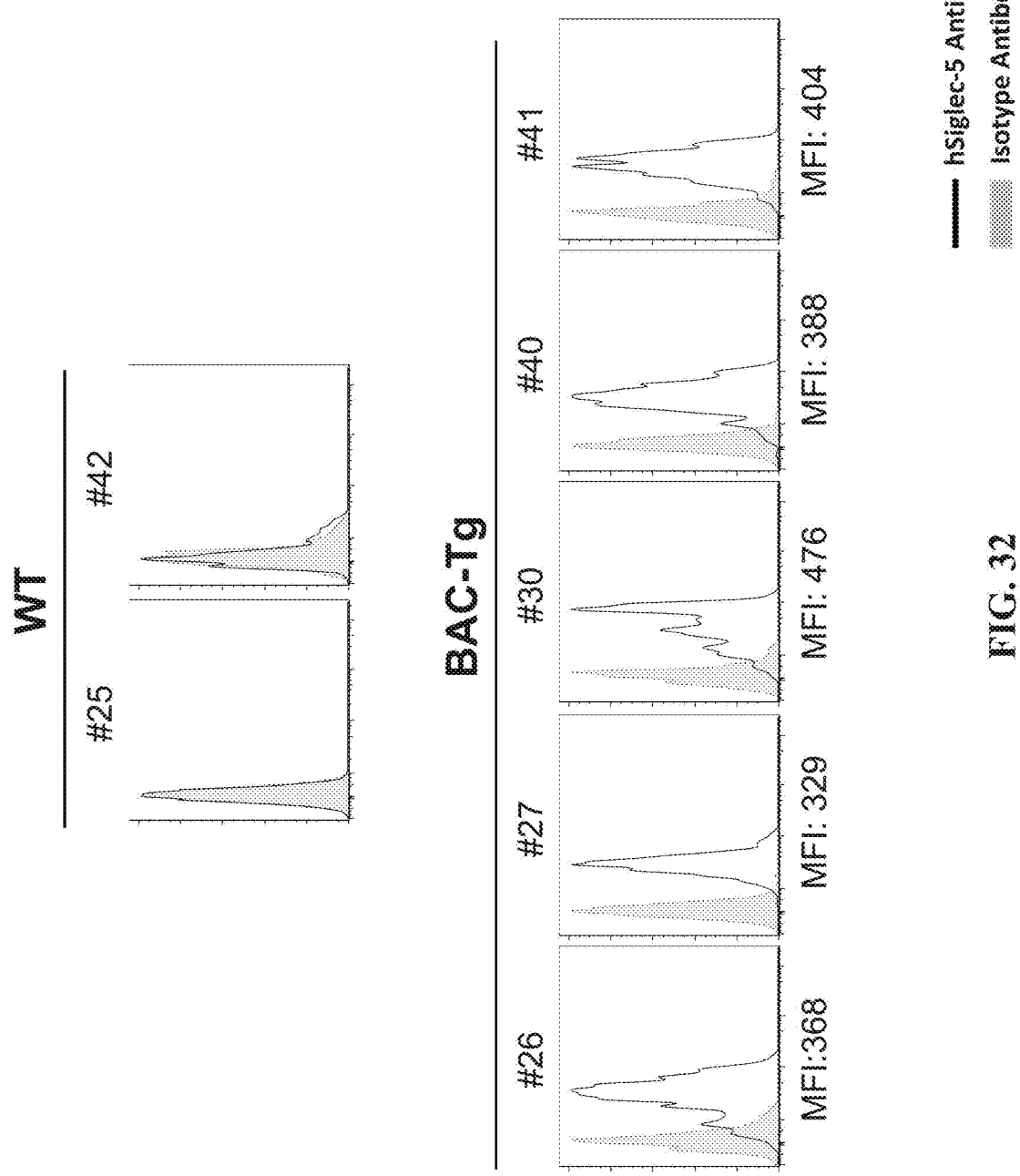
FIG. 32 shows results of FACS analysis demonstrating the expression pattern of human Siglec-5 on CD11b$^+$/Ly6G$^+$ primary cells from the spleen of control non-transgenic mice (#25 and #42) and BACCTD-2026P14 transgenic mice (#26, #27, #30, #40, and #41) stained with an isotype control antibody (grey) or an anti-human Siglec-5 antibody (black line).
Figure 33:
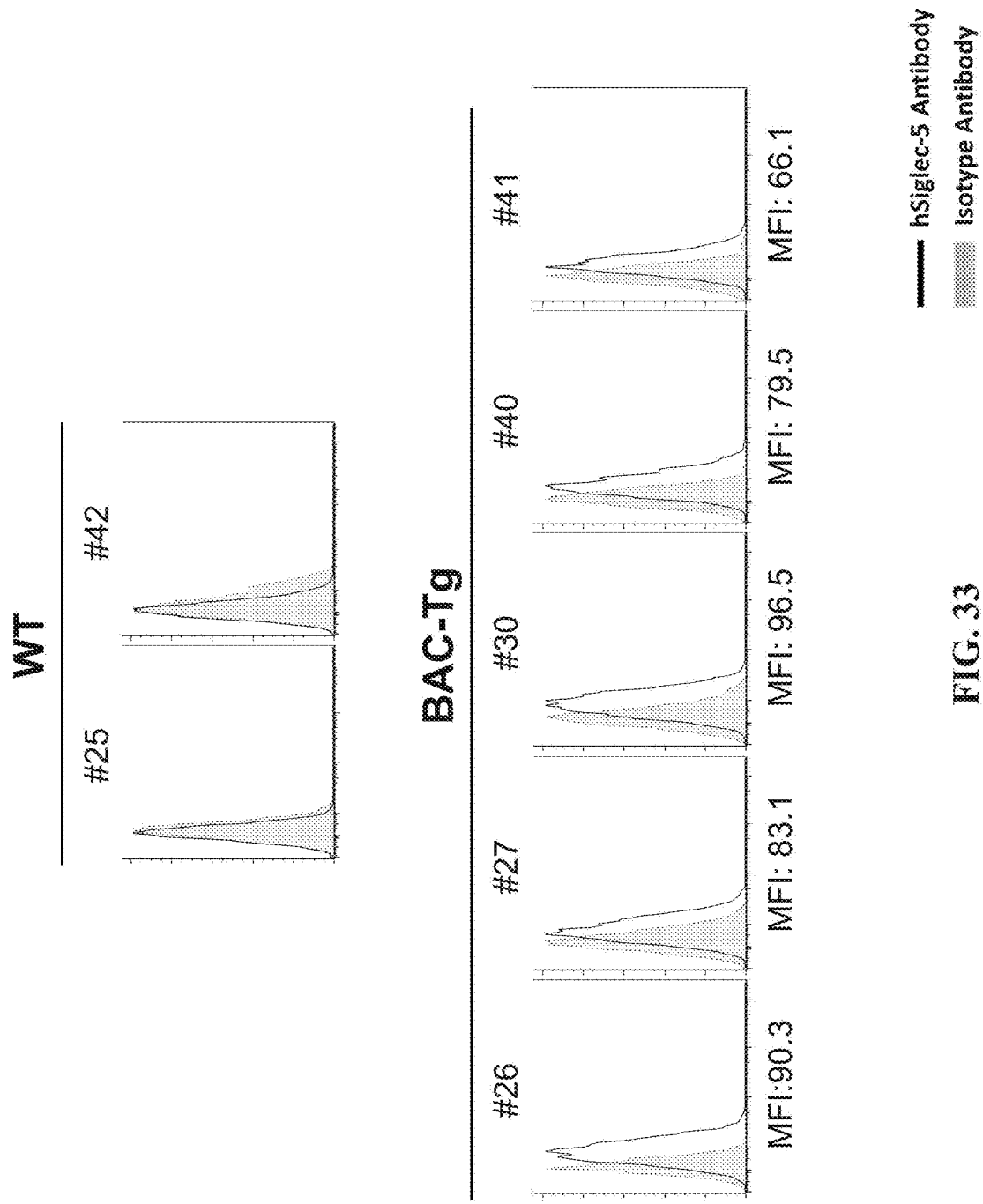
FIG. 33 shows results of FACS analysis demonstrating the expression pattern of human Siglec-5 on CD11b$^+$/Ly6G$^-$ primary cells from peripheral blood of control non-transgenic mice (#25 and #42) and BACCTD-2026P14 transgenic mice (#26, #27, #30, #40, and #41) stained with an isotype control antibody (grey) or an anti-human Siglec-5 antibody (black line).
Figure 34:
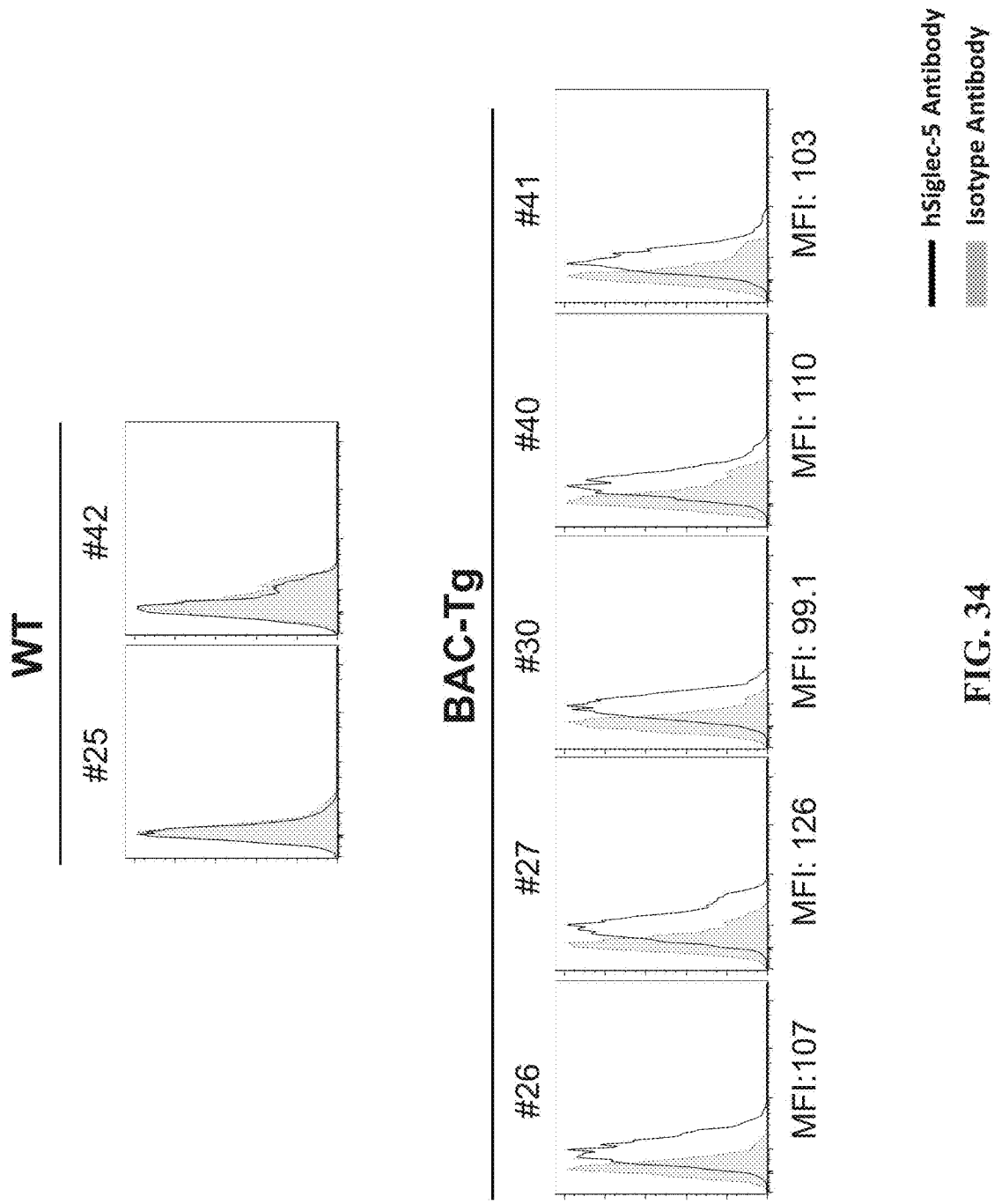
FIG. 34 shows results of FACS analysis demonstrating the expression pattern of human Siglec-5 on CD11b$^+$/Ly6G$^-$ primary cells from the spleen of control non-transgenic mice (#25 and #42) and BACCTD-2026P14 transgenic mice (#26, #27, #30, #40, and #41) stained with an isotype control antibody (grey) or an anti-human Siglec-5 antibody (black line).

Monocytes, dendritic cells, and macrophages isolated from a human patient expressed Siglec-5 on their surface (FIG. 30). The expression of human Siglec-5 on relevant mouse immune cells was tested to determine whether these transgenic mice expressed human Siglec-5 in a similar pattern to the expression of Siglec-5 on human immune cells. Human Siglec-5 expression was positive on CD11b$^+$/Ly6G$^+$ cells from peripheral blood (FIG. 31) and spleens (FIG. 32) in mice from the mouse #95 founder line (mouse #26, #27, #30, #40, and #41), and negative on non-transgenic control mice. Similarly, human Siglec-5 expression was positive on CD11b$^+$/Ly6G$^-$ cells from peripheral blood (FIG. 33) and spleens (FIG. 34). This data showed that Siglec-5 was successfully expressed on these immune cell types in all of the transgenic mice tested.

Figure 35A:
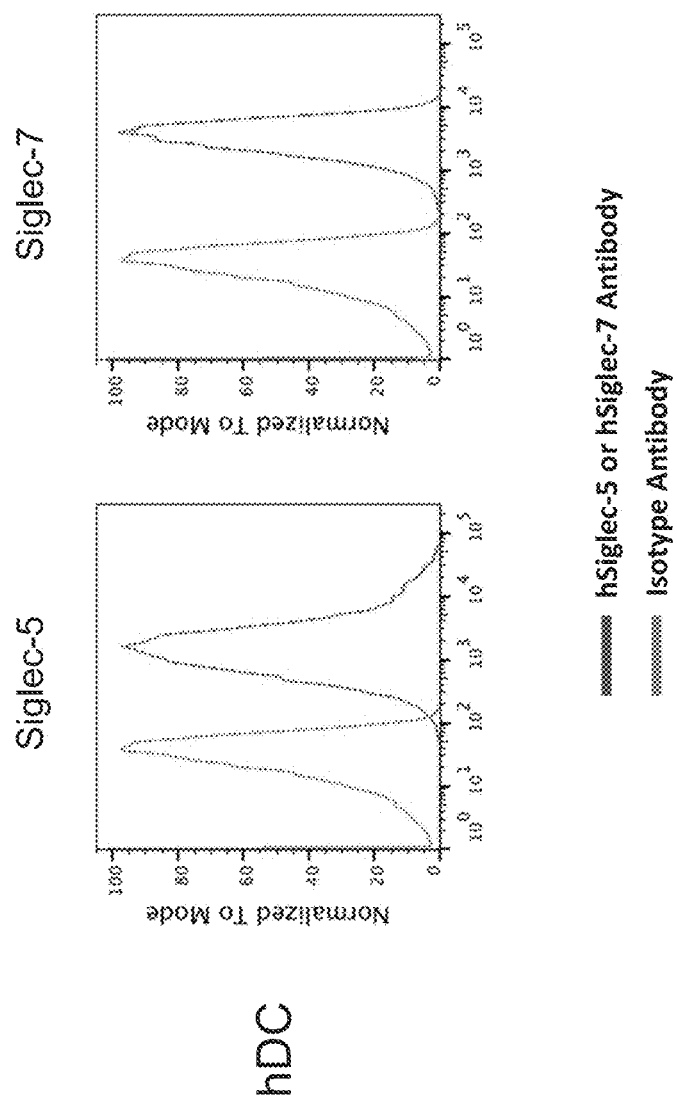
FIGS. 35A-B show human Siglec-5 and human Siglec-7 expression patterns on dendritic cells isolated from mice and humans.
Figure 35B:
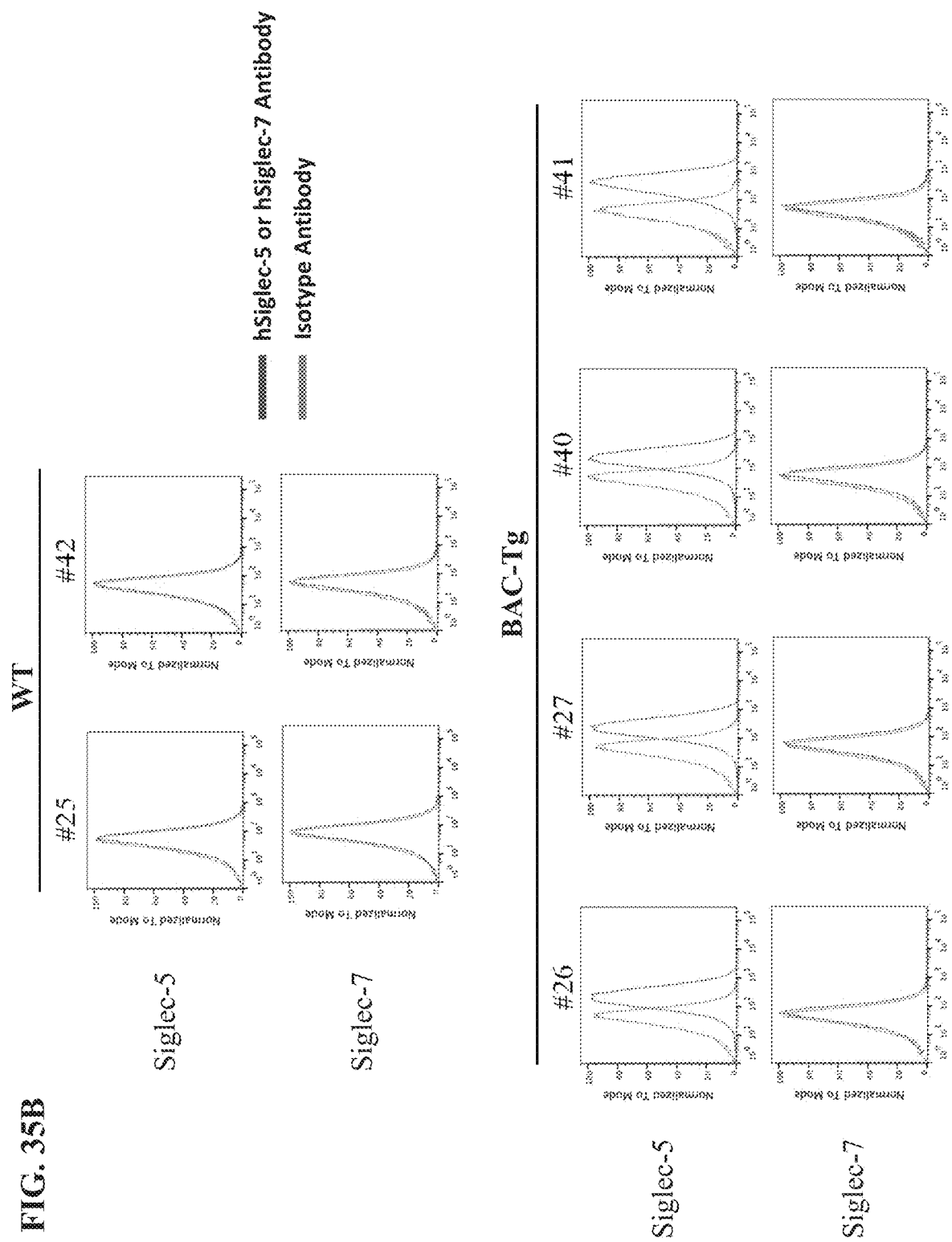

Finally, the expression pattern of human Siglec-5 on dendritic cells in the transgenic mice was tested. Dendritic cells isolated form a human patient expressed both Siglec-5 and Siglec-7 on their surface (FIG. 35A). Bone-marrow derived dendritic cells (BM-DCs) in mice from the mouse #95 founder line (mouse #26, #27, #30, #40, and #41) were also observed to express human Siglec-5 on their surface, while BM-DCs in non-transgenic control mice were Siglec-5 negative (FIG. 35B). None of the mice had observable expression of human Siglec-7, as these mice did not carry a human Siglec-7 transgene.

Taken together, this data suggested that transgenic animals were successfully generated that carried the human Siglec-5 and Siglec-14 genes. Further, these transgenic mice were capable of expressing human Siglec-5 on a number of relevant immune cell types, similar to the expression of Siglec-5 observed on human immune cells.

Example 4: Generation of Transgenic Mice Harboring Human Siglec-11 and Siglec-16

Methodologies

Identifying BACs of interest: Bacterial Artificial Chromosomes (BACs) harboring the human Siglec genes Siglec-11 and Siglec-16 with all intronic and exonic sequences were identified using the UCSC genome browser and the CloneDB from NCBI. BAC clones were further selected to identify those clones harboring a minimum of at least 10 kilobases of 5' and 3' flanking sequences in addition to the indicated Siglec genes to maximize the likelihood of identifying BAC clones that include the relevant human gene regulatory sequences in addition to human Siglec-5 and Siglec-14.

Isolating and purifying BAC clones: BAC clones meeting all of the selection requirements were isolated and purified as described in Example 1.

Generating transgenic animals: Mice harboring BAC clones of interest were generated as described in Example 1.

Results

Figure 36:
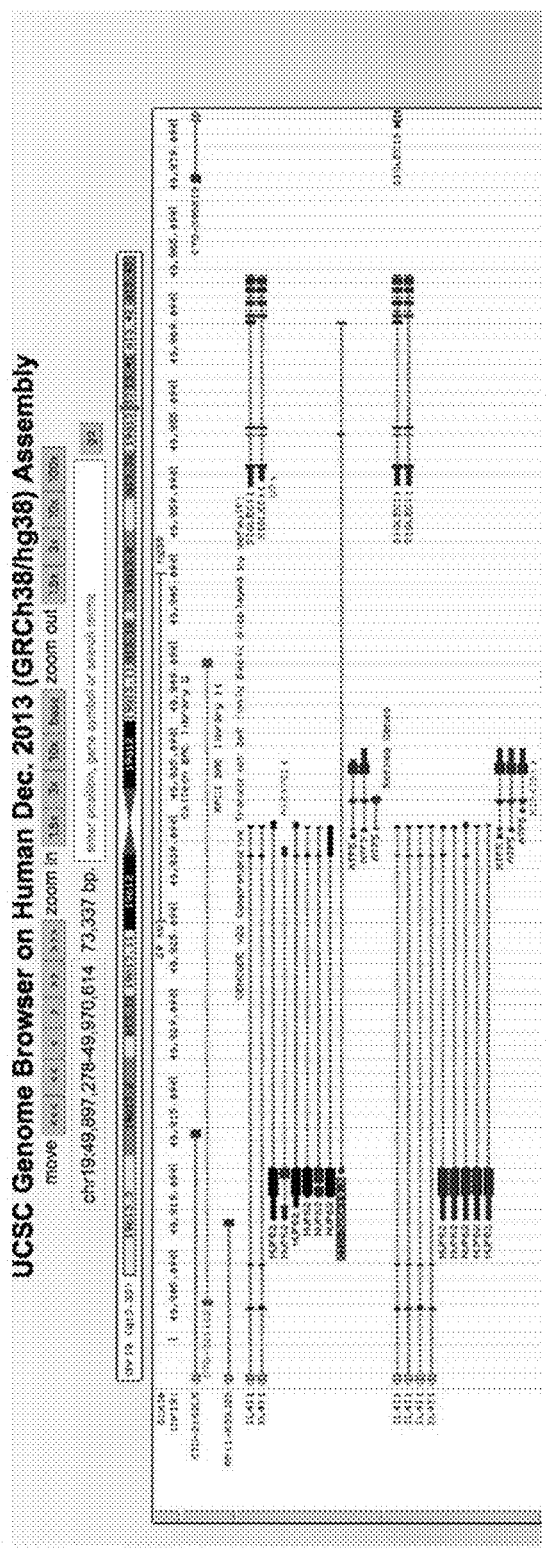
FIG. 36 shows a UCSC genome browser map of the genes, including Siglec-11 and Siglec-16, on a region of human Chromosome 19 containing the bacterial artificial chromosome (BAC) BACCTC-326K19.

To obtain mice coordinately expressing multiple human Siglec genes, Bacterial Artificial Chromosomes (BACs) harboring key human Siglec genes with sufficient flanking sequences were identified using the UCSC genome browser and the CloneDB from NCBI. One BAC clone (BACCTC-326K19) was identified that was predicted to contain the coding sequences for the human genes Siglec-11 and Siglec-16. Maps of the human chromosomal region of interest encompassing BACCTC-326K19 are shown in FIG. 36 (from the UCSC genome browser). The chromosomal DNA within BACCTC-326K19 spanned 118,595 nucleotides of the human genome, covering nucleotide positions 49,893,498-50,039,937 on human chromosome 19, based on the hg38 build of the UCSC genome browser (the human Siglec genes are found within a cluster on chromosome 19). Sequences at the ends of the BAC clone were confirmed, as was the presence of the 5' end of the human Siglec-11 gene sequence.

Transgenic mice harboring BACCTC-326K19 were generated by pronuclear injection of the BAC DNA into C57BL6/j zygotes. The resulting pups were genotyped to identify founder animals harboring the human transgenes. These founder animals were then bred to non-transgenic animals, and progeny animals were then analyzed to monitor expression of human Siglec-11 and Siglec-16.

```
                              SEQUENCES

All polypeptide sequences are presented N-terminal to C-terminal unless otherwise noted.
Human CD33 polypeptide-isoform 1
                                                              (SEQ ID NO: 1)
MPLLLLLPLLWAGALAMDPNFWLQVQESVTVQEGLCVLVPCTFFHPIPYYDKNSPVHGYWFREGAIISRDSPVATNKLDQEVQEETQG
RFRLLGDPSRNNCSLSIVDARRRDNGSYFFRMERGSTKYSYKSPQLSVHVTDLTHRPKILIPGTLEPGHSKNLTCSVSWACEQGTPPI
FSWLSAAPTSLGPRTTHSSVLIITPRPQDHGTNLTCQVKFAGAGVTTERTIQLNVTYVPQNPTTGIFPGDGSGKQETRAGVVHGAIGG
AGVTALLALCLCLIFFIVKTHRRKAARTAVGRNDTHPTTGSASPKHQKKSKLHGPTETSSCSGAAPTVEMDEELHYASLNFHGMNPSK
DTSTEYSEVRTQ Human CD33 polypeptide-isoform 2
                                                              (SEQ ID NO: 2)
MPLLLLLPLLWAGALAMDPNFWLQVQESVTVQEGLCVLVPCTFFHPIPYYDKNSPVHGYWFREGAIISRDSPVATNKLDQEVQEETQG
RFRLLGDPSRNNCSLSIVDARRRDNGSYFFRMERGSTKYSYKSPQLSVHVTDLTHRPKILIPGTLEPGHSKNLTCSVSWACEQGTPPI
FSWLSAAPTSLGPRTTHSSVLIITPRPQDHGTNLTCQVKFAGAGVTTERTIQLNVTYVPQNPTTGIFPGDGSGKQETRAGVVHGAIGG
AGVTALLALCLCLIFFIVKTHRRKAARTAVGRNDTHPTTGSASPVR Human CD33 polypeptide-isoform 3
                                                              (SEQ ID NO: 3)
MPLLLLLPLLWADLTHRPKILIPGTLEPGHSKNLTCSVSWACEQGTPPIFSWLSAAPTSLGPRTTHSSVLIITPRPQDHGTNLTCQVK
FAGAGVTTERTIQLNVTYVPQNPTTGIFPGDGSGKQETRAGVVHGAIGGAGVTALLALCLCLIFFIVKTHRRKAARTAVGRNDTHPTT
GSASPKHQKKSKLHGPTETSSCSGAAPTVEMDEELHYASLNFHGMNPSKDTSTEYSEVRTQ Human Siglec-5 polypeptide
                                                              (SEQ ID NO: 4)
MLPLLLLPLLWGGSLQEKPVYELQVQKSVTVQEGLCVLVPCSFSYPWRSWYSSPPLYVYWFRDGEIPYYAEVVATNNPDRRVKPETQG
RFRLLGDVQKKNCSLSIGDARMEDTGSYFFRVERGRDVKYSYQQNKLNLEVTALIEKPDIHFLEPLESGRPTRLSCSLPGSCEAGPPL
TFSWTGNALSPLDPETTRSSELTLTPRPEDHGTNLTCQMKRQGAQVTTERTVQLNVSYAPQTITIFRNGIALEILQNTSYLPVLEGQA
LRLLCDAPSNPPAHLSWFQGSPALNATPISNTGILELRRVRSAEEGGFTCRAQHPLGFLQIFLNLSVYSLPQLLGPSCSWEAEGLHCR
CSFRARPAPSLCWRLEEKPLEGNSSQGSFKVNSSSAGPWANSSLILHGGLSSDLKVSCKAWNIYGSQSGSVLLLQGRSNLGTGVVPAA
LGGAGVMALLCICLCLIFFLIVKARRKQAAGRPEKMDDEDPIMGTITSGSRKKPWPDSPGDQASPPGDAPPLEEQKELHYASLSFSEM
KSREPKDQEAPSTTEYSEIKTSK Human Siglec-7 polypeptide-isoform 1
                                                              (SEQ ID NO: 5)
MLLLLLLPLLWGRERVEGQKSNRKDYSLTMQSSVTVQEGMCVHVRCSFSYPVDSQTDSDPVHGYWFRAGNDISWKAPVATNNPAWAVQ
EETRDRFHLLGDPQTKNCTLSIRDARMSDAGRYFFRMEKGNIKWNYKYDQLSVNVTALTHRPNILIPGTLESGCFQNLTCSVPWACEQ
GTPPMISWMGTSVSPLHPSTTRSSVLTLIPQPQHHGTSLTCQVTLPGAGVTTNRTIQLNVSYPPQNLTVTVFQGEGTASTALGNSSSL
SVLEGQSLRLVCAVDSNPPARLSWTWRSLTLYPSQPSNPLVLELQVHLGDEGEFTCRAQNSLGSQHVSLNLSLQQEYTGKMRPVSGVL
LGAVGGAGATALVFLSFCVIFIVVRSCRKKSARPAADVGDIGMKDANTIRGSASQGNLTESWADDNPRHHGLAAHSSGEEREIQYAPL
SFHKGEPQDLSGQEATNNEYSEIKIPK Human Siglec-7 polypeptide-isoform 2
                                                              (SEQ ID NO: 6)
MLLLLLLPLLWGRERVEGQKSNRKDYSLTMQSSVTVQEGMCVHVRCSFSYPVDSQTDSDPVHGYWFRAGNDISWKAPVATNNPAWAVQ
EETRDRFHLLGDPQTKNCTLSIRDARMSDAGRYFFRMEKGNIKWNYKYDQLSVNVTDPPQNLTVTVFQGEGTASTALGNSSSLSVLEG
QSLRLVCAVDSNPPARLSWTWRSLTLYPSQPSNPLVLELQVHLGDEGEFTCRAQNSLGSQHVSLNLSLQQEYTGKMRPVSGVLLGAVG
GAGATALVFLSFCVIFIVVRSCRKKSARPAADVGDIGMKDANTIRGSASQGNLTESWADDNPRHHGLAAHSSGEEREIQYAPLSFHKG
EPQDLSGQEATNNEYSEIKIPK Human Siglec-7 polypeptide-isoform 3
                                                              (SEQ ID NO: 7)
MLLLLLLPLLWGRERVEGQKSNRKDYSLTMQSSVTVQEGMCVHVRCSFSYPVDSQTDSDPVHGYWFRAGNDISWKAPVATNNPAWAVQ
EETRDRFHLLGDPQTKNCTLSIRDARMSDAGRYFFRMEKGNIKWNYKYDQLSVNVTE Human Siglec-7 polypeptide-isoform 4
                                                              (SEQ ID NO: 8)
MLLLLLLPLLWGRERVEGQKSNRKDYSLTMQSSVTVQEGMCVHVRCSFSYPVDSQTDSDPVHGYWFRAGNDISWKAPVATNNPAWAVQ
EETRDRFHLLGDPQTKNCTLSIRDARMSDAGRYFFRMEKGNIKWNYKYDQLSVNVTG
```

SEQUENCES

Human Siglec-9 polypeptide-isoform 1

(SEQ ID NO: 9)

```
MLLLLLLPLLWGRERAEGQTSKLLTMQSSVTVQEGLCVHVPCSFSYPSHGWIYPGPVVHGYWFREGANTDQDAPVATNNPARAVWEETR
DRFHLLGDPHTKNCTLSIRDARRSDAGRYFFRMEKGSIKWNYKHHRLSVNVTALTHRPNILIPGTLESGCPQNLTCSVPWACEQGTPP
MISWIGTSVSPLDPSTTRSSVLTLIPQPQDHGTSLTCQVTFPGASVTTNKTVHLNVSYPPQNLTMTVFQGDGTVSTVLGNGSSLSLPE
GQSLRLVCAVDAVDSNPPARLSLSWRGLTLCPSQPSNPGVLELPWVHLRDAAEFTCRAQNPLGSQQVYLNVSLQSKATSGVTQGVVGG
AGATALVFLSFCVIFVVVRSCRKKSARPAAGVGDTGIEDANAVRGSASQGPLTEPWAEDSPPDQPPPASARSSVGEGELQYASLSFQM
VKPWDSRGQEATDTEYSEIKIHR
```

Human Siglec-9 polypeptide-isoform 2

(SEQ ID NO: 10)

```
MLLLLLLPLLWGRERAEGQTSKLLTMQSSVTVQEGLCVHVPCSFSYPSHGWIYPGPVVHGYWFREGANTDQDAPVATNNPARAVWEETR
DRFHLLGDPHTKNCTLSIRDARRSDAGRYFFRMEKGSIKWNYKHHRLSVNVTALTHRPNILIPGTLESGCPQNLTCSVPWACEQGTPP
MISWIGTSVSPLDPSTTRSSVLTLIPQPQDHGTSLTCQVTFPGASVTTNKTVHLNVSYPPQNLTMTVFQGDGTVSTVLGNGSSLSLPE
GQSLRLVCAVDAVDSNPPARLSLSWRGLTLCPSQPSNPGVLELPWVHLRDAAEFTCRAQNPLGSQQVYLNVSLQSKATSGVTQGVVGG
AGATALVFLSFCVIFVVVRSCRKKSARPAAGVGDTGIEDANAVRGSASQILNHFIGFPTFLGLGFEFLLNLRDLCCHPDSEFYVYHFS
HFRLIKNIAGEIVWSLEGKILWLLDVSDFFHWFFLICVG
```

Human Siglec-11 polypeptide-isoform 1

(SEQ ID NO: 11)

```
MVPGQAQPQSPEMLLLPLLLPVLGAGSLNKDPSYSLQVQRQVPVPEGLCVIVSCNLSYPRDGWDESTAAYGYWFKGRTSPKTGAPVAT
NNQSREVEMSTRDRFQLTGDPGKGSCSLVIRDAQREDEAWYFFRVERGSRVRHSFLSNAFFLKVTALTKKPDVYIPETLEPGQPVTVI
CVFNWAFKKCPAPSFSWTGAALSPRRTRPSTSHFSVLSFTPSPQDHDTDLTCHVDFSRKGVSAQRTVRLRVAYAPKDLIISISHDNTS
ALELQGNVIYLEVQKGQFLRLLCAADSQPPATLSWVLQDRVLSSSHPWGPRTLGLELRGVRAGDSGRYTCRAENRLGSQQQALDLSVQ
YPPENLRVMVSQANRTVLENLGNGTSLPVLEGQSLRLVCVTHSSPPARLSWTRWGQTVGPSQPSDPGVLELPPIQMEHEGEFTCHAQH
PLGSQHVSLSLSVHYPPQLLGPSCSWEAEGLHCSCSSQASPAPSLRWWLGEELLEGNSSQGSFEVTPSSAGPWANSSLSLHGGLSSGL
RLRCKAWNVHGAQSGSVFQLLPGKLEHGGGLGLGAALGAGVAALLAFCSCLVVFRVKICRKEARKRAAAEQDVPSTLGPISQGHQHEC
SAGSSQDHPPPGAATYTPGKGEEQELHYASLSFQGLRLWEPADQEAPSTTEYSEIKIHTGQPLRGPGFGLQLEREMSGMVPK
```

Human Siglec-11 polypeptide-isoform 2

(SEQ ID NO: 12)

```
MVPGQAQPQSPEMLLLPLLLPVLGAGSLNKDPSYSLQVQRQVPVPEGLCVIVSCNLSYPRDGWDESTAAYGYWFKGRTSPKTGAPVAT
NNQSREVEMSTRDRFQLTGDPGKGSCSLVIRDAQREDEAWYFFRVERGSRVRHSFLSNAFFLKVTALTKKPDVYIPETLEPGQPVTVI
CVFNWAFKKCPAPSFSWTGAALSPRRTRPSTSHFSVLSFTPSPQDHDTDLTCHVDFSRKGVSAQRTVRLRVAYAPKDLIISISHDNTS
ALELQGNVIYLEVQKGQFLRLLCAADSQPPATLSWVLQDRVLSSSHPWGPRTLGLELRGVRAGDSGRYTCRAENRLGSQQQALDLSVQ
YPPENLRVMVSQANRTVLENLGNGTSLPVLEGQSLRLVCVTHSSPPARLSWTRWGQTVGPSQPSDPGVLELPPIQMEHEGEFTCHAQH
PLGSQHVSLSLSVHWKLEHGGGLGLGAALGAGVAALLAFCSCLVVFRVKICRKEARKRAAAEQDVPSTLGPISQGHQHECSAGSSQDH
PPPGAATYTPGKGEEQELHYASLSFQGLRLWEPADQEAPSTTEYSEIKIHTGQPLRGPGFGLQLEREMSGMVPK
```

Human Siglec-14 polypeptide (SEQ ID NO: 13)

```
MLPLLLLLPLLWGGSLQEKPVYELQVQKSVTVQEGLCVLVPCSFSYPWRSWYSSPPLYVYWFRDGEIPYYAEVVATNNPDRRVKPETQG
RFRLLGDVQKKNCSLSIGDARMEDTGSYFFRVERGRDVKYSYQQNKLNLEVTALIEKPDIHFLEPLESGRPTRLSCSLPGSCEAGPPL
TFSWTGNALSPLDPETTRSSELTLTPRPEDHGTNLTCQVKRQGAQVTTERTVQLNVSYAPQNLAISIFFRNGTGTALRILSNGMSVPI
QEGQSLFLACTVDSNPPASLSWFREGKALNPSQTSMSGTLELPNIGAREGGEFTCRVQHPLGSQHLSFILSVQRSSSSCICVTEKQQG
SWPLVLTLIRGALMGAGFLLTYGLTWIYYTRCGGPQQSRAERPG
```

Human Siglec-16 polypeptide (SEQ ID NO: 14)

```
MLLLPLLLPVLGAGSLNKDPSYSLQVQRQVPVPEGLCVIVSCNLSYPRDGWDESTAAYGYWFKGRTSPKTGAPVATNNQSREVAMSTR
DRFQLTGDPGKGSCSLVIRDAQREDEAWYFFRVERGSRVRHSFLSNAFFLKVTALTQKPDVYIPETLEPGQPVTVICVFNWAFKKCPA
PSFSWTGAALSPRRTRPSTSHFSVLSFTPSPQDHDTDLTCHVDFSRKGVSAQRTVRLRVASLELQGNVIYLEVQKGQFLRLLCAADSQ
PPATLSWVLQDRVLSSSHPWGPRTLGLELPGVKAGDSGRYTCRAENRLGSQQRALDLSVQYPPENLRVMVSQANRTVLENLRNGTSLR
VLEGQSLRLVCVTHSSPPARLSWTWGEQTVGPSQPSDPGVLQLPRVQMEHEGEFTCHARHPLGSQRVSLSFSVHCKSGPMTGVVLVAV
GEVAMKILLLCLCLILLRVRSCRRKAARAALGMEAADAVTD
```

Human CD33 genomic sequence (SEQ ID NO: 15)

```
tctgctcacacaggaagccctggaagctgcttcctcagacatgccgctgctgctactgctgcccctgctgtgggcaggtgagtggctg
tggggagaggggttgtcgggctgggccgagctgaccctcgtttcccacaggggccctggctatggatccaaatttctggctgcaagt
gcaggagtcagtgacggtacagagggtttgtgcgtcctcgtgcctgccctgcacttcttccatacctccatacgacgaagaactcc
ccagttcatggttactggttccgggaaggagccattatatccaggactctccagttggccacaaacaagctagatcaagaagtacagg
aggagactcagggcagattccgcctccttggggatcccagtaggaacaactgctccctgagcatcgtagacgccaggaggagggataa
tggttcatacttctttcggatggagagaggaagtaccaaatacagttacaaatctccccagctctctgtgcatgtgacaggtgaggca
caggcttcagaagtggccgcaaggggaagttcatgggtactgcagggcagggctgggatgggaccctggtactgggaggggtttaggg
taaagcctgtcgtgcttagcgggggaggcttgaccagaggttgatcttctctcaggccctcacctggaccctcctcctgattctgcat
ccctctttctcctcactagacttgacccacaggcccaaaatcctcatccctggcactctagaacccggccactccaaaaacctgacc
tgctctgtgtcctgggcctgtgagcagggaacaccccgatcttctcctggttgtcagctgcccccacctccctgggcccaggacta
ctcactcctcggtgctcataatcaccccacggccccaggaccacggcaccaacctgacctgtcaggtgaagttcgctggagctggtgt
gactacggagagaaccatccagctcaacgtcacctgtaagtgctgggccaggatgctgggtccctgagggtgtaggggagacaggat
gggctggtgctggggacattagtgtcctggaggcctggctgagttcgggagccagaaggacatgagccctgtccctctgcatttct
gtggtttctggcaggagtaaggggaaatgcctacccctatctcatctctaccccaactgaaggaaatcctctcttcctctcctagat
gttccacagaacccaacaactggtatctttccaggagatggctcaggtaggaaggagcctcccgcctgggctgttactgacattga
gtctgtgtcaggtttggtcagatctggactttcagagtcaaatgttcagaggcaaggcctgcagttagacacgggtagacatcaggca
ccttggaaaaggatatttggggatgactagcaacttcccccttgccatccaaataatgctctttgtctccctcctgtctctgaatgt
cttggggtattttatttttaattgatatgtaataatagtacatatttatggatggcatagtgatgtttccatactaataatgtatagt
```

| SEQUENCES |
|---|
| aatcagatcagggtaatagcatatccatcatcttgaacatttattatttcattgttgttgggaacattcaatatcccctttctagcta |
| tttgaagctatctattattgttaagcatagtcatcctacagtggtatagaacaccagaacttattcttcctttccaggtgtaatctag |
| tatccttaacaaatctctctccttatcattgttcccctaaccttcccagcccttattattctctgttctacttttttacttctatgaa |
| atcaacttcttgtagcttccacttatgagtgagaacatgtggtattcaacttctgttcctagcttatttcatttaacataatgtcct |
| ctagttcaatctatgttatagtgaataacaagatttcattatttttatggctgaatgataatccattgtgtatatacgccacatttc |
| ctttatttattcatctgttgttggacacttaggtttatttcatatcttcctattgtggataatgctgcaataaacattgaggtgcaga |
| cgtttcttcaatatactgatttcctttcctttctataaatgcccagtagtggggttgctggatcatatggtagttctatttgtagttt |
| tttgagaaacttccatactcttctccatagtggttatactagtttacattctggtcaaaagtatataagagttccctcttctctacat |
| cctcaccatcatttgttaattttcatctttttttatcatagtcctcccaactggggtgatgttacctcattgtggttttgatttgca |
| tttccctggtgattggtgacgttgagcattttcatatacacttgttggccatctgtatatcttttcttgagaaatgtctactcagat |
| aatttgcccattttttaaatgagattgggtttcttttgccattgagatgtatgagttcctcgtatgttctggatatgaatcacttgtcag |
| atgaatagctgacaaatattttctccctattctgtaggttgccttttcactctgttggttgtttccttctgcatagaagcttttttagc |
| ttgatatcatctcatttatttacttttgcttttgttgcttgtgctagtgaggtcttactcataaaatatttttccagaccaatgtcct |
| aaagcatttcccctatgttttttttctagtattttttaaattttgtgtcttatattcaggtctttgatccattttgaattgattttttgt |
| ataggacgagaggtgtgagtctaatgtcattcttctgcatatggcaccagttttcccagcatcatttattaaagaaactgctcttcc |
| tcaatgagtgttcttcatgcatttgtcaaaattcagttggctgtagatcgtggattaatttcggtgttctctattatgtattattggt |
| gtatgtatctgcttttatgccaatatcatgctgttttggttactacagctttgtagttttgaaatctttaaattttttgaaattttgaa |
| attttctagttttgaaattttgaaatcttgtagtgttgatacctccagctttgttctttttgcttgggattgctttgaccattcaggc |
| tattttttagttccatatgaattttaagattgtttcctctaattctgtgaagaattacattgatattttgatagagccaggtttgaatc |
| tgtagattcttttgggtagtataatcattttagcaatattaatctgatggtaaggaagtgtctttccatttgtttgtatcctct |
| tcagtttatttcctcagtgtttttgtagtttttcttattaaggcttgtcacctccttggttaaattttattcctaggtatacttcattct |
| cttatagctattgtaaatgtgattgccttcctgatttattttcagctaattcattgtgtgtagaaatgctactgattttttgtatattg |
| attttgcatcctgcaaatttactaaattcatttatccagttctgagagttttattgttagagtctttaggtttttgttttgttttgttt |
| tgttttgttttgtttttgagatggaatttcaccatgttgcaagctggtcttgatctcctggcctcaagcaatctgcccactttggc |
| ctcctaaagtgctggaattacaggcatgagccaccacgcctggccaagtcttttaggtttttgtatgttatttgcagagacaatttgac |
| ttccgcctttccagttttggatggttttttatttctttctcttgcctaattgctctggctaggactttcagtactatgtaaaataagagt |
| cataacagtggacatccagttcctagaggaaaagatttcagcttttctccattcagtatgatgttagccatgggtttgtcatatatgg |
| ccttttttgtgttgaggtacttttccttctataccctaatttattgagagtttctatcatgaaacaatattgaattttaacacatgctttt |
| ttattctgcaactatttaggtgatcatacggtttatgtccttcattctgttgacatatgtataacatttattgatttgcatatgttga |
| atcattcttgccttctgggattaatccccactttatcatggtatgttatcttttgatgtattgttggatttgatttgctactattt |
| gttgaatattttgcatctatgttcatcagggatattggcctctagttttcttttttttattgtctccttctgattttggtgtcatgg |
| ttatgctggccttgtagaatgagttaggaagagttgcctccacttcaattttttgaagtagtttgagaagagttggcataatttttt |
| ttctttaaaggttcagtaaagttcagcactgaagccatccagccctggaatttcttttgttgggggggctttttattattcattcaatc |
| tcattacttgttgtttgtctgctgaagttttctatacctcttgattcaatctcggtagattatatgtgccaggaacttatccattt |
| cttctagactttcaaatttgttggcatattgttcatagtagtgtctaagatcctgtgtatttctgtggtaaccattgtgacatcttct |
| tttttatttatgattttattaattttttatgtcttctgtctctttcttagtttagctaatgattgtcaattttatttattttttccaaaa |
| agcgaacttgttcattgattttttttaattcatttatttctgctctgatcttttatgattttctttccattgtgctgattttggatttg |
| gtttgttcttgcttttctagtttcttgaaatgcacagttaaatggtttacttgaaatttgtctaattgtttgatgtaggcatttatttc |
| tctcaagttgtctcttaaaactgttttttgctgtgtcccataggttttggtatattttatttctattttatttattttgagaaatttt |
| taaatatcattcttaatttcttccttcactattggtcatttagaatcattttgtttcatttctgtgtatttgtatagtttgcatgttt |
| ccttggtattgattttttagttttattcaattgtagtcaaataagatactttgatacatttttgttttaaaaattttttggcacttgtt |
| ttgtgttctaacatatggtcgatccttgggaatgttgcacatgctgatgaaacatgtgtattctgcagctgtcggttgaaatgttct |
| gtaaatatcttaggttcatttggtatatggtgcagtttaaatccaacgtttatttgttaatcttgtctagatgatttgttcaatgctg |
| agagtggggcgttgaagtcctcaactattattgtattggagtctatctctccctttatatctaataatatttgctttacatatctggg |
| tgctctggtgttgtgtgcatatgtatttacagttgttatattatagtgctgaactgacccccttataataataataatgtccttctttg |
| tctcttttacagctttgacttgtagtccgttttgtctgagataagtatagctattcctgcttccttttcatttccacttgggtagaata |
| tcttttttccatctcttcctttcagtctatgtgtgtcttctaggtgagataagttcttgtaagcagtatatagctgtgttggtagaa |
| gggctgaggcagggcttgcttgtctgacataatgtaaaagagtcttggaacatgtcctgggtccagggtctcaaacccctcgtggcct |
| atggaacaccaagctctgtgcctaagggtggaaggctgccctgccacactgcaatctaagcccagggcataaaaccctcgtggcttg |
| gaaagaatccagggctctgggcataaaacccctcatagcctctggaatgtgtccagacttgctggcccctctgctcctctctcccag |
| gatcataaattgattgtatcttgagtgaaaagaacttgttctcccattatttcaagtagcagagcatatgctaaaccgtcacagctatg |
| cttgatgcaccgctacctttctacccaaagtcctcacgttctcacttgtctatccccacttctgcacgtcctcaccacctgcttctt |
| tgtttgattaccaataaatagtgtgggctcccagagctcggggcctttcacagcctccatactagcgtcggcccccctggactcacttta |
| tgtactattaacttgtcttgtctcattcctttgactccgctggacttcgtggccccacggcctagtgttggatctgatcaccccaac |
| aagctgagtctagattttcttttcattcattcaggcagtccatatatttaaatgggacaatttaatccatttacatacacattatta |
| ttaataggttattttcatttcattgattgttttctgattgttttatatattcctggttccttacttccctctttattgtttcttttg |
| tggttggctgatgttttttttttttttgtagtgataagattttgattccttttctcttttcttctttgtgtatgggctgtcagtgagtttt |
| aagttcacgtgtttttgccttttcacttccagatgtaagactccctttgagcatttcttttctttttctctcttattttttatta |
| ttttttttttgagaaagtgtctcactctgtcgcccaggcaggagtgcagtggcatgatcacgctcactagtctcgacctcctggg |
| cttaagcaatcttcctgccttaacctcccaagtagctgggactacaggcatgtgccaccacgcccagctaattttttgtgtttcttgta |
| gaggtagggtgttgccatttgcctaagctggtctcaaattaaagagctcaagtggtccacctgcctgccttcacctcccaatgtgctg |
| ggattataggcatgagccacactgtgcctggccccttgagcatttcttgtaaggcagtctaagagttgataagaattcccttagtttt |
| tgcttatctatgaaatattttatttctccttcttttctgaaagatagcttttctgggtatagtattttttgactgttaagttttttatc |
| tttcagtactttgagtatgtcatcccattctatcctggcctatataatgttactgctgagaaactcactgttagtctaataaggataa |
| tcctatatgtgactagatacttttaccttgctgtttttacaattcttttacttgacttttgacaatttggcataatgagctttggagag |
| gacttgcttgggttgaatattttgagagtactttgagcttcctggacctggatgtccttctagttcccaaggcttgggaagttttcac |
| ctattactggattaaatatgttttctacacctttccattctctttcctcctccggaaataccataatgtgaatatttgcttgattgtg |
| tcccatgagtcctgtaggtttccttcgttctatttattctctatttttaccctgcctgtctatttcagaagatctgtctcaagtt |
| cagaaattattttttcttcttgacctagcctgttgttgaagctctcgattgcggttttttatttcatttattgagttctcagctgtag |
| gagttctgctttgttcttttatataatatctatctctctgttaaatttctctttcaagtcatgaattaaaacaatgggacacaggtgc |
| ccaactacttggctgacctgggggcatatctgctggaggtgccaacatggctgttttgcagggctgagatgaagctgaatgactcttg |
| gctggcctaggtgtgttttgccaggagtagcactcagagcttttatctaggtttgggatgtgagtgtaagactgctcagctggccta |
| gggggtgtaccagccagtggtagcccatgggcgtgtttctcaggcctggaatgcaagcacattctgcctgggtcatgtctaaaaggg |
| ttggctcacaaggctgtttctcaggccctaattgtgggagagtggcctttgggcaggccagagtcatgtccacgaaggcgtctgggc |
| accgtaaggctgtttctcagagcctgtgtgtgagcacataaccactaccccagcctggggatgtatcaactctttgttggctcagagg |
| tctctcccattcaggtgagcatgcacagtagtttggccaactcaattgtgtgttcgccctgagtgggactataagacctttcctccag |
| ctggaagtacgggcagcagggggttggtttctctgctgttcagggcagagtcccagccaatcctgggcccaggctccatgcagctcta |

| SEQUENCES |
|---|
| attgtggtattcagccactactgcaggtttagtggaatgaagatgcacaatgataaagaggtgcatgccactggcccccagaggaggg |
| tgcactccagagatggctgtggtctcaagatggttctgtgttgtagcagcttgcccgcaggggctggttagggagttgggagtgcaca |
| ccaaatgctccatgcagctgtgtgaattcctggcagctcttccaactgtgctgaggacttgtgaggactgtaagattaacctgtagta |
| aggaatgtaggtatctgcagtggcactggaggttggttggattcctctgcttatcatttccctacaaggggaaatccttcctgtctct |
| gggacaaaccaatctgggctgggagatggagctgcaaagcccgggtgcctccatgctgccctcctgggtttccaattaccacaggta |
| actctccactcccttgctgcactacactactctcccttcgacactccactcaaatctttgctgtggtttattcattgccttggtcctt |
| tcttgtctggtgacacggggggaggatgagctccaggcacctccggtgagccattttgctccaatggggggcatttttttttaataggtt |
| ttattttttcagagtagtttttgtttcacagcaaaattgagtggaatcttctagtcgctgatcatcttgggagcatttataaatgaacc |
| ttatttttcatgaagaaattgagcagaagatactaagacttcccgtatgccctctacccttacacatagtttccccggccatcagcat |
| cccccatcagagtggtacatttgttacagtcaataaaactacattgacatatcattgtcacctgaagcccatagtttacattaaagtt |
| cactcttggtgttgtacattttacaggcttttttaaaaatgtataatgacatgaatccaccatgagagtatcatatagaatagtcacac |
| ttccctaaaaatctctttagggcattttttttctactgtccataccctcaaccctctagccctggcctctgtccaaagaccagtgctctct |
| ccactgccctattccaattaataatggcatctggcacctcagtggacagtgagcccagtgagagcaggaacagttccctcagtagtgg |
| ttatcaaactgttaacaatgatgctcagagacacgcccctgactctgagtgttgggacctagaaggcacagccaggcaggtccaggag |
| aactgtctgggtctaagaaggtctgagaaccacctccctgcccaccctgcttccaggccctttttaaggccaaaaggaccacctttg |
| accctaagtgatggggccagtgggaagaaagaagagacaaggcctatcagcattccagtgctttctctctctctcatccaagaggctc |
| agagcttcacagtccttcaggggctatgtctgaggttcatttcagaaagacccagggtggagaggaacctgagtcctaggagagatga |
| tgtttgtgcaccagagagagggtgggacaagaggtgtcaggtgcactgtgtacttcatctcatggtcgtggtcaatattgatgtc |
| tatgatgggtgggaagatctaggagctaaacccatttggaggtgaagtcaccctctctacatgctggagaggaggatacacatac |
| ctgtttatctagattagaattcaccccaaatcttttttgtcgcagggaaacaagagaccagacaggagtggttcatggggccattg |
| gaggagctggtgttacagccctgctcgctctttgtctctgcctcatcttcttcatgtgagcattttctctgggtcaggcatgggccag |
| aggtgaagaggatggacctggtgtagaagggtcctgagggggctgtgagggctggagaaagggcaggggtgtgatgatgtacagaat |
| ccagcctgtggccactgggataggcgtgggtctattccagggccctgatctcagatgtccaaggagtgggaggtagagggagaccttg |
| tgactaagtcttgtttgagggctcctggattaatcccaccctttacctgccaaagtccctcattccaggctcataacaatggccccac |
| agcctgagaaaaccaggctcaaagaccctggtgtctcccatcagagtgaagacccacaggaggaaagcagccaggacagcagtgggca |
| ggaatgacacccacccttaccacagggtcagcctccccggtgagtgatggggcatcctggcatccagtctgtcctgcagacacctcctc |
| ccaatgtggcccaccgtcatgccccattcagcatttccagaactgagcttattgtctttcctcctgtttaacagtgtaggttttaata |
| tttttcaggtacgttgaggccaacagatcaggagatgatggccattgaaaagatagtttcttggccgggcacagtgtttcacacctgc |
| aatcccagcaccttggaggccaaggcgggcggatcacgaggtcaggagattgagactaccctggctaacatggtgaaacccccgtctc |
| tactaaaaatacaaaaaattagccagatgtggtggctggcgcctgtagtcccagctacttgggaggctgaggcaggagaatggtatga |
| acccgggaggcagagcttgtagtgagccgacatagcaccactgcactccagcctgggtgacagagagagactctgtcccaaaagaaa |
| aaaaaaatagtttcttattcaccgttcccgagagggcacaccacaccatgcaaggccatatggagaagcaccagggtcagtcaggaag |
| cagagggagcaaggagaaaaatgggacaaggccttcactgtgcttttcatggaaaagaatggccaagacagggtaagcaagctaggca |
| ggtttaggattggctacttagaacaatttcagcagactctggggtataggagttgtctctagttgtctggtacatggccctgggttta |
| ttaaggaggattgtggtctggagtgtaagagctcaataaaggatccagctggtagtgtgggctttagattgactggtttgcacatgaa |
| aggtgcacttgtatgcaagtcctttattagctctagaaatctactatccttgggaaaggcagtctctcaagggtcagtaatgccccag |
| atgtcaaaacatcagaaacacttggttgacacaccccaaacatacttctcctgatgggtctccatctcgctgatggcactcttgtc |
| cccattacccaaccagagacatggcccctcctgtcccagtcctccatctcttcctgtgccagtatgctacgatgcatgtctgagctt |
| cctctgaacacggcttaacacaaccactcctgagccgagagccccctcttactccttattctgctgcagcctcacctcccatttctcct |
| ctccagaacattagcatcacctcccttaaaaggtcattgtcccatcattcccaagtttgaaatgcactgcttctctacactcctgaaag |
| attggcattccaacaacttggtctggcatttggagcaggaaaaccagagtcccctttcagtgctatgctcccccaacattagccactca |
| atcacctcaagcagggcaagctttctcatctcagaatcattgctgggctgtccctcctcctcatatgcctaatagctacctgcccaa |
| ctccagtgcatccttcaagctctgattttttttttaatttatttaactctgactaaagtgaacaccacagtaaagttttttgaacacag |
| ggtcaaccagcacccattcattctgaaatatctatataatcccatttgccaattgctctaggtccttgtgccattctgtatttttata |
| aacacacagtttacaaatataaaatattcctcctatcgggggcttaacatttattgggaaagggatgaaaataatgaacaaataagc |
| agtgcaaatatacatgaaataggcatgaaataagtgctatggcaggaaatgaaatgggagaacggattggacagtcctggggggccaaa |
| gaatggcctttgggcaaacacctgcagaaagaaagtgagtacagtatgagcagtagagaatcatcaaggaagcagcaagtaccatggc |
| tctgaggccggaacacatctgatgttttagagaaacaaagtaggacagtgtggataaggcagagttacgtgttggggggtggagtgtgg |
| actgaacaatggtaggtaggaaatgaggttgaagagacatattgcaaatattgcaggatcctaagtccatcatagtttattgatg |
| cgtttagagcagaagagtgacatgaactgacactcattttagtgggagtcactctggctgctctgtgagaaactctagtatgtagtat |
| agaagagaagataccagaatagaagatacacagataatcaagccaagagatgactgactcagacttagtcccaagtaagaataatgaa |
| tctgatgtggagaaatttgggttccggatacatcttgaaggtggagtcaacagtatttgcaagtggagtgatggagtgcatgcaaggca |
| tgagcaaagatagctcacgggctctgctcgataagtgtctcagatgtcataggtgggccacagatatcatgatgtcatggatgtcc |
| aagaagacccccatagatgtcatagatgtctatagatgccaatgatgatgttcatgtgtcaaactcagaattcaaacttaaaaaatcaa |
| attgccaatgattaaaattgccatccttgaaggagaagtctattttcaagtgtatatcaaacattatttttggttaccgtaagtttgag |
| gtgcctctgagacatccatgtggagatgacaagtagcaggcaagtgtctggagctcagaagagggctccacgtgggagacacagaggt |
| tgggagcttccctatcaacatccaataatcgatgaatctacaaagaagagaagggtccacagacacagccctggaaccctccagcat |
| ttaatgttagggagatgaggtgtaaatggtgagaaagctgagaatgaataggagccaatgaccaggaaattgcaggctgtagtgttgg |
| tggccaagggaagatggggcttcatggaggagaggttggtcatttgtttcaaatgctggtaagtctggtaagatggaatctgaagaaat |
| ggctatttgaatgtagctaagtggtatgacagcaaagcagatctgattttttctgctggaggaagatctcttgactagagagagttcaa |
| gagagaatgggaggagaagaggcagaaactgtgagttgaaggactcttttgagaaacactgccccaaatctagaaccaagaaatgggc |
| ctgcaccagcaaatggttgtaccctgtagacttgccatttctccagcatctgctcctgtgtctcttatgataccatgttccctgtttg |
| tgtagggctttgcaccacttgaactaactgcattcccatagcttcccctaccacaccatgagctccacaaggaaaagcctggttttta |
| ttagacctccatcattctactctctcctgttcatctgcacactgtcacaatttgcaattaccagtctgttttctgtcttcatccctgc |
| agtactggaaatcacagggccctgctctgctctgtccctcctgaggatccagtgccagcacataggaggtcccagagacctggga |
| ccgagttcagggtcaacagatgctgtgactttggaaatttacctaagctctctgagacctagtttcctggtctgtaaaatggattaaaat |
| aatagatgccaaagatgatgtcagtgtagctgcccagaatttttccacattagtctctgtgagtattcaagagaattgcgaatcaatc |
| aatacgtgctacatgtgttagataatgaataagtagagccttaattaattaacatttgatgaaagaatgaaagagtgaataaatgttc |
| tgtcagagtcaaatttacttcattgaccctctttgccttctcctggtcccctcctcactgccctgctctaaccccttctttcctct |
| ccataagaaacaccagaagagtccaagttacatggcccactcaagcctcaagctgttcaggtgcgccctactgtgggatggat |
| gaggagctgcattatgcttccctcaactttcatgggatgaatcctccaaggacacctccaccgaatactcagagtcaggacccagt |
| gaggaacccacaagagcatcaggctcagctagaagatccacatcctctacaggtcggggaccaaaggctgattcttggagatttaaca |
| ccccacaggcaatgggtttatagacattatgtgagtttcctgctatattaacatcatcttagactttgcaagcagagagtcgtgaat |
| caaatctgtgctctttcatttgctaagtgtatgatgtcacacaagctccttaaccttccatgtctccatttttcttctctgtgaagtag |
| gtataagaagtcctatctcatagggatgctgtgagcattaaataaaggtacacatggaaaacaccagtc |

-continued

SEQUENCES

Human Siglec-5 genomic sequence (SEQ ID NO: 16)
```
gtgcgcgtccacagctctcactcaccctccggcttcctgtcggggctttctcagccccaccccacgtttggacatttggagcatttcc
ttccctgacagccggacctgggactgggctggggccctggcggatggagacatgctgcccctgctgctgctgcccctgctgtgggggg
gtgagtgagctgagggaggagggacaggcacaggggtgagaaggggggctggagctgcagctgagcttctgtgtcccccagggtccc
tgcaggagaagccagtgtacgagctgcaagtgcagaagtcggtgacggtgcaggagggcctgtgcgtccttgtgccctgctccttctc
ttaccccctggagatcctggtattcctctcccccactctacgtctactggttccgggacggggagatcccatactacgctgaggttgtg
gccacaaacaacccagacagaagagtgaagccagagacccagggccgattccgcctccttggggatgtccagaagaagaactgctccc
tgagcatcggagatgccagaatggaggacacgggaagctatttcttccgcgtggagagaggaagggatgtaaaatatagctaccaaca
gaataagctgaacttggaggtgacaggtatggcagggaccccaggagaggaccctgggacgtggagaccccgtatgagaacagggac
aggagttgggcaggggcggctggaggaggtgtaggacttggggcaggtcggggcctggccactctcggggtcacaccttac
gtcctcaagccctggggcccaggtatctccctgtctcctcctcagccctgatagagaaacccgacatccactttctggagcctctgg
agtccggccgcccacaaggctgagctgcagcctccaggatcctgtgaagcgggaccacctctcacattctcctggacggggaatgc
cctcagcccctggaccccgagaccacccgctcctcggagctcaccctcaccccaggcccgaggaccatggcaccaacctcacctgt
cagatgaaacgccaaggagctcaggtgaccacggagagaactgtccagctcaatgtctcctgtgagtggtgctggggacacagctgag
tcctcaagggcagtgggagtgaggggtgtgtgtgtgtgtgtgtgtgtgtgtgtgtaaggaagacagagagaaacaaaacaataa
cttgagaaacctgtgtgtggatctaagccttgggatctgcggggagtgagacaggacagccttccccgcttggtgggtttctgtggc
tcctcttgggtacctcctgggcccatgcccatctcactcctcactgctgaagcaagtttatatctttttatcccagatgctccaca
gaccatcaccatcttcaggaacggcataggtaggaaagacctcctctctgaagctgggacctgcctctgggtctgtctctgagcagag
gtagagaatcagagcttgaatgcaatcagatttgggaagagcaagaatgagaattactgcctctggcttccaccttctgtgagcccc
atgtgcaggcacatatgcacacacgcacatacacacgcacacatgcacacacgcacacacacacgcacacacacacatgcatatacac
cacacacatacacatgcaatacaccacacacacacgcacatacacacacatgcacacaggcacacatgcacacacaccacacacat
atgcacacacacacacaggcacatacacacgcacatgcacacacacgcacacatgcacatacacacacacacatatgcagatacaccc
acacacgcacacatgtacgtacacccgcacacgcacacacacacgcacacaggtgcacactcatgcactctgctcaaagcagtgaaca
gactttagaccccacccatctcccatccctcctgtggtctggttctttccacagtcactaaggaccactccatgcccctctcatctca
gtcagcccagctctgtggttcttctctcacccttccactcctgcatcctcagtcttatttcctgtcacattagcggactgtatttccc
aacgccaccgggggctctctgtcctctctccaccacagtccaggcatgtaccagtgagatattgagcctcctctggagacatgagact
cagacactttttggtcagttcctgagtgtgcaaaggcccagcctttgaaccaggatgcaatcaagccagcataggccaggggaggaga
gggagatgtcatctggatcctgggaaggagggaaggatagggactgtcagcctccctggccccatctctctttccccacccttctctc
cccaaagccctagagatcctgcaaaacacctcatacctttccggtcctggagggccaggctctgcggctgctctgtgatgctcccagca
accccctgcacacctgagctggttccagggctccccctgccctgaacgccaccccatctccaataccgggatcttggagcttcgtcg
agtaaggtctgcagaagaaggaggcttcacctgccgcgctcagcaccgctgggcttcctgcaaattttctgaatctctcagtttac
tgtgagtgtgggggcagctggagcaggaactgcatggtattaaagaaggaagaggcccctgctgagttctgtcctcctccccacag
ccctcccacagttgctgggccctcctgctcctgggaggctgagggtctgcactgcagatgctccttcgagcccggccggcccctc
cctgtgctggcggcttgaggagaagccgctggaggggaacagcagccagggctcattcaaggtcaactccagctcagctgggccctgg
gccaacagctccctgatcctccacgggggggctcagctccgacctcaaagtcagctgcaaggcctggaacatctatgggtcccagagcg
gctctgtcctgctgctgcaaggtcaggggggcgtattgcagagggcagggcctgaggggagggcatggatcccagagtgatggatgg
tgggagagaggctggactggtggtgggagacaggggttcttcatctcctgtctgagcagggccctggagcaagttgcccagcaggt
gggaggacaagagtctgagtcctgggagtgagttattgcacgcccctcttttctgcagggagatcgaacctcgggacaggagtggttc
ctgcagcccttggtggtgctggtgtcatggccctgctctgtatctgtctgtgcctcatcttcttttaatgtaagtcttggtcccagg
gaaggtacagggtggtgtttgtagggagtaggagagactgaatctcagaaacacagagctaaggccagaggtggtgatgtgtcttgt
ggttccagatgctcaggagtctgaggcaggaggatcacttgatcatggaggttgaggctgcagtgagccaggattgtgccaatgcact
ccatcctgggcctcagagtgagagaccctgtcttaaaagaaaaacaaaacaaaacaaaaagcagaactgagtagatccgagaggtct
tctttctttttttctttctaatagctttattgagatacatgtttttgtacaattcatccactgaaagtgtacgagtcaatggctttaa
gtatattgacagagttatgcatctgtcaccaaaatcaattttagaacattttcatcagcctaaagtgaaaaacgaagacataaagaaa
ccttgcacccctttagctatcactcctgcttctttccccccagcccttaacctattccatgtctctgtggatttgtctgtcctgaagttgc
agttgtactttgtgtgaatggaatcacgcgatatgtggtcctttgtggctggcttctttcactcggcctaatgttttcaagattcatc
tatgttgtagcatgcatcgatacttcattcctttttgttttcaaataatattccattatataaatggaacgcatttgatttgtgggtt
cagctgttgacgggtacttgggttgcctctgcttcttggctatgatgcataacactgctatgaccattcctgccatggttttgtgtgt
aagaggggctctatatgatggaaattcagtccatggccaccctgaccaaatccctggttatccaggaggatggagccctcactccgaa
gtcaggaaggtctccgagtttagttccggggcctggatggcttcattgtcattttcaccatcttagcatgggatgggacaacccgcta
acccgtgcctgggtggtcccagctgcactgtgctggttctcttccttaggtgaaagcccgcaggaagcaagcagctgggagaccaga
gaaaatggatgatgaagaccccattatgggtaccatcacctcggtgagtggttgggggatcttctcatgtgcatgtccactcggaaag
tccaggctgagctcttcagcattccaccaaacccactcctccctcatcacctgggagtctcttctctcctgttctccccttcatat
cccagagccaggaaatcattatgtcccattcaaccttctttgttttgtttgtttgtttgttttgagatggagtttcactcttg
ttacccaggctggagtgcaatggtgcgatcttggctcactgcaaactccaactccaggttcaagcgattctcctgcctcagcctccc
aagtagctgggattacaggcgcacaccatgccccggctaattttttgtattttagtagagacgggggtttcaccatgttggccaggctggtctcgaactcctgacc
tcaggtgatctgcctgcctcagcctcccaaagtgctgggattacaggtgtgagccaccgcgtgcggccaatatctgtggaattcttga
aggacaggggctggggcttcttttagccctgcagttttctctcctgctgtttctgtccagctgtctcctctcctcttttataaatt
gatcagtgttgccccgaacgaattgtccaaaatgcttagttcatgaccaagctgtcatgactggaacaagcatcatttacttttact
ttttcacttttggttcataatatgataaataactgcaaaccccaccatccaacctaagacctaacacattggtgataacttgtatccacc
tgtgttgctccctgatccattcccagtaaccactgttgtgaatcttgtcttcctagtgttgtcacatatatgtaggcttatgccacta
tttagttttaatgtttatgaatctacagaggtatcatgttccacgcacacttcttggacttgctttgtagactcaacattgtatta
tgattcattcatgttgtataaagttgcagttgtattcattttcctgcttataatatatatattttttgagacagggtctgactccat
tgcccaggttggagtgcagtggtgcgatctcggctcattgcaacctccacctcccggttcaagcaactctcctgcctcagcttcctg
agtagctgggattacaggcatgtaccaccacgcaaggctcattttgcatttttagtagcgatggggtttcaccatgttggccagtct
```

-continued

| SEQUENCES |
|---|
| ggtcttgatccacccaccttgacctcccaaagtgctgggattataggtgtgacggcttataatattatattttatgattgtgtctatc |
| acctaagctcatattgatgcacacttgagttgtttccatttgagccgttctgaacattcttatccttgtctcaccgtactaacacaca |
| cgagctttcctttagcatcacctaaagattgagttgccgcatcgctggaatgggcatcttacaaggtcatgaaaaatggc |
| tttccaaagcaattatatccatttatactctcatctatgcctaggaaatcttgttgttctgtaatctctccaacttgcttttctcagt |
| tttggaggctattttactatctcactatggtattgatttgcatttcctcggttaccagtgaagatgaaaaatctctctctgctttcat |
| cttctataaaacacctggtcacatctggatcccattttcctattgggtgtttgacttttcttaatgaatttgttggagggcttata |
| cattttacactatttttctcattgtatgtgttgtaaatataaatatcttctcccaatgcgtagcttgtcttcacttcttaaagtgat |
| cttcaatgaacataagttcctagttgtaatataatcatattcacaaatcctctcttttctattgagtaccttttggatctcattaaaa |
| aaaatttcacccatcctaagattagaaagatattcaaatatagtttctactaaaagttttatgcttttattttaattttgtgggtac |
| atattagatgtatatatttatggggtacatgaactgtttcaatagaggcatgcagtgtgaaataaacacttcatgaagaattgggtac |
| ccagcccctcaagcattgatccgttgagttgcaaacaatccagaagcaacctaagtgtccatcaatagatgaatggataaagaaaatg |
| ttgtgcatatacacaatggagtactattcagccataaaaaagaatgagatccagtcattgcaacaacatggatggaactggagatca |
| ttatgttaagtgaaataaggcaggcacagaaagacaaacattgcatgttctcacatattgtgggatctaagaataaaaaaaaaattga |
| actgatggacatagagagtatgcttttcttttgacatttaagtactcactctgtctggggttgacttttgtgtatggtgtatagtgtt |
| gatccatatatgtttctccttcatttctgaatagtccttctccttctccattgagcaacatgccaattctgccatgtattaaaattc |
| tatatatttgtcggtctcttttctgtggtctctattctactccaatagtcaatttttactgtccctgagtcatcactgtctatataatc |
| aaaataagtcctgatatagagtacagcaaaacctcttccttaatctccttcaatagtatcttgaccattcttggtccttttttttttt |
| cactttaatgttagaatcaggttgtcaaggccgggcgcggtggctcacgcctgtaatcccagcactttgggaggccgaggtgggtgga |
| tcacgaggtcaggagatcgagaccatcctggctcacacggtgaaacccccgtctttactaaaaatacaaaaaaaaaaaaaattagccag |
| gcgtggtggtgggcacctgtagtcccagctactcgggaggctgaggcaggaatggcgtgaacctgggaggcagagcttgcagtgag |
| cggagatcgcgccagtgcactccagcctgggtgacagaacacgactccgtctcaaaacaaaacaaaacaaaaaacaaaaaagcaaaac |
| aaaacaaaacaaaaaagaatcaggttgtcaaattccaaaaaatacattgaatctatagctcaatgtggaaaaaatttacttgtttaga |
| aattcatgccttcttatccatgacagtaggtcttttctctctctattcctttaaatattttaagtgttttaaagagataatgtagagt |
| ttcttcacacaggtcttacacattctttgttattttcttcctaaatacccagttttttgttgctattgtaaatgctatcttttaaaag |
| tgcattttctgattccttatcagaatgcagaatgaaagtatttaaaaaatataagagggttttttttttgtaattaaaaaaaatcacaa |
| gttggtcttgcatgtgtcctttagcatcttcttgctttggtagctggagaattcttagatcttatttataagcctgctgatctcttct |
| ttttcagaaatatagataccatctgaaaaattagtgatattcctattttttaactgtcatggcttgctgaatcaaagcagctgggtttg |
| atgcaagtgtaatgctatttttcttaaagaatcaactcatccttttgggcttcaggtactgagcaagaaatgcctgtcctcatgtatac |
| tctgcagatgtatttctcttctaacagatgtcagatttcaacaaatgacccactgtcctgaataatcactttttttgaggaagtgagg |
| acacgcaaacctaacctcatcggcaacgaagtctgtgtaacacctcagactgtgggcagtttgtgactatggatggtttgaagaat |
| agccagttaccttcatttccccaccatttggcaacacagaacttctcctttttctttcctatattgatggggttgaatttctcagct |
| gggttccttgagggggattcactataactgtgcatctctctcatagtgacacccatctcctctgggatgtcagctctctggatttagaga |
| attgtcataattctctcagtaaatgcagcaagtaaaactcattttttaattgattttcattccttccaacttgccaagctcccttatta |
| gttcaaataactagtatatagaaattgaagtattttaaataaattttttttcaattaaaacaaaatcacaaattaggccaggtttggtg |
| gctcatgcctgtaatcccagaactttgggaggctgaggcaggaggatctcttgaggccaggagttcaaggccaggggataacacagtg |
| agccctccatctctacaaaaagaaaaaaaatcacacattgatcttgggtattatttagaatgttttgggatttcaaattagatgatta |
| tatcatctgcaaaataataacagtttattctctccctttgctccctaagcacttcttttccttttttcttgtttcaatatgctgggtgagat |
| tatggtcaaagttgagtagacatagtgaccatgggcatcttttgctactgctgattttgaaggaaatgcacccaatatcctgccactt |
| ggttctgtgaactttcatcaggttaaggaagttcctttctatcactaaataagttttatcctaaacttctgttgtattttttgaatg |
| catctactgataggatttttcctacttaatctgttaccatggggaatgacaattaaagattttctggtatgaaactactcctgcat |
| tcctgggagaaaaccatattattcatagcattttttttaatactccagtaggttgtttgatcagtcttttgctcagcacttttgcgtcta |
| tatgcatggtcaaatacacttgtcattttccttttttcctcctgtttcttctgtttgggtatcaagataagattgagaaattgggggact |
| agtctctcttttctactgtctggaagagtgtgtataaaactgaaatgacttgtttcctgaatgattgatagatgtcacttatcaaac |
| tacctgggcctggtggcgtcactgatgtgcaattttcctaatttaatcattttatgtattcttcagcgagctttattctagggacgtgt |
| tcctttcacctaagttatatatatatatatattttgacaaaaggatatggtggcatttctcttgtcttttatattattttgttttttgtcg |
| agattacttccccttttagaaatattcctgacattggttatttgtgacttcttctctttttttctagctaaatcttgttaattgcttc |
| cctattttattatcagtttcaaggaaccaactttgggattgtagaattttctcactgtatctttgttttctgttttattgattttta |
| ctctcattttctcagcaccttccttctacttgttttggtttattctgatgatctttgataaattttaagctggatacttagcttctt |
| agtgtctatattttcattctctataaaacgtagttagggataaatttctctcagaatttcattttcatcccattgcacaaatttgat |
| atgtattatttgaataacattcagttgtggatattgttaaaacaacattgtgatttcttcttgaatcttaaattatttgggattaaa |
| aattccaaaggtatgaagattttaaacatcttcataattaaattctaagtagatgcttttggtcagaatacatggttttatgatat |
| ctactttaaaatttgttgagacttgatctgtggcctgtataacatgaatttttgtaaatgtttccctgtgtgcttaagaataatgta |
| tgttttttagcgcgggtgcggtggctcatacctgtaatcccagcacttttgggaggccgaggtgggcagatcacaaaggtcaggagttcaag |
| accagcctggccaatatggtgaaaccccgtctctactaaaaatataaaaattacctgggcatgctggatggtggcaggcacctgtagt |
| cccagctactcaggaggctgaggcaggagaatcgtatgaacccaggaggtggaggttgcagtgagccaagatcgtgccactgcactcc |
| agcctgggcaacaatgtatatttttatttcttaaattaacagtccagtgtgttaattgtaatgttcaaatccaaatcttcagatgtc |
| aacagatcttcccaacatgtcaatacttgagagaggtgtgttgaaatcttacattatgataagtgtatttgtcaatttcttactgtaat |
| tctaacaattgtgtttcttatatttgatgtacttttaaattaaaaccatatattttagaaaagcattatatcttctcagtgaactgaa |
| cattttatcaaacatagtaattctttctcttcatagtggtgctttttttttttttttttttttggagacagagtctcactctgtc |
| acccaggcggcagtgcagtggcacgatctcggctcactgcaacttccacctcctgggttcaagcaattctcctgcttcagcctcctga |
| gtagctgggattacaggtgcccgccaccatgcccaggtaattttttgtattttagtggagacagggttttatcatgttgaccgggctg |
| gtcttgaactcctgggctcaagtgatctgcccacctcgtcctcccaaagtgctgggattacaggtgagccactgtgcccggctcat |
| aatgatgcttttttgctttaaagtctgttcgactggatgtttttttttttttttttttttttaggcagggtctcactcactcatgcg |
| ggctggaatgaagcggcatgtggatcttaatatagctactctagtttcttattgattagttagatgcctgatactttttcattttctc |
| ccatcctcccaacatttatgtatttatgctctaccagtgattttgtaaacagtatataaccaggttttaaaaaatccaatttgaca |
| tcccttgttgagtttactctgctggtatttattatggttactgacatatgtggatttctttctactattttaccttttacttttcactt |
| agtccacttttttcaatattttcattttctccttttcttacttagaagcttaatatcttgccgggcacagtggtgcatacctgtaattc |
| cagctacttgggagggtgaggtaggagcatcgcttgagcccaggactttgaatctagtatgagcaacatagcaagactctcgcctcaa |
| aaaaaaattaatatctctgtcttcacatctaacaaaaagaattttggtgcgcttttatatctcttggcctctcttccttcaactcttta |
| caatgttgatattttctacaaatgtgcagttttgttctgtgttattatgaacatacttagcattttctctattatttgattttttaaa |
| aaatatacagctacacattttgttgaggtattttgtcacctttctattccatacttatcacagatttttctgttcttctttctctttct |
| ctcttttttttgaattctttccccccagtggttttcagtttgggttcctcaaggctctgaagacttatatgcctggaaatatattt |
| tatcccttacattttaattttatttggcaggatatacattctaaaattaaagtgattttccttttggtgcttaaactccaccccact |
| gtttcttgcatttagtattgctgttaagacatcttacgtcattcttaatctcacatattgtaggtaatccactcattttccctggaa |
| actttttataattttctctttggttctgatattcttaagatccactgtcctgtgtctaggcatgggattccctgcatctttttcttgc |
| actcgtgggccctttcagctgaggtgtttcatcttctttaactctggaaattttgtttccactatttttttcaaatattttttcctttt |
| tctacttttttttttttttttaaggtggagtcttgctctgtcgcccaggctggagtgcagtggcgcgatctcctctcactgcaagctcc |

SEQUENCES

```
gcctcccgggttcacgccattctcctgcctcagccctccgagtagttgggactacaggcgcccgccaccatgcccggctaattttttg
tattttagtagagacggggtttcaccgtcttagccaggatggtcttgatctcctgaccttgtgatccgccagcctcggcctcccaaa
gtactggcatgagccaccacaccggcctatttcttttttatcttatttgaaaactattattatctaaatgttcaagtgttttttttt
tttgttttttttttttgacagtctcactctgttgcccaggctggagtgcagtggcacaatctcggctcactgcaatctctgcctctg
ggttcaagtgaatcttgtgcctcagcctcccgagtagctgggattacaggtgcacatcatcacgcctggctaattttttgtatttttt
agagacaggattttgccatgtcggccaagctgatcttgaactcctgacctcaagtgatctgcctgccttggccttccaaagtgctagg
attacaggcatgagccaccacgcctggccagttttctatttctatcttccatctatcttaacctttttctcatatgttctagtcttca
tccttccctacttccttttagggataacttctgacggcccttctagctcactaatttgccctcaattatagtcattctattctccatc
ccatccattgggctcttcctatgatattttttcagatattttccacatggcccttttttgcatcaagtacacaattacataattccttatt
atgtttcacattcattttgcatgcacactttgttattgacaaagtttcttatgcttgttttcatgctgctaatattgccacatctttt
tagtgcatgtaatatgctcagtttagcttcttgaccaaagcgtcctagtacttgtgcttctagtggtctatcaggttctgttggtttg
cttttcttcaaaggtgcccagccttctgagctgtgagctcacattccctcggggttattggctactctggcagtgtttcttgaatgag
ggaagggcagatgctggcctgtgtcaggcttactgagccaaagaaatgacagggacgccgggcacggtggctcacgcctataatccca
gcactttgggaggccgaggtgggcagatcacctgaggtcgggagtttgaggccagcccaaccaacatggagaaactccgtctctacta
aaaatacaaaattagccaggtgtggtggcacatgcctgtaatcccagctactcgggaggctgaggcagggaatctcttgaacctggg
aggtggaggttgcagtgagccgagatcatgccattgcactccagcctgggcaacaacagtgaagcatcgtctcaaaaaaagagaaatg
actgggacaagcccagggtggatcccctcaagaacccaaaccacaccaaccagtcccacttcctatcacccagtaaggcagctta
agtcatccctccatctcagaccctcgtggagaagcaacattggtcaaggactctcgttgcattgtgatccaccagccctgggagttt
ggagtggagaaaatggcaaggagaatgtcaaagaccagtgagcttccacctccgttctccttctcctcacccagtgggcctctggtg
cttacccaacacatgcctgttggacactggcacatcataatcctgtccatactctgaattctgcagtgaggggcagacaatgtttgtc
ccactggaagggtagaggagagaaaggagcagaattcaagtatgtttgggctaacccatcctctcaacaagccagctgtcccccgcc
cagttctcccaccccttttcttcaaatgagccttaactttccctagggatatcagtgtgattgattgatcataaattgatttgtaaa
gttttgttcacccaggagctccatcttagttccatcattggtaggtcttggagaacagagccggtgtatgaattcactcttttgaca
agaactatggtagagagaagcttttgttttctccttttattttaaccattctgcacactttcatgccataggcagaatggtaaag
cgaggcacagcatggtccctggagtttgacgtcctgcattcaggttctagatttcacccacttgcaagctgtgtgaccttggataagct
aatgaacctctctgttttttttgttttctcctatagaaattgggttattaatatgctagtatctgtctcggattgttacaaggagtgct
tagtaaagtggcaagctcacagggagctcacttataactgttacccagtattacttttccttctgtctaacaaggaactgcatgacgg
ggaggtatttgggtggtttcagtctgcttatgtcctcatttatacgaacggcatctagcccaaagaaagcactcagcaaagagctat
tgagtgaaagggtgaacatactgcattgtcctatttactaatctgagctgtgcctttctcttcagttgtcaatttcaccctttttatt
tcatataccgcacacctattgatagacatatgtctttatttcttcctttgcctgcataatgctggtgtgcatagccacttttcattt
tatttcatctttcttgtgcctaatataagcagctctctccagaaagtctatttttttctgacacaatgaagccattttccctaactg
cggagtccttttaaaaaaactgtatggccaggtgtggtggctcacacctgtaatcccaccactctggaaggctaagctgggccagtcg
cttagcccaggagtttgagaccaacctgggtaacgtggcgaaaccctgtctttacaaaaattagctgggcatggtggctctgtgcctgt
ggtctcagctactcaggaagctgaggtgggaggattgcttgagccaggacgggaggttgcagtgagacgaaatcacaccactgccct
ccagcctggatgacagagtgaaactctgtctcaaaaagaaaacttctgagctactgtttgaagactcacgttgctttcaacatatttt
ccatagcgtgatgggtagggatatgggtgaaggtgggagaggaaagaaattgcttacttgtatctggttaccatctttgctgggggaca
ggatctgctccattttgtttctcttttcatggaaactgggtccaggatcagaattgccatctcttttctggtttctgcacataagacacct
tgtaacctatgccgaaggtatacatttgcttcatcaataatccgctcctcctgcctaggtcagggtctatgtctgatttctcacactg
tacgtgcccagaacctgaaacaggggagacagggctgagttcgaatcctggcctcgccatgtattagatgaataaccctgggcaagct
acttaacctctctccacctcagtttccctgtgtgtaaggtggggataattagaatatcttttatactgttgtgggttttttttttggtg
atgattcaatgtgattagtaagtcctcaatatgtgtctgatcaatcatagtattacaaaattgaaagaatgagcgaatagttgagtt
cacaggaaatgtatatggacaggtggggccgggatttgaacccagccctgtctgccctgtgccggttcctgggcacgtacagtgtgag
aaatcagacatagaccctgacctaggcagcctatggcctgtccttaggaggagtggattataaaaggatgaattgataaatgtcacat
cagcccaacttccctgtgggaaccatttgttgtatttttctcttatttggtgttgaggtctctcttttggggagtggtcataaaatcta
gcccgccttgaatgggaaccccagagatctggccatcatgttcacgtgtgactttcacagaatactccttatcctggcacaccac
ctgctgcctgagtgcccagcctgtgacccctctcacagcaaacttgtttatcctgcagattccctgcagctttcctatgacctgt
gtccggtttattccaccaagacagctattctctaggagagccttgaccagaaagaagtgaggttcaggtctgttgggcgggtggga
cacagaggagacagcacaacaaaacacatgaaataacagaagcagtttattactcacaggtcccagagagaagatagcacagcaagcc
tggaagggcgaatggaaagggggaactgaccaggacgcaagtgctcatccagtgggtagggggcagagagagaggagagagagagaa
gaacccatgagccaaagccttaattagagtccagggcataatctaagcaggcttcccacagggagttctaactgggggtttagagcta
gcaggcaggagttctgtggagccacactgtgactgagaggtggttgctgcagtatatctgcgcagcctatgagggacacaggagtcaa
tacgtaagtcaagtaggttgtagctgtatgtcccatagggagctggtcacaaggagatggttgtataaggcagacatttggattaacc
accttggggaactgggaggagggtagagaattggaaattgtgtccaggtgactaagccctgcttctggcatgagaaagtccaacttaca
ttcaaaataaatcccaaggcaacatataaatataagaactcattattctacacctgcctctttattcctactgtgacacctttccttc
ccctttactcagggttccaggaagaagccctggccagacagcccggagatcaagcatctcctcctggggatgccctccttggaag
aacaaaaggagctccattatgcctcccttagttttttctgagatgaagtcgagggagcctaaggaccaggaggcccaagcaccacgga
gtactcggagatcaagacaagtgaggattgtgcccagagttcagtcctggctggaggagccacagcctgtctggggaaaggaca
agtcagggaccacttgctgaagcacgaaggagccttgtgcaatgttaacattaactgatgtttaagtgctccaagcagatggaatta
gagaggtgggctcaaatctaggccctggcactgtcatcaagcaattcactgcatccctctgtgcctcagtttccattctgtaaatca
gagatcatgcatgctacctcaaaggttgttgtgaacattaaagaaatcaacacatggaaatcaaccaacatgggtcctgaacagggc
gttgtgctcagtgctttctggtctctcttccttgaatagaaaggtcctgctggcaagttctctcaaggctggggatgaccaggcacaa
aaaacagggcagcaatatgttggtgtcactcccctccaaaacctctcgaagactccctaggaaaagaccagccccctcagcctggcac
ttggttcatgatgtgggatcttatatccttgccagagtcatatctttgcccactttttacctgcaatccttgcatcatattcctttggc
tccagtcctcattttatgagacccataggaatccttccaacagccaaagagttgagtctaactctttcctgcccaaacccattcacgg
ccccctggccttagacaatatatcacaagcatctcccctgacacataaagtc
```

Human Siglec-7 genomic sequence (SEQ ID NO: 17)
```
gcagttcctgagagaagaaccctgaggaacagacgttccctcgcggccctggcacctccaacccagatatgctgctgctgctgctgc
tgcccctgctctggggagggagagggtggaaggacagaagagtaaccgaaggattactcgctgacgatgcagagttccgtgaccgt
gcaagagggcatgtgtgtccatgtgcgctgctccttctcctacccagtggacagccagactgactctgacccagttcatggctactgg
ttccgggcagggaatgatataagctggaagatccagtggccacaaaccccagctgggcagtgcaggagggaaactcgggaccgat
tccacctccttggggacccacagaccaaaaattgcaccctgagcatcagatgccagaatgagtgatgcggggagatacttctttcg
tatggagaaggaaatataaaatggaattataaatatgaccagctctctgtgaacgtgacaggtaaggcacgggctccaagagaggcc
aaaggcaaatgtgatgagggctttagggcacggctgagacgggacacatgtcctgggaggggccggggtgatggactcaggagagg
agctggaccagagcctgagcttccccaggaccgcaccttggatgcccctcctgatcctgcaggccctccctcaccagccctgaccc
acaggcctgacatcctcatcctgcctctgacgctggcattgtggcatgtggggccttatgactccttgttttggggcctgtcctaggc
```

| SEQUENCES |
|---|
| atggccggggtttagcaccatcccaggcctctccccaccagatgccagaagcacccactccacccatgcagtgagacaataacaatta |
| tctccacacattgttaaacgtcctggggggttaagtcctccccagttgagagccttaggtctacacaacccgtgactctctcaggcc |
| aggccagggaggaagcacttcctggcgcaaaccaagggcagcagaggcacctgagcctggacagggagactcagcacacaggccctcc |
| atctctcatgccctgaggtcctcggagatccacatttagatgctcaaaagacaggagggacctccacgatggtccagaggccgggagg |
| gcaggacctacgtgtctggtgcaggccctggtgctccagggaagcccggaggtaggaggtgggacacggtctcttctcctccctgggt |
| gggtctctagggtctctgagcttcagggtttccttcactctgtgcagagggaaccagttcctatagcatgtgggtttgtagtttctct |
| ttcgtgctgggttgaggtctccagctcctctccagccctctccagcccctgtgggtcccacagccctgcccctcctctccctccca |
| cttctctgctcacacaaggagcccaggaaccctctgtctcagagatgctgctgcctctcttgtgggcaaatgaagagagggacagtcg |
| gggctgggctgagcctcatttcccacagcgtcccaggccccactgtcaagatacaggctggaggtgctggagttggtgatggtgcag |
| gagggctagtgcgtctctgtgccctgcagtgtcctttaaccctattacaactgaactgactctagccctgtccatggatgctggttta |
| agaaagggatcaatatacaatggaataatccagtggccacaaacatcccaaatggaaaagtgcaggagacacggggccgattccacct |
| cctggggacctgaagaccaacaactgctccctgagcatccagagatgccaggaagggggatttgaggaactactacttccaggtggag |
| agaggacagataagatggaattacaaaacgaagcagctctctgtgaatgtgacagataaggcacaggctccaggagacaccacaggga |
| aagtcatgggggtggcagcgaaagcctgggatggggcccctgccctgggagagggctgagggtgaagcgagttgggctcagggcaga |
| agctgaaccagagcctgagcttcccccagggctgtaccatggatcctctgtcctgatcctgagtcccctctcttcaccagccttgac |
| ccacaggcccaacatccttatccccggtaccctgagtctggctgcttccagaatctgacctgctctgtgccctgggcctgtgagcag |
| gggacgcccctatgatctcctggatggggacctctgtgtcccccctgcaccctccaccaccccgctcctcagtgctcaccctcatcc |
| cacagcccagcaccacggcaccagcctcacctgtcaggtgaccttgcctggggccggcgtgaccacgaacaggaccatccaactcaa |
| tgtgtcctgtgagtgctgagccaggacgccctggtccctgatgagggggggacgtccctgagggcagaggatggggtcagggctcgac |
| actgggtgctgggtcccagaatctgggctggtgtgggatcaggaggacgctggctccgcctttcccccatttatgcagctcctggggag |
| acagggccagtgtcccagcccctcacagtgatgcaggtctccatgtctttctgtcccagaccctcctcagaacttgactgtgactgtc |
| ttccaaggagaaggcacaggtaggatggaccccctccctggggctggggagcagggccttcagctcagggcagggccaggtccctc |
| ctcatcctggactcaccctggtgatatgagactcccttgtagttgaaccaggcctcctcccatccttagcctctgtggccacctga |
| gcacctgtcctcttccccccactccccctcagactcttgcacacacaccctcctcagccctgcagccaggacagggggaaatacatata |
| gcaggagcagccttttgggcctcttatcttccatctcctgaatatgccacctaactcgtctttttattttacccaataqttttgagcta |
| cgttctttggatacatgctataatcacgtgggcaaaaattttaaattcacagtaaaatgtgtccccagaatcaaccagggtctgtcc |
| aggctgtcctgagccttggtttgtgcacctggaagatctcagaggtggtttgatgtcagcagtgagactgtttgcaccctcttctagg |
| gatgtgtgattccactgtctgaatagtctctgattttgtggcatctccctaatggaagatcatggcactaattttatcctacggcac |
| gaacactgcaatgaataatgttgtatctactcccacaaggaatatctaagtgtataggataaattcctaaaagcacattttaccagtg |
| tcatatgttctttctgattttgaaagatatggtgaagttgtcctcaaataaaggtgggcaagtttacattcccaacagtgagcggtga |
| acataagtatgtccctgcaccagcctacatcactctctgttccattcccagtctcattctgtatccttcctccctgtttcaatcact |
| ttgtctctttgaacctccaactttttctctacagcatccacagctctggggaacagctcatctctttcagtcctagagggccagtctc |
| tgcgcttggtctgtgctgttgacagcaatcccctgccaggctgagctggacctggaggagtctgacctgtaccctcacagccctc |
| aaaccctctggtactggagctgcaagtgcacctggggatgaaggggaattcacctgtcgagctcagaactctctgggttcccagcac |
| gtttccctgaacctctccctgcaacaggagtacacaggtgggtaaggagggggctggaggaggagaacacacctgccccaccctcatg |
| ggccacccactgcccctgagcttcaaggggagctcagctctggtctgtgctcagctgtgaggcctggaacttccctgcaacccaggg |
| cactgctgtcctcttcctgccaggaaaggtgtgtaaggcaggaagggggaggagtgggtcttggaggggaggagctggggcctggac |
| aggtgtgtttggggagacacgtgccttgcttttccagtgcctggactagggtgacaagcaaggcactcacttctgggcacacgacta |
| aaaaacaaaaaataaaacaactcagcaagcaagtgaaataatattggatgtgattatctttattaaaaactaaaaattattgcaaaat |
| aatttgacagtgaatacaaatcaaaatttcaaatacaggcaggctgtgcttaccactctcatgcctcagtgacctcaggagttgtccc |
| ttcctcctccctcccattcttgccctttgtttctgggaaggggggattagggtacccaagttggggggccttataggaagtgggaggaga |
| agagacccagttcttggagttggatcaccaaaacaattccaatccatcctcaggcaaaatgaggcctgtatcaggagtgttgctgggg |
| gcggtcgggggagctggagccacagccctggtcttcctctccttctgtgtcatcttcattgtgtgagcactgaccctagggagggagg |
| gagagtcctggggagggcggactgggagcaggatccctgaagccagagctggaagggactgcatgggtcaagagcttggggcaagaa |
| tgagctcacgggtgcgtggcaagaatttcaagagcgccctttgctctgtggggctccacatctctgtggtgaacctttgggccccaccaccca |
| ggaggcaggagcctctgtttttcaacactggggtctctgggactggaccaccctcctcccacctcagttaccctccagcgcccaaca |
| ggaaatacagggcaggggttggtctgcccactgcaccccgatctgaccacactgaaaggctctctggtctcttcactcagagtgaggt |
| cctgcaggaagaaatcggcaaggccagcagcggacgtgggagacataggcatgaaggatgcaaacaccatcaggggctcagcctctca |
| ggtgagtgatatgggcgtctccacaccagcatccagctgggacatctcccacaggatggcctccaggattttctctgcttatcatggc |
| caaaattatctcctcatctcctcctccttcccaccatccagcttctcctgcaggattcccatcttgctgactgcatgacagtccctc |
| ctacctactttctctcgggccaggcatggaggaggagttatctcctctctgtcctcccttcttctctatagctccacattcaccaaa |
| tcttgtccattttttcctccctaagaatggctagcattgctcccaccccaccaatcctaaactctctcaatgctgaggcctgaggatc |
| tctgtcttggacttcctcacctccctgcctcttgtgtcccctgccctgatgggaggaatcattcagaagccatcatcgatcagtttct |
| ttgcatctggacagctgttcccaccccaacactgtctagagcagaagccagaaaatactatctggaaaggccagataggaaatattt |
| ttggctttctggcctacacagtctcattgcagctcctcaactctactgatgtagcaggaaatcagccgtagaccatgtgtaaatgatt |
| agctggctgtgtgccagtaaaactttatttataaaaacaagctgtgggtagaatttgtcccaagggctctagtttgacaagccctaac |
| ctagagaaaaagcccaaacttcataactgcagccctgcacattctcgtctcttaaacatctacctctctagcagggctggaattagtg |
| tgagatgagtgaggtcctggcctagcatgcaaaatttaaggaaggtgccaaaaatctcagtaattgtgatagttttaaaaaaaaactctt |
| attttaggtttgggggtacatgtgcaggtttgttacatacataaactctggtcagaggggtttgtggtacagattattttgtcaccca |
| ggtcctaagcctagtacccacagttatttttttctgttcctctctcctcccaccctccacctttcaagtgggcccagtgtctgtt |
| gttctcttctttgtgttcatgagttctcatcatttagctctcactgataagtgagaacatgcagtatttggttttctgttcctgtgtt |
| cgtttgctaaggataatggcctccagctccatccatgttcccacaaaagacatagccatttcattgaatggtgcacagtattcca |
| tggtgtatttgtaccatatttctttatccattctgtcatggatgggcatttaggttaattttcatatatttgctattgaatagtac |
| tacaatgaacatttgcttgtatgtgtcttatggtagaatgattttttattactctgagtataaaaccagtaatgtgattgctatgtca |
| aatgatagttctgcttttagctcttcaggaaattaccatactgctttccacagtggttgaactaatttacactcctgccgacagtata |
| agtgttccctttctctgcagccttgccagcctctgtgatttttttttactttttaaaagtagccattctgactggtgtgagatgatat |
| ttcattgtggttctgatttgcgtttctctagtgatcagcgataatgagctttttctcatatgtctgttggccaaaaatgtctgtttcat |
| gtcctttgctcacttttaatggggttgttttttctcttgtaaatttgtttaagttccttatagatgctggatattagacctttgccta |
| atgcatagtttgcaagtattttctcccattccggttgtttactctgttgatggttattttgctgtgcaggagctcttaagtttaatt |
| agatcccatttgtcaattttgcttttgttgtgattgcttggcatctttgtcaggaaatctttgcctgtttatccagaacgatattg |
| cctacattgtcttccagagtttttatagttttgagttttacatttaagttttttaacccatctcgagttgatttttatatgtggtataa |
| ggaagcagtcccactcaatcttctgcatgtggctagacagttatcccagccacatttattgaatcaggagtccttttccccattgctt |
| tttttgtcagctttgttgaagatcaaattgtttaggtgtgtggcttatttctgggctctcattccgttccattggtctatgtgtc |
| tgtttttgtaccactaccatgctgtttggttactgtagacttgtaatatagtttaaatttgggtaacgtgatgcctccaggttttct |
| ttttgcttaggattgccttggctatttgggcacttttttggtttcatatgaattttaaaattgttttttctagttctgtgaagaatct |
| cattggtagtttgatagaaatagcattgaatgtataaattcttttgggcagtatggccattttaatgattttgattcttttttatccat |
| gagcatagtatgttttttccatttgtgtcaccctttgatttatttgagcagtgttttgtaattctcattgtagagttctttcacctccct |

-continued

SEQUENCES ggttagctgtatttctaaaaattttattcttttttgtggcaattgtgaatgggattgtgttcctaatgtgactcttggcttggtagttc
ctgatgtatagaaatactagtgattttctatattgattttgtatcctgaaactttgctgaagttatttatcatttaagaagcttttg
ggctgggactacgaggttttctagatatagaatcatgcatctgcaaagagggatagtttaaattcctctcttcctatttggatgctct
ttatttctttctcttgcctgattgctctggccagaatttccaatactacgttaaacaggagtggtgagagagggcatccttgtcttgt
gctggctttcaaggggaatgctttcagcttttccatattcaatatgatgttggctctgcgttcaccatagatagctcttattatttg
agatatgttcctttaatacctagtttactgagagtttttaacacgaagcgatgctgaattttatcaaaagccttttctgcatctattg
agataatcatgtgttttttgtctttagttctgtttgtggtgaatcacatttattgatttgtgtatgttgaaccaacatgaagccgac
ttgatcatattggattaaccttctgatgtgctgatggattcagtttgcaagtatttttgttgaggattttttgcatcaatgttcatcaag
gatattggcccgaagttttcttcttttgttgtgtcttcgccagattttggtatcaggatgatactggcctcataagaatgagttaggga
agagtcagtcttcctccgtatttgggaatagtttcagtaggaacagaaggaggctcagatctgacatttattgtgtgattgaagagcc
ttccaggcagagggaggagcaaagcaaggcccaggcacaggaagaggaaaggagaggagccatgggacatctgtgtgattagacagag
ggaggcaggactgagagcaggaaatgacttttggaggagttgagcctatgtgaattgtgtctgactgcacaggctactgtgagcatttg
gagagttttgagcagaaggacatgatcagacgagattgggtccgttcaggggtggtatagctgtagaccagaagaacatgatcaactttt
cattttcatgggattcctctggccactgtgtgcagaagagaccgtgtgtgtggcaggggaaggagagagcataggaggtagacaggag
gctggtgaacatccaggcagaaggtggtgttggctggaaccaagatagcagcagtggtagacatgactgtctcccagatgaattctg
cagtggaacctactgggatttgttaatgaattggaattgaagtgtgagccacagaaagggagcaagaattacttccagatttttgccc
tgagcagtgggaagaatggaggtgccaatcattgaggctgagaagattgcagaagaaatggatttgggaaagaaaaggaggagttcag
attgaataggttgagttttgtgtgtcttggacaagaacgcgggggtttgaattataccactggatcaaagactatagtcaggagaaa
ggagtgggctggggtacagatttgggagtcattagcctattgatggcatgaagccaacacagtggataagatcacaaggcaaaggta
aagaagaaaagaacccggggctgctctgatatttaaggtcagggagacctgaagcaattggcaaagaggttgccaagaaggtgaggtg
gacccagaaaagcatgatgtcctatagttgagtcaagaaggccttctgtgtagggaaggtgagcagctgggtcctctgctgctgaaaa
gtccaggaaggagaagactgcaaggtggacatttagactcagccacttaagtggtagtcacagtgaccttgatagtagcagtgcttag
acttggtatgtgtgtgaatattaatttgagtaatcaagagagaatctggcaagcaaaatcactgacagttccatggagcatcttctgc
acaggggagcagcagggaagggctgcgatgaaggaggaccctcccaggcagcctctgtcactctctgctgtgtgagtctgtattagtt
tcctgtggctgctgtgacaaattaccatgcattctcctggcttccaacaacacacatggattaaagttctgaaggtcacaaccccaaaa
tgggtgtcactgggccaaaatcaaggcattggcaggcagggctggttccttctggaggctccaggggaggatgcaatttctcacccttt
tctggcttctagaggcacctgcattccttggctcaagtccctcctctgtttgcaaggcaagtagcctggcatcttccaatctctcta
agccctcctcctttcacttgtaaggactcctgtcattccactgggcccacccaaataatccaggataacctccccatgtcaatatcct
taacctagctccatctgtaaagtcccttagcaatgtaacgtaacagattcacaggttcaggggattagggtatggacattttgggg
agcagttatacttcttatcagaggatataatttctttgactgagttgtcctccccataccaccgaactgtgagcttcctaagagcagg
tgccccatccaaatcaaggccctgtaattctctctcacttagcctcttcctgcccatcttataattcacacatagatattcgtttgtt
tgacagtcattttttgccaaattccctcaattaaaaagtgagtttcaggaggtcagggccaacacctactgtgtccaccacagtccatc
cagcacccggatcagggcttcacacacagagggcccagcaggactccaggctttggggtcagaaggaagggactggattgggtcccg
gcataacagggagtttgggtacgctacttcttcatggagttgttgcgggaagttaataagattaataaacaccaaacaagttgctca
ataagtgttaaatattgcaggaaagtataaatgaaggagatttctataaaatgaacgtgggatagaggcaggaactcatgaagtttaa
ttctatacagaggaatatatccgaaccaaccaaccgatcaaacaacttgtgactctccctgccttatcctataccactgctctgtct
gactctcactctctctccattcagggtaacctgactgagtcctgggcagatgataaccccccgacaccatggcctggctgcccactcct
cagggaggaaagagagatccagtatgcacccctcagctttcataaggggggagcctcaggacctatcaggacaagaagccaccaacaa
tgagtactcagagatcaagatccccaagtaagaaaatgcagaggctcgggcttgtttgagggttcacgaccccctccagcaaaggagtc
tgaggctgattccagtagaattagcagccctcaatgctgtgcaacaagacatcagaacttattcctcttgtctaactgaaaatgcatg
cctgatgaccaaactctcccttttccccatccaatcggtccacactccccgccctggcctctggtacccaccattctcctctgtacttc
tctaaggatgactactttagattccgaatatagtgagattgtaacgtg Human Siglec-9 genomic sequence (SEQ ID NO: 18)

tagggcctcctctaagtcttgagcccgcagttcctgagagaagaaccctgaggaacagacgttccctcgcggccctggcacctctaac
cccagacatgctgctgctgctgctgcccctgctctggggagggagagggcggaaggacagacaagtaaactgctgacgatgcagagt
tccgtgacggtgcaggaaggcctgtgtgtccatgtgcccctgctccttctcctaccctcgcatggctggatttaccctggccagtag
ttcatggctactggttccgggaaggggccaatacagaccaggatgctccagtggccacaaacaaccccagctcgggcagtgtgggagga
gactcgggaccgattccaccctccttggggaccccacataccaagaattgcaccctgagcatcagagatgccagaagaagtgatgcgggg
agatacttctttcgtatggagaaaggaagtataaaatggaattataaacatcaccggctctctgtaatgtgacaggtaaggcacagg
ctccaggaaaggccacagggaaggtcatgggggcggcagggaaaggctgggatggagcccctgccccaggagagggcttagggtgaa
gcgagttggctcagggcaggagctggaccagagcctgagctccccccagggctgcaccatggatcctctgacctgatcctgagtcccc
ctctcttcaccagccttgacccacaggccaacatcctcatcccaggcaccctggagtccggctgccccccagaatctgacctgctctg
tgccctgggcctgtgagcagggacacccccatgatctcctggatagggacctccgtgtcccccctggaccctccaccaccccgctc
ctcggtgctcaccctcatcccacagcccaggaccatggcaccagcctcacctgtcaggtgaccttccctggggccagcgtgaccacg
aacaagaccgtccatctcaacgtgtcctgtgagtgctgggccgggacgcctgggtccctgatggggtgagcgtcaagcctggacactg
ggtgctgggtcccggaatctgggctggtggtgggtcaggaggacactggctctgccttccctgtttatgcggctcctggggacagac
agggccagtgtcccagccctcacagtgatgcgggtctccatgtctttctgtcccagacccgcctcagaacttgaccatgactgtctt
ccaaggagacggcacaggtaggatggagctccctccctgggggctggaggagcagggccttcaggtcaggatggggctggcttattcct
caacctggactcactttggcaaacagggatgtccttgtgggtgaactcagggcccctctgtatccttaggccccaaggccacttgttc
ccatcctcccatcacctccccttggactccccccacacaccccccctccgcctcaaacaagaagaggggtgcattcacacagcaggacc
aggctttgaggctccttctccatgtatctccctgaatacatctccaccctttatctgtttatttctgatagttctgatctaagtacttctg
gacaggtgataaatgtccatgggcaaaaattcaaattgcagagcaaaggctctcctccgatgcctgccccctccccagaaccaacca
ctgtccatccaggctgccctgagtctcggtttgtacacctggaggatctcagaggtggtttgacgtccgtagtgagactgtccgcacc
ctcctctagggctgtgtgtgagtccactgcatggatggactctgattttgtggcatctcctaatggaagatcacggcactaatttcat
cctacggcaggatagaacaatcttgtatctacttccacaggaatatctaagcctgtgggttaagttcctaaaagcaaaatgtagctac
attatatatgttctttcttatttttgaaagataagcccaaactgttctcgatgaagcggggagaagtttacattcccagcagtgagtggtg
aaagtgtgtgtttcagaacttcagtctatgtctgtgtgtcagttgctgtcatcagtctcttctgtatccttccttttttctccagat
ctatgtatctctgaccctctgtctcttttctacagtatccacagtcttgggaaatggctcatctctgtcactcccagagggccag
tctctgcgcctggtctgtgcagttgatgcagttgacagcaatccccctgccaggctgagcctgagctggagaggcctgaccctgtgcc
cctcacagcccctcaaaccggggttgctggactgcctctgggtgcctgagctgaatttcacctgcagagctcagaaccc
tctcggctctcagcaggtctacctgaacgtctccctgcagagtgagtgcaccagtatgctgggagggcctggagaggagaacacacc
tcctccaccccttagtaactgctgagcgtggaccttcagagaggagctccgctctggtctgtgctcagctgtgaggtctgaacttccc
tgggacccacagcaccactgtcctcttcctgccagggaagggtgtggggtgggagagggcaggagtggatctcagaggggcagga
tggggccggacaggtgtgtttagggagacaagcgccttcttcttgcagggctgaactggagtcacacaactgagatacttgctttgagc
atcaaattaaaaaaaagaaaaagcccagcaagtcagcaatcaaatgaaatcatattgcaatgcaataatcttttaaaaaaagtaaaaa

```
                                    SEQUENCES ttgaatgcaaaacaaattcattaatggataaaatattaaaattgtgaaaaaaaccccaaaaggaatggctggcacttgcacgcctca
ctggcctcaggaagagtctctccatgtcctgctctctcattcctgttctttgtgtctggaaagggaagtggaaatagaagtctag
gaccctacaggaagtgggaggagaagagaccaattctctatgatatatcacaaaaataactcccatctgtcaacaggcaaagccaca
tcaggagtgactcagggggtggtcgggggagctggagccacagccctggtcttcctgtccttctgcgtcatcttcgttgtgtaagcat
ggaccctagagagggagggagggagagccctgggggaggacaggctggaagctggatccctgaagccagagctggagggacctggatg
ggtcaagagcttggggcaagaaggaggtcacaggtgcatggtgagaattccatgtgggcctgtgtttgaggagctttgagtctgtggc
aaaccttggtacccactgtccaggagaagagagcctctgttctcaacctggggtctctaagactggaccactgctttcccacctcag
tcaccctgcagtccttaatagaaacacatggggtacctggtctgcccaccgcacccaatctgaccacactgaaaggctctctg
gtctcttcactcagagtgaggtcctgcaggaagaaatcggcaaggccagcagcgggcgtgggagatacgggcatagaggatgcaaacg
ctgtcagggggttcagcctctcaggtgagtgatgtggactctccacagccagcatgtagcctggacacctcccacaggatgaccccag
gactaatcagctgggcgtagccaaagttacctcctctctgttcttcctttcttctctgtagcccaaatcacaatgtttggttggttt
cctccctaagaacagcttttattgtctctgctccctatcctgacccttcattgctgaggcctgaggatctctgtctttgttccctc
acctgtctgcctgtctcctctcctttcctgcctgggggggactgtccagaagacatcatcgtccagttcctctgcatttgaacagctgt
tcccccacccctcaataccgtttagagcagaagcagcaaatactatctgtcagggacagatagaaactattttcggcttcatgggcc
acacagtctcattgcagctcctcaaatctgctgttgtagcaagaaagaagccatatacccctgtgtaaacaaatgaatatggctgtgtg
ccaataaaactattcacaaacataaagagtgggctggatctgactcagatactgtagtttgacaaccccctgatctagagtaaaaatcc
caaactctatagcctgcagcagtgcacattctgactttttttttgttttttttttttttgttgttgttgttttgagacagagtcttgc
tctgtcgcccaggctggagtgcagtggtgcgatctctgctcactgcaacttccaccttccgggttcaagccattctcctgcctcagcc
tccgagtagctgggactacaggcgcctgccaccacgcccagctaatttttttttgtattttagtagagacggggtttcactgtgttag
ccaggatggtctcagtctctgaccttgtgatctgcccaccttggcttcccgaagtgctgggattacaggcgtgagccactgtgaccg
gccacattctgaccttttaagcacctacctctccactagggcaagaacaaggtgaagtgagtgaggctgttgcctcaagtgcatttt
ttcgtttgtttgttttttgtttttttgagatggagtctcgctctgtcacccaggatgtagtgcagtggcacaatcttggctactgcaac
ctctgcctcctaggttcaagcgattctcctgcctcagcctcctgagtagctgggattaaaggtgcacaccaccacacctggctaattt
tgtatttttagtagagacagggtttcaccatgttggccaggctggtctcaaactcctgacctcaggtgatccgctacctcagcctcc
tgaaagagctgggattacagatgtgagccaccgcgcccatcctcactgtctgctctgactcacttctctctcccatgtctcagggcc
cctgactgaaccttgggcagaagacagtccccccagaccagcctccccagcttctgcccgctcctcagtgggggaaggagagctccag
tatgcatccctcagcttccagatggtgaagccttgggactcgcggggacaggaggccactgacaccgagtactcggagatcaagatcc
acagatgagaaactgcagagactcaccctgattgagggatcacagcccctccaggcaagggagaagtcagaggctgattcttgtagaa
ttaacagccctcaacgtgatgagctatgataacactatgaattatgtgcagagtgaaaagcacacaggcttttagagtcaaagtatctc
aaacctgaatccacactgtgccctccctttttatttttttaactaaaagacagacaaattccta Human Siglec-11 genomic sequence
                                                                                (SEQ ID NO: 19)
cgaggctcctcctctgtggatggtcactgccctccaccaggcttcctgctggaggagtttccttcccagccaggccggcccagaagc
cagatggtcccgggacaggcccagcccagagcccagagatgctgctgctgccctgctgctgcccgtgctgggggcgggtgagtggg
tcggtggctgggggtcccaggcaggggctgggctgccgctgagcctctgcatctccccagggtccctgaacaaggatcccagttaca
gtcttcaagtgcagaggcaggtgccggtgccggagggcctgtgtgtcatcgtgtcttgcaacctctcctacccccgggatggctgggga
cgagtctactgctgcttatggctactggttcaaaggacggaccagcccaaagacgggtgctcctgtggccactaacaaccagagtcga
gaggtggaaatgagcacccgggaccgattccagctcactggggatcccggcaaagggagctgctccttggtgatcagagacgcgcaga
gggaggatgaggcatggtacttcttcggtggagagaggaagccgtgtgagacatagtttcctgagcaatgcgttcttctctaaaagt
aacaggtatggaatggggtgggaaccctgcctgtcacactgggggaccctgggacaggctatgggctgagcagagagggctct
cagggaccctgcagcacaagaatctcccaccggtctctgtcccagccctgactaagaagcctgatgtctacatccccgagaccctg
gagcccggcagccggtgacggtcatctgtgtgtttaactgggctttcaagaaatgtccagccccttctttctcctggacggggggctg
ccctctcccctagaagaaccagaccaagcacctcccacttctcagtgctcagcttcacgcccagccccaggaccacgacaccgacct
cacctgccatgtggacttctccagaaagggtgtgagcgcacagaggaccgtccgacctcgctgtggcctgtgagtgtggcctgggaggg
tggggcgtcagacagccccggtgggtggggaggtggaggagcccagcgggacagtgagtggctcccagctcaggagcatccagggag
aggaagctgtgggtccaggatgccggctcagccctgggagggggatgggaatggcgtctgatcctctgtccacatgtgtgagccct
ggagctggttgtcacttgtccatcctgggatgttcccactttcttttccctgagggagttttttccaggtgtgaggaacaaattgtcc
ctccctgaagccagctcacaatcttgttgcagatgccccccaaagaccttattatcagcatttcacatgacaacacgtcaggtactgag
ggccttcgggctgggctgggccagtcctcctttagggatgaaaaggcttcaggggggtgaggggattgtgggcctacaccctgccg
ctcccacccattctctctctccacccccacccccctctctctttccctgtcttcagccctggaactccagggaaacgtcatatatctggaa
gttcagaaaggccagttcctgcggctcctctgtgctgctgacagccagccccctgccacgctgagctgggtcctgcaggacagagtcc
tctcctcgtcccacccctggggcccagaaccctggggctggagctgcgtggggtaagggccggggattcagggcgctacacctgccg
agcggagaacaggcttggctcccagcagcaagccctggacctctctgtgcagtgtgagtgtgcctagcagggggcctggagtccattgg
gagggcagagggatacagggctgggctcagggtcccagagctgaggggtcttgaaccccaggcctcggggactgaccttcttacct
gtgtagaccctcatgcagtttgtgtctgggactcagtgggtgattctgccctgcccttctatcccacccacttccccccacctcagtgt
ccaggatagttcccttttacccagagggaagccctggtctgtctagagccggtcccctgtctccatttcagatcctccagagaacctg
agagtgatggtttcccaagcaacaggacaggtaggaaaggagacaggaggagccaggggcctctcagtgccaaactgggggcccaggag
tctgagggtccccacacaggagggtccctgagccctgagctgcacgtcgattctgctcttccttccctagtcctggaaaacctcgg
gaacggcacatccctcccggtcctggagggccaaagcctgcgcctggtctgtgtcacccacagcagccccccagccaggctgagctgg
acccggtggggacagaccgtgggccctcccagccctcagaccccggggtcctggagctgccacccattcaaatggagcacgaaggag
agttcacctgccacgctcagcaccctctgggctcccagccagctctctctcagcctctccgtgcactgtgagtggggggaaagggagacac
ctgggtcccaggaagggccctgctgagtcctgctctccctcccccacagaccctccacagctgctgggccctcctgctcctggag
gctgagggtctgcactgcagctgctcctccaggccagcccggccccctctctgcgctggtggcttggggaggagctgctggaggggga
acagcagtcagggctccttcgaggtcaccccagctcagccgggccctgggccaacagctccctgagcctccatggagggctcagctc
cggcctcaggctccgctgtaaggcctggaacgtccacggggcccagagtggctctgtcttccagctgctaccaggtgaggggactgtg
gggggctgaggttcagggagaaaggagacaggatcctagaaagatgaaggttcaagttgtggggagagggtgtgggctgtgggaa
gggatgggacaaagtccctgctctgtggctggtagttgttgcgggaaactgaggaacggagagagcaatatgtggaacaggaggatt
gtttatttaaggtaagttccagcttagtggatttacatttcaaaagctgagcattaaataaagacaaagaaggggttttttttgtttt
ttggttttttttttgagatggagtctcgctctgtcagcaaggctggagtgcagtggctcgatctcggctcactgcaacctctgcctcc
cggattcaagcaattctcctgcctcagccacctgagtagctgggattacaggcatgcgccaccacgcccagctaatttttttgtattt
ttagtttcactatgttggccaggctggtctcgaactcctgacctttgattcacgcacctggaccctcccaaagtgctgggattacagg
cgtgtgccaccgcgcccggctaaagcagtgtgtttataagcggacttacaaaagtaaaacaaaagcggttaattatatagtgcataac
ttgtggccttgtagctgtgtcaaaagaaaaacaagaactggttaaatacagacatttgtgaaacataattgtgcttaagaagccaggg
aaaggagtaacagtaaaagaatttgtctttttttttttttctttaaccttgctctggaagggtgtgtctggagcccattcctttggc
cttggcttttaaacagtgttatttttatacctgtccttgaagtgagcttgctaggcatagaaagacttgggtttttttgtttttttt
ttaacccttgccttgcctgttacttttttgggagtgaatgaatgcatatttattttttaaattttttgcctcagtttccccttttgatg
```

| SEQUENCES |
|---|
| tttttttataaaagaagtttaatagaaggcattactattacttaattctgcatgaagagacactttttttctttagacaaaggttgata |
| tttatgcagagccgttagctgagtggtagtttgcctagctgctattgcctttatagttgattgaatgcttccaacaaggagagctaag |
| agacaagggagtattcggcaacttcctagtatggccagaaccacttttattaaagtcttgaaccctctgcaaaatgaaaaccagtcct |
| taaagagagaatctggagaccacccttccaagtttgaactggaacatgggctaattttttttatttttgcagttattttttataattgc |
| cttttcattgtcagcgattttaggcagcagttagttagattgaacttttttacatttttttttttctgggctaggagtagtccaaagc |
| taacctgttctgatagataacattcttcattttttgtgggttgctgggccagtaaatctaatgcatttgctgttttattagtgatgatt |
| tcaagtactgcctgcaacctttatgatgcggttaagcatgtaaataggagtgtggtatcccccatgacccattttgtgcccaggtagctg |
| gcctatactattgaattattttttcagggggttaattttgtgtcttttcaatttttttaattttttattttttgtgtgtgttttgcattt |
| ttttttaactttattatagacaggataccttaaagtttctccctgttgcagtgggaataggaagaaagacggtctaattgtttcaagca |
| cacaggcccctgtccatttagctggcaactgttgatatgcccatggcctacagatccaacaaagactaggaggtgcttgccaagtatt |
| tggagctttcggctgatagtaggtgtgattaaagaagagaaacagggaaccggatttggatgaggtcatttgcattcatcttttgcccc |
| gccacaaagtgtttcttagtgttttatcgtcatattgctgtcctaagcagtttagttcttttactgggtttgtaaaaacttttcccca |
| gcgagcaacacagtatttcctgataatagaagttttaagagccagacgcttgaacttgtgggcgtcggttcgggagaagagtcagtt |
| aaattatttgtggcattaactttttttgctttccaaggccattggtcttccgtgttagtccctccgcaaacatagtatgaggaaatgc |
| ctaggctgccgacaatgttttaggcagccgagcaaacaggttttctgctaaaggagtgggctctggtaacaggattacaggtgtgag |
| ccactgcgcccggccataagtacaagttcttttttttttttttttgagacggagtctcgctctgttgcctggctggagtgcagtgg |
| cgccatctctgctcactgcaagctccaactcccaggttcacgccattctcctgcctcagcctcccgagtagctgggactacaggcgcc |
| cgccaccaagcccggctaatttttttgtattttactagagacaggtttcacagtgttagccaggatggtctcaatctcctgaccct |
| gtgatctgtccacctcggcctcccaaagtgctgggattacaggtgtgagccgccatgcccggcctgctaattttttcttttatgaggg |
| ctgctgccaacagattggccttttttttaagcctatgttctgcttccttttttccttgagttatcctgctcctacagctggccag |
| tgggactgggctacggcgtgggccccgcccctgtgcacgcacgcactgccatctatctttactgtttctttctgattttttcttttttc |
| cttttttcacacttacttttttgggctaggtaggatctgcacagccgtagtccacccctgggccgttataggcccagaggcttggtaga |
| tgcctgccgcaagttgtaagaattatgcctttctttttttttttttttggcttttttttctggggccagtcccgccccgctctttt |
| tccagatagagccaggctgaggagggactaaaccctctggtgtgcctagctgcttggtgcctccgcttgttgcttttcgctctttcccg |
| ttttgttctctggtcatgtttcatgtacatcttggtggtcactttttataagctgggtggcattcatgcctgcagctgccgcttgacgt |
| caccctgggcttgccctacaaatgctgtgtttaccatgcgctgattttcagcagcctcagggtcaaatagggtgtaaggccggaatgc |
| ttcacaaagtttttttataaaactgacttgggctctcgtcagctctctgaagcacttttgaaattttttcgtatattaattgctttcttt |
| ccaccagcttttatccccttgcagaagtgtctcttggtacctttgcaaatgctgaagctgagttgcatcctctggggttccagttgggat |
| cttggtatgagaactgaccttgagtgtatgcctgagcattcactgcatctgctggtgcatgggggttttagccaggggagagctgccta |
| tgttactctcctgcgcttttttagtgttaaataacgttaggaaaagctgcctgcaatctggccaggttggactgtgtgtcagaaagacg |
| gattgcgtcagatctataagagcttgaggcttctccatgtaggaggggagtatggtgtttccagttcagtagatcagtagctcagtagt |
| cagaaagggctgatagatgaaggtgcgttgcccccccacctccgaacctggcctggttattacaataagtgggtcctcacatctccct |
| gacaggcatttgcatagctcgagcaggcatttgcatagctcaagcacgggccagatctgagacagcctgcttgactattttgactcct |
| tccctggccttttgaggctccagtcctcccttccggggtcagactcagggcatgctagctcctgaattttggttcctggagggctgttg |
| gcctcagtaaagggggtaggctgggacatatggaggaggaatttctgtttcctctggcagctgttgcaaaactggcttctcttgctc |
| tttctggggttttctttttaacttcgtgtcagtcggtgaagctgctcttacttttttattttttggctcgggctacaagtgtttttgcaata |
| agctgctaaacagggcttgatccaggttagtcttgtctgtgctgtatttaaccatgaatcaatataaggaaattgatcgggatactca |
| ggctgtcctcagaccctatcaccatctttaatacatgcccaattgtttcctagtctacagttcttcggtcagccatccaacatcaa |
| aagaaagtcattctaattcaaagagagttctcaacctttggggggttagcttaacttttataatcccctgcaaaacctttcttaaagtt |
| ttgtaacatgcacttcaatggagtaagttttgatggactttccttctattccttccttttacggcccagcacactcactcttcctctag |
| tttcggccaactataccatctcctattacgggagttttcagaagctacttggcttttggagagttccttattcctgctacaactctgag |
| ctgtagggcagctcctattagccatacgcagatcaccactagtcttagttggccccacactttgctcggagcaccagtccacactaa |
| gagaattgtgacttcccattttgtggctgatcagcctaataaggcttcttcatttacacactgttacacacttccccactcccagttc |
| ctaagttcctaattagggtggtaagccactctcgccacctccagttttcttttcctaatcgacttagcaaaccattctcacatcctgt |
| gatggttggggtgtgagtttcatccaaatcgacgagccactctcgctgccccccaaccctctgggtcggactgttaggcacccccgcaa |
| gaagtgatcagcctcccccttccatccctatgggatgggtcctgccttggtccccaaaaggttactgttggttcctgacgtacactgttt |
| ctgaaatcattctgtagctcctttcaggttttgttgtgctgctgggtaggggcgccggctcaggggagagctgatttctcctccaggc |
| tgaagttcacccagtggcacctggggtcacaggtctcctgaggcccggggctccagccccagaggcaaaggaggcagtaaacctacc |
| gtctctggtcccttcgtggtcgccaaaaatgctgcgggaaactggagactggtgagaccgatacggagaacaggaggattgtttattt |
| taggtgcaaaccggctcagtggactcgcatctaaaaagctgagcatgaaacaaagacagagcgaggtttttatgagcagacttacaaa |
| agtaaaacagaggcagttaattttaggataggtgacataatttatagtatagcataacttgtggccttgcatagctggtggccttgta |
| gctgtatcaaaggaaaaaaaagaactggctaaatacagacatttgtaaaacatagttatgcttaagaagccagggaaaggagtaac |
| agtaaaggaatttgtttttctttcttgttttcctttcaaccttgctctggaaggggtgtgtctggagcctattccttttggccttggct |
| ttttaaacagtattatcttataactgtccttgaagtgagccttgctaagcagaggaaaagttgttctttttttaacccttttccttgcc |
| tgttacttttcttggagtgaatgaatgcatatttatttttaaatttctgcctcagttgggatgaagaatccgagagctctaggtctg |
| tgggaggaaggggcaggagggtctcagggccaggagggcaccaccccaaaccctgctcccatgcagggaagctggagcatgggggagg |
| acttggcctgggggctgccctgggagctggcgtcgctgccctgctcgcttttctgttcctgccttgtcgtcttcaggtaagcatcggag |
| ggcaggcaatgcagggtgtgggaagggtgagggttctagaatcccagacagtcccagctgcaggaatctagatggggcagtgggtgtg |
| agaactaggcctgggcaagaggatcagagcagggtctgctccagagccctgatctgggccatctatgagggtccccagttctcact |
| atggaagtcaccccgtggatatgtccccaccccactgggctctgcagccttccagcctctgctaagccatgtgggtagcagtttcccc |
| aggctctggaccagcctggaggctgaagggcactgcctcctccctcagggtgaagatctgcaggaaggaagctcgcaagagggcagca |
| gctgagcaggacgtgccctccaccctgggacccatctcccaggtgagacccacagctgtctgctgggccctgcctgttccccttt |
| ccttgatggccatgggtagtcctcttggtgacttgcagaatcattgtgcccaaatagggttttgctcctgggtcccatcaatgcag |
| tcccaagtcccatgatctgggaggcacccctcccactgctccctacatcccctcccagaaccaagggccccccaggcctgtccatact |
| ctgcctgtgctcagatccagtggaccctccacctcccactcctcatttcctcctgcatcccgactcctttgccctccctcctatctc |
| tcctcctcaacacaggatgccagagagtcctttcctcagatgactattgtctactacaaagctaagggtccccatcctcacttctgac |
| accaaccacagttgtggggtcccacgaccactctgaggttggataacccccctaggactcgcaggtcactgagagctgtgatcctc |
| gtggtgatggtttatagtgaccgatacagatgaaaatcatggacaggaagaggtgctcagggcaggtccaggagataccaaacccaca |
| gcttccgtggcctttcccaggggagccatggggacagcacccaattctcccagcaaggaagtgtgacagatgcacggagcatcaggg |
| caccgctcacctgggaagctccaccaaacctgggtccaggttcactgggggtggtcacgcaggcatggggacttgccactgactt |
| cagttcctcagcccctgcagagccaaactgatgctacgtaggcccgcgtaagtcccagtgctggcgtaaactatgtggcctggctt |
| gtggtcccaggtcaacagggatgctcctaccagcaggatattccaaggccctacattagaggttccttcccagcaccctgggcacaaac |
| ggttgaagctttctctgggcaaggggaatcctttacttccagtaaccttttcttcttgagctcctagctcagtttcacaattgtgtcc |
| gagtagatcttccaaggtcttttgaggtcagtccaggtccgagcaaatccctgtctttctcacacctcctccttcctgggcatccactt |
| ataatttgcaattagatagtaacttcattgactatagcttaatgtgtctacttcttcttccatactgcaagctgcctgagatcaggg |
| gtggtgtctcctagttcccccgggaatatccaggggctggcacaggggagctgttccataaggcagcgggcactggagtcagagaaa |
| cctggacgtgaatcctggcctgaccgctacttagatgtgcggggtttgggtatttactcagccttcatttctccatctgatcatggag |

| SEQUENCES |
| --- |
| acaatagtgtctccccagtggattgtggtgaggattttatgagtctggattgtggtgaggattttatgagtctggcagtgaattacca<br>agagctagatgttattgttctcaaatatttgctgaatgagtgaatgaatgaatgagtgaatgaatgagggcccagctgacctttgtgg<br>aatgagtaggtgaaacaggaaatactcaatttccagatcctcttgtgcatcctccttgctctcgcttagcccccatgaccctaatttg<br>accccctttctccccctgcattcagggtcaccagcatgaatgctcggcaggcagctcccaagaccacccgcccccaggtgcagccacct<br>acaccccggggaaggggaagagcaggagctccactatgcctccctcagcttccagggcctgaggctctgggagcctgcggaccagga<br>ggcccccagcaccaccgagtactcggagatcaagatccacacaggacagccctgaggggccaggctttgggcttcaattggagagg<br>gagatgtcagggatggttccaaagtgaagaggtctccatggcaacaggacaccagcaagtgtgtgggagtcgcactggtgtgacggcc<br>agaactggactcagatttcagccccatccccaatgaagagcttgagtttgaagattatactttttttgagacagggtctgactctgtc<br>ctccaggccagagtccagtggtgcaatctcagctcactgtagcctcaacctgccaggttgaagtgagcctcccatttcagcctcccaa<br>gtagctgggactacaattgtgagccaccatgccaggtcattgttatattttagtagagacagggttttgccatgtttccctggctg<br>gtctcagactcctgggctcaagcaatctgcccgcctctgcctcccaaagtgctggattacagacgtgagccaccacagctggctgaa<br>gattatactttcaattcagagcgagtttgaagatgacactttgaggcatcgtgtctatggttcattactacagaagcttctctggatg<br>tgtaaagcacaggaaaccaggcagaggaggcacagggtgctctccagaacgagaagccagctcctggagttgtttgctgcaactgcca<br>ttccccgttgatgaccatgctcttccttcagaagagggagagtgagaggaccaagtccaagtggtccccatttgaacatttaaaaaaa<br>aaaaaaaggctgggcatggtggctcacgcctgtaatctcaacactttgggaggctgaagtgggtggatcacaagtcaggagttcaaga<br>ccagcctgggcaagatggtgaaaccccatctctactaaaaatacaaaaattagccgggcatggtggcgggcgcctaaaatcccagcta<br>ctcgggagactaggcagagaattggttgaacccgggaggtggaggttgcagtgagccgagatcgtcccactgcactccagcctgggca<br>acagagtgagactctgtttctaaatAAATaaatgaa |

Human Siglec-14 genomic sequence (SEQ ID NO: 20)

actcaccctccggcttcctgtcggggctttctcagcccaccccacgtttggacatttggagcatttccttccctgacagccggacct
gggactgggctggggccctggcggatggagacatgctgccctgctgctgctgccctgctgtgggggggtgagtgagctgagggagg
agggacaggcacagggtgagaaggggggctggagctgagcttctgtgtccccccaggtccctgcaggagaagccagtgta
cgagctgcaagtgcagaagtcggtgacggtgcaggagggcctgtgcgtccttgtgccctgctccttctcttaccctggagatcctgg
tattcctctcccccactctacgtctactggttccgggacggggagatcccatactacgctgaggttgtggccacaaacaacccagaca
gaagagtgaagccagagacccagggccgattccgcctccttgggatgtccagaagaagaactgctccctgagcatcggagatgccag
aatggaggacacgggaagctatttcttccgcgtggagagaggaagggatgtaaaatatagctaccaacagaataagctgaacttggag
gtgacaggtatggcaggaaccctaggagaggaccctgggacgtggagaccccgtatgagaacagggacaggagttgggcaggggcgg
ctggaggaggtgtaggacttggggcaggtcggggcctgaggcctggccactctcggggtcacaccttacgtcctcaagccctgggc
ccaggtatctccctgtctcctcctcagccctgatagagaaaccgacatccactttctggagcctctggagtccggccgcccacaag
gctgagctgcagccttccaggatcctgtgaagcgggaccacctctcacattctcctggacggggaatgccctcagcccctggacccc
gagaccacccgctcctcggagctcaccctccaccccaggccgaggaccatggccaccaacctcacctgtcaggtgaaacgccaaggag
ctcaggtgaccacggagagaactgtccagctcaatgtctcctgtgagtggtgctggggacacagctgagtccccaagggcagtgggag
tgaggggggtgtgtgtgtgtgtgtgtgtgtgtgtagaagagagagagagagaaagagaatgataaccagggaaaactcgtgtgtgggc
aggaaggacagcggtccccacctggtgggtttctgtggcccctccttgggtcctcccgggaccacgccatccctcttgtcacctct
gaagctggtgctgtatctttctatcccagatgctccacagaacctcgccatcagcatcttcttcagaaatggcacaggcacaggtagg
aaagaccctcttccctctgggcgtgtgatgggagccttctattagctcagggttcagcattgggagaggagaccctccctcacccctc
agcccctgggtctgggtccttcctgctcccaaccccccaatcccagtcactaagatcttgcacgaacagacctagtatttcttttggc
ttctccctttctctgctctcttttcagatttatttttttcattgtgagaaaatacacatagcacaaaatttgtcatcttagccattt
taaagagtacagttcagcagtgttaaatgtgttcacattgttgcaaaaccaaactgcagagtcctttttatctggcaaaactgaaact
ttgtacccactgaacagcgactttccacttccccctcctgccaccgagcagtcaccattctacttttctgtctctgtgagtttgagta
ctcaggacacgctgttcccttttcttgaatttctgcctgctccgatgtcctctgatgcatgccctgcttcatctctaactgatcgtcc
tttttgggagccttcgactttcccacctcccacagctctgtcccagaacccagttcttccctccacattcctgagtaatccgatctc
tccttgaccctgtcctgatgcctcccacaactttatatccagcccttttctctgaggcacagatctgcacattagccaccctccctcgg
atgcttctcggctcctccttccctgttgatcccagggctgttctggacatcgctgtagacagcaccctttctcatcagctgtttcatg
agtccgcaagtcttaacaccttttacttcaccaatcatcacttccctcctcatcccttggttccaggccagctcaagtctcgtgctc
aaccctggcccattgcccagcctcctcccagcctccctgcctcctatcccacttctctccagtccgggacctacttggctccagcag
gatcttctagatccagtgctaactctgtttcccttgcttatagccccctcttgctttccaggataaagcccaaggccctcaatctgg
cacccaatgctccaaaagatctgagcctgcttctacctccattatcgtgtcttgggagctctgggtcctccctgacaggttgcggatc
taggagcctcttcctcgtctgcctgtctcagttcttggcacgtctgcacctgagctgcccatccacttctccttaatgtgagaactc
ctcctcatcgtctttctcagctcagccaccttctttctggtagcctgacctgatcaccaagtcctcatcctttcacccatgactag
cccattctcagcactcaccacacacagtcttgtctttcttcttgcagctcagtgggaggaatggggagaattgggcctcccagctccac
tcacctggctgtgcttctcttttcccagccctgcggatcctgagcaatggcatgtcggtgccatccaggagggccagtccctgttcct
cgcctgcacagttgacagcaaccccctgcctcactgagcggttccggagggaaaagccctcaatccttcccagacctcaatgtct
gggaccctggagctgcctaacataggagctagagagggaggggaattcacctgccggttcagcatccgctgggctcccagcacctgt
ccttcatccttctgtgcagagtgagttgcaggacaggtgctgagggtagacagcccggtgaggtattcaggttggtgggagggactg
aggcctggtaacagcaccttaccttctccttctcccaggaagctcctcttcctgcatatgtgtaactgagaaacagcagggctcctg
gcccctcgtcctcacctgatcagggggctctcatgggggctggcttcctcctcacctatggcctcacctggatctactataccagg
tgagccggactgcctgtctccaggaagctcctgagttccaggtggggctgagctgtcctgccccaggacagctcagcccacctggaa
ttagaactgaagtggctggtgctgatctgaggccatgttggctctgcaggtgtggaggccccagcagagcagggctgagaggcctg
gctgagccctccgctcaagacagaactgaggtgtggacacttagccctgtgggacacatgcaggacatcactgtcagcttctttct
ggaagctcacatcccactgactaccctcttttccttcctgccccataccccttctacttattccctctgcttgtgagtcttgcccc
accacacctgcatcccatctgcacccatccctctccacctgccttctcttccctctccatccaccatctccagccctgtgaagg
gaatgtactttcggtcttatacccccattaccattacccaaaagttacctttttttttttttttttttttgagacagagtctcact
ctgttgcacaggctggagttcagtggcacaatctccgttcactgcaacctccacctctgggttcaagcaattctcctgcctcagcct
ccctagtagctgggattacaggtgcctgccaccacatccagttaatttttttttttttgtatgttagtagagatggggttttaccatgt
tggccaggtctcgaactcctgacctcaagcaatccactgcattggcctcccaaagtgctggcattacaggtatgagccaccgtgcctg
gctgccaaaagttaccttcttaacactttgaatttctggtctcctcagcttccctatccatataggcacagagaggcagcatttgtttt
ccagttaaaactctacctcattgtgattattatccaatacaattgttacaaaataagtaaaactttttatgaaacaatacaacataact
gattttactcttttaa Human Siglec-16 genomic sequence (SEQ ID NO: 21)

actgcccctccaccaggcttcctgctggaggagtttccttcccagccaggccggcccagaagccagatggtcccgggacaggcccagc
cccagagcccagagatgctgctgctgcccctgctgctgcccgtgctgggggcgggtgagtgggtcggtggctgggggtcccaggcagg
ggctggggctgccgctgagcctctgcatctccccagggtccctgaacaaggatcccagttacagtcttcaagtgcagaggcaggtgcc -continued

| SEQUENCES |
|---|
| ggtgccggagggcctgtgtgtcatcgtgtcttgcaacctctcctaccccgggatggctgggacgagtctactgctgcttatggctac |
| tggttcaaaggatggaccagcccaaagacgggtgctcctgtggccactaacaaccagagtcgagaggtggaaatgagcacccgggacc |
| gattccagctcactgggatcccggcaaagggagctgctccttggtgatcagagacgcgcagagggaggatgaggcatggtacttctt |
| tcgggtggagagaggaagccgtgtgagacatagtttcgtgaacaatttgttctaaaagtaacaggtatggaatggggtgggaacccct |
| gcctgtcacactggggagggaccctggggacaggctatgggctgagcagagagggctttcagggaccctgcagcacaagaattcccc |
| accccggtctctgcccagccctgactcagaagcctgatgtctacatccccgagaccctggagcccgggcagccggtgacggtcatct |
| gtgtgtttaactgggctttcaagaaatgtccagcccctctttctccttggacgggggctgccctctcccctagaagaaccagaccaag |
| cacctcccacttctcagtgctcagcttcacgcccagccccaggaccacgacaccgacctcacctgccatgtggacttctccagaaag |
| ggtgtgagcgcacagaggaccgtccgactccgtgtggcctgtgagtgtggcctgggaggtgggcgtgcagacagcccggtgggtg |
| ggaggtggaggagcccagcaggacagtgagtggctcccagctcaggagcatccaggagaggaagctgtggggtcccaggatgccgg |
| ctcagccctgggaggggatgggaatggcgtctgatcctctgtccacatgtgtgagcctggagctggttgtcacttgtccatcctgg |
| gatgttcccactttcttttccctgagggagtttttttccaggtgtgaggaacaaattgtccctccctgaagccagctcacaatcttgtt |
| gcagatgccccaaagaccttattatcagcatttcacatgacaacacgtcaggtactgagggccttcgggctggggctgggccagtcc |
| tctttagggatgaaaaggcttcagggggtgagggatgtggtcctcttttgcagccccctcccacccattctctctctccacccc |
| accctctctctttccctgtcttcagccctggaactccaggaaaacgtcatatatctggaagttcagaaaggccagttcctgcggctcc |
| tctgtgctgctgacagccagcccctgccacgctgagctgggtcctgcaggacagagtcctctcctcgtcccaccctgggcccag |
| aaccctggggctggagctgcgtggggtaagggccggggattcagggcgctacacctgccgagcggagaacaggcttggctcccagcag |
| cgagccctggacctctctgtgcagtgtgagtgtgcctagcaggggcctggagtccattgggagggcagagggatacaggggctgggct |
| cagtgtcccagagctgagggggtcttgaaccccaggcctcggggactgaccttcttacctgtgtagaccctcatgcagtttgtgtctg |
| ggactcagtgggtgattctgccctgcccttctatcccaccacttccccaccctcagtctccaggacgcttccctttgcccagaggga |
| agtccctggtccgtctagagccggtccccctgtctccatttcagatcctccagagaacctgagagtgatggtttcccaagcaaacagga |
| caggtaggaaaggagacagaggagccagggcctctcagtgccaaattgggggcccaggtgtctggagggtcccatgcaggcgggtcc |
| ctgagccctgagctgcacgtcgattctgcctcttccttcccagtcctggaaaacctgaggaacggcacatccctccgggtcctggag |
| ggccaaagcctgcgtctggtctgtgtcacacacagcagccccccagccaggctgagctggaacagccgcaggactacttcaaggtcacccc |
| cccagccctcagacccgtggggtcctggagctgcctcgggttcaaatggagcacgaaggagagttcacctgccacgctcggcacccgct |
| gggctcccagccgcgtctctctcagcttctccgtgcactgtgagtggggaaagggacacctgggtcccaggaagggcccctgctgag |
| tcctgtcctccctcccacagagcccccccagctgctgggaccctcctgctcctgggaggctgagggtctgcactgcagctgctcctcc |
| caaggcagcccggccccgtctctgccctggtggattggtggggagctgcggagggaaaacagcagccaggactacttcaaggtcacccc |
| cagctcagccgggccctgggcaacagctccctgatcctccaaggggggcttggctccaacctcaggctcacctttgaggcccagaa |
| cgtccatgggcccagagctctctgattcctggcggacagtcagggtataggtggggaggcctgggctcaccaggtcctgcatccag |
| ggatgtaggaagggcctggagaaccaagttgcaataagagaggaaggattcggaagtgtggtttagaaggtgaatgggccttatccca |
| cttttccaggcaaatcagggcccatgacggggtggttctggtggctgttggggaggtggctatgaagatcctgcttctctgcctctg |
| cctcatcctcctcaggtgagccctgccccagggaccaaggggagggcgagagggcaaaggatacaccgctgaatcccagaatctca |
| atcctggggtacttggacagttaaagaggcctgtggccaggcagaggctgagttgatcgtgatgattccacacgggccagtgttgtc |
| agtccccaactctggaccaatgtccaggctggggaggttcctgcttgtatcaggaggtcctgggggctaggcctgctctctctgcct |
| cagtcccctccaaccccttagcagggcacaggaggtgagtctgctgccctcttccccccatccagccacactcacaggccctggtc |
| tcttcaccagagtgaggtcttgcaggaggaaggcagcaaggcagcattgggcatggaggctgcagacgctgtcacggactaatctc |
| caggtgagtgtcgtgggcctcttaccctccaacatcccgctggacacctcccccctcgatggccccaaggactgctccactcaacttgg |
| ccataactgactcatcacctccctttccaagcccacttctcttgttgagagcccatccctctgatgacatggtagcccatctctaa |
| cgtcagaacccgggtgtgggtgtccaccttgacctccctcctcctccagatcccaaaaatcactagcacttgtccctcctcctaagt |
| acaggtcaccttggagccctttctccatcctggcccggtcatgcctgggcctcacctcttccctggtcgctgaacccacctcacct |
| cttgcctccatctctcccaacagactccagactgcttccagatgcctcctcatccagttc |

---

What is claimed is:

1. A method of screening candidate agents, the method comprising
   i) administering one or more candidate agents to a transgenic mouse, wherein the genome of the transgenic mouse comprises two or more human genes, wherein the two or more human genes are selected from the group consisting of CD33, Siglec-5, Siglec-7, Siglec-9, Siglec-11, Siglec-14, and Siglec-16, wherein the two or more human genes are expressed in one or more cells of the transgenic mouse, and wherein the one or more cells are selected from the group consisting of myeloid cells, natural killer (NK) cells, T cells, microglia, and any combination thereof; and
   ii) determining whether the one or more candidate agents binds to and/or modulates the function and/or activity of at least one of the two or more human genes in the transgenic mouse.

2. A method of screening candidate agents, the method comprising
   i) administering one or more candidate agents to a transgenic mouse, wherein the genome of the transgenic mouse comprises two or more human genes, wherein the two or more human genes are selected from the group consisting of CD33, Siglec-5, Siglec-7, Siglec-9, Siglec-11, Siglec-14, and Siglec-16, wherein the two or more human genes are expressed in one or more cells of the transgenic mouse, and wherein the one or more cells are selected from the group consisting of myeloid cells, natural killer (NK) cells, T cells, microglia, and any combination thereof; and
   ii) determining the effect of the one or more candidate agents on one or more activities and/or functions associated with the expression of at least one of the two or more human genes in the transgenic mouse.

3. The method of claim 2, wherein the candidate agent inhibits one or more activities and/or functions associated with the expression of human CD33, human Siglec-5, human Siglec-7, human Siglec-9, human Siglec-11, human Siglec-14, and/or human Siglec-16 genes in the transgenic mouse.

4. The method of claim 2, wherein the one or more candidate agents are two or more candidate agents.

5. The method of claim 4, wherein the two or more candidate agents target two or more of the human genes.

6. The method of claim 4, wherein each of the two or more candidate agents targets a human gene selected from the group consisting of CD33, Siglec-5, Siglec-7, Siglec-9, Siglec-11, Siglec-14, and Siglec-16, and wherein each of the two or more candidate agents targets a different human gene.

7. The method of claim 2, wherein the one or more activities and/or functions associated with expression of the two or more human genes are selected from the group consisting of:
   (a) immune cell suppression;
   (b) decreased expression of one or more pro-inflammatory cytokines, optionally wherein the one or more pro-inflammatory cytokines are selected from a group consisting of IFN-a4, IFN-beta, IL-1β, IL-1alpha, TNF-α, IL-6, IL-8, CRP, IL-20 family members, LIF, IFN-gamma, OSM, CNTF, GM-CSF, IL-11, IL-12, IL-17, IL-18, CRP, MCP-1, and MIP-1-beta;
   (c) decreased expression of one or more pro-inflammatory cytokines in one or more cells selected from the group consisting of macrophages, neutrophils, NK cells, dendritic cells, bone marrow-derived dendritic cells, monocytes, osteoclasts, T cells, T helper cells, cytotoxic T cells, granulocytes, and microglial cells;
   (d) increased expression of one or more anti-inflammatory cytokines, optionally wherein the one or more anti-inflammatory cytokines are selected from the group consisting of IL4, IL10, IL13, IL35, IL16, TGF-beta, IL1ra, G-CSF, and soluble receptors for TNF, IFN-beta1a, IFN-beta1b, and IL6;
   (e) increased expression of one or more anti-inflammatory cytokines in one or more cells selected from the group consisting of macrophages, neutrophils, NK cells, dendritic cells, bone marrow-derived dendritic cells, monocytes, osteoclasts, T cells, T helper cells, cytotoxic T cells, granulocytes, and microglial cells;
   (f) inhibition of extracellular signal-regulated kinase (ERK) phosphorylation;
   (g) decreasing tyrosine phosphorylation on one or more cellular proteins, optionally, wherein the one or more cellular proteins comprises ZAP-70 and the tyrosine phosphorylation occurs on Tyr-319 of ZAP-70;
   (h) decreased expression of C—C chemokine receptor 7 (CCR7);
   (i) inhibition of microglial cell chemotaxis toward CCL19-expressing and CCL21-expressing cells;
   (j) decreasing T cell proliferation induced by one or more cells selected from the group consisting of dendritic cells, bone marrow-derived dendritic cells, monocytes, microglia, M1 microglia, activated M1 microglia, M2 microglia, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, and M2 NK cells;

(k) inhibition of osteoclast production, decreased rate of osteoclastogenesis, or both;

(l) decreasing survival of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia;

(m) decreasing proliferation of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia;

(n) inhibiting migration of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia;

(o) inhibiting one or more functions of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia;

(p) inhibiting maturation of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia;

(q) inhibition of one or more types of clearance selected from the group consisting of apoptotic neuron clearance, nerve tissue debris clearance, non-nerve tissue debris clearance, bacteria clearance, other foreign body clearance, disease-causing protein clearance, disease-causing peptide clearance, and tumor cell clearance; optionally wherein the disease-causing protein is selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides and the tumor cell is from a cancer selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer;

(r) inhibition of phagocytosis of one or more of apoptotic neurons, nerve tissue debris, non-nerve tissue debris, bacteria, other foreign bodies, disease-causing proteins, disease-causing peptides, disease-causing nucleic acids, or tumor cells; optionally wherein the disease-causing nucleic acids are antisense GGCCCC (G2C4) repeat-expansion RNA, the disease-causing proteins are selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and the tumor cells are from a cancer selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, or thyroid cancer;

(s) inhibition of tumor cell killing by one or more of microglia, macrophages, neutrophils, NK cells, dendritic cells, bone marrow-derived dendritic cells, neutrophils, T cells, T helper cells, or cytotoxic T cells;

(t) inhibiting anti-tumor cell proliferation activity of one or more of microglia, macrophages, neutrophils, NK cells, dendritic cells, bone marrow-derived dendritic cells, neutrophils, T cells, T helper cells, or cytotoxic T cells;

(u) inhibition of anti-tumor cell metastasis activity of one or more of microglia, macrophages, neutrophils, NK cells, dendritic cells, bone marrow-derived dendritic cells, neutrophils, T cells, T helper cells, or cytotoxic T cells;

(v) inhibition of one or more ITAM motif containing receptors, optionally wherein the one or more ITAM motif containing receptors are selected from the group consisting of TREM1, TREM2, Sirp beta, FcgR, DAP10, and DAP12;

(w) inhibition of signaling by one or more pattern recognition receptors (PRRs), optionally wherein the one or more PRRs are selected from the group consisting of receptors that identify pathogen-associated molecular patterns (PAMPs), receptors that identify damage-associated molecular patterns (DAMPs), and any combination thereof;

(x) inhibition of one or more receptors comprising the motif D/EX$_{0-2}$YxxL/IX$_{6-8}$ YxxL/I (SEQ ID NO: 22);

(y) inhibition of signaling by one or more Toll-like receptors;

(z) inhibition of the JAK-STAT signaling pathway;

(aa) inhibition of nuclear factor kappa-light-chain-enhancer of activated B cells (NFκB);

(bb) de-phosphorylation of an ITAM motif containing receptor;

(cc) decreased expression of one or more inflammatory receptors, optionally wherein the one or more inflammatory receptors comprise CD86 and the one or more inflammatory receptors are expressed on one or more of microglia, macrophages, neutrophils, NK cells, dendritic cells, bone marrow-derived dendritic cells, neutrophils, T cells, T helper cells, or cytotoxic T cells;

(dd) decreasing expression of one or more ITAM-dependent genes, optionally wherein the one more ITAM-dependent genes are activated by nuclear factor of activated T cells (NFAT) transcription factors;

(ee) promoting differentiation of one or more of immunosuppressor dendritic cells, immunosuppressor macrophages, immunosuppressor neutrophils, immunosuppressor NK cells, myeloid derived suppressor cells, tumor-associated macrophages, tumor-associated neutrophils, tumor-associated NK cells, and regulatory T cells;

(ff) rescuing functionality of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells;

(gg) increasing infiltration of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells into tumors;

(hh) increasing the number of tumor-promoting myeloid/granulocytic immune-suppressive cells in a tumor, in peripheral blood, or in another lymphoid organ;

(ii) enhancing tumor-promoting activity of myeloid-derived suppressor cells;

(jj) increasing expression of tumor-promoting cytokines in a tumor or in peripheral blood, optionally wherein the tumor-promoting cytokines are TGF-beta or IL-10;

(kk) increasing tumor infiltration of tumor-promoting FoxP3+ regulatory T lymphocytes;

(ll) enhancing tumor-promoting activity of myeloid-derived suppressor cells (MDSC);

(mm) decreasing activation of tumor-specific T lymphocytes with tumor killing potential;

(nn) decreasing infiltration of tumor-specific NK cells with tumor killing potential;

(oo) decreasing the tumor killing potential of NK cells;

(pp) decreasing infiltration of tumor-specific B lymphocytes with potential to enhance immune response;

(qq) decreasing infiltration of tumor-specific T lymphocytes with tumor killing potential;

(rr) increasing tumor volume;

(ss) increasing tumor growth rate;

(tt) increasing metastasis;

(uu) increasing rate of tumor recurrence;

(vv) decreasing efficacy of one or more immune-therapies that modulate anti-tumor T cell responses, optionally wherein the one or more immune-therapies are immune-therapies that target one or more target proteins selected from the group consisting of PD1/PDL1, CTLA4, CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG, DR-5, and any combination thereof, or cancer vaccines;

(ww) inhibition of PLCγ/PKC/calcium mobilization;

(xx) inhibition of PI3K/Akt, Ras/MAPK signaling; and (yy) any combination thereof.

8. The method of claim 2, wherein the transgenic mouse suffers from a disease, disorder, and/or injury.

9. The method of claim 2, wherein administering the one or more candidate agents reduces or eliminates one or more signs and/or symptoms of a disease, disorder, and/or injury.

10. The method of claim 8, wherein the disease, disorder, and/or injury is one or more of autoimmunity, susceptibility to infection, cancer, proliferative disorders, and neurodegenerative disorders.

11. The method of claim 8, wherein the disease, disorder, and/or injury is one or more of dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV infection, and *Haemophilus influenza* infection.

12. The method of claim 2, wherein the effect of the one or more candidate agents is selected from the group consisting of:
    (a) reducing cell surface levels of one or more polypeptides encoded by the human CD33, Siglec-5, Siglec-7, Siglec-9, Siglec-11, Siglec-14, or Siglec-16 genes;
    (b) competing for binding with a natural ligand of one or more polypeptides encoded by the human CD33, Siglec-5, Siglec-7, Siglec-9, Siglec-11, Siglec-14, or Siglec-16 genes;
    (c) reducing T cell proliferation and/or phagocytosis;
    (d) increasing the survival of macrophages, neutrophils, NK cells, and/or dendritic cells;
    (e) inducing CCR7 and/or F-actin in microglia, macrophages, neutrophils, NK cells, and/or dendritic cells;
    (f) increasing expression of one or more inflammatory cell surface markers on macrophages, neutrophils, and/or NK cells;
    (g) suppressing myeloid-derived suppressor cell (MDSC) proliferation, activation, and/or function;
    (h) reducing IL-10 secretion from one or more myeloid cells;
    (i) inducing SYK and/or ERK activation and/or phosphorylation; and
    (j) any combination thereof.

13. The method of claim 1, wherein:
    the genome comprises the human genes Siglec-5 and Siglec-14;
    the genome comprises the human genes Siglec-11 and Siglec-16;
    the genome comprises the human genes CD33, Siglec-7, and Siglec-9; or
    the genome comprises the human genes CD33, Siglec-5, Siglec-7, Siglec-9, Siglec-11, Siglec-14, and Siglec-16.

14. The method of claim 1, wherein:
    the two or more human genes comprise all intronic and exonic sequences of one or more of the two or more human genes;
    the two or more human genes comprise at least one flanking sequence at the 5' and/or 3' end of one or more of the two or more human genes;
    the two or more human genes comprise at least one flanking sequence at the 5' and/or 3' end of one or more of the two or more human genes, and the flanking sequence is at least 10,000 base pairs in length;
    the two or more human genes comprise at least one flanking sequence at the 5' and/or 3' end of one or more of the two or more human genes, and the flanking sequence comprises one or more human transcriptional regulatory elements; or
    the two or more human genes comprise at least one flanking sequence at the 5' and/or 3' end of one or more of the two or more human genes, the flanking sequence comprises one or more human transcriptional regulatory elements, and the one or more human transcriptional regulatory elements directs expression of the two or more of human genes.

15. The method of claim 1, wherein:
    the human CD33 encodes a polypeptide at least 95% identical to a polypeptide encoded by the nucleic acid sequence of SEQ ID NO: 15, or encodes a polypeptide at least 95% identical to a sequence selected from the group consisting of SEQ ID NOS: 1-3;
    the human Siglec-5 gene encodes a polypeptide at least 95% identical to a polypeptide encoded by the nucleic acid sequence of SEQ ID NO: 16, or encodes a polypeptide at least 95% identical to SEQ ID NO: 4;
    the human Siglec-7 gene encodes a polypeptide at least 95% identical to a polypeptide encoded by the nucleic acid sequence of SEQ ID NO: 17, or encodes a polypeptide at least 95% identical to a sequence selected from the group consisting of SEQ ID NOS: 5-8;
    the human Siglec-9 gene encodes a polypeptide at least 95% identical to a polypeptide encoded by the nucleic acid sequence of SEQ ID NO: 18, or encodes a polypeptide at least 95% identical to SEQ ID NO: 9 or SEQ ID NO: 10;
    the human Siglec-11 gene encodes a polypeptide at least 95% identical to a polypeptide encoded by the nucleic acid sequence of SEQ ID NO: 19, or encodes a polypeptide at least 95% identical to SEQ ID NO: 11 or SEQ ID NO: 12;
    the human Siglec-14 gene encodes a polypeptide at least 95% identical to a polypeptide encoded by the nucleic acid sequence of SEQ ID NO: 20, or encodes a polypeptide at least 95% identical to SEQ ID NO: 13; or
    the human Siglec-16 gene encodes a polypeptide at least 95% identical to a polypeptide encoded by the nucleic acid sequence of SEQ ID NO: 21, or encodes a polypeptide at least 95% identical to SEQ ID NO: 14.

16. The method of claim 1, wherein:
    the myeloid cells are selected from the group consisting of myeloid-derived suppressor cells, granulocyte-like myeloid-derived suppressor cells, monocyte-like myeloid-derived suppressor cells, monocytes, macrophages, bone marrow-derived macrophages, M1 macrophages, activated M1 macrophages, M2 macrophages, neutrophils, M1 neutrophils, activated M1 neutrophils, M2 neutrophils, basophils, eosinophils, erythrocytes, dendritic cells, bone marrow-derived dendritic cells, megakaryocytes, and any combination thereof;
    the NK cells are selected from the group consisting of M1 NK cells, activated M1 NK cells, M2 NK cells, and any combination thereof;
    the T cells are selected from the group consisting of T helper cells, cytotoxic T cells, regulatory T cells (Tregs), and any combination thereof; or
    the microglia are selected from the group consisting of brain microglia, M1 microglia, activated M1 microglia, M2 microglia, and any combination thereof.

17. The method of claim 1, wherein expression of the two or more human genes in the one or more cells of the transgenic mouse recapitulates the expression pattern of the two or more human genes in a corresponding human cell.

18. The method of claim 1, wherein the two or more human genes are co-expressed, and co-expression of the two or more human genes suppresses one or more myeloid immune cell functions.

19. The method of claim 18, wherein the one or more myeloid immune cell functions are selected from the group consisting of:
    (a) phagocytosis;
    (b) antigen presentation;
    (c) immune cell recruitment;
    (d) immune cell maturation, migration, proliferation, differentiation, and/or survival;
    (e) modulation of adaptive immune cells such as B cells and T cells;

(f) expression and/or secretion of one or more cytokines and/or chemokines;
(g) tumor infiltration, tumor cell recognition, and/or tumor cell killing;
(h) releasing granules (degranulation) or neutrophil extracellular traps (NETs);
(i) anti-parasitic activities;
(j) bactericidal activities;
(k) clearance of cellular debris and/or protein aggregates; and
(l) any combination thereof.

20. The method of claim 1, wherein expression of the two or more human genes humanizes the Siglec repertoire on the one or more cells of the transgenic mouse.

21. The method of claim 1, wherein the transgenic mouse comprises a genome comprising one or more non-functional murine genes, wherein the one or more non-functional murine genes are selected from the group consisting of murine CD33, murine Siglec-5, murine Siglec-7, murine Siglec-9, murine Siglec-11, and any combination thereof.

22. The method of claim 1, wherein the transgenic mouse comprises a genome comprising a non-functional murine CD33 gene, a non-functional murine Siglec-5 gene, a non-functional murine Siglec-7 gene, a non-functional murine Siglec-9 gene, and a non-functional murine Siglec-11 gene.

* * * * *

SEQUENCE LISTING

<160> NUMBER OF SEQ ID NOS: 22

<210> SEQ ID NO 1
<211> LENGTH: 364
<212> TYPE: PRT
<213> ORGANISM: Homo sapiens

<400> SEQUENCE: 1

Met Pro Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
            20                  25                  30

Glu Gly Leu Cys Val Leu Val Pro Cys Thr Phe Phe His Pro Ile Pro
        35                  40                  45

Tyr Tyr Asp Lys Asn Ser Pro Val His Gly Tyr Trp Phe Arg Glu Gly
    50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp

```
                100             105             110
Asn Gly Ser Tyr Phe Arg Met Glu Arg Gly Ser Thr Lys Tyr Ser
            115                 120                 125
Tyr Lys Ser Pro Gln Leu Ser Val His Val Thr Asp Leu Thr His Arg
    130                 135                 140
Pro Lys Ile Leu Ile Pro Gly Thr Leu Glu Pro Gly His Ser Lys Asn
145                 150                 155                 160
Leu Thr Cys Ser Val Ser Trp Ala Cys Glu Gln Gly Thr Pro Pro Ile
                165                 170                 175
Phe Ser Trp Leu Ser Ala Ala Pro Thr Ser Leu Gly Pro Arg Thr Thr
            180                 185                 190
His Ser Ser Val Leu Ile Ile Thr Pro Arg Pro Gln Asp His Gly Thr
                195                 200                 205
Asn Leu Thr Cys Gln Val Lys Phe Ala Gly Ala Gly Val Thr Thr Glu
    210                 215                 220
Arg Thr Ile Gln Leu Asn Val Thr Tyr Val Pro Gln Asn Pro Thr Thr
225                 230                 235                 240
Gly Ile Phe Pro Gly Asp Gly Ser Gly Lys Gln Glu Thr Arg Ala Gly
                245                 250                 255
Val Val His Gly Ala Ile Gly Gly Ala Gly Val Thr Ala Leu Leu Ala
                260                 265                 270
Leu Cys Leu Cys Leu Ile Phe Phe Ile Val Lys Thr His Arg Arg Lys
            275                 280                 285
Ala Ala Arg Thr Ala Val Gly Arg Asn Asp Thr His Pro Thr Thr Gly
    290                 295                 300
Ser Ala Ser Pro Lys His Gln Lys Lys Ser Lys Leu His Gly Pro Thr
305                 310                 315                 320
Glu Thr Ser Ser Cys Ser Gly Ala Ala Pro Thr Val Glu Met Asp Glu
                325                 330                 335
Glu Leu His Tyr Ala Ser Leu Asn Phe His Gly Met Asn Pro Ser Lys
            340                 345                 350
Asp Thr Ser Thr Glu Tyr Ser Glu Val Arg Thr Gln
        355                 360

<210> SEQ ID NO 2
<211> LENGTH: 310
<212> TYPE: PRT
<213> ORGANISM: Homo sapiens

<400> SEQUENCE: 2

Met Pro Leu Leu Leu Leu Leu Pro Leu Leu Trp Ala Gly Ala Leu Ala
1               5                   10                  15
Met Asp Pro Asn Phe Trp Leu Gln Val Gln Glu Ser Val Thr Val Gln
            20                  25                  30
Glu Gly Leu Cys Val Leu Val Pro Cys Thr Phe Phe His Pro Ile Pro
        35                  40                  45
Tyr Tyr Asp Lys Asn Ser Pro Val His Gly Tyr Trp Phe Arg Glu Gly
    50                  55                  60
Ala Ile Ile Ser Arg Asp Ser Pro Val Ala Thr Asn Lys Leu Asp Gln
65                  70                  75                  80
Glu Val Gln Glu Glu Thr Gln Gly Arg Phe Arg Leu Leu Gly Asp Pro
                85                  90                  95
Ser Arg Asn Asn Cys Ser Leu Ser Ile Val Asp Ala Arg Arg Arg Asp
            100                 105                 110
```

Asn Gly Ser Tyr Phe Phe Arg Met Glu Arg Gly Ser Thr Lys Tyr Ser
            115                 120                 125

Tyr Lys Ser Pro Gln Leu Ser Val His Val Thr Asp Leu Thr His Arg
130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
                180                 185                 190

His Ser Ser Val Leu Ile Ile Thr Pro Arg Pro Gln Asp His Gly Thr
                195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Val Val His Gly Ala Ile Gly Gly Ala Gly Val Thr Ala Leu Leu Ala
                260                 265                 270

Leu Cys Leu Cys Leu Ile Phe Phe Ile Val Lys Thr His Arg Arg Lys
                275                 280                 285

Ala Ala Arg Thr Ala Val Gly Arg Asn Asp Thr His Pro Thr Thr Gly
            290                 295                 300

Ser Ala Ser Pro Val Arg
305                 310

<210> SEQ ID NO 3
<211> LENGTH: 237
<212> TYPE: PRT
<213> ORGANISM: Homo sapiens

<400> SEQUENCE: 3

Met Pro Leu Leu Leu Leu Pro Leu Leu Trp Ala Asp Leu Thr His
1               5                   10                  15

Arg Pro Lys Ile Leu Ile Pro Gly Thr Leu Glu Pro Gly His Ser Lys
                20                  25                  30

Asn Leu Thr Cys Ser Val Ser Trp Ala Cys Glu Gln Gly Thr Pro Pro
            35                  40                  45

Ile Phe Ser Trp Leu Ser Ala Ala Pro Thr Ser Leu Gly Pro Arg Thr
    50                  55                  60

Thr His Ser Ser Val Leu Ile Ile Thr Pro Arg Pro Gln Asp His Gly
65                  70                  75                  80

Thr Asn Leu Thr Cys Gln Val Lys Phe Ala Gly Ala Gly Val Thr Thr
                85                  90                  95

Glu Arg Thr Ile Gln Leu Asn Val Thr Tyr Val Pro Gln Asn Pro Thr
            100                 105                 110

Thr Gly Ile Phe Pro Gly Asp Gly Ser Gly Lys Gln Glu Thr Arg Ala
        115                 120                 125

Gly Val Val His Gly Ala Ile Gly Gly Ala Gly Val Thr Ala Leu Leu
    130                 135                 140

Ala Leu Cys Leu Cys Leu Ile Phe Phe Ile Val Lys Thr His Arg Arg
145                 150                 155                 160

Lys Ala Ala Arg Thr Ala Val Gly Arg Asn Asp Thr His Pro Thr Thr
                165                 170                 175

```
Gly Ser Ala Ser Pro Lys His Gln Lys Ser Lys Leu His Gly Pro
            180                 185                 190

Thr Glu Thr Ser Ser Cys Ser Gly Ala Ala Pro Thr Val Glu Met Asp
        195                 200                 205

Glu Glu Leu His Tyr Ala Ser Leu Asn Phe His Gly Met Asn Pro Ser
    210                 215                 220

Lys Asp Thr Ser Thr Glu Tyr Ser Glu Val Arg Thr Gln
225                 230                 235

<210> SEQ ID NO 4
<211> LENGTH: 551
<212> TYPE: PRT
<213> ORGANISM: Homo sapiens

<400> SEQUENCE: 4

Met Leu Pro Leu Leu Leu Pro Leu Leu Trp Gly Gly Ser Leu Gln
1               5                   10                  15

Glu Lys Pro Val Tyr Glu Leu Gln Val Gln Lys Ser Val Thr Val Gln
                20                  25                  30

Glu Gly Leu Cys Val Leu Val Pro Cys Ser Phe Ser Tyr Pro Trp Arg
            35                  40                  45

Ser Trp Tyr Ser Ser Pro Pro Leu Tyr Val Tyr Trp Phe Arg Asp Gly
    50                  55                  60

Glu Ile Pro Tyr Tyr Ala Glu Val Val Ala Thr Asn Asn Pro Asp Arg
65              70                  75                  80

Arg Val Lys Pro Glu Thr Gln Gly Arg Phe Arg Leu Leu Gly Asp Val
                85                  90                  95

Gln Lys Lys Asn Cys Ser Leu Ser Ile Gly Asp Ala Arg Met Glu Asp
            100                 105                 110

Thr Gly Ser Tyr Phe Phe Arg Val Glu Arg Gly Arg Asp Val Lys Tyr
        115                 120                 125

Ser Tyr Gln Gln Asn Lys Leu Asn Leu Glu Val Thr Ala Leu Ile Glu
    130                 135                 140

Lys Pro Asp Ile His Phe Leu Glu Pro Leu Glu Ser Gly Arg Pro Thr
145                 150                 155                 160

Arg Leu Ser Cys Ser Leu Pro Gly Ser Cys Glu Ala Gly Pro Pro Leu
                165                 170                 175

Thr Phe Ser Trp Thr Gly Asn Ala Leu Ser Pro Leu Asp Pro Glu Thr
            180                 185                 190

Thr Arg Ser Ser Glu Leu Thr Leu Thr Pro Arg Pro Glu Asp His Gly
        195                 200                 205

Thr Asn Leu Thr Cys Gln Met Lys Arg Gln Gly Ala Gln Val Thr Thr
    210                 215                 220

Glu Arg Thr Val Gln Leu Asn Val Ser Tyr Ala Pro Gln Thr Ile Thr
225                 230                 235                 240

Ile Phe Arg Asn Gly Ile Ala Leu Glu Ile Leu Gln Asn Thr Ser Tyr
                245                 250                 255

Leu Pro Val Leu Glu Gly Gln Ala Leu Arg Leu Leu Cys Asp Ala Pro
            260                 265                 270

Ser Asn Pro Pro Ala His Leu Ser Trp Phe Gln Gly Ser Pro Ala Leu
        275                 280                 285

Asn Ala Thr Pro Ile Ser Asn Thr Gly Ile Leu Glu Leu Arg Arg Val
    290                 295                 300

Arg Ser Ala Glu Glu Gly Gly Phe Thr Cys Arg Ala Gln His Pro Leu
```

```
                305                 310                 315                 320
Gly Phe Leu Gln Ile Phe Leu Asn Leu Ser Val Tyr Ser Leu Pro Gln
                325                 330                 335

Leu Leu Gly Pro Ser Cys Ser Trp Glu Ala Glu Gly Leu His Cys Arg
                340                 345                 350

Cys Ser Phe Arg Ala Arg Pro Ala Pro Ser Leu Cys Trp Arg Leu Glu
                355                 360                 365

Glu Lys Pro Leu Glu Gly Asn Ser Ser Gln Gly Ser Phe Lys Val Asn
                370                 375                 380

Ser Ser Ser Ala Gly Pro Trp Ala Asn Ser Ser Leu Ile Leu His Gly
385                 390                 395                 400

Gly Leu Ser Ser Asp Leu Lys Val Ser Cys Lys Ala Trp Asn Ile Tyr
                    405                 410                 415

Gly Ser Gln Ser Gly Ser Val Leu Leu Leu Gln Gly Arg Ser Asn Leu
                420                 425                 430

Gly Thr Gly Val Val Pro Ala Ala Leu Gly Gly Ala Gly Val Met Ala
                435                 440                 445

Leu Leu Cys Ile Cys Leu Cys Leu Ile Phe Phe Leu Ile Val Lys Ala
                450                 455                 460

Arg Arg Lys Gln Ala Ala Gly Arg Pro Glu Lys Met Asp Asp Glu Asp
465                 470                 475                 480

Pro Ile Met Gly Thr Ile Thr Ser Gly Ser Arg Lys Lys Pro Trp Pro
                    485                 490                 495

Asp Ser Pro Gly Asp Gln Ala Ser Pro Pro Gly Asp Ala Pro Pro Leu
                500                 505                 510

Glu Glu Gln Lys Glu Leu His Tyr Ala Ser Leu Ser Phe Ser Glu Met
                515                 520                 525

Lys Ser Arg Glu Pro Lys Asp Gln Glu Ala Pro Ser Thr Thr Glu Tyr
                530                 535                 540

Ser Glu Ile Lys Thr Ser Lys
545                 550

<210> SEQ ID NO 5
<211> LENGTH: 467
<212> TYPE: PRT
<213> ORGANISM: Homo sapiens

<400> SEQUENCE: 5

Met Leu Leu Leu Leu Leu Pro Leu Leu Trp Gly Arg Glu Arg Val
1               5                   10                  15

Glu Gly Gln Lys Ser Asn Arg Lys Asp Tyr Ser Leu Thr Met Gln Ser
                20                  25                  30

Ser Val Thr Val Gln Glu Gly Met Cys Val His Val Arg Cys Ser Phe
                35                  40                  45

Ser Tyr Pro Val Asp Ser Gln Thr Asp Ser Asp Pro Val His Gly Tyr
                50                  55                  60

Trp Phe Arg Ala Gly Asn Asp Ile Ser Trp Lys Ala Pro Val Ala Thr
65                  70                  75                  80

Asn Asn Pro Ala Trp Ala Val Gln Glu Glu Thr Arg Asp Arg Phe His
                85                  90                  95

Leu Leu Gly Asp Pro Gln Thr Lys Asn Cys Thr Leu Ser Ile Arg Asp
                100                 105                 110

Ala Arg Met Ser Asp Ala Gly Arg Tyr Phe Phe Arg Met Glu Lys Gly
                115                 120                 125
```

```
Asn Ile Lys Trp Asn Tyr Lys Tyr Asp Gln Leu Ser Val Asn Val Thr
    130                 135                 140

Ala Leu Thr His Arg Pro Asn Ile Leu Ile Pro Gly Thr Leu Glu Ser
145                 150                 155                 160

Gly Cys Phe Gln Asn Leu Thr Cys Ser Val Pro Trp Ala Cys Glu Gln
                165                 170                 175

Gly Thr Pro Pro Met Ile Ser Trp Met Gly Thr Ser Val Ser Pro Leu
            180                 185                 190

His Pro Ser Thr Thr Arg Ser Ser Val Leu Thr Leu Ile Pro Gln Pro
        195                 200                 205

Gln His His Gly Thr Ser Leu Thr Cys Gln Val Thr Leu Pro Gly Ala
    210                 215                 220

Gly Val Thr Thr Asn Arg Thr Ile Gln Leu Asn Val Ser Tyr Pro Pro
225                 230                 235                 240

Gln Asn Leu Thr Val Thr Val Phe Gln Gly Glu Gly Thr Ala Ser Thr
                245                 250                 255

Ala Leu Gly Asn Ser Ser Ser Leu Ser Val Leu Glu Gly Gln Ser Leu
            260                 265                 270

Arg Leu Val Cys Ala Val Asp Ser Asn Pro Pro Ala Arg Leu Ser Trp
        275                 280                 285

Thr Trp Arg Ser Leu Thr Leu Tyr Pro Ser Gln Pro Ser Asn Pro Leu
    290                 295                 300

Val Leu Glu Leu Gln Val His Leu Gly Asp Glu Gly Glu Phe Thr Cys
305                 310                 315                 320

Arg Ala Gln Asn Ser Leu Gly Ser Gln His Val Ser Leu Asn Leu Ser
                325                 330                 335

Leu Gln Gln Glu Tyr Thr Gly Lys Met Arg Pro Val Ser Gly Val Leu
            340                 345                 350

Leu Gly Ala Val Gly Gly Ala Gly Ala Thr Ala Leu Val Phe Leu Ser
        355                 360                 365

Phe Cys Val Ile Phe Ile Val Val Arg Ser Cys Arg Lys Lys Ser Ala
    370                 375                 380

Arg Pro Ala Ala Asp Val Gly Asp Ile Gly Met Lys Asp Ala Asn Thr
385                 390                 395                 400

Ile Arg Gly Ser Ala Ser Gln Gly Asn Leu Thr Glu Ser Trp Ala Asp
                405                 410                 415

Asp Asn Pro Arg His His Gly Leu Ala Ala His Ser Ser Gly Glu Glu
            420                 425                 430

Arg Glu Ile Gln Tyr Ala Pro Leu Ser Phe His Lys Gly Glu Pro Gln
        435                 440                 445

Asp Leu Ser Gly Gln Glu Ala Thr Asn Asn Glu Tyr Ser Glu Ile Lys
    450                 455                 460

Ile Pro Lys
465

<210> SEQ ID NO 6
<211> LENGTH: 374
<212> TYPE: PRT
<213> ORGANISM: Homo sapiens

<400> SEQUENCE: 6

Met Leu Leu Leu Leu Leu Pro Leu Leu Trp Gly Arg Glu Arg Val
1               5                   10                  15

Glu Gly Gln Lys Ser Asn Arg Lys Asp Tyr Ser Leu Thr Met Gln Ser
            20                  25                  30
```

```
Ser Val Thr Val Gln Glu Gly Met Cys Val His Val Arg Cys Ser Phe
        35                  40                  45

Ser Tyr Pro Val Asp Ser Gln Thr Asp Ser Asp Pro Val His Gly Tyr
        50                  55                  60

Trp Phe Arg Ala Gly Asn Asp Ile Ser Trp Lys Ala Pro Val Ala Thr
65                  70                  75                  80

Asn Asn Pro Ala Trp Ala Val Gln Glu Glu Thr Arg Asp Arg Phe His
                85                  90                  95

Leu Leu Gly Asp Pro Gln Thr Lys Asn Cys Thr Leu Ser Ile Arg Asp
            100                 105                 110

Ala Arg Met Ser Asp Ala Gly Arg Tyr Phe Phe Arg Met Glu Lys Gly
        115                 120                 125

Asn Ile Lys Trp Asn Tyr Lys Tyr Asp Gln Leu Ser Val Asn Val Thr
        130                 135                 140

Asp Pro Pro Gln Asn Leu Thr Val Thr Val Phe Gln Gly Glu Gly Thr
145                 150                 155                 160

Ala Ser Thr Ala Leu Gly Asn Ser Ser Leu Ser Val Leu Glu Gly
                165                 170                 175

Gln Ser Leu Arg Leu Val Cys Ala Val Asp Ser Asn Pro Pro Ala Arg
        180                 185                 190

Leu Ser Trp Thr Trp Arg Ser Leu Thr Leu Tyr Pro Ser Gln Pro Ser
        195                 200                 205

Asn Pro Leu Val Leu Glu Leu Gln Val His Leu Gly Asp Glu Gly Glu
        210                 215                 220

Phe Thr Cys Arg Ala Gln Asn Ser Leu Gly Ser Gln His Val Ser Leu
225                 230                 235                 240

Asn Leu Ser Leu Gln Gln Glu Tyr Thr Gly Lys Met Arg Pro Val Ser
                245                 250                 255

Gly Val Leu Leu Gly Ala Val Gly Gly Ala Gly Ala Thr Ala Leu Val
                260                 265                 270

Phe Leu Ser Phe Cys Val Ile Phe Ile Val Arg Ser Cys Arg Lys
        275                 280                 285

Lys Ser Ala Arg Pro Ala Ala Asp Val Gly Asp Ile Gly Met Lys Asp
290                 295                 300

Ala Asn Thr Ile Arg Gly Ser Ala Ser Gln Gly Asn Leu Thr Glu Ser
305                 310                 315                 320

Trp Ala Asp Asp Asn Pro Arg His His Gly Leu Ala Ala His Ser Ser
                325                 330                 335

Gly Glu Glu Arg Glu Ile Gln Tyr Ala Pro Leu Ser Phe His Lys Gly
            340                 345                 350

Glu Pro Gln Asp Leu Ser Gly Gln Glu Ala Thr Asn Asn Glu Tyr Ser
        355                 360                 365

Glu Ile Lys Ile Pro Lys
    370

<210> SEQ ID NO 7
<211> LENGTH: 145
<212> TYPE: PRT
<213> ORGANISM: Homo sapiens

<400> SEQUENCE: 7

Met Leu Leu Leu Leu Leu Pro Leu Leu Trp Gly Arg Glu Arg Val
1               5                   10                  15

Glu Gly Gln Lys Ser Asn Arg Lys Asp Tyr Ser Leu Thr Met Gln Ser
```

```
                    20                  25                  30

Ser Val Thr Val Gln Glu Gly Met Cys Val His Val Arg Cys Ser Phe
         35                  40                  45

Ser Tyr Pro Val Asp Ser Gln Thr Asp Ser Asp Pro Val His Gly Tyr
     50                  55                  60

Trp Phe Arg Ala Gly Asn Asp Ile Ser Trp Lys Ala Pro Val Ala Thr
 65                  70                  75                  80

Asn Asn Pro Ala Trp Ala Val Gln Glu Glu Thr Arg Asp Arg Phe His
                 85                  90                  95

Leu Leu Gly Asp Pro Gln Thr Lys Asn Cys Thr Leu Ser Ile Arg Asp
                100                 105                 110

Ala Arg Met Ser Asp Ala Gly Arg Tyr Phe Phe Arg Met Glu Lys Gly
            115                 120                 125

Asn Ile Lys Trp Asn Tyr Lys Tyr Asp Gln Leu Ser Val Asn Val Thr
        130                 135                 140

Glu
145

<210> SEQ ID NO 8
<211> LENGTH: 145
<212> TYPE: PRT
<213> ORGANISM: Homo sapiens

<400> SEQUENCE: 8

Met Leu Leu Leu Leu Leu Pro Leu Leu Trp Gly Arg Glu Arg Val
 1               5                  10                  15

Glu Gly Gln Lys Ser Asn Arg Lys Asp Tyr Ser Leu Thr Met Gln Ser
                 20                  25                  30

Ser Val Thr Val Gln Glu Gly Met Cys Val His Val Arg Cys Ser Phe
             35                  40                  45

Ser Tyr Pro Val Asp Ser Gln Thr Asp Ser Asp Pro Val His Gly Tyr
     50                  55                  60

Trp Phe Arg Ala Gly Asn Asp Ile Ser Trp Lys Ala Pro Val Ala Thr
 65                  70                  75                  80

Asn Asn Pro Ala Trp Ala Val Gln Glu Glu Thr Arg Asp Arg Phe His
                 85                  90                  95

Leu Leu Gly Asp Pro Gln Thr Lys Asn Cys Thr Leu Ser Ile Arg Asp
                100                 105                 110

Ala Arg Met Ser Asp Ala Gly Arg Tyr Phe Phe Arg Met Glu Lys Gly
            115                 120                 125

Asn Ile Lys Trp Asn Tyr Lys Tyr Asp Gln Leu Ser Val Asn Val Thr
        130                 135                 140

Gly
145

<210> SEQ ID NO 9
<211> LENGTH: 463
<212> TYPE: PRT
<213> ORGANISM: Homo sapiens

<400> SEQUENCE: 9

Met Leu Leu Leu Leu Pro Leu Leu Trp Gly Arg Glu Arg Ala Glu
 1               5                  10                  15

Gly Gln Thr Ser Lys Leu Leu Thr Met Gln Ser Ser Val Thr Val Gln
                 20                  25                  30

Glu Gly Leu Cys Val His Val Pro Cys Ser Phe Ser Tyr Pro Ser His
```

```
                35                  40                  45
Gly Trp Ile Tyr Pro Gly Pro Val His Gly Tyr Trp Phe Arg Glu
 50                  55                  60

Gly Ala Asn Thr Asp Gln Asp Ala Pro Val Ala Thr Asn Asn Pro Ala
 65                  70                  75                  80

Arg Ala Val Trp Glu Glu Thr Arg Asp Arg Phe His Leu Leu Gly Asp
                 85                  90                  95

Pro His Thr Lys Asn Cys Thr Leu Ser Ile Arg Asp Ala Arg Arg Ser
                100                 105                 110

Asp Ala Gly Arg Tyr Phe Phe Arg Met Glu Lys Gly Ser Ile Lys Trp
                115                 120                 125

Asn Tyr Lys His His Arg Leu Ser Val Asn Val Thr Ala Leu Thr His
                130                 135                 140

Arg Pro Asn Ile Leu Ile Pro Gly Thr Leu Ser Gly Cys Pro Gln
145                 150                 155                 160

Asn Leu Thr Cys Ser Val Pro Trp Ala Cys Glu Gln Gly Thr Pro Pro
                165                 170                 175

Met Ile Ser Trp Ile Gly Thr Ser Val Ser Pro Leu Asp Pro Ser Thr
                180                 185                 190

Thr Arg Ser Ser Val Leu Thr Leu Ile Pro Gln Pro Gln Asp His Gly
                195                 200                 205

Thr Ser Leu Thr Cys Gln Val Thr Phe Pro Gly Ala Ser Val Thr Thr
210                 215                 220

Asn Lys Thr Val His Leu Asn Val Ser Tyr Pro Pro Gln Asn Leu Thr
225                 230                 235                 240

Met Thr Val Phe Gln Gly Asp Gly Thr Val Ser Thr Val Leu Gly Asn
                245                 250                 255

Gly Ser Ser Leu Ser Leu Pro Glu Gly Gln Ser Leu Arg Leu Val Cys
                260                 265                 270

Ala Val Asp Ala Val Asp Ser Asn Pro Pro Ala Arg Leu Ser Leu Ser
                275                 280                 285

Trp Arg Gly Leu Thr Leu Cys Pro Ser Gln Pro Ser Asn Pro Gly Val
                290                 295                 300

Leu Glu Leu Pro Trp Val His Leu Arg Asp Ala Ala Glu Phe Thr Cys
305                 310                 315                 320

Arg Ala Gln Asn Pro Leu Gly Ser Gln Gln Val Tyr Leu Asn Val Ser
                325                 330                 335

Leu Gln Ser Lys Ala Thr Ser Gly Val Thr Gln Gly Val Val Gly Gly
                340                 345                 350

Ala Gly Ala Thr Ala Leu Val Phe Leu Ser Phe Cys Val Ile Phe Val
                355                 360                 365

Val Val Arg Ser Cys Arg Lys Lys Ser Ala Arg Pro Ala Ala Gly Val
                370                 375                 380

Gly Asp Thr Gly Ile Glu Asp Ala Asn Ala Val Arg Gly Ser Ala Ser
385                 390                 395                 400

Gln Gly Pro Leu Thr Glu Pro Trp Ala Glu Asp Ser Pro Pro Asp Gln
                405                 410                 415

Pro Pro Pro Ala Ser Ala Arg Ser Ser Val Gly Glu Gly Glu Leu Gln
                420                 425                 430

Tyr Ala Ser Leu Ser Phe Gln Met Val Lys Pro Trp Asp Ser Arg Gly
                435                 440                 445

Gln Glu Ala Thr Asp Thr Glu Tyr Ser Glu Ile Lys Ile His Arg
450                 455                 460
```

<210> SEQ ID NO 10
<211> LENGTH: 479
<212> TYPE: PRT
<213> ORGANISM: Homo sapiens

<400> SEQUENCE: 10

```
Met Leu Leu Leu Leu Pro Leu Leu Trp Gly Arg Glu Arg Ala Glu
1               5                   10                  15

Gly Gln Thr Ser Lys Leu Leu Thr Met Gln Ser Ser Val Thr Val Gln
            20                  25                  30

Glu Gly Leu Cys Val His Val Pro Cys Ser Phe Ser Tyr Pro Ser His
            35                  40                  45

Gly Trp Ile Tyr Pro Gly Pro Val Val His Gly Tyr Trp Phe Arg Glu
    50                  55                  60

Gly Ala Asn Thr Asp Gln Asp Ala Pro Val Ala Thr Asn Asn Pro Ala
65                  70                  75                  80

Arg Ala Val Trp Glu Glu Thr Arg Asp Arg Phe His Leu Leu Gly Asp
                85                  90                  95

Pro His Thr Lys Asn Cys Thr Leu Ser Ile Arg Asp Ala Arg Arg Ser
            100                 105                 110

Asp Ala Gly Arg Tyr Phe Phe Arg Met Glu Lys Gly Ser Ile Lys Trp
        115                 120                 125

Asn Tyr Lys His His Arg Leu Ser Val Asn Val Thr Ala Leu Thr His
    130                 135                 140

Arg Pro Asn Ile Leu Ile Pro Gly Thr Leu Glu Ser Gly Cys Pro Gln
145                 150                 155                 160

Asn Leu Thr Cys Ser Val Pro Trp Ala Cys Glu Gln Gly Thr Pro Pro
                165                 170                 175

Met Ile Ser Trp Ile Gly Thr Ser Val Ser Pro Leu Asp Pro Ser Thr
            180                 185                 190

Thr Arg Ser Ser Val Leu Thr Leu Ile Pro Gln Pro Gln Asp His Gly
        195                 200                 205

Thr Ser Leu Thr Cys Gln Val Thr Phe Pro Gly Ala Ser Val Thr Thr
    210                 215                 220

Asn Lys Thr Val His Leu Asn Val Ser Tyr Pro Pro Gln Asn Leu Thr
225                 230                 235                 240

Met Thr Val Phe Gln Gly Asp Gly Thr Val Ser Thr Val Leu Gly Asn
                245                 250                 255

Gly Ser Ser Leu Ser Leu Pro Glu Gly Gln Ser Leu Arg Leu Val Cys
            260                 265                 270

Ala Val Asp Ala Val Asp Ser Asn Pro Pro Ala Arg Leu Ser Leu Ser
        275                 280                 285

Trp Arg Gly Leu Thr Leu Cys Pro Ser Gln Pro Ser Asn Pro Gly Val
    290                 295                 300

Leu Glu Leu Pro Trp Val His Leu Arg Asp Ala Ala Glu Phe Thr Cys
305                 310                 315                 320

Arg Ala Gln Asn Pro Leu Gly Ser Gln Gln Val Tyr Leu Asn Val Ser
                325                 330                 335

Leu Gln Ser Lys Ala Thr Ser Gly Val Thr Gln Gly Val Val Gly Gly
            340                 345                 350

Ala Gly Ala Thr Ala Leu Val Phe Leu Ser Phe Cys Val Ile Phe Val
        355                 360                 365

Val Val Arg Ser Cys Arg Lys Lys Ser Ala Arg Pro Ala Ala Gly Val
```

```
                    370                 375                 380
Gly Asp Thr Gly Ile Glu Asp Ala Asn Ala Val Arg Gly Ser Ala Ser
385                 390                 395                 400

Gln Ile Leu Asn His Phe Ile Gly Phe Pro Thr Phe Leu Gly Leu Gly
                405                 410                 415

Phe Glu Phe Leu Leu Asn Leu Arg Asp Leu Cys Cys His Pro Asp Ser
                420                 425                 430

Glu Phe Tyr Val Tyr His Phe Ser His Phe Arg Leu Ile Lys Asn Ile
                435                 440                 445

Ala Gly Glu Ile Val Trp Ser Leu Glu Gly Lys Ile Leu Trp Leu Leu
450                 455                 460

Asp Val Ser Asp Phe Phe His Trp Phe Phe Leu Ile Cys Val Gly
465                 470                 475

<210> SEQ ID NO 11
<211> LENGTH: 698
<212> TYPE: PRT
<213> ORGANISM: Homo sapiens

<400> SEQUENCE: 11

Met Val Pro Gly Gln Ala Gln Pro Gln Ser Pro Glu Met Leu Leu Leu
1               5                   10                  15

Pro Leu Leu Leu Pro Val Leu Gly Ala Gly Ser Leu Asn Lys Asp Pro
                20                  25                  30

Ser Tyr Ser Leu Gln Val Gln Arg Gln Val Pro Val Pro Glu Gly Leu
                35                  40                  45

Cys Val Ile Val Ser Cys Asn Leu Ser Tyr Pro Arg Asp Gly Trp Asp
                50                  55                  60

Glu Ser Thr Ala Ala Tyr Gly Tyr Trp Phe Lys Gly Arg Thr Ser Pro
65                  70                  75                  80

Lys Thr Gly Ala Pro Val Ala Thr Asn Asn Gln Ser Arg Glu Val Glu
                85                  90                  95

Met Ser Thr Arg Asp Arg Phe Gln Leu Thr Gly Asp Pro Gly Lys Gly
                100                 105                 110

Ser Cys Ser Leu Val Ile Arg Asp Ala Gln Arg Glu Asp Glu Ala Trp
                115                 120                 125

Tyr Phe Phe Arg Val Glu Arg Gly Ser Arg Val Arg His Ser Phe Leu
                130                 135                 140

Ser Asn Ala Phe Phe Leu Lys Val Thr Ala Leu Thr Lys Lys Pro Asp
145                 150                 155                 160

Val Tyr Ile Pro Glu Thr Leu Glu Pro Gly Gln Pro Val Thr Val Ile
                165                 170                 175

Cys Val Phe Asn Trp Ala Phe Lys Lys Cys Pro Ala Pro Ser Phe Ser
                180                 185                 190

Trp Thr Gly Ala Ala Leu Ser Pro Arg Arg Thr Arg Pro Ser Thr Ser
                195                 200                 205

His Phe Ser Val Leu Ser Phe Thr Pro Ser Pro Gln Asp His Asp Thr
                210                 215                 220

Asp Leu Thr Cys His Val Asp Phe Ser Arg Lys Gly Val Ser Ala Gln
225                 230                 235                 240

Arg Thr Val Arg Leu Arg Val Ala Tyr Ala Pro Lys Asp Leu Ile Ile
                245                 250                 255

Ser Ile Ser His Asp Asn Thr Ser Ala Leu Glu Leu Gln Gly Asn Val
                260                 265                 270
```

```
Ile Tyr Leu Glu Val Gln Lys Gly Gln Phe Leu Arg Leu Leu Cys Ala
            275                 280                 285

Ala Asp Ser Gln Pro Pro Ala Thr Leu Ser Trp Val Leu Gln Asp Arg
            290                 295                 300

Val Leu Ser Ser Ser His Pro Trp Gly Pro Arg Thr Leu Gly Leu Glu
305                 310                 315                 320

Leu Arg Gly Val Arg Ala Gly Asp Ser Gly Arg Tyr Thr Cys Arg Ala
                325                 330                 335

Glu Asn Arg Leu Gly Ser Gln Gln Ala Leu Asp Leu Ser Val Gln
            340                 345                 350

Tyr Pro Pro Glu Asn Leu Arg Val Met Val Ser Gln Ala Asn Arg Thr
            355                 360                 365

Val Leu Glu Asn Leu Gly Asn Gly Thr Ser Leu Pro Val Leu Glu Gly
            370                 375                 380

Gln Ser Leu Arg Leu Val Cys Val Thr His Ser Ser Pro Pro Ala Arg
385                 390                 395                 400

Leu Ser Trp Thr Arg Trp Gly Gln Thr Val Gly Pro Ser Gln Pro Ser
                405                 410                 415

Asp Pro Gly Val Leu Glu Leu Pro Pro Ile Gln Met Glu His Glu Gly
                420                 425                 430

Glu Phe Thr Cys His Ala Gln His Pro Leu Gly Ser Gln His Val Ser
            435                 440                 445

Leu Ser Leu Ser Val His Tyr Pro Pro Gln Leu Leu Gly Pro Ser Cys
            450                 455                 460

Ser Trp Glu Ala Glu Gly Leu His Cys Ser Cys Ser Ser Gln Ala Ser
465                 470                 475                 480

Pro Ala Pro Ser Leu Arg Trp Trp Leu Gly Glu Glu Leu Leu Glu Gly
                485                 490                 495

Asn Ser Ser Gln Gly Ser Phe Glu Val Thr Pro Ser Ser Ala Gly Pro
            500                 505                 510

Trp Ala Asn Ser Ser Leu Ser Leu His Gly Gly Leu Ser Ser Gly Leu
            515                 520                 525

Arg Leu Arg Cys Lys Ala Trp Asn Val His Gly Ala Gln Ser Gly Ser
530                 535                 540

Val Phe Gln Leu Leu Pro Gly Lys Leu Glu His Gly Gly Gly Leu Gly
545                 550                 555                 560

Leu Gly Ala Ala Leu Gly Ala Gly Val Ala Ala Leu Leu Ala Phe Cys
                565                 570                 575

Ser Cys Leu Val Val Phe Arg Val Lys Ile Cys Arg Lys Glu Ala Arg
            580                 585                 590

Lys Arg Ala Ala Ala Glu Gln Asp Val Pro Ser Thr Leu Gly Pro Ile
            595                 600                 605

Ser Gln Gly His Gln His Glu Cys Ser Ala Gly Ser Ser Gln Asp His
            610                 615                 620

Pro Pro Pro Gly Ala Ala Thr Tyr Thr Pro Gly Lys Gly Glu Glu Gln
625                 630                 635                 640

Glu Leu His Tyr Ala Ser Leu Ser Phe Gln Gly Leu Arg Leu Trp Glu
                645                 650                 655

Pro Ala Asp Gln Glu Ala Pro Ser Thr Thr Glu Tyr Ser Glu Ile Lys
                660                 665                 670

Ile His Thr Gly Gln Pro Leu Arg Gly Pro Gly Phe Gly Leu Gln Leu
            675                 680                 685

Glu Arg Glu Met Ser Gly Met Val Pro Lys
```

```
                        690                 695

<210> SEQ ID NO 12
<211> LENGTH: 602
<212> TYPE: PRT
<213> ORGANISM: Homo sapiens

<400> SEQUENCE: 12

Met Val Pro Gly Gln Ala Gln Pro Ser Pro Glu Met Leu Leu Leu
1               5                   10                  15

Pro Leu Leu Leu Pro Val Leu Gly Ala Gly Ser Leu Asn Lys Asp Pro
                20                  25                  30

Ser Tyr Ser Leu Gln Val Gln Arg Gln Val Pro Val Pro Glu Gly Leu
            35                  40                  45

Cys Val Ile Val Ser Cys Asn Leu Ser Tyr Pro Arg Asp Gly Trp Asp
    50                  55                  60

Glu Ser Thr Ala Ala Tyr Gly Tyr Trp Phe Lys Gly Arg Thr Ser Pro
65              70                  75                  80

Lys Thr Gly Ala Pro Val Ala Thr Asn Asn Gln Ser Arg Glu Val Glu
                85                  90                  95

Met Ser Thr Arg Asp Arg Phe Gln Leu Thr Gly Asp Pro Gly Lys Gly
                100                 105                 110

Ser Cys Ser Leu Val Ile Arg Asp Ala Gln Arg Glu Asp Glu Ala Trp
            115                 120                 125

Tyr Phe Phe Arg Val Glu Arg Gly Ser Arg Val Arg His Ser Phe Leu
    130                 135                 140

Ser Asn Ala Phe Phe Leu Lys Val Thr Ala Leu Thr Lys Lys Pro Asp
145                 150                 155                 160

Val Tyr Ile Pro Glu Thr Leu Glu Pro Gly Gln Pro Val Thr Val Ile
                165                 170                 175

Cys Val Phe Asn Trp Ala Phe Lys Lys Cys Pro Ala Pro Ser Phe Ser
            180                 185                 190

Trp Thr Gly Ala Ala Leu Ser Pro Arg Arg Thr Arg Pro Ser Thr Ser
    195                 200                 205

His Phe Ser Val Leu Ser Phe Thr Pro Ser Pro Gln Asp His Asp Thr
210                 215                 220

Asp Leu Thr Cys His Val Asp Phe Ser Arg Lys Gly Val Ser Ala Gln
225                 230                 235                 240

Arg Thr Val Arg Leu Arg Val Ala Tyr Ala Pro Lys Asp Leu Ile Ile
                245                 250                 255

Ser Ile Ser His Asp Asn Thr Ser Ala Leu Glu Leu Gln Gly Asn Val
            260                 265                 270

Ile Tyr Leu Glu Val Gln Lys Gly Gln Phe Leu Arg Leu Leu Cys Ala
    275                 280                 285

Ala Asp Ser Gln Pro Pro Ala Thr Leu Ser Trp Val Leu Gln Asp Arg
290                 295                 300

Val Leu Ser Ser Ser His Pro Trp Gly Pro Arg Thr Leu Gly Leu Glu
305                 310                 315                 320

Leu Arg Gly Val Arg Ala Gly Asp Ser Gly Arg Tyr Thr Cys Arg Ala
                325                 330                 335

Glu Asn Arg Leu Gly Ser Gln Gln Ala Leu Asp Leu Ser Val Gln
            340                 345                 350

Tyr Pro Pro Glu Asn Leu Arg Val Met Val Ser Gln Ala Asn Arg Thr
    355                 360                 365
```

```
Val Leu Glu Asn Leu Gly Asn Gly Thr Ser Leu Pro Val Leu Glu Gly
    370                 375                 380

Gln Ser Leu Arg Leu Val Cys Val Thr His Ser Ser Pro Pro Ala Arg
385                 390                 395                 400

Leu Ser Trp Thr Arg Trp Gly Gln Thr Val Gly Pro Ser Gln Pro Ser
                405                 410                 415

Asp Pro Gly Val Leu Glu Leu Pro Pro Ile Gln Met Glu His Glu Gly
                420                 425                 430

Glu Phe Thr Cys His Ala Gln His Pro Leu Gly Ser Gln His Val Ser
                435                 440                 445

Leu Ser Leu Ser Val His Trp Lys Leu Glu His Gly Gly Leu Gly
450                 455                 460

Leu Gly Ala Ala Leu Gly Ala Gly Val Ala Ala Leu Leu Ala Phe Cys
465                 470                 475                 480

Ser Cys Leu Val Val Phe Arg Val Lys Ile Cys Arg Lys Glu Ala Arg
                485                 490                 495

Lys Arg Ala Ala Ala Glu Gln Asp Val Pro Ser Thr Leu Gly Pro Ile
                500                 505                 510

Ser Gln Gly His Gln His Glu Cys Ser Ala Gly Ser Ser Gln Asp His
                515                 520                 525

Pro Pro Pro Gly Ala Ala Thr Tyr Thr Pro Gly Lys Gly Glu Glu Gln
530                 535                 540

Glu Leu His Tyr Ala Ser Leu Ser Phe Gln Gly Leu Arg Leu Trp Glu
545                 550                 555                 560

Pro Ala Asp Gln Glu Ala Pro Ser Thr Thr Glu Tyr Ser Glu Ile Lys
                565                 570                 575

Ile His Thr Gly Gln Pro Leu Arg Gly Pro Gly Phe Gly Leu Gln Leu
                580                 585                 590

Glu Arg Glu Met Ser Gly Met Val Pro Lys
595                 600

<210> SEQ ID NO 13
<211> LENGTH: 396
<212> TYPE: PRT
<213> ORGANISM: Homo sapiens

<400> SEQUENCE: 13

Met Leu Pro Leu Leu Leu Leu Pro Leu Leu Trp Gly Gly Ser Leu Gln
1               5                   10                  15

Glu Lys Pro Val Tyr Glu Leu Gln Val Gln Lys Ser Val Thr Val Gln
                20                  25                  30

Glu Gly Leu Cys Val Leu Val Pro Cys Ser Phe Ser Tyr Pro Trp Arg
            35                  40                  45

Ser Trp Tyr Ser Ser Pro Pro Leu Tyr Val Tyr Trp Phe Arg Asp Gly
        50                  55                  60

Glu Ile Pro Tyr Tyr Ala Glu Val Val Ala Thr Asn Asn Pro Asp Arg
65                  70                  75                  80

Arg Val Lys Pro Glu Thr Gln Gly Arg Phe Arg Leu Leu Gly Asp Val
                85                  90                  95

Gln Lys Lys Asn Cys Ser Leu Ser Ile Gly Asp Ala Arg Met Glu Asp
                100                 105                 110

Thr Gly Ser Tyr Phe Phe Arg Val Glu Arg Gly Arg Asp Val Lys Tyr
            115                 120                 125

Ser Tyr Gln Gln Asn Lys Leu Asn Leu Glu Val Thr Ala Leu Ile Glu
        130                 135                 140
```

```
Lys Pro Asp Ile His Phe Leu Glu Pro Leu Glu Ser Gly Arg Pro Thr
145                 150                 155                 160

Arg Leu Ser Cys Ser Leu Pro Gly Ser Cys Glu Ala Gly Pro Pro Leu
                165                 170                 175

Thr Phe Ser Trp Thr Gly Asn Ala Leu Ser Pro Leu Asp Pro Glu Thr
            180                 185                 190

Thr Arg Ser Ser Glu Leu Thr Leu Thr Pro Arg Pro Glu Asp His Gly
        195                 200                 205

Thr Asn Leu Thr Cys Gln Val Lys Arg Gln Gly Ala Gln Val Thr Thr
    210                 215                 220

Glu Arg Thr Val Gln Leu Asn Val Ser Tyr Ala Pro Gln Asn Leu Ala
225                 230                 235                 240

Ile Ser Ile Phe Phe Arg Asn Gly Thr Gly Thr Ala Leu Arg Ile Leu
                245                 250                 255

Ser Asn Gly Met Ser Val Pro Ile Gln Glu Gly Gln Ser Leu Phe Leu
            260                 265                 270

Ala Cys Thr Val Asp Ser Asn Pro Pro Ala Ser Leu Ser Trp Phe Arg
        275                 280                 285

Glu Gly Lys Ala Leu Asn Pro Ser Gln Thr Ser Met Ser Gly Thr Leu
    290                 295                 300

Glu Leu Pro Asn Ile Gly Ala Arg Glu Gly Gly Glu Phe Thr Cys Arg
305                 310                 315                 320

Val Gln His Pro Leu Gly Ser Gln His Leu Ser Phe Ile Leu Ser Val
                325                 330                 335

Gln Arg Ser Ser Ser Cys Ile Cys Val Thr Glu Lys Gln Gln Gly
            340                 345                 350

Ser Trp Pro Leu Val Leu Thr Leu Ile Arg Gly Ala Leu Met Gly Ala
        355                 360                 365

Gly Phe Leu Leu Thr Tyr Gly Leu Thr Trp Ile Tyr Tyr Thr Arg Cys
    370                 375                 380

Gly Gly Pro Gln Gln Ser Arg Ala Glu Arg Pro Gly
385                 390                 395

<210> SEQ ID NO 14
<211> LENGTH: 481
<212> TYPE: PRT
<213> ORGANISM: Homo sapiens

<400> SEQUENCE: 14

Met Leu Leu Leu Pro Leu Leu Leu Pro Val Leu Gly Ala Gly Ser Leu
1               5                   10                  15

Asn Lys Asp Pro Ser Tyr Ser Leu Gln Val Gln Arg Gln Val Pro Val
            20                  25                  30

Pro Glu Gly Leu Cys Val Ile Val Ser Cys Asn Leu Ser Tyr Pro Arg
        35                  40                  45

Asp Gly Trp Asp Glu Ser Thr Ala Ala Tyr Gly Tyr Trp Phe Lys Gly
    50                  55                  60

Arg Thr Ser Pro Lys Thr Gly Ala Pro Val Ala Thr Asn Asn Gln Ser
65                  70                  75                  80

Arg Glu Val Ala Met Ser Thr Arg Asp Arg Phe Gln Leu Thr Gly Asp
                85                  90                  95

Pro Gly Lys Gly Ser Cys Ser Leu Val Ile Arg Asp Ala Gln Arg Glu
            100                 105                 110

Asp Glu Ala Trp Tyr Phe Phe Arg Val Glu Arg Gly Ser Arg Val Arg
```

```
            115                 120                 125
His Ser Phe Leu Ser Asn Ala Phe Phe Leu Lys Val Thr Ala Leu Thr
130                 135                 140

Gln Lys Pro Asp Val Tyr Ile Pro Glu Thr Leu Glu Pro Gly Gln Pro
145                 150                 155                 160

Val Thr Val Ile Cys Val Phe Asn Trp Ala Phe Lys Lys Cys Pro Ala
                165                 170                 175

Pro Ser Phe Ser Trp Thr Gly Ala Ala Leu Ser Pro Arg Arg Thr Arg
                180                 185                 190

Pro Ser Thr Ser His Phe Ser Val Leu Ser Phe Thr Pro Ser Pro Gln
                195                 200                 205

Asp His Asp Thr Asp Leu Thr Cys His Val Asp Phe Ser Arg Lys Gly
        210                 215                 220

Val Ser Ala Gln Arg Thr Val Arg Leu Arg Val Ala Ser Leu Glu Leu
225                 230                 235                 240

Gln Gly Asn Val Ile Tyr Leu Glu Val Gln Lys Gly Gln Phe Leu Arg
                245                 250                 255

Leu Leu Cys Ala Ala Asp Ser Gln Pro Pro Ala Thr Leu Ser Trp Val
                260                 265                 270

Leu Gln Asp Arg Val Leu Ser Ser His Pro Trp Gly Pro Arg Thr
                275                 280                 285

Leu Gly Leu Glu Leu Pro Gly Val Lys Ala Gly Asp Ser Gly Arg Tyr
        290                 295                 300

Thr Cys Arg Ala Glu Asn Arg Leu Gly Ser Gln Gln Arg Ala Leu Asp
305                 310                 315                 320

Leu Ser Val Gln Tyr Pro Pro Glu Asn Leu Arg Val Met Val Ser Gln
                325                 330                 335

Ala Asn Arg Thr Val Leu Glu Asn Leu Arg Asn Gly Thr Ser Leu Arg
                340                 345                 350

Val Leu Glu Gly Gln Ser Leu Arg Leu Val Cys Val Thr His Ser Ser
                355                 360                 365

Pro Pro Ala Arg Leu Ser Trp Thr Trp Gly Glu Gln Thr Val Gly Pro
        370                 375                 380

Ser Gln Pro Ser Asp Pro Gly Val Leu Gln Leu Pro Arg Val Gln Met
385                 390                 395                 400

Glu His Glu Gly Glu Phe Thr Cys His Ala Arg His Pro Leu Gly Ser
                405                 410                 415

Gln Arg Val Ser Leu Ser Phe Ser Val His Cys Lys Ser Gly Pro Met
                420                 425                 430

Thr Gly Val Val Leu Val Ala Val Gly Glu Val Ala Met Lys Ile Leu
        435                 440                 445

Leu Leu Cys Leu Cys Leu Ile Leu Leu Arg Val Arg Ser Cys Arg Arg
        450                 455                 460

Lys Ala Arg Ala Ala Leu Gly Met Glu Ala Ala Asp Ala Val Thr
465                 470                 475                 480

Asp
```

<210> SEQ ID NO 15
<211> LENGTH: 14941
<212> TYPE: DNA
<213> ORGANISM: Homo sapiens

<400> SEQUENCE: 15
tctgctcaca caggaagccc tggaagctgc ttcctcagac atgccgctgc tgctactgct     60

```
gccectgctg tgggcaggtg agtggctgtg gggagagggg ttgtcgggct gggccgagct    120
gaccctcgtt tccccacagg ggccctggct atggatccaa atttctggct gcaagtgcag    180
gagtcagtga cggtacagga gggtttgtgc gtcctcgtgc cctgcacttt cttccatccc    240 atacectact acgacaagaa ctccccagtt catggttact ggttccggga aggagccatt    300
atatccaggg actctccagt ggccacaaac aagctagatc aagaagtaca ggaggagact    360
cagggcagat tccgcctcct tggggatccc agtaggaaca actgctccct gagcatcgta    420
gacgccagga ggagggataa tggttcatac ttctttcgga tggagagagg aagtaccaaa    480
tacagttaca aatctcccca gctctctgtg catgtgacag gtgaggcaca ggcttcagaa    540
gtggccgcaa gggaagttca tgggtactgc agggcagggc tgggatggga ccctggtact    600
gggaggggtt taggggtaaa gcctgtcgtg cttagcgggg gagcttgacc agaggttgat    660
cttctctcag gccctcacct ggaccctccc tcctgattct gcatcccctc tttctcctca    720
ctagacttga cccacaggcc caaaatcctc atccctggca ctctagaacc cggccactcc    780
aaaaacctga cctgctctgt gtcctgggcc tgtgagcagg aacacccccc gatcttctcc    840
tggttgtcag ctgcccccac ctccctgggc cccaggacta ctcactcctc ggtgctcata    900
atcaccccac ggccccagga ccacggcacc aacctgacct gtcaggtgaa gttcgctgga    960
gctggtgtga ctacggagag aaccatccag ctcaacgtca cctgtaagtg ctgggccagg   1020
atgctggggt ccctgagggt gtaggggaga caggatgggc tggtgctggg acatttagt    1080 gtcctggagg cctggctgag ttcgggagcc agaaggacat gagccctgtc ccttctgcat   1140
ttctgtggtt tctggcagga gtaagggaaa atgcctaccc ttatctcatc tctaccccca   1200
actgaaggaa atcctctctt cctctcctag atgttccaca gaacccaaca actggtatct   1260
ttccaggaga tggctcaggt aggaaggagc ctccccgcct ggggctgtta ctgacattga   1320
gtctgtgtca ggtttggtca gatctggact ttcagagtca aatgttcaga ggcaaggcct   1380
gcagttagac acgggtagac atcaggcacc ttggaaaagg atatttgggg atgactagca   1440
acttccccct tgcccatcca aataatgctc tttgtctccc tcctgtctct gaatgtcttg   1500
gggtatttta tttttaattg atatgtaata atagtacata tttatggatg gcatagtgat   1560
gtttccatac taataatgta tagtaatcag atcagggtaa tagcatatcc atcatcttga   1620
acatttatta tttcattgtt gttgggaaca ttcaatatcc cctttctagc tatttgaagc   1680
tatctattat tgttaagcat agtcatccta cagtggtata gaacaccaga acttattctt   1740
cctttccagg tgtaatctag tatccttaa caaatctctc tccttatcat tgttccccta    1800
accttcccag cccttattat tctctgttct acttttact tctatgaaat caacttcttg     1860
tagcttccac ttatgagtga aacatgtgg tattcaactt tctgttccta gcttatttca     1920
tttaacataa tgtcctctag ttcaatctat gttatagtga ataacaagat ttcattattt   1980
tttatggctg aatgataatc cattgtgtat atacgccaca tttcctttat ttattcatct   2040
gttgttggac acttaggttt atttcatatc ttcctattgt ggataatgct gcaataaaca   2100
ttgaggtgca gacgtttctt caatatactg atttccttc cttctataa atgcccagta     2160 gtggggttgc tggatcatat ggtagttcta tttgtagttt tttgagaaac ttccatactc   2220
ttctccatag tggttatact agtttacatt ctggtcaaaa gtatataaga gttccctctt   2280
ctctacatcc tcaccatcat tgttaatttt tcatcttttt tttatcatag tcctcccaac   2340 tgggggtgatg ttacctcatt gtggttttga tttgcatttc cctggtgatt ggtgacgttg  2400
```

```
agcatttttc atatacactt gttggccatc tgtatatctt ttcttgagaa atgtctactc    2460 agataaatttg cccatttttta aatgagaattg ggtttctttg ccattgagat gtatgagttc    2520
ctcgtatgtt ctggatatga atcacttgtc agatgaatag ctgacaaata ttttctccta    2580
ttctgtaggt tgccttttca ctctgttggt tgttttccttt ctgcatagaa gcttttttagc    2640 ttgatatcat ctcatttatt tacttttgct tttgttgctt gtgctagtga ggtcttactc    2700
ataaaatatt tttccagacc aatgtcctaa agcatttccc ctatgttttt ttctagtatt    2760
ttttaaattt tgtgtcttat attcaggtct ttgatccatt ttgaattgat ttttgtatag    2820
gacgagaggt gtgagtctaa tgtcattctt ctgcatatgg caccagtttt cccagcatca    2880
tttattaaag aaactgctct ttcctcaatg agtgttcttc atgcatttgt caaaattcag    2940
ttggctgtag atcgtggatt aatttcggtg ttctctatta tgtattattg gtgtatgtat    3000
ctgcttttat gccaatatca tgctgttttg gttactacag ctttgtagtt ttgaaatctt    3060 taaattttg aaattttgaa attttctagt tttgaaattt tgaaatcttg tagtgtgata    3120
cctccagctt tgttcttttt tgcttgggat tgctttgacc attcaggcta ttttttagttc    3180 catatgaatt ttaagattgt ttcctctaat tctgtgaaga attacattga tattttgata    3240
gagccaggtt tgaatctgta gatttctttg ggtagtataa tcattttagc aatattaatt    3300
catctgatga gtaaggaatg tcttttccatt tgtttgtatc ctcttcagtt tatttcctca    3360
gtgttttgta gttttttctta ttaaggcttg tcacctcctt ggttaaattt attcctaggt    3420
atacttcatt ctcttatagc tattgtaaat gtgattgcct tcctgattta ttttcagcta    3480
attcattgtg tgtagaaatg ctactgattt ttgtatattg atttttgcatc ctgcaaattt    3540 actaaattca tttatcagtt ctgagagttt tattgttaga gtctttaggt ttttgttttg    3600
ttttgttttg ttttgttttg ttttgagat ggaatttcac catgttggcc aagctggtct    3660
tgatctcctg gcctcaagca atctgcccac tttggcctcc taaagtgctg gaattacagg    3720
catgagccac cacgcctggc caagtctttta ggttttgta tgttattgc agagacaatt    3780 tgacttccgc ctttccagtt tggatggttt ttatttctttt ctcttgccta attgctctgg    3840
ctaggacttt cagtactatg taaaataaga gtcataacag tggacatcca gttcctagag    3900
gaaaagattt cagcttttct ccattcagta tgatgttagc catgggtttg tcatatatgg    3960 cctttttttgt gttgaggtac tttccttcta tacctaattt attgagagtt tctatcatga    4020
aacaatattg aattttaaca catgcttttt attctgcaac tatttaggtg atcatacggt    4080
ttatgtcctt cattctgttg acatatgtat aacattatt gatttgcata tgttgaatca    4140
ttcttgcctt tctgggatta atcccacttt atcatggtat gttatctttt tgatgtattg    4200
ttggatttga tttgctacta ttttgttgaa tattttgca tctatgttca tcagggatat    4260
tggcctctag ttttctttt ttattgtctc ctttctgatt ttggtgtcat ggttatgctg    4320
gccttgtaga atgagttagg aagagttgcc tccacttcaa tttttttggaa tagtttgaga    4380 agagttggca taattttttt ttctttaaag gttcagtaaa gttcagcact gaagccatcc    4440
agccctggaa ttttctttgt tggggggcct tttattattc attcaatctc attacttgtt    4500
gtttgtctgc tgaagttttc tataccttct tgattcaatc tcggtagatt atatgtgtcc    4560
aggaacttat ccattcttc tagactttca aatttgttgg catattgttc atagtagtgt    4620
ctaagatcct gtgtatttct gtggtaacca ttgtgacatc ttcttttta tttatgattt    4680 tattaattttt tatgtcttct gtctctttct tagtttagct aatgattgtc aattttatttt    4740 attttttccaa aaagcgaact tgttcattga ttttttttta atttcattta tttctgctct    4800
```

```
gatctttatg atttctttca ttgtgctgat tttggatttg gtttgttctt gctttctagt    4860
ttcttgaaat gcacagttaa atggtttact tgaaatttgt ctaattgttt gatgtaggca    4920
tttatttctc tcaagttgtc tcttaaaact gttttgctg tgtcccatag gttttggtat    4980
attttatttc tattttttatt tattttgaga aattttaaa tatcattctt aatttcttcc    5040
ttcactattg gtcatttaga atcattttgt ttcatttctg tgtatttgta tagtttgcat    5100
gtttcccttg gtattgattt ttagtttat tcaattgtag tcaaataaga tacttgatac    5160
attttggttt ttaaaaattt ttggcacttg ttttgtgttc taacatatgg tcgatccttg    5220
ggaatgttgc acatgctgat gaaaccatgt gtattctgca gctgtcggtt gaaatgttct    5280
gtaaatatct taggttcatt tggtatatgg tgcagtttaa atccaacgtt tatttgttaa    5340
tcttgtctag atgatttgtt caatgctgag agtggggcgt tgaagtcctc aactattatt    5400
gtattggagt ctatctctcc ctttatatct aataatattt gctttacata tctgggtgct    5460
ctggtgttgt gtgcatatgt atttacagtt gttatattat agtgctgaac tgacccctt    5520 ataataatat aatgtccttc tttgtctctt tacagctttt gacttgtagt ccgttttgtc    5580
tgagataagt atagctattc ctgcttcctt tcatttccac ttgggtagaa tatctttttc    5640
catctcttcc ttttcagtct atgtgtgtct tctaggtgag ataagtttct tgtaagcagt    5700
atatagctgt gttggtagaa gggctgaggc agggcttgct tgtctgacat aatgtaaaag    5760
agtcttggaa catgtcctgg gtccagggtc tcaaacccct cgtggcctat ggaacaccaa    5820
gctctgtgcc taagggtgga aggctgccct gccacactgc aatctaagcc cagggcataa    5880 aaccctcgt ggcttggaaa gaatccaggg ctctgggcat aaaacccctc atagcctctg    5940
gaatgtgtcc agacttgctg gccccttgct ccttgctctc ccaggatcat aaaattgattg    6000 tatcttgagt gaaaagaact tgttctccat tatttcaagt agcagagcat atgctaaacc    6060
gtcacagcta tgcttgatgc accgctacct ttctaccca aagtcctcac gttctcactt    6120
gtctatcccc acttctgcac gtcctcacca cctgcttctt tgtttgatta ccaataaata    6180
gtgtgggctc ccagagctcg gggccttcac agcctccata ctagcgtcgg cccccctggac    6240 tcactttatg tactattaac ttgtcttgtc tcattccttt gactccgctg gacttcgtgg    6300
cccccacggc ctagtgttgg atctgatcac cccaacaagc tgagtctaga ttttcttttc    6360
attcattcag gcagtccata tattttaaat gggacaatta aatccattta catacacatt    6420
attattaata ggttattttc atttcattga ttgttttctg attgttttat atattcctgg    6480
ttccttactt cccctcttat tgtttctttt tgtggttggc tgatgttttt tttttttttg    6540
tagtgataag atttgattcc tttctctttc ttctttgtgt atgggctgtc agtgagtttt    6600
aagttcacgt gttttttgcct tttcacttcc agatgtaaga ctccctgag catttctttt    6660 cttttttcttc tcttatttat ttttattatt ttttttttga gaaagtgtct cactctgtcg    6720
cccaggcagt agtgcagtgg catgatcacg gctcactata gtctcgacct cctgggctta    6780
agcaatcttc ctgccttaac ctcccaagta gctgggacta caggcatgtg ccaccacgcc    6840
cagctaattt ttgtgtttct tgtagaggta gggtgttgcc atttgcctaa gctggtctca    6900
aattaaagag ctcaagtggt ccacctgcct gccttcacct cccaatgtgc tgggattata    6960
ggcatgagcc acactgtgcc tggccccttg agcatttctt gtaaggccag tctaagagtg    7020
attagaattc ccttagtttt tgcttatcta tgaaatattt tatttctcct tctttttctga    7080 aagatagctt ttctgggtat agtatttttg actgttaagt ttttatctt tcagtacttt    7140
```

```
gagtatgtca tcccattcta tcctggccta tataatgtta ctgctgagaa actcactgtt    7200
agtctaataa ggataatcct atatgtgact agatacttt accttgctgt ttttacaatt     7260
ctttacttga cttttgacaa tttggcataa tgagctttgg agaggacttg cttgggttga    7320
atattttgag agtactttga gcttcctgga cctggatgtc cttctagttc ccaaggcttg    7380
ggaagttttc acctattact ggattaaata tgttttctac accttttcca ttctcttctc    7440
ctcctggaaa taccataatg tgaatatttg cttgattgtg tcccatgagt cctgtaggtt    7500
tccttcgttc tatttattc tcttatttt acctgcctgt gttatttcag aagatctgtc      7560
ttcaagttca gaaattattt tttcttcttg acctagcctg ttgttgaagc tctcgattgc    7620
ggttttttat ttcatttatt gagttctcag ctgtaggagt tctgctttgt tcttttatat    7680
aatatctatc tctctgttaa atttctcttt caagtcatga attaaaacaa tgggacacag    7740
gtgcccaact acttggctga cctgggggca tatctgctgg aggtgccaac atggctgttt    7800
tgcagggctg agatgaagct gaatgactct tggctggcct aggtgtgttt ttgccaggag    7860
tagcactcag agctttatct agggtttggg atgtgagtgt aagactgctc agctggccta    7920
gggggtgtac cagccagtgg tagcccatgg ggctgtttct caggcctgga atgcaagcac    7980
attctgcctg gggtcatgtc taaaagggtt ggctcacaag gctgtttctc aggccctaat    8040
tgtgggagag tggcctttgg gcaggccaga gtcatgtcca cagaaggcgt ctgggcaccg    8100
taaggctgtt tctcagagcc tgtgtgtgag cacataacca ctaccccagc ctgggatgt     8160 atcaactctt tgttggctca gaggtctctc ccattcaggt gagcatgcac agtagtttgg    8220
ccaactcaat tgtgtgttcg ccctgagtgg gactataaga cctttcctcc agctggaagt    8280
acgggcagca ggggttggtt tctctgctgt tcagggccag agtcccagcc aatcctgggc    8340
ccaggctcca tgcagctcta attgtggtat tcagccacta ctgcaggttt agtggaatga    8400
agatgcacaa tgataaagag gtgcatgcca ctggccccca gaggagggtg cactccagag    8460
atggctgtgg tctcaagatg gttctgtgtt gtagcagctt gcccgcaggg gctggttagg    8520
gagttgggag tgcacaccaa atgctccatg cagctgtgtg aattcctggc agctcttcca    8580
actgtgctca gagcttgtga ggactgtaag attaacctgt agtaaggaat gtaggtatct    8640
gcagtggcac tggaggttgg ttggattcct ctgcttatca tttccctaca aggggaaatc    8700
cttcctgtct ctgggacaaa ccaatctggg ctggggagat ggagctgcaa agcccgggtg    8760
cctccatgct gccctcctgg gtttccaatt accacaggta actctccact cccttgctgc    8820
actacactac tctcccttcg acactccact caaatctttg ctgtggttta ttcattgcct    8880
tggtcctttc ttgtctggtg acacggggga ggatgagctc caggcacctc cggtgagcca    8940
ttttgctcca atgggggcat ttttttttaa taggttttat ttttcagagt agttttgtt    9000 tcacagcaaa attgagtgga atcttctagt cgctgatcat cttgggagca tttataaatg    9060
aaccttattt ttcatgaaga aattgagcag aagatactaa gacttcccgt atgccctcta    9120
cccttacaca tagtttcccc ggccatcagc atccccatc agagtggtac atttgttaca     9180
gtcaataaaa ctacattgac atatcattgt cacctgaagc ccatagttta cattaaagtt    9240
cactcttggt gttgtacatt ttacaggctt tttaaaaatg tataatgaca tgaatccacc    9300
atgagagtat catatagaat agtcacactt ccctaaaaat ctctttaggg cattttttc     9360 tactgtccat acctcaaccc ttagccctgg cctctgtcca aagaccagtg ctctctccac    9420
tgccctattc caattaataa tggcatctgg cacctcagtg gacagtgagc ccagtgagag    9480
caggaacagt tccctcagta gtggttatca aactgttaac aatgatgctc agagacacgc    9540
```

```
ccctgactct gagtgttggg acctagaagg cacagccagg caggtccagg agaactgtct    9600
gggtctaaga aggtctgaga accacctccc tgccccaccc tgcttccagg cccttttttaa   9660 ggccaaaagg accacctttg accctaagtg atggggccag tgggaagaaa gaagagacaa    9720
ggcctatcag cattccagtg cttctctct ctctcatcca agaggctcag agcttcacag    9780
tccttcaggg gctatgtctg aggttcattt cagaaagacc cagggtggag aggaacctga    9840
gtcctaggag agatgatgtt ttgtgcacca gagagagagg gtgggacaag aggtgtcagg    9900
tgcactgtgt acttcatctc atggtcgtgg tcaatattga tgtctatgat gggtgggaag    9960
atctaggagc taaaccccat tttggaggtg aagtcacccc tctctacatg ctggagagga   10020
ggatacacat acctgtttat ctagattaga attcacccca aatctttttt gtctgcaggg   10080
aaacaagaga ccagagcagg agtggttcat ggggccattg gaggagctgg tgttacagcc   10140
ctgctcgctc tttgtctctg cctcatcttc ttcatgtgag catttctct gggtcaggca    10200 tgggccagag gtgaagagga tggacctggt gtagaagggt cctggagggg ctgtgagggc   10260
tggagaaagg gcagggggtg tgatgatgta cagaatccag cctgtggcca ctgggatagg   10320
cgtgggtcta ttccagggcc ctgatctcag atgtccaagg agtgggaggt agagggagac   10380
cttgtgacta agtcttgttt gagggctcct ggattaatcc cacccttttac ctgccaaagt   10440 ccctcattcc aggctcataa caatggcccc acagcctgag aaaaccaggc tcaaagaccc   10500
tggtgtctcc catcagagtg aagacccaca ggaggaaagc agccaggaca gcagtgggca   10560
ggaatgacac ccaccctacc acagggtcag cctccccggt gagtgatggg gcatcctggc   10620
atccagtctg tcctgcagac acctcctccc aatgtggccc accgtcatgc cccattcagc   10680
atttccagaa ctgagcttat tgtctttcct cctgtttaac agtgtaggtt ttaatatttt   10740
tcaggtacgt tgaggccaac agatcaggag atgatggcca ttgaaaagat agtttcttgg   10800 ccggcacag tgtttcacac ctgcaatccc agcacctttg gaggccaagg cgggcggatc    10860
acgaggtcag gagattgaga ctatcctggc taacatggtg aaaccccgtc tctactaaaa   10920
atacaaaaaa ttagccagat gtggtggctg gcgcctgtag tcccagctac ttgggaggct   10980
gaggcaggag aatggtatga acccgggagg cagagcttgt agtgagccga catagcacca   11040
ctgcactcca gcctgggtga cagagagaga ctctgtccca aaaagaaaaa aaaaatagtt   11100
tcttattcac cgttcccgag agggcacacc acaccatgca aggccatatg gagaagcacc   11160
agggtcagtc aggaagcaga gggagcaagg agaaaatggg acaagagcct tcactgtggc   11220
tttcatggaa aagaatgggc aagacagggt aagcaagcta gcaggtttta ggattggcta   11280
cttagaacaa tttcagcaga ctctggggta taggagttgt ctctagttgt ctggtacatg   11340
gccctgggtt tattaaggag gattgtggtc tggagtgtaa gagctcaata aaggatccag   11400
ctggtagtgt gggctttaga ttgactggtt tgcacatgaa aggtgcactt gtatgcaagt   11460
cctttattag ctctagaaat ctactatcct tgggaaaggc agtctctcaa gggtcagtaa   11520
tgccccagat gtcaaaacat cagaaacact tggttgacac accctaaac atacttctcc    11580 tgatgggttc tccatctcgc tgatggcact cttgtcccca ttacccaacc agagacatgg   11640 cccccctcctg tcccagtcct ccatctcttc ctgtgccagt atgctacgat gcatgtctga   11700
gcttcctctg aacacggctt aacacaacca ctcctgagcc gagagcccct cttactcctt   11760
attctgctgc agcctcacct cccatttctc ctctccagaa cattagcatc acctcccctaa  11820 aaggtcattg tcccatcatt cccaagtttg aaatgcactg cttctctaca ctcctgaaag   11880
```

```
attggcattc aacaacttg gtctggcatt tggagcagga aaaccagagt cccttcagt    11940 gctatgctcc cccaacatta gccactcaat cacctcaagc agggcaagct ttctcatctc   12000
agaatcattg ctgggctgtc ccctcctcct catatgccta atagctacct gcccaactcc   12060
agtgcatcct tcaagctctg atttttttt taatttattt aactctgact aaagtgaaca   12120
ccacagtaaa gttttgaac acagggtcaa ccagcaccca ttcattctga aatatctata   12180
taatcccatt tgccaattgc tctaggtcct tgtgccattc tgtattttta taaacacaca   12240
gtttacaaat ataaaatatt cctcctatcg ggggcttaac atttattggg gaaagggatg   12300
aaaataatga acaaataagc agtgcaaata tacatgaaat aggcatgaaa taagtgctat   12360
ggcaggaaat gaaatgggag aacggattgg acagtcctgg gggccaaaga atggcctttg   12420
ggcaaacacc tgcagaaaga aagtgagtac agtatgagca gtagagaatc atcaaggaag   12480
cagcaagtac catggctctg aggccggaac acatctgatg ttttagagaa acaaagtagg   12540
acagtgtgga taaggcagag ttacgtgttg ggggtggagt gtggactgaa caatggtagg   12600
taggaaatga ggttgaagag acataggagc tgcaaatatt gcaggatcct aagtccatca   12660
tagttattga tgcgtttaga gcagaagagt gacatgaact gacactcatt ttagtgggag   12720
tcactctggc tgctctgtga gaaactctag tatgtagtat agaagagaag ataccagaat   12780
agaagataca cagataatca agccaagaga tgactgactc agacttagtc ccaagtaaga   12840
ataatgaatc tgatgtggag aaattgggtt ccggatacat cttgaaggtg gagtcaacag   12900
tatttgcaag tggagtgatg gagtgcatgc aaggcatgag caaagatagc tcacgggctc   12960
tgctcgataa gtgtctcaga tgtcataggt gggtccacag atatcataga tgtcatggat   13020
gtccaagaag accccataga tgtcatagat gtctatagat gccaatgatg atgttcatgt   13080
ggttaactca gaattcaaac ttaaaaaatc aaattgccaa tgattaaaat tgccatcctt   13140
gaaggagaag tctattttca agtgtatatc aaacattatt ttggttaccg taagtttgag   13200
gtgcctctga gacatccatg tggagatgac aagtagcagg caagtgtctg gagctcagaa   13260
gagggctcca cgtgggagac acagaggttg ggagcttccc tatcaacatc caataatcga   13320
tgaatctaca aagaagagaa ggggtccaca gacacagccc tggaaccctc cagcatttaa   13380
tgttagggag atgaggtgta aatggtgaga aagctgagaa tgaataggag ccaatgacca   13440
ggaaattgca ggctgtagtg ttggtggcca agggaagatg gggcttcatg gaggagaggt   13500
tggtcatttg tttcaaatgc tggtaagtct ggtaagatgg aatctgagaa atggctattt   13560
gaatgtagct aagtggtatg acagcaaagc agatctgatt tttctgctgg aggaagatct   13620
cttgactaga gagagttcaa gagagaatgg gaggagaaga ggcagaaact gtgagttgaa   13680
ggactctttt gagaaacact gccccaaatc tagaaccaag aaatgggcct gcaccagcaa   13740
atggttgtac cctgtagact tgccatttct ccagcatctg ctcctgtgtc tcttatgata   13800
ccatgttccc tgtttgtgta gggctttgca ccacttgaac taactgcatt cccatagctt   13860 ccctaccac accatgagct ccacaaggaa agcctgggt tttattagac ctccatcatt   13920
ctactctctc ctgttcatct gcacactgtc acaatttgca attaccagtc tgtttctgtc   13980
ttcatcccct gcagtactgg aaatcacagg gccctgctc tgctctgctc cctcctgagg   14040
atccagtgcc cagcacatag gaggtcccag agacctggga ccgagttcag ggtcaacaga   14100
tgtgtgactt tggaaattac ctaagctctc tgagacctag tttcctggtc tgtaaaatgg   14160
attaaaataa tagatgccaa agatgatgtc agtgtagctg cccagaattt ttccacatta   14220
gtctctgtga gtattcaaga gaattgcgaa tcaatcaata cgtgctacat gtgttagata   14280
```

```
atgaataagt agagccttaa ttaattaaca tttgatgaaa gaatgaaaga gtgaataaat    14340
gttctgtcag agtcaaattt acttcattga ccctctttgc cttctcctgg tccccctcct    14400
cactgccctg ctctaacccc cttctttcct ctccataaga aacaccagaa gaagtccaag    14460
ttacatggcc ccactgaaac ctcaagctgt tcaggtgccg cccctactgt ggagatggat    14520
gaggagctgc attatgcttc cctcaacttt catgggatga atccttccaa ggacacctcc    14580
accgaatact cagaggtcag gacccagtga ggaacccaca agagcatcag gctcagctag    14640
aagatccaca tcctctacag gtcggggacc aaaggctgat tcttggagat ttaacacccc    14700
acaggcaatg ggtttataga cattatgtga gtttcctgct atattaacat catcttagac    14760
tttgcaagca gagagtcgtg gaatcaaatc tgtgctcttt catttgctaa gtgtatgatg    14820
tcacacaagc tccttaacct tccatgtctc cattttcttc tctgtgaagt aggtataaga    14880
agtcctatct catagggatg ctgtgagcat taaataaagg tacacatgga aaacaccagt    14940
c                                                                   14941
```

<210> SEQ ID NO 16
<211> LENGTH: 18972
<212> TYPE: DNA
<213> ORGANISM: Homo sapiens

<400> SEQUENCE: 16

```
gtgcgcgtcc acagctctca ctcaccctcc ggcttcctgt cggggctttc tcagccccac      60
cccacgtttg acatttggaa gcatttcctt ccctgacagc cggacctggg actgggctgg     120
ggccctggcg gatggagaca tgctgcccct gctgctgctg cccctgctgt ggggggggtga    180 gtgagctgag ggaggaggga caggcacagg ggtgagaagg ggggctggag ctgcagctga    240
gcttctgtgt cccccccaggg tccctgcagg agaagccagt gtacgagctg caagtgcaga    300
agtcggtgac ggtgcaggag ggcctgtgcg tccttgtgcc ctgctccttc tcttaccct     360 ggagatcctg gtattcctct cccccactct acgtctactg gttccgggac ggggagatcc    420
catactacgc tgaggttgtg gccacaaaca acccagacag aagagtgaag ccagagaccc    480
agggccgatt ccgcctcctt ggggatgtcc agaagaagaa ctgctccctg agcatcggag    540
atgccagaat ggaggacacg ggaagctatt tcttccgcgt ggagagagga agggatgtaa    600
aatatagcta ccaacagaat aagctgaact tggaggtgac aggtatgca gggaccccag    660 gagaggaccc tgggacgtgg agaccccgt atgagaacag ggacaggagt tgggcagggg    720
cggctggagg aggtgtagga cttggggcag gtcggggcct gaggcctggc cactctcggg    780
gtcacacctt acgtcctcaa gcccctgggg ccaggtatc tccctgtctc ctcctcagcc    840
ctgatagaga aacccgacat ccactttctg gagcctctgg agtccggccg ccccacaagg    900
ctgagctgca gccttccagg atcctgtgaa gcgggaccac ctctcacatt ctcctggacg    960
gggaatgccc tcagccccct ggaccccgag accaccgct cctcggagct cacccctcacc   1020 cccaggcccg aggaccatgg caccaacctc acctgtcaga tgaaacgcca aggagctcag   1080
gtgaccacgg agaaactgt ccagctcaat gtctcctgtg agtggtgctg gggacacagc    1140
tgagtcctca agggcagtgg gagtgagggg tgtgtgtgtg tgtgtgtgtg tgtgtgtgtg    1200
tgtaaggaag acagagagaa acaaaacaat aacttgagaa accttgtgtg tggatctaag    1260
ccttgggatc tgcggggagt gagacaggac agccttcccc gcttggtggg tttctgtggc    1320
tcctctttgg gtacctcctg ggcccatgcc catctcactc ctcactgctg aagccaagtt    1380
```

```
tatatctttt tatcccagat gctccacaga ccatcaccat cttcaggaac ggcataggta    1440
ggaaagacct cctctctgaa gctgggacct gcctctgggt ctgtctctga gcagaggtag    1500
agaatcagag cttgaatgca atcagatttg ggaagagcaa gaatgagaat tactgccttc    1560
tggcttccac cttctgtgag ccccatgtgc aggcacatat gcacacacgc acatacacac    1620
gcacacatgc acacacgcac acacacacgc acacacacac atgcatatac accacacaca    1680
tacacatgca ataccacaca cacacacgca catacacaca cacatgcaca caggcacaca    1740
tgcacacaca ccacacacat atgcacacac acacatacac cacacaggca catgcacata    1800
cacacgcaca catgcacata caccacacac acatatgcag atacacccac acacgcacac    1860
atgtacgtac acccgcacac gcacacacac acgcacacag gtgcacactc atgcactctg    1920
ctcaaagcag tgaacagact ttagaccccca cccatctccc atccctcctg tggtctggtt    1980
ctttccacag tcactaagga ccactccatg cccctctcat ctcagtcagc ccagctctgt    2040
ggttcttctc tcacccttcc actcctgcat cctcagtctt atttcctgtc acattagcgg    2100
actgtatttc ccaacgccac cgggggctct ctgtcctctc tccaccacag tccaggcatg    2160
taccagtgag atattgagcc tcctctggag acatgagact cagacacttt tggtcagttt    2220
cctgagtgtg caaaggccca gcctttgaac caggatgcaa tcaagccagc ataggccagg    2280
ggaggagagg gagatgtcat ctggatcctg ggaaggaggg aaggataggg actgtcagcc    2340
tccctggccc catctctctt tccccaccct tctctcccca aagccctaga gatcctgcaa    2400
aacacctcat accttccggt cctggagggc caggctctgc ggctgctctg tgatgctccc    2460 agcaacccccc ctgcacacct gagctggttc cagggctccc ctgccctgaa cgccaccccc    2520
atctccaata ccgggatctt ggagcttcgt cgagtaaggt ctgcagaaga aggaggcttc    2580
acctgccgcg ctcagcaccc gctgggcttc ctgcaaattt ttctgaatct ctcagtttac    2640
tgtgagtgtg ggggcagctg gagcaggaac tgcatggtat aaagaaggaa gaggcccccc    2700
tgctgagttc tgtcctcccct ccccacagcc ctcccacagt tgctgggccc ctcctgctcc    2760
tgggaggctg agggtctgca ctgcagatgc tcctttcgag cccggccggc cccctccctg    2820
tgctggcggc ttgaggagaa gccgctggag gggaacagca gccagggctc attcaaggtc    2880
aactccagct cagctgggcc ctgggccaac agctccctga tcctccacgg ggggctcagc    2940
tccgacctca agtcagctg caaggcctgg aacatctatg ggtcccagag cggctctgtc    3000
ctgctgctgc aaggtcaggg ggcgtattgc agagggcagg ggcctgaggg gaggggcatg    3060
gatcccagag tgatggatgg tgggagagag aggctggact ggtggtgggg agacagggtt    3120
cttcatctcc tgtctgagca gggccctgga gcaagttgcc cagcaggtgg gaggacaaga    3180
gtctgagtcc tgggagtgag ttattgcacg cccctctttt ctgcagggag atcgaacctc    3240
gggacaggag tggttcctgc agcccttggt ggtgctggtg tcatggccct gctctgtatc    3300
tgtctgtgcc tcatcttctt tttaatgtaa gtcttggtcc cagggaaggt acagggtggt    3360
gtttgtaggg agtaggagag actgaatctc agaaacacag agctaaggcc agaggtggtg    3420
atgtgtgctt gtggttccag atgctcagga gtctgaggca ggaggatcac ttgatcatgg    3480
aggttgagnc tgcagtgagc caggattgtg ccaatgcact ccatcctggg cctcagagtg    3540
agagaccctg tcttaaaaga aaacaaaac aaaacaaaaa gcagaactga gtagatccag    3600
agaggtcttc tttctttttt tcttttctaa tagcttatt gagatacatg ttttgtacaa    3660
ttcatccact gaaagtgtac gagtcaatgg ctttaagtat attgacagag ttatgcatct    3720
gtcaccaaaa tcaattttag aacatttttca tcagcctaaa gtgaaaaacg aagacataaa    3780
```

```
gaaaccttgc accccttagc tatcactcct gcttctttcc cccagcccta acctattcca      3840
tgtctctgtg gatttgtctg tcctgaagtt gcagttgtac tttgtgtgaa tggaatcacg      3900
cgatatgtgg tcctttgtgg ctggcttctt tcactcggcc taatgttttc aagattcatc      3960
tatgttgtag catgcatcga tacttcattc ctttttgttt tcaaataata ttccattata      4020
taaatggaac gcatttgatt tgtgggttca gctgttgacg ggtacttggg ttgcctctgc      4080
ttcttggcta tgatgcataa cactgctatg accattcctg ccatggtttt gtgtgtaaga      4140
gggggtctat atgatggaaa ttcagtccat ggccaccctg accaaatccc tggttatcca      4200
ggaggatgga gccctcactc cgaagtcagg aaggtctccg agtttagttc cggggcctgg      4260
atggcttcat tgtcатттте accatcttag catgggatgg acaacccgc taacccgtgc      4320
ctgggtggtc ccagctgcac tgtgctggtt tctttcctta gagtgaaagc ccgcaggaag      4380
caagcagctg ggagaccaga gaaatggat gatgaagacc ccattatggg taccatcacc      4440
tcggtgagtg gtttggggat cttctcatgt gcatgtccac tcggaaagtc caggctgagc      4500
tcttcagcat tccaccaaac ccactcctcc ctcatcacct gggagttctc ttctctcctg      4560
ttctccccct tcatatccca gagccaggaa atcattatgt cccattcaac cттсттгgтт      4620
ttgtttgttt gtttgtttgt ttttgagatg gagттгсаст сттgттасссс aggctggagt      4680
gcaatggtgc gatcttggct cactgcaaac tccacctccc aggttcaagc gатгстсстg      4740
cctcagcctc ccaagtagct gggattacag gcgcacacca ccatgcccgg ctaattttt g      4800
тат тттт тагт agagacggga тттт gccatg ttag gcaggc agttcttgaa ctcctgacct      4860
caggtgatcc gcccgcctcg gcctcccaaa gtgctgggat tacaggcgta agccaccgcg      4920
cccggccacc aaccttcttt ctaaaagtaa aactaacttg ttccttt gctc ат c ттс ссtс      4980
cccacctcta ctgaccacag agcctgcctc actt cctccc tgcctccatc tctcatt cca      5040
aactt caggc tgccagaatc atcgccccaa aactatt аст ccccaggcag cctggagttt      5100
caatgtt gtt gtt gtt т gtt cct gtt gctt agagaat cag gcccatgtt c cttgccccac      5160
accaggtggc cacttcagcc tgtttctgtc ctctgatcct gccccgtggc ctggccacgc      5220
tggccttctg tctc cat acg gacctgctgt cctac aac tt tgagcccttg caagtatagt      5280
ttcttccacc ttccttccc tgtttccacc agactacctc atctaatcct tccagctcta      5340
атстсагтат стgстастст agтсат ttcc cctcctgttg atatctgccc cttctcttct      5400
gtgtttacag ccctcatgc atccccgtcc ccat cacaca tcaccactgc cttt acctgt      5460
ctccaccccac tcat сататс тgтагаатт с тт тт тт татт т татт тт тт т ggagacggag      5520
tcctgctctg tcacccaggc tggagtgcac tggcgcaacc tcggctcact gcaacctctg      5580
cctcccaggc tcaagcaatt tcctgcctc agcctcccaa gtagctggga ttacaggcat      5640
gсасс acc tg gстаатт tt т gтат tt т tag tagagacggg gt тт c accat gtt ggccagg      5700
gtggtctcga act сст gacc tcaggtgatc tgcctgcctc agcctcccaa agtgctggga      5760
ttacaggtgt gagccaccgc gtgcggccaa tatc tgtgga att cttgaag gacaggggct      5820
gggcttctt tagcccctgc agttttctct cctgct gttt ct gtccagcg тgтстссtст      5880
ссtсттт тат ааа ат т gатс т agt gtt gcc ccgaacgaat tgtccaaaat gctt agttca      5940
т gacc aagct gtcatgactg gaacaagcat catttacttt tacttttt са сттт ggттса      6000
taatatgata aataactgca aaccca ccat ccaacct aag acctaacaca ттggтgаtaaa      6060
cttgtatcca cctgtgttgc ccct gatcc att cccagta accactgttg tgaatcttgt      6120
```

```
cttcctagtg ttgtcacata tatgtaggct tatgccacta tttagtttta attgtttatg    6180
aatctacaga gggtatcatg ttccacgcac acttcttgga cttgctttgt agactcaaca    6240
ttgtattatg attcattcat gttgtataaa gttgcagttg tattcatttt tcctgcttat    6300
aatatatata ttttttgaga cagggtctga ctccattgcc caggttggag tgcagtggtg    6360
cgatctcggc tcattgcaac ctccacctcc cgggttcaag caactctcct gcctcagctt    6420
cctgagtagc tgggattaca ggcatgtacc accacgcaag gctcattttt gcatttttag    6480
tagcgatggg gtttcaccat gttggccagt ctggtcttga tccacccacc ttgacctccc    6540
aaagtgctgg gattataggt gtgacggctt ataatattat attttatgat tgtgtctatc    6600
acctaagctc atattgatgc acacttgagt tgtttccatt tgagccgttc tgaacattct    6660
tatccttgtc tcaccgtact aacacacacg agctttcctt tagcatcacc taaagattga    6720
gttgccgcat cgctgggcat gtgaatgggc atctttacaa ggtcatgaaa aatggctttc    6780
caaagcaatt atatccattt atactctcat ctatgcctag gaaatcttgt tgttctgtaa    6840
tctctccaac ttgcttttct cagtttttgga ggctatttta ctatctcact atggtattga    6900
tttgcatttc ctcggttacc agtgaagatg aaaaatctct ctctgctttc atcttctata    6960
aaacacctgg tcacatctgg atcccatttt cctattgggt gtttgacttt ttcttaatga    7020
atttgttgga gggctttata cattttttaca ctattttttct cattgtatgt gttgtaaata    7080
taaatatctt ctcccaatgc gtagcttgtc ttcacttctt aaagtgatct tcaatgaaca    7140
taagttccta gttgtaatat aatcatattc acaaatcctc tcttttctat tgagtaccttt   7200 ttggatctca ttaaaaaaaa tttcacccat cctaagatta gaaagatatt caaatatagt    7260
ttctactaaa agttttatgc tttttatttt aattttgtgg gtacatatta gatgtatata    7320
tttatggggt acatgaactg tttcaataga ggcatgcagt gtgaaataaa cacttcatga    7380
agaattgggt acccagcccc tcaagcattg atccgttgag ttgcaaacaa tccagaagca    7440
acctaagtgt ccatcaatag atgaatggat aaagaaaatg ttgtgcatat acacaatgga    7500
gtactattca gccataaaaa agaatgagat ccagtcattt gcaacaacat ggatggaact    7560
ggagatcatt atgttaagtg aaataaggca ggcacagaaa gacaaacatt gcatgttctc    7620
acatatttgt gggatctaag aataaaaaaa aattgaactg atggacatag agagtatgct    7680
tttcttttga catttaagta ctcactctgt ctggggttga cttttgtgta tggtgtatag    7740
tgttgatcca tatatgtttc tccttcattt ctgaatagtc cttctcccttt ctccattgag    7800 caacatgcca attctgccat gtattaaaat tctatatatt tgtcggtctc tttctgtggt    7860
ctctattcta ctccaatagt caattttact gtccctgagt catcactgtc tataaattca    7920
aaaataagtc ctgatataga gtacagcaaa acctcttcct taatctcctt caatagtatc    7980
ttgaccattc ttggtccttt tttttttttca ctttaatgtt agaatcaggt tgtcaaggcc    8040
gggcgcggtg gctcacgcct gtaatcccag cactttggga ggccgaggtg ggtggatcac    8100
gaggtcagga gatcgagacc atcctggctc acacggtgaa accccgtctt tactaaaaat    8160
acaaaaaaaa aaaaaattag ccaggcgtgg tggtgggcac ctgtagtccc agctactcgg    8220
gaggctgagg caggagaatg gcgtgaacct gggaggcaga gcttgcagtg agcggagatc    8280
gcgccagtgc actccagcct gggtgacaga acacgactcc gtctcaaaac aaaacaaaac    8340
aaaaaacaaa aaagcaaaac aaacaaaac aaaaagaat caggttgtca aattccaaaa    8400
aatacattga atctatagct caatgtggaa aaaatttact tgtttagaaa ttcatgcctt    8460
cttatccatg acagtaggtc tttctctctc tattcctttta aatatttta agtgttttaa    8520
```

```
agagataatg tagagtttct tcacacaggt cttacacatc ttttgttatt tttcttccta   8580
aataccagtt tttgttgcta ttgtaaatgc tatcttttta aaagtgcatt ttctgattcc   8640
ttatcagaat gcagaatgaa agtatttaaa aaatataaga gggttttttt ttgtaattaa   8700
aaaaaatcac aagttggtct tgcatgtgtc ctttagcatc ttcttgcttt ggtagctgga   8760
gaattcttag atcttattta taagcctgct gatctcttct ttttcagaaa tatagatacc   8820
atctgaaaaa ttagtgatat tcctattttt aactgtcatg gcttgctgaa tcaaagcagc   8880
tgggtttgat gcaagtgtaa tgctatttc ttaaagaatc aactcatcct tttgggcttc   8940
aggtactgag caagaaatgc ctgtcctcat gtatactctg cagatgtatt tctcttctaa   9000
cagatgtcag attcaacaa atgacccact gtcctgaata atcactttt ttgaggaagt   9060 gaggacacgc aaacctaacc tcatctggca acggaagtct gtgtaacacc tcagactgtg   9120
ggcagtttgt gactatggat ggtttgaaga atagccagtt accttcatt tccccaccat   9180 ttggcaacac agaacttctc cttttctttt cctatattga tggggttgaa tttctcagct   9240
gggttccttg aggggattca ctataactgt gcatctcttc atagtgacac ccatctcctc   9300
tgggatgtca gctctctgga tttagagaat tgtcataatt ctctcagtaa atgcagcaag   9360
taaaactcat ttttaattga tttcatttcc ttccaacttg ccaagctccc ttattagttc   9420
aaataactag tatatagaaa ttgaagtatt ttaaataaat ttttttcaat taaaacaaaa   9480
tcacaaatta ggccaggttt ggtggctcat gcctgtaatc ccagaacttt gggaggctga   9540
ggcaggagga tctcttgagg ccaggagttc aaggccaggg gataacacag tgagccctcc   9600
atctctacaa aaagaaaaaa aatcacacat tgatcttggg tattatttag aatgttttgg   9660
gatttcaaat tagatgatta tatcatctgc aaaataataa cagtttatt cttccctttg    9720 tcctaagcac ttcttttcctt tttcttgttt caatatgctg ggtgagatta tggtcaaagt   9780
tgagtagaca tagtgaccat gggcatcttt tgctactgct gattttgaag gaaatgcacc   9840
caatatcctg ccacttggtt ctgtgaactt tcatcaggtt aaggaagttc ctttctatca   9900
ctaaataagt tttatccta aacttctgtt gtattttttg aatgcatcta ctgataggat    9960 ttttttcctac ttaatctgtt accatgggga atgacaatta aagattttc tggtatgaaa  10020 ctactcctgc attcctggga gaaaaccata ttattcatag catttttta atactccagt   10080 aggttgtttg atcatctttt gctcagcact tttgcgtcta tatgcatggt caaatacact  10140
tgtcattttc cttttcctc ctgtttcttc tgtttgggta tcaagataag attgagaaat   10200
tggggactag tctctctttt tctactgtct ggaagagtgt gtataaaact gaaatgactt   10260
gtttcctgaa tgattgatag atgtcactta tcaaactacc tgggcctggt ggcgtcacta   10320
tgtgcaattt tcctaattta atcattttat gtattcttca gcgagcttta ttctagggac   10380
gtgttccttt cacctaagtt atatatatat atatattttg acaaaaggat atgggtggca   10440
ttcttttgtc tttatattat ttgttttgt cgagattact tccccttta gaatattcc     10500 tgacattggt tatttgtgac ttcttctt ttttctagct aaatcttgtt aattgctttc    10560
cctattttat tatcagtttc aaggaaccaa cttttgggat tgtagaattt tctcactgta  10620
tctttgtttt ctgtttatt gatttttact ctcattttct cagcaccttc cttctacttg   10680
ttttggttta ttctgatgat ctttgataaa ttttaagct ggatacttag cttcttagtg    10740
tctatatttt cattctctat aaaacgtagt tagggataaa tttctctcag aatttcattt  10800
tcatcccatt gcacaaattt tgatatgtat tatttgaata acattcagtt gtggatattg  10860
```

```
ttaaaacaac attgtgattt cttctttgaa tcttaaatta tttgggatta aaaattccaa  10920
aggtatgaag attttaaaca tctttcataa ttaaattcta agtagatgct ttttggtcag  10980
aatacatggt tttatgatat ctacttttaa aatttgttga gacttgatct gtggcctgta  11040
tacaatgaat ttttgtaaat gtttccctgt gtgcttaaga ataatgtatg tttttagccg  11100
ggtgcggtgg ctcatacctg taatcccagc actttgggag gccgaggtgg gcagatcaca  11160
aggtcaggag ttcaagacca gcctggccaa tatggtgaaa ccccgtctct actaaaaata  11220
taaaaattac ctgggcatgc tggatggtgg caggcacctg tagtcccagc tactcaggag  11280
gctgaggcag gagaatcgta tgaacccagg aggtggaggt tgcagtgagc caagatcgtg  11340
ccactgcact ccagcctggg caacaatgta tattttttat ttcttaaatt aacagtccag  11400
tgtgttaatt gtaatgttca aatccaaatc ttcagatgtc aacagatctt cccaacatgt  11460
caatacttga gagaggtgtg ttgaaatctt acattatgat aatgtatttg tcaatttctt  11520
actgtaattc taacaattgt gtttcttata tttgatgtac ttttaaatta aaaccatata  11580
ttttagaaaa gcattatatc ttctcagtga actgaacatt ttatcaaaca tagtaattct  11640
ttctcttcat agtggtgctt tttttttttt tttttttttt ttggagacag agtctcactc  11700
tgtcacccag gcggcagtgc agtggcacga tctcggctca ctgcaacttc cacctcctgg  11760
gttcaagcaa ttctcctgct tcagcctcct gagtagctgg gattacaggt gccgccacc   11820
atgcccaggt aattttgta ttttagtgg agacagggtt ttatcatgtt gacgggctg   11880
gtcttgaact cctgggctca agtgatctgc ccacctcgtc ctcccaaagt gctgggatta  11940
caggtgtgag ccactgtgcc cggctcataa tgatgctttt tgctttaaag tctgttcgac  12000
tggatgtttt ttttttttt tttttttttt taggcagggt ctcactcact catgcgggct  12060
ggaatgaagc ggcatgtgga tcttaatata gctactctag tttcttattg attagttaga  12120
tgcctgatac ttttcatt tctcccatcc tcccaacatt ttatgtattt atgctctacc   12180
agtgatttt gtaaacagta tataaccagg ttttaaaaaa tccaatttga catcccttgt   12240
tgagtttact ctgctggtat ttattatggt tactgacata tgtggatttc tttctactat  12300
tttaccttt actttcactt agtcccactt tttcaatatt tcattttct cctttcttac   12360
ttagaagctt aatatcttgc cgggcacagt gatgcatacc tgtaattcca gctactggg   12420
agggtgaggt aggagcatcg cttgagccca ggactttgaa tctagtatga gcaacatagc  12480
aagactctcg cctcaaaaaa aaattaatat ctctgtctta catctaacaa aaagaatttt  12540
ggtgcgcttt tatatctctt ggcctctctt ccttcaactc tttacaatgt tgatattttc  12600
tacaaatgtg cagttttgt tctgtgttat tatgaacata cttagcattt ttctattatt   12660
tgatttttta aaaatatac agctacacat tttgttgagg tattttgtca cctttctatt   12720
ccatacttat cacagatttt ctgttcttct ttctctttct ctctttttat ttgaattctt  12780
ccccccagtg ggttttcagt ttgggttcct caaggcttct gaagactat atgcctggaa    12840
atatatttta tccccttaca ttttaatttt atttggcagg atatacattc taaaattaaa  12900
gtgattttcc tttggtgctt taaactccac cccactgttt cttgcattta gtattgctgt  12960
taagacatct tacgtcattc ttaatctcac atatttgtag gtaatccact cattttccct  13020
ggaaacttt ataatttct ctttggttct gatattctta agatccactg tcctgtgtct    13080
aggcatggga ttccctgcat cttttttct gcactcgtgg ggccctttca gctgaggtgt   13140
ttcatcttct ttaactctgg aaattttgtt tccactattt ttttcaaata ttttttcctt  13200
tctacttttt tttttttttt aaggtggagt cttgctctgt cgcccaggct ggagtgcagt  13260
```

```
ggcgcgatct cctctcactg caagctccgc ctcccgggtt cacgccattc tcctgcctca   13320
gccctccgag tagttgggac tacaggcgcc cgccaccatg cccggctaat tttttgtatt   13380
tttagtagag acggggtttc accgtcttag ccaggatggt cttgatctcc tgaccttgtg   13440
atccgccagc ctcggcctcc caaagtactg gcatgagcca ccacacccgg cctatttctt   13500
ttttatctta tttgaaaact attattatct aaatgttcaa gtgtttttt tttttgtttt    13560 tttttttga cagtctcact ctgttgccca ggctggagtg cagtggcaca atctcggctc    13620
actgcaatct ctgcctcctg ggttcaagtg aatcttgtgc ctcagcctcc cgagtagctg    13680
ggattacagg tgcacatcat cacgcctggc taatttttgt atttttttag agacaggatt    13740
ttgccatgtc ggccaagctg atcttgaact cctgacctca agtgatctgc ctgccttggc   13800 cttcaaagt gctaggatta caggcatgag ccaccacgcc tggccagttt tctatttcta    13860
tcttccatct atcttaacct ttttctcata tgttctagtc ttcatccttc cctacttcct    13920
tttaggggat acttctgacg gcccttctag ctcactaatt tgccctcaat tatagtcatt    13980
ctattctcca tcccatccat tgggctcttc ctatgatatt tttcagatat ttccacatgg    14040 cccttttgc atcaagtaca caattacata attccttatt atgtttcaca ttcattttgc     14100
atgcacactt tgttattgac aaagtttctt atgcttgttt tcatgctgct aatattgcca    14160 catctttta gtgcatgtaa tatgctcagt ttagcttctt gaccaaagcg tcctagtact     14220
tgtgcttcta gtggtctatc aggttctgtt ggtttgcttt tcttcaaagg tgcccagcct    14280
tctgagctgt gagctcacat tcccctgggg ttattggcta ctctggcagt gtttcttgaa    14340
tgagggaagg gcagatgctg gcctgtgtca ggcttactga gccaaagaaa tgacagggac    14400
gccgggcacg gtggctcacg cctataatcc cagcactttg ggaggccgag gtgggcagat    14460
cacctgaggt cgggagtttg aggccagccc aaccaacatg gagaaactcc gtctctacta    14520
aaaatacaaa attagccagg tgtggtggca catgcctgta atcccagcta ctcgggaggc    14580
tgaggcaggg gaatctcttg aacctgggag gtggaggttg cagtgagccg agatcatgcc    14640
attgcactcc agcctgggca acaacagtga agcatcgtct caaaaaaaga gaaatgactg   14700
ggacaagccc cagggtggat cccctcaaga acccaaacca cacccaacca gtcccacttc   14760
ctatcacccc agtaaggcag cttaagtcat ccctccatct tcagaccctc gtggagaagc    14820
aacattggtc aaggactctc gttgcattgt gatccaccag ccctgggagt ttggagtgga    14880
gaaaatggca aggagaatgt caaagaccag tgagcttcca cctccgttct ccttctcctc    14940
accccagtgg gcctctggtg cttacccaac acatgcctgt ggacactgg cacatcataa     15000 tcctgtccat actctgaatt ctgcagtgag gggcagacaa tgtttgtccc actggaaggg    15060
tagaggagag aaaggagcag aattcaagta tgtttgggct aacccatcct ctcaacaagc    15120
cagctgtccc cccgcccagt tctcccaccc cttttcttca aatgagcctt aactttcccc    15180
tagggatatc agtgtgattg attgatcata aattgatttg taaagttttg ttcacccagg    15240
agctccatct ttagttccat cattggtagg tcttggagaa cagagccggt gtatgaattc    15300
actcttttga caagaactat ggtagagaga gctttgtttt ctcctttatt ttaccttaa     15360 ccattctgca cactttcatg ccataggcag aatggtaaag cgaggcacag catggtccct    15420
ggagtttgac gtcctgcatt caggttctag attcacccac ttgcaagctg tgtgaccttg    15480
gataagctaa tgaacctctc tgttttttg ttttctccta tagaaattgg gttattaata     15540
tgctagtatc tgtctcggat tgttacaagg agtgcttagt aaagtggcaa gctcacaggg    15600
```

```
agctcactta taactgttac ccagtattac ttttccttct gtctaacaag gaactgcatg    15660
acggggaggt atttgggtgg tttcagtctg ctttatgtcc tcatttatac gaacggcatc    15720
tagcccaaag aaagcactca gcaaagagct attgagtgaa agggtgaaca tactgcattg    15780
tcctatttac taatctgagc tgtgcctttt cttcagttg tcaatttcac ccttttatt     15840 tcatataccg cacacctatt gatagacata tgtctttatt tcttcctttg cctgcataat    15900
gctggtgtgc atagccactt tttcatttta tttcatcttt cttgtgccta atataagcag    15960
ctctctccag aaagtctatt tttttctgac acaatgaagc cattttccc taactgcgga    16020 gtccttttaa aaaactgta tggccaggtg tggtggctca cacctgtaat cccaccactc    16080
tggaaggcta agctgggcca gtcgcttagc ccaggagttt gagaccaacc tgggtaacgt    16140
ggcgaaaccc tgtctttaca aaattagct gggcatggtg gcttgtgcct gtggtctcag    16200
ctactcagga agctgaggtg ggaggattgc ttgagccagg gacgggaggt tgcagtgaga    16260
cgaaatcaca ccactgccct ccagcctgga tgacagagtg aaactctgtc tcaaaaagaa    16320
aacttctgag ctactgtttg aagactcacg ttgctttcaa catattttcc atagcgtgat    16380
gggtagggat atgggtgaag gtgggagagg aaagaaattg cttacttgta tctggttacc    16440
atctttgctg gggacaggat ctgctccatt ttgtttctct ttcatggaaa ctgggtccag    16500
gatcagaatt gccatctctt ttctggtttg cacataagac accttgtaac ctatgccgaa    16560
ggtatacatt tgcttcatca ataatccgct cctcctgcct aggtcagggt ctatgtctga    16620
tttctcacac tgtacgtgcc cagaacctga acaggggag acagggctga gttcgaatcc     16680
tggcctcgcc atgtattaga tgaataaccc tgggcaagct acttaacctc tctccacctc    16740
agtttccctg tgtgtaaggt ggggataatt agaatatctt ttatactgtt gtgggttttt    16800
ttttggtgat gattcaatgt gattagtaag tcctcaatat ggtctgatca atcatagtat    16860
tacaaatttt tgaaagaatg agcgaatagt tgagttcaca ggaaatgtat atggacaggt    16920
ggggccggga tttgaaccca gccctgtctg ccctgtgccg gttcctggc acgtacagtg      16980 tgagaaatca gacatagacc ctgacctagg cagcctatgg cctgtcctta ggaggagtgg    17040
attataaaag gatgaattga taaatgtcac atcagcccaa cttccctgtg gaaccatttt    17100
gttgtatttt tctcttattt ggtgttgagg tctctctttg gggagtggtc ataaaatcta    17160
gcccggcctt gaatgggaac cccagagatc tggccatcat gttcacagtg tgactttcac    17220
agaatactcc tttatcctgg cacaccacct gctgcctgag tgcccagcct gtgacccct     17280 ctcacagcaa acttgtttat cctggcagat tcccttgcag cttttcctatg acctgtgtcc    17340 ggtttattcc caccaagaca gctattctct aggagagcct tgaccagaaa agaagtgagg    17400
ttcaggtctg ttgggcgggt gggacacaga ggagacagca caacaaaaca catgaaataa    17460
cagaagcagt ttattactca caggtcccag agagaagata gcacagcaag cctggaaggg    17520
cgaatggaaa ggagggaact gaccaggacg caagtgctca tccagtgggt aggggggaag    17580
agagagagag agagagagaa gaacccatga gccaaagcct taattagagt ccaggggcata   17640 atctaagcag gcttcccaca gggagttcta actgggggtt tagagctagc aggcaggagt    17700
tctgtggagc cacactgtga ctgagaggtg gttgctgcag tatatctgcg cagcctatga    17760
gggacacagg agtcaatacg taagtcaagt aggttgtagc tgtatgtccc ataggagct     17820 ggtcacaagg agatggttgt ataaggcaga catttggatt aaccaccttg gggaactggg    17880
aggaggtaga gaattggaaa ttgtgtccag gtgactaagc cctgcttctg gcatgagaaa    17940
gtccaactta cattcaaaat aaatcccaag gcaacatata aatataagaa ctcattattc    18000
```

```
tacacctgcc tctttattcc tactgtgaca cctttccttc cccttta ctc agggttccag    18060 gaagaagccc tggccagaca gccccggaga tcaagcatct cctcctgggg atgcccctcc    18120
cttggaagaa caaaaggagc tccattatgc ctcccttagt ttttctgaga tgaagtcgag    18180
ggagcctaag gaccaggagg ccccaagcac cacggagtac tcggagatca agacaagcaa    18240
gtgaggattt gcccagagtt cagtcctggc tggaggagcc acagcctgtc tggggaaag     18300 gacaagtcag ggaccacttg ctgaagcacg aagagccctt gtggcaatgt taacattaac    18360
tgatgtttaa gtgctccaag cagatggaat tagagaggtg ggctcaaatc taggccctgg    18420
cactgtcatc aagcaattca ctgcatccct ctgtgcctca gtttcccatt ctgtaaatca    18480
gagatcatgc atgctacctc aaaggttgtt gtgaacatta agaaatcaa cacatggaaa     18540 tcaaccaaca tgggtcctgg aacagggcgt tgtgctcagt gctttctggt ctctcttcct    18600
tgaatagaaa ggtcctgctg gcaagttctc tcaaggctgg ggatgaccag gcacaaaaaa    18660
cagggcagca atatgttggt gtcactcccc ttcccaaaac tcttcgaaga ctccctagga    18720
aagaccagcc cctcagcctg gcacttggtt catgatgtgg gatcttatat ccttgccaga    18780
gtcatatctt tgcccacttt tacctgcaat ccttgcatca tattcctttg gctccagtcc    18840
ttcatttatg agacccatag gaatccttcc aacagccaaa gagttgagtc taactctttc    18900
ctgcccaaac ccattcacgg cccctggcc ttagacaata tcacaagc atctcccctg       18960 acacataaag tc                                                         18972

<210> SEQ ID NO 17
<211> LENGTH: 11226
<212> TYPE: DNA
<213> ORGANISM: Homo sapiens

<400> SEQUENCE: 17
gcagttcctg agagaagaac cctgaggaac agacgttccc tcgcggccct ggcacctcca      60
accccagata tgctgctgct gctgctgctg cccctgctct gggggaggga gagggtggaa    120
ggacagaaga gtaaccggaa ggattactcg ctgacgatgc agagttccgt gaccgtgcaa    180
gagggcatgt gtgtccatgt gcgctgctcc ttctcctacc cagtggacag ccagactgac    240
tctgacccag ttcatggcta ctggttccgg gcagggaatg atataagctg gaaggctcca    300
gtggccacaa acaacccagc ttgggcagtg caggaggaaa ctcgggaccg attccacctc    360
cttggggacc cacagaccaa aaattgcacc ctgagcatca gagatgccag aatgagtgat    420
gcggggagat acttctttcg tatggagaaa ggaaatataa aatggaatta taaatatgac    480
cagctctctg tgaacgtgac aggtaaggca cgggctccaa gagaggccaa aggcaaatgt    540
gatgagggct ttagggcacg gctgagacgg gacacatgtc ctgggagggg ccggggggtg    600
atggactcag agaggagct ggaccagagc ctgagcttcc ccaggaccgc accttggatg    660
cccctcctga tcctgcaggc ccctcccctc accagccctg acccacaggc ctgcatcct     720 catcctgcct ctgacgctgg cattgtggca tgtggggcct tatgactcct tgttttgggg    780
cctgtcctag gcatggccgg ggtttagcac catcccaggc ctctccccac cagatgccag    840
aagcacccac tccaccccatg cagtgagaca ataacaatta tctccacaca ttgttaaacg   900
tcctgggggg ttaagtcctc cccagttgag agccttaggt ctacacaacc ccgtgactct    960
ctcaggccag gccagggagg aagcacttcc tggcgcaaac caagggcagc agaggcacct   1020
gagcctggac agggagactc agcacacggc ccctccatct ctcatgccct gaggtcctcg   1080
```

-continued

```
gagatccaca tttagatgct caaaagacag gagggacctc cacgatggtc cagaggccgg     1140
gagggcagga cctacgtgtc tggtgcaggc cctggtgctc cagggaagcc cggaggtagg     1200
aggtgggaca cggtctcttc tcctccctgg gtgggtctct agggtctctg agcttcaggg     1260
tttccttcac tctgtgcaga gggaaccagt tcctatagca tgtgggtttg tagtttctct     1320
ttcgtgctgg gttgaggtct ccagctcctc tccagcccct ctccagcccc ctgtgggtcc     1380
cacagccctg cccctcctct ccctcccact tctctgctca cacaaggagc ccaggaaccc     1440
tctgtctcag agatgctgct gcctctcttg tgggcaaatg aagagaggga cagtcggggc     1500
tgggctgagc ctcatttccc cacagcgtcc caggccccac tgtcaagata caggctggag     1560
gtgctggagt tggtgatggt gcaggagggc tagtgcgtct ctgtgccctg cagtgtcctt     1620
taaccctatt acaactgaac tgactctagc cctgtccatg gatgctggtt taagaaaggg     1680
atcaatatac aatggaataa tccagtggcc acaaacatcc caaatggaaa agtgcaggag     1740
acacggggcc gattccacct ccttggggac ctgaagacca caactgctc cctgagcatc       1800 agagatgcca ggaaggggga tttgaggaac tactacttcc aggtggagag aggacagata     1860
agatggaatt acaaaacgaa gcagctctct gtgaatgtga cagataaggc acaggctcca     1920
ggagacacca caggaaaagg tcatgggggt ggcagcgaaa gcctgggatg gggcccctgc     1980
cctgggagag ggctgagggt gaagcgagtt gggctcaggg cagaagctga accagagcct     2040
gagcttcccc cagggctgta ccatggatcc tctgtcctga tcctgagtcc ccctctcttc     2100
accagccttg acccacaggc ccaacatcct tatccccggt accctggagt ctggctgctt     2160
ccagaatctg acctgctctg tgccctgggc ctgtgagcag gggacgcccc ctatgatctc     2220
ctggatgggg acctctgtgt cccccctgca cccctccacc cccgctcct cagtgctcac       2280 cctcatccca cagccccagc accacggcac cagcctcacc tgtcaggtga ccttgcctgg     2340
ggccggcgtg accacgaaca ggaccatcca actcaatgtg tcctgtgagt gctgagccag     2400
gacgccctgg tccctgatga gggggggacg tccctgaggg cagaggatgg ggtcagggct     2460
cgacactggg tgctgggtcc cagaatctgg gctggttgtg ggatcaggag gacgctggct     2520
ccgccttccc catttatgca gctcctgggg agacagggcc agtgtcccca gccctcacag     2580
tgatgcaggt ctccatgtct ttctgtccca gaccctcctc agaacttgac tgtgactgtc     2640
ttccaaggag aaggcacagg taggatggag ccccctccct ggggctgggg gagcagggcc     2700
ttcagctcag ggcagggcca ggtccctcct catcctggac tcaccctggt gatatgagac     2760
tcccttgtag ttgaacccag gcctcctccc catccttagc ctctgtggcc acctgagcac     2820
ctgtcctctt cccccactc ccctcagact cttgcacaca caccctcctc agccctgcag       2880
ccaggacagg gggaaatac tatagcagga gcagcctttg ggcctcttat cttccatctc      2940
ctgaatatgc cacctaactc gtcttttat tttacccaat agttttgagc tacgttcttt       3000
tggatacatg ctataatcac gtgggcaaaa atttaaatt cacagtaaaa tgtgtccccca      3060 gaatcaacca gggtctgtcc aggctgtcct gagccttggt ttgtgcacct ggaagatctc     3120
agaggtggtt tgatgtcagc agtgagactg tttgcaccct cttctaggga tgtgtgtgat     3180
tccactgtct gaatagtctc tgattttgtg gcatctccta atggaagatc atggcactaa     3240
ttttatccta cggcacgaac actgcaatga ataatgttgt atctactccc acaaggaata     3300
tctaagtgta taggataaat tcctaaaagc acatttacc agtgtcatat gttctttctg       3360
attttgaaag atatggtgaa gttgtcctca aataaaggtg gcaagttta cattcccaac       3420 agtgagcggt gaacataagt atgtccctgc accagcctac atcactctct gttccattcc     3480
```

```
ccagtctcat tctgtatcct tcctccctgt ttcaatcact ttgtctcttt gaacctccaa    3540 cttttttctct acagcatcca cagctctggg gaacagctca tctctttcag tcctagaggg   3600
ccagtctctg cgcttggtct gtgctgttga cagcaatccc cctgccaggc tgagctggac    3660
ctggaggagt ctgaccctgt acccctcaca gccctcaaac cctctggtac tggagctgca    3720
agtgcacctg ggggatgaag gggaattcac ctgtcgagct cagaactctc tgggttccca    3780
gcacgtttcc ctgaacctct ccctgcaaca ggagtacaca ggtgggtaag ggaggggctg    3840
gaggaggaga acacacctgc cccaccctca tgggccaccc actgcccctg agcttcaagg    3900
gggagctcag ctctggtctg tgctcagctg tgaggcctgg aacttccctg caacccaggg    3960
cactgctgtc ctcttcctgc caggaaaggt gtgtaaggca ggaagagggg aggagtgggt    4020 cttgagggg aggagctggg gcctggacag gtgtgtttgg ggagacacgt gccttgcttt     4080
ccagtgcctg gactagggtg acacaagcaa ggcactcact tctgggcaca cgactaaaaa    4140
acaaaaaata aaacaactca gcaagcaagt gaaataatat tggatgtgat tatctttatt    4200
aaaaactaaa aattattgca aaataatttg acagtgaata caaatcaaaa tttcaaatac    4260
aggcaggctg tgcttaccac tctcatgcct cagtgacctc aggagttgtc ccttcctcct    4320
ccctcccatt cttgccctt gtttctggga aggggatta gggtacccaa gttgggggcc      4380
ttataggaag tgggaggaga agagacccag ttcttggagt tggatcacca aaacaattcc    4440
aatccatcct caggcaaaat gaggcctgta tcaggagtgt tgctgggggc ggtcggggga   4500
gctggagcca cagccctggt cttcctctcc ttctgtgtca tcttcattgt gtgagcactg    4560
accctaggga gggagggaga gtcctggggg agggcggact gggagcagga tccctgaagc    4620
cagagctgga agggactgca tgggtcaaga gcttggggca agaatgagct cacgggtgcg    4680
tggcaagaat tcaagagcg cccttgtctg tggggctcca catctgtggt gaaccttggg     4740
ccccaccacc caggaggcag gagcctctgt tttcaacact ggggtctctg ggactggacc    4800
accctcctcc cacctcagtt acccctccag cgccccaaca ggaaatacag ggcagggggtt   4860 ggtctgccca ctgcaccccg atctgaccac actgaaaggc tctctggtct cttcactcag    4920
agtgaggtcc tgcaggaaga aatcggcaag gccagcagcg gacgtgggag acataggcat    4980
gaaggatgca aacaccatca gggggctcagc ctctcaggtg agtgatatgg gcgtctccac   5040
acccagcatc cagctgggac atctcccaca ggatggcctc caggatttct ctgcttatca    5100
tggccaaaat tatctcctca tctcctcctc cttcccacca tccagcttct cctgcaggat    5160
tccccatctt gctgactgca tgacagtccc tcctacctac tttctctcgg gccaggcatg    5220
gaggaggagt tatctcctct ctgtcctccc tttcttctct atagctccac attcaccaaa    5280
tcttgtccat ttttcctccc taagaatggc tagcattgct cccacccca ccaatcctaa     5340 actctctcaa tgctgaggcc tgaggatctc tgtcttggac ttcctcacct ccctgcctct    5400 tgtgtccct gccctgatgg gaggaatcat tcagaagcca tcactgatca gtttcttgc      5460 atctggacag ctgttccac ccccaacact gtctagagca aagccagaa atactatct       5520 ggaaaggcca gataggaaat attttttggct ttctggccta cacagtctca ttgcagctcc   5580
tcaactctac tgatgtagca ggaaatcagc cgtagaccat gtgtaaatga ttagctggct    5640
gtgtgccagt aaaactttat ttataaaaac aagctgtggg tagaatttgt cccaagggct    5700
ctagtttgac aagccctaac ctagagaaaa agcccaaact tcataactgc agccctgcac    5760
attctcgtct cttaaacatc tacctctcta gcagggctgg aattagtgtg agatgagtga    5820
```

```
ggtcctggcc tagcatgcaa aatttaagaa ggtgccaaaa atctcagtaa ttgtgatagt    5880
tttaaaaaaa actcttattt taggtttggg ggtacatgtg caggtttgtt acatacataa    5940
actctggtca gagggggtttg tggtacagat tattttgtca cccaggtcct aagcctagta   6000
ccccacagtt attttttttct gttcctctct ctcctcccac cctccacctt caagtgggcc   6060
ccagtgtctg ttgttctctt ctttgtgttc atgagttctc atcatttagc tctcactgat    6120
aagtgagaac atgcagtatt tggttttctg ttcctgtgtt cgtttgctaa ggataatggc    6180
ctccagctcc atccatgttc ccacaaaaga cataatctca ttctttttta tggctgcaca    6240
gtattccatg gtgtatttgt accatatttt ctttatccat tctgtcatgg atgggcattt    6300
aggttaattt catatatttg ctattgtgaa tagtactaca atgaacattt gcttgtatgt    6360
gtctttatgg tagaatgatt tttattactc tgagtataaa accagtaatg tgattgctat    6420
gtcaaatgat agttctgctt ttagctcttc aggaaattac catactgctt tccacagtgg    6480
ttgaactaat ttacactcct gccgacagta taagtgttcc cttttctctg cagccttgcc    6540
agcctctgtg atttttttta cttttttaaaa gtagccattc tgactggtgt gagatgatat    6600
ttcattgtgg ttctgatttg cgtttctcta gtgatcagcg ataatgagct ttttctcata    6660
tgtctgttgg ccaaaaatgt ctgttcatgt cctttgctca cttttttaatg gggttgtttt    6720 tctcttgtaa atttgtttaa gttccttata gatgctggat attagacctt tgcctaatgc    6780
atagtttgca agtattttct cccattccgg ttgtttactc tgttgatggt ttattttgct    6840
gtgcaggagc tcttaagttt aattagatcc catttgtcaa ttttttgcttt tgttgtgatt    6900 gctttggcat ctttgtcagg aaatctttgc ctgtttatcc agaacgatat tgcctacatt    6960
gtcttccaga gtttttatag ttttgagttt tacatttaag ttttttaaccc atctcgagtt    7020 gattttttata tgtggtataa ggaagcagtc ccactcaatc ttctgcatgt ggctagacag    7080
ttatcccagc accatttatt gaatcaggag tcctttcccc attgcttttt tttgtcagct    7140
ttgttgaaga tcaaattgtt gtaggtgtgt ggctttattt ctgggctctc tattccgttc    7200
cattggtcta tgtgtctgtt tttgtaccac taccatgctg ttttggttac tgtagacttg    7260
taatatagtt taaatttggg taacgtgatg cctccaggtt ttcttttttgc ttaggattgc    7320 cttggctatt tgggcacttt tttggtttca tatgaattttt aaaattgttt tttctagttc    7380
tgtgaagaat ctcattggta gtttgataga aatagcattg aatgtataaa tttctttggg    7440
cagtatggcc attttaatga ttttgattct ttttatccat gagcatagta tgttttttcca   7500 tttgtgtcac ctttgattta tttgagcagt gtttttgtaat tctcattgta gagttctttc    7560
acctccctgg ttagctgtat ttctaaaaat tttattcttt ttgtggcaat tgtgaatggg    7620
attgtgttcc taatgtgact cttggcttgg tagttcctga tgtatagaaa tactagtgat    7680
ttttctatat tgattttgta tcctgaaact ttgctgaagt tatttatcat ttaagaagct    7740
tttgggctgg gactacgagg ttttctagat atagaatcat gcatctgcaa agagggatag    7800
tttaaattcc tctcttccta tttggatgct ctttatttct ttctcttgcc tgattgctct    7860
ggccagaatt tccaatacta cgttaaacag gagtggtgag agagggcatc cttgtcttgt    7920
gctggctttc aagggaatg ctttcagctt ttccatattc aatatgatgt tggctctgcg    7980
ttcaccatag atagctctta ttattttgag atatgttcct ttaataccta gtttactgag    8040 agttttttaac acgaagcgat gctgaatttt atcaaaagcc ttttctgcat ctattgagat   8100
aatcatgtgt ttttgtctttt agttctgttt gtgtggtgaa tcacatttat tgatttgtgt    8160
atgttgaacc aacatgaagc cgacttgatc atattggatt aaccttctga tgtgctgatg    8220
```

```
gattcagttt gcaagtattt tgttgaggat ttttgcatca atgttcatca aggatattgg   8280
cccgaagttt tcttcttttg ttgtgtcttc gccagatttt ggtatcagga tgatactggc   8340
ctcatagaat gagttaggga agagtcagtc ttcctccgta tttgggaata gtttcagtag   8400
gaacagaagg aggctcagat ctgacattta ttgtgtgatt gaagagcctt ccaggcagag   8460
ggaggagcaa agcaaggccc aggcacagga agaggaaagg agaggagcca tgggacatct   8520
gtgtgattag acagagggag gcaggactga gagcaggaaa tgactttgga ggagttgagc   8580
ctatgtgaat tgtgtctgac tgcacaggct actgtgagca tttggagagt tttgagcaga   8640
aggacatgat cagacgagat tgggtccgtt cagggtggta tagctgtaga ccagaagaac   8700
atgatcaact ttcattttca tgggattcct ctggccactg tgtgcagaag agaccgtgtg   8760
tgtggcaggg gaaggagaga gcataggagg tagacaggag gctggtgaac atcccaggca   8820
gaaggtggtg ttggctggaa ccaagatagc agcagtggta gacatgactg tctcccagat   8880
gaattctgca gtgaaccta ctgggatttg ttaatgaatt ggaattagaa tgtgagccac   8940
agaaagggag caagaattac ttccagattt ttgccctgag cagtgggaag aatggaggtg   9000
ccaatcattg aggctgagaa gattgcagaa gaaatggatt tgggaaagaa aaggaggagt   9060
tcagattgaa taggttgagt tttgtgtgtc tttggacaag aacgcggggg tttgaattat   9120
accactggat caaagactat agtcaggaga aaggagtggg ctgggggtac agatttggga   9180
gtcattagcc tattgatggc atgaagccaa cacagtggat aagatcacaa ggcaaaggta   9240
aagaagaaaa gaacccgggg ctgctctgat atttaaggtc agggagacct gaagcaattg   9300
gcaaagaggt tgccaagaag gtgaggtgga cccagaaaag catgatgtcc tatagttgag   9360
tcaagaaggc cttctgtgta gggaaggtga gcagctgggt cctctgctgc tgaaaagtcc   9420
aggaaggaga agactgcaag gtggacattt agactcagcc acttaagtgg tagtcacagt   9480
gaccttgata gtagcagtgc ttagacttgg tatgtgtgtg aatattaatt tgagtaatca   9540
agagagaatc tggcaagcaa aatcactgac agttccatgg agcatcttct gcacagggga   9600
gcagcaggga agggctgcga tgaaggagga ccctcccagg cagcctctgt cactctctgc   9660
tgtgtgagtc tgtattagtt tcctgtggct gctgtgacaa attaccatgc atttcctggc   9720
ttccaacaac acacatggat taaagttctg aaggtcacaa ccccaaaatg ggtgtcactg   9780
ggccaaaatc aaggcattgg caggcagggc tggttccttc tggaggctcc aggggaggat   9840
gcaatttctc acccttcctg gcttctagag gcacctgcat tccttggctc aagtcccttc   9900
ctctgtttgc aaggcaagta gcctggcatc ttccaatctc tctaagccct cctcctttca   9960
cttgtaagga ctcctgtcat tccactgggc ccacccaaat aatccaggat aacctcccca  10020
tgtcaatatc cttaacctag ctccatctgt aaagtcccct tagcaatgta acgtaacaga  10080
ttcacaggtt tcagggatt agggtatgga cattttgggg agcagttata cttcttatca  10140
gaggatataa tttctttgac tgagttgtcc tccccatacc accgaactgt gagcttccta  10200
agagcaggtg ccccatccaa atcaaggccc tgtaattctc tctcacttag cctcttcctg  10260
cccatcttat aattcacaca tagatattcg tttgtttgac agtcattttt gccaaattcc  10320
ctcaattaaa aagtgagttt caggaggtca gggccaacac ctactgtgtc caccacagtc  10380
catccagcac ccggatcagg gcttcacaca cagagggccc cagcaggact ccaggctttg  10440
gggtcagaag gaagggactg gattgggtcc cggcataaca gggagtttgg gtacgctact  10500
ttcttcatgg agttgttgcg ggaagttaat aagattaata aacaccaaac aagttgctca  10560
```

| | |
|---|---|
| ataagtgtta aatattgcag gaaagtataa atgaaggaga tttctataaa atgaacgtgg | 10620 |
| gatagaggca ggaactcatg aagtttaatt ctatacagag gaatatatcc gaaccaacca | 10680 |
| accgatcaaa caacttgtga ctctccctgc cttatcctat ttccactgct ctgctctgac | 10740 |
| tctcttctct ctctccattc agggtaacct gactgagtcc tgggcagatg ataaccccg | 10800 |
| acaccatggc ctggctgccc actcctcagg ggaggaaaga gagatccagt atgcacccct | 10860 |
| cagctttcat aagggggagc ctcaggacct atcaggacaa gaagccacca acaatgagta | 10920 |
| ctcagagatc aagatcccca gtaagaaaa tgcagaggct cgggcttgtt tgagggttca | 10980 |
| cgaccctcc agcaaaggag tctgaggctg attccagtag aattagcagc cctcaatgct | 11040 |
| gtgcaacaag acatcagaac ttattcctct tgtctaactg aaaatgcatg cctgatgacc | 11100 |
| aaactctccc tttccccatc caatcggtcc acactcccg ccctggcctc tggtacccac | 11160 |
| cattctcctc tgtacttctc taaggatgac tactttagat tccgaatata gtgagattgt | 11220 |
| aacgtg | 11226 |

<210> SEQ ID NO 18
<211> LENGTH: 5431
<212> TYPE: DNA
<213> ORGANISM: Homo sapiens

<400> SEQUENCE: 18

| | |
|---|---|
| tagggcctcc tctaagtctt gagcccgcag ttcctgagag aagaaccctg aggaacagac | 60 |
| gttccctcgc ggccctggca cctctaaccc cagacatgct gctgctgctg ctgcccctgc | 120 |
| tctggggag ggagagggcg gaaggacaga caagtaaact gctgacgatg cagagttccg | 180 |
| tgacggtgca ggaaggcctg tgtgtccatg tgccctgctc cttctcctac ccctcgcatg | 240 |
| gctggattta ccctggccca gtagttcatg gctactggtt ccgggaaggg gccaatacag | 300 |
| accaggatgc tccagtggcc acaaacaacc cagctcgggc agtgtgggag gagactcggg | 360 |
| accgattcca cctccttggg gacccacata ccaagaattg caccctgagc atcagagatg | 420 |
| ccagaagaag tgatgcgggg agatacttct ttcgtatgga gaaggaagt ataaaatgga | 480 |
| attataaaca tcaccggctc tctgtgaatg tgacaggtaa ggcacaggct ccaggaaagg | 540 |
| ccacagggaa aggtcatggg ggcggcaggg aaaggctggg atggagcccc tgccccagga | 600 |
| gagggcttag ggtgaagcga gttggctcag ggcaggagct ggaccagagc ctgagctccc | 660 |
| cccagggctg caccatggat cctctgacct gatcctgagt cccctctct tcaccagcct | 720 |
| tgacccacag gccaacatc ctcatcccag gcacctgga gtccggctgc cccagaatc | 780 |
| tgacctgctc tgtgccctgg gcctgtgagc aggggacacc ccctatgatc tcctggatag | 840 |
| ggacctccgt gtccccctg gacccctcca ccacccgctc ctcggtgctc accctcatcc | 900 |
| cacagcccca ggaccatggc accagcctca cctgtcaggt gaccttccct ggggccagcg | 960 |
| tgaccacgaa caagaccgtc catctcaacg tgtcctgtga gtgctgggcc gggacgcctg | 1020 |
| ggtccctgat ggggtgagcg tcaagcctgg acactgggtg ctgggtcccg gaatctgggc | 1080 |
| tggtggtggg gtcaggagga cactggctct gccttccctg tttatgcggc tcctggggac | 1140 |
| agacagggcc agtgtcccca gccctcacag tgatgcgggt ctccatgtct ttctgtccca | 1200 |
| gacccgcctc agaacttgac catgactgtc ttccaaggag acggcacagg taggatggag | 1260 |
| ctccctccct ggggctggag gagcagggcc ttcaggtcag gatggggctg gcttattcct | 1320 |
| caacctggac tcactttggc aaacagggat gtccttgtgg gtgaactcag ggcccctctg | 1380 |
| tatccttagg ccccaaggcc acttgttccc atcctcccat cacctccctt ggactccccc | 1440 |

```
acacaccccc ccctcagcct caaacaagaa gagggtggca ttcacacagc aggaccaggc    1500
tttgaggctc cttctcatgt atctcctgaa tacatctcca cccttatctg tttatttctg    1560
atagttctga tctaagtact tctggacagg tgataaatgt ccatgggcaa aaattcaaat    1620
tgcagagcaa aggctctcct ccgatgcctg ccccccctccc cagaaccaac cactgtccat    1680
ccaggctgcc ctgagtctcg gtttgtacac ctggaggatc tcagaggtgg tttgacgtcc    1740
gtagtgagac tgtccgcacc ctcctctagg gctgtgtgtg agtccactgc atggatggac    1800
tctgattttg tggcatctcc taatggaaga tcacggcact aatttcatcc tacggcagga    1860
tagaacaatc ttgtatctac ttccacagga atatctaagc ctgtgggtta agttcctaaa    1920
agcaaaatgt agctacatta tatgttcttt cttattttga aagataagcc caaactgttc    1980
tcgatgaagc ggggagaagt ttacattccc agcagtgagt ggtgaaagtg tgtgtttcca    2040
gaacttcagt ctatgtctgt gtgtcagttg ctgtcatcag tctctttctg tatccttcct    2100 tttctccag atctatgtat ctctctgacc ctctgtctct tttctacag tatccacagt    2160 cttgggaaat ggctcatctc tgtcactccc agagggccag tctctgcgcc tggtctgtgc    2220
agttgatgca gttgacagca atcccctgc caggctgagc ctgagctgga gaggcctgac    2280
cctgtgcccc tcacagccct caaacccggg ggtgctggag ctgccttggg tgcacctgag    2340
ggatgcagct gaattcacct gcagagctca gaaccctctc ggctctcagc aggtctacct    2400
gaacgtctcc ctgcagagtg agtgcaccag tatgctgggg aggggctgga gaggagaaca    2460
cacctcctcc acccttagta actgctgagc gtggaccttc agagaggagc tccgctctgg    2520
tctgtgctca gctgtgaggt ctggaacttc cctgggaccc acagcaccac tgtcctcttc    2580
ctgccaggga agggttgtgg ggtggggaga gggcaggagt ggatctcaga ggggacagga    2640
tggggccgga caggtgtgtt tagggagaca agcgcctttc tttgcagggc tgaactggag    2700
tcacacaact gagatacttg ctttgagcat caaattaaaa aaaagaaaaa gcccagcaag    2760
tcagcaatca aatgaaatca tattgcaatg caataatctt ttaaaaaaag taaaaattga    2820
atgcaaaaca aattcattaa tggataaaat attaaaattg tgaaaaaaaa ccccaaaagg    2880
aatggctggc acttgcacgc ctcactggcc tcaggaagag tctctccatg tcctgctctc    2940
tctcattcct gttctttgtg tctggaaagg ggaagtggaa atagaagtct aggaccctac    3000
aggaagtggg aggagaagag acccaattct ctatgatata tcacaaaaat aactcccatc    3060
tgtcaacagg caaagccaca tcaggagtga ctcaggggt ggtcggggga gctggagcca    3120
cagccctggt cttcctgtcc ttctgcgtca tcttcgttgt gtaagcatgg ccctagaga    3180 gggagggagg gagagccctg ggggaggaca ggctggaagc tggatccctg aagccagagc    3240
tggagggacc tggatgggtc aagagcttgg ggcaagaagg aggtcacagg tgcatggtga    3300
gaattccatg tgggcctgtg tttgaggagc tttgagtctg tggcaaacct tggtacccac    3360
tgtccaggag aagagagcct ctgttctcaa ccttggggtc tctaagactg accactgct    3420 ttcccacctc agtcaccct gcagtcccttt aataggaaac acatgggggt acctggtctg    3480
cccaccgcac cccaatctga ccacactgaa aggctctctg gtctcttcac tcagagtgag    3540
gtcctgcagg aagaaatcgg caaggccagc agcgggcgtg ggagatacgg gcatagagga    3600
tgcaaacgct gtcagggggtt cagcctctca ggtgagtgat gtggactctc cacagccagc    3660
atgtagcctg gacacctccc acaggatgac ccccaggact aatcagctgg gcgtagccaa    3720
agttacctcc tctctgttct tcctttcttc tctgtagccc caaatcacaa tgtttggttg    3780
```

```
gtttcctccc ctaagaacag cttttattgt ctctgctccc tatcctgacc cttcattgct    3840
gaggcctgag gatctctgtc ttttgttccc tcacctgtct gcctgtctcc tctcctttcc    3900
tgcctggggg gactgtccag aagacatcat cgtccagttc ctctgcattt gaacagctgt    3960
tcccccaccc ctcaataccg tttagagcag aagccagcaa atactatctg tcagggacag    4020
atagaaacta ttttcggctt catgggccac acagtctcat gcagctcct  caaatctgct    4080 gttgtagcaa gaaagaagcc atatacctg  tgtaaacaaa tgaatatggc tgtgtgccaa    4140
taaaactatt cacaaacata aagagtgggc tggatatgac tcagatactg tagtttgaca    4200 accctgatc  tagagtaaaa atcccaaact ctatagcctg cagcagtgca cattctgact    4260 tttttgttt  tttttttttt ttgttgttgt tgttttgag  acagagtctt gctctgtcgc    4320
ccaggctgga gtgcagtggt gcgatctctg ctcactgcaa cttccacctt ccgggttcaa    4380
gccattctcc tgcctcagcc tccggagtag ctgggactac aggcgcctgc caccacgccc    4440
agctaatttt tttgtatttt tagtagagac ggggtttcac tgtgttagcc aggatggtct    4500
cagtctcctg accttgtgat ctgcccacct tggcttcccg aagtgctggg attacaggcg    4560
tgagccactg tgaccggcca cattctgacc ttttaagcac ctacctctcc actagggcaa    4620
gaacaagggt gaagtgagtg aggctgttgc ctcaagtgca ttttttcgtt tgtttgtttt    4680
tgttttttga gatggagtct cgctctgtca cccaggatgt agtgcagtgg cacaatcttg    4740
gcttactgca acctctgcct cctaggttca agcgattctc ctgcctcagc ctcctgagta    4800
gctgggatta aggtgcaca  ccaccacacc tggctaattt tgtattttta gtagagacag    4860
ggtttcacca tgttggccag gctggtctca aactcctgac ctcaggtgat ccgcctacct    4920
cagcctcctg aagagctggg attacagatg tgagccaccg cgcccatcc  tcactgtctg    4980 ctctgactca cttctctctc ccatgtctca ggggccctg  actgaacctt gggcagaaga    5040
cagtccccca gaccagcctc cccagcttc  tgcccgctcc tcagtggggg aaggagagct    5100
ccagtatgca tccctcagct tccagatggt gaagccttgg gactcgcggg gacaggaggc    5160
cactgacacc gagtactcgg agatcaagat ccacagatga gaaactgcag agactcaccc    5220
tgattgaggg atcacagccc ctccaggcaa gggagaagtc agaggctgat tcttgtagaa    5280
ttaacagccc tcaacgtgat gagctatgat aacactatga attatgtgca gagtgaaaag    5340
cacacaggct ttagagtcaa agtatctcaa acctgaatcc acactgtgcc ctccctttta    5400
tttttttaac taaaagacag acaaattcct a                                   5431

<210> SEQ ID NO 19
<211> LENGTH: 12180
<212> TYPE: DNA
<213> ORGANISM: Homo sapiens

<400> SEQUENCE: 19
cgaggctcct cctctgtgga tggtcactgc ccctccacca ggcttcctgc tggaggagtt      60
tccttcccag ccaggccggc ccagaagcca gatggtcccg ggacaggccc agccccagag     120
cccagagatg ctgctgctgc ccctgctgct gcccgtgctg ggggcgggtg agtgggtcgg     180
tggctggggg tccaggcag  ggctgggc  tgccgctgag cctctgcatc tccccagggt     240
ccctgaacaa ggatcccagt tacagtcttc aagtgcagag gcaggtgccg tgccggagg      300 gcctgtgtgt catcgtgtct tgcaacctct cctaccccg  ggatggctgg gacgagtcta     360
ctgctgctta tggctactgg ttcaaaggac ggaccagccc aaagacgggt gctcctgtgg     420
ccactaacaa ccagagtcga gaggtggaaa tgagcacccg ggaccgattc cagctcactg     480
```

```
gggatcccgg caaagggagc tgctccttgg tgatcagaga cgcgcagagg gaggatgagg    540
catggtactt ctttcgggtg gagagaggaa gccgtgtgag acatagtttc ctgagcaatg    600
cgttctttct aaaagtaaca ggtatggaat ggggtgggaa ccoctgcctg tcacactggg    660 gagggaccct ggggacaggc tatgggctga gcagagaggg ctctcaggga cccctgcagc    720
acaagaatct cccacccggt ctctgtccca gccctgacta agaagcctga tgtctacatc    780
cccgagaccc tggagcccgg gcagccggtg acggtcatct gtgtgtttaa ctgggctttc    840
aagaaatgtc cagccccttc tttctcctgg acggggggctg ccctctcccc tagaagaacc    900
agaccaagca cctcccactt ctcagtgctc agcttcacgc ccagccccca ggaccacgac    960
accgacctca cctgccatgt ggacttctcc agaaagggtg tgagcgcaca gaggaccgtc   1020
cgactccgtg tggcctgtga gtgtggcctg gagggtggg gcgtgcagac agccccggtg   1080 ggtgggagg tggaggagcc cagcgggaca gtgagtggct cccagctcag gagcatccag    1140
ggagaggaag ctgtggggtc ccaggatgcc ggctcagccc tgggaggggg atgggaatgg   1200
cgtctgatcc tctgtccaca tgtgtgagcc ctggagctgg ttgtcacttg tccatcctgg   1260
gatgttccca ctttctttc cctgaggag tttttttccag gtgtgaggaa caaattgtcc    1320
ctccctgaag ccagctcaca atcttgttgc agatgcccc aaagaccta ttatcagcat     1380 ttcacatgac aacacgtcag gtactgaggg ccttcgggct ggggctgggc cagtcctctt   1440
tagggatgaa aaggcttcag gggggtgagg ggatgtggtc ctctttgcag cccccccctcc   1500 cacccattct ctctctccac ccccacccte tctctttccc tgtcttcagc cctggaactc   1560
cagggaaacg tcatatatct ggaagttcag aaaggccagt tcctgcggct cctctgtgct   1620
gctgacagcc agcccctgc cacgctgagc tgggtcctgc aggacagagt cctctcctcg    1680
tcccacccct ggggcccag aaccctgggg ctggagctgc gtggggtaag ggccggggat    1740
tcagggcgct acacctgccg agcggagaac aggcttggct cccagcagca agccctggac   1800
ctctctgtgc agtgtgagtg tgcctagcag gggcctggag tccattggga gggcagaggg   1860
atacaggggc tgggctcagg gtcccagagc tgaggggtc ttgaaccccca ggcctcgggg   1920 actgaccttc ttacctgtgt agaccctcat gcagtttgtg tctgggactc agtgggtgat   1980
tctgccctgc ccttctatcc cacccacttc ccccacctca gtgtccagga tagttccctt   2040
tacccagagg gaagcccctg gtctgtctag agccggtccc ctgtctccat ttcagatcct   2100
ccagagaacc tgagagtgat ggtttcccaa gcaaacagga caggtaggaa aggagacaga   2160
ggagccaggg cctctcagtg ccaaactggg ggcccaggag tctggagggt ccccacacag   2220
gagggtccct gagccctgag ctgcacgtcg attctgcctc ttccttcct agtcctggaa    2280 aacctcggga acggcacatc cctcccggtc ctggagggca aaagcctgcg cctggtctgt   2340
gtcacccaca gcagccccc agccaggctg agctggaccc ggtggggaca gaccgtgggc   2400
ccctcccagc cctcagaccc cggggtcctg gagctgccac ccattcaaat ggagcacgaa   2460
ggagagttca cctgccacgc tcagcaccct ctgggctccc agcacgtctc tctcagcctc   2520
tccgtgcact gtgagtgggg gaaagggac acctgggtcc caggaagggg ccctgctga    2580 gtcctgtcct ccctccccac agaccctcca cagctgctgg gcccctcctg ctcctgggag   2640
gctgagggtc tgcactgcag ctgctcctcc caggcagcc cggcccccctc tctgcgctgg    2700 tggcttgggg aggagctgct ggaggggaac agcagtcagg gctccttcga ggtcaccccc   2760
agctcagccg ggccctgggc caacagctcc ctgagcctcc atgagggct cagctccggc    2820
```

```
ctcaggctcc gctgtaaggc ctggaacgtc cacggggccc agagtggctc tgtcttccag    2880
ctgctaccag gtgaggggac tgtgggggc tgaggttcag ggagaaagga gacaggatcc    2940
tagaaagatg aaggttcaag gttgtgggga gagggtgtgg gcgtggtggg aagggatggg    3000
gacaaagtcc ctgctctgtg gctggtagtt gttgcgggaa actgaggaac ggagagagca    3060
atatggagaa caggaggatt gtttatttaa ggtaagttcc agcttagtgg atttacattt    3120
caaaagctga gcattaaata aagacaaaga aggggttttt tttgtttttt ggttttttt    3180 ttgagatgga gtctcgctct gtcagcaagg ctggagtgca gtggctcgat ctcggctcac    3240
tgcaacctct gcctcccgga ttcaagcaat tctcctgcct cagccacctg agtagctggg    3300
attacaggca tgcgccacca cgcccagcta atttttttgt attttttagtt tcactatgtt    3360 ggccaggctg gtctcgaact cctgaccttg tgattcacgc acctggacct cccaaagtgc    3420
tgggattaca ggcgtgtgcc accgcgcccg gctaaagcag tgtgtttata agcggactta    3480
caaaagtaaa acaaaagcgg ttaattatat agtgcataac ttgtggcctt gtagctgtgt    3540
caaaagaaaa acaagaactg gttaaataca gacatttgtg aaacataatt gtgcttaaga    3600
agccagggaa aggagtaaca gtaaaagaat ttgtctttt ttttttttct ttaaccttgc    3660
tctggaaggg gtgtgtctgg agcccattcc tttggccttg gctttttaaa cagtgttatt    3720
ttatacctgt ccttgaagtg agcttgctag gcatagaaag acttgggttt ttttttgtttt    3780 tttttaacc cttgccttgc ctgttacttt tttgggagtg aatgaatgca tatttatttt    3840
taaatttttg cctcagtttc cccctttga tgtttttat aaaagaagtt aatagaagg    3900 cattactatt acttaattct gcatgaagag acactttttt tctttagaca aaggttgata    3960
tttatgcaga gccgttagct gagtggtagt ttgcctagct gctattgcct ttatagttga    4020
ttgaatgctt ccaacaagga gagctaagag acaagggag attcggcaac ttcctagtat    4080
ggccagaacc acttttatta aagtcttgaa ccctctgcaa aatgaaaacc agtccttaaa    4140
gagagaatct ggagaccacc ctttccaagt ttgaactgga acatgggcta attttttttat    4200 ttttgcagtt attttttataa ttgccttttc attgtcagcg atttttaggc agcagttagt    4260
tagattgaac ttttttacatt ttttttttttc tgggctagga gtagtccaaa gctaacctgt    4320
tctgatagat aacattcttc attttttgtgg gttgctgggc cagtaaatct aatgcatttg    4380
ctgttttatt agtgatgatt tcaagtactg cctgcaacct tatgatgcgg ttaagcatgt    4440
aaataggagt gtggtatccc catgacccat tttgtgccca ggtagctggc ctatactatt    4500
gaattatttt ttcaggggt taatttgtgt ctttttcaatt ttttttaattt ttattttttgt    4560 gtgtgtgttt gcatttttttt taactttatt atagacagga tacttaaaag tttctccctg    4620
ttgcagtggg aataggaaga aagacggtct aattgtttca agcacacagg cccctgtcca    4680
tttagctggc aactgttgat atgcccatgg cctacagatc caacaaagac taggaggtgc    4740
ttgccaagta tttggagctt tcggctgata gtaggtgtga tttaaagaag agaaacaggg    4800
aacggatttg gatgaggtca tttgcattca tctttgcccc gccacaaagt gtttcttagt    4860
gttttatcgt catattgctg tcctaagcag tttagttctt ttactgggtt tgtaaaaact    4920
tttccccagc gagcaacaca gtatttcctg ataatagaag ttttttaagag ccagacgctt    4980 gaacttgtgg gcgtcggttc gggagaagag tcagttaaat tattttgtgg cattaacttt    5040
tttgctttcc aaggccattg gtcttccgtg ttagtccctc cgcaaacata gtatgaggaa    5100
atgcctaggc tgccgacaat gttttaggc agccgagcaa acaggtttc tgctaaagga    5160 gtgggctctg gtaacaggat tacaggtgtg agccactgcg cccggccata agtacaagtt    5220
```

| | | | | | |
|---|---|---|---|---|---|
| cttttttttt | tttttttga | gacggagtct | cgctctgttg | ccctggctgg | agtgcagtgg | 5280 |
| cgccatctct | gctcactgca | agctccaact | cccaggttca | cgccattctc | ctgcctcagc | 5340 |
| ctcccgagta | gctgggacta | caggcgcccg | ccaccaagcc | cggctaattt | ttttgtattt | 5400 |
| ttactagaga | cagggtttca | cagtgttagc | caggatggtc | tcaatctcct | gaccctgtga | 5460 |
| tctgtccacc | tcggcctccc | aaagtgctgg | gattacaggt | gtgagccgcc | atgcccggcc | 5520 |
| tgctaatttt | tctttttatg | agggctgctg | ccaacagatt | ggcctttttt | tttaagccta | 5580 |
| tgttctgctt | cctttttcct | tcctgagtta | tcctgctcct | acagctggcc | agtgggactg | 5640 |
| ggctacggcg | tgggccccgc | ccctgtgcac | gcacgcactg | ccatctatct | ttactgtttc | 5700 |
| tttctgattt | ttcttttttc | cttttcaca | cttactttt | tgggctaggt | aggatctgca | 5760 |
| cagccgtagt | ccacccctgg | gccgttatag | gcccagaggc | ttggtagatg | cctgccgcaa | 5820 |
| gttgtaagaa | ttatgccttt | ctttttttt | tttttttgg | ctttttttct | ggggccagtc | 5880 |
| cccgccccgc | tcttttcca | gatagagcca | ggctgaggag | agggactaaa | cccttggtgt | 5940 |
| gcctagctgc | ttggtgcctc | gcttgttgct | ttcgctcttt | cccgttttgt | tctctggtca | 6000 |
| tggttcatgt | acatcttggt | ggtcactttt | ataagctggg | tggcattcat | gcctgcagct | 6060 |
| gccgcttgac | gtcaccctgg | gcttgcccta | caaatgctgt | gtttaccatg | cgctgatttt | 6120 |
| cagcagcctc | agggtcaaat | agggtgtaag | gccggaatgc | ttcacaaagt | ttttataaa | 6180 |
| actgacttgg | gctctcgtca | gctctctgaa | gcacttttga | aattttcgt | atattaattg | 6240 |
| cttctttcc | accagctttt | atcccttgca | gaagtgtctc | ttggtaccctt | tgcaaatgct | 6300 |
| gaagctgagt | tgcatcctct | gggttccagt | tgggatcttg | gtatgagaac | tgaccttgag | 6360 |
| tgtatgcctg | agcattcact | gcatctgctg | gtgcatgggg | ttttagccag | gggagagctg | 6420 |
| cctatgttac | tctcctgcgc | ttttagtgt | taaataacgt | taggaaaagc | tgcctgcaat | 6480 |
| ctggccaggt | tggactgtgt | gtcagaaaga | cggattgcgt | cagatctata | agagcttgag | 6540 |
| gcttctccat | gtaggaggga | gtatggtgtt | tccagttcag | tagatcagta | gctcagtagt | 6600 |
| cagaaagggc | tgatagatga | aggtgcgttg | ccccccacct | ccgaacctgg | ccttggttat | 6660 |
| tacaataagt | gggtcctcac | atctccctga | caggcatttg | catagctcga | gcaggcattt | 6720 |
| gcatagctca | agcacggcca | gatctgagac | agcctgcttg | actattttga | cttccttccc | 6780 |
| tggccttttg | aggctccagt | ccttccctttc | ggggtcagac | tcagggcatg | ctagctcctg | 6840 |
| aatttggttc | ctggagggct | gttggcctca | gtaaggggg | gtaggctggg | acatatggag | 6900 |
| gaggaatttc | tgtttcctct | ggcagctgtt | gcaaaactgg | cttctcttgc | tctttctggg | 6960 |
| gttttctttt | taacttcgtg | tcagtcggtg | aagctgctct | tactttatt | tttggctcgg | 7020 |
| gctacaagtg | ttttgcaata | agctgctaaa | cagggcttga | tccaggttag | tcttgtctgt | 7080 |
| gctgtattta | accatgaatc | aatataagga | aattgatcgg | gatactcagg | ctgtcctcag | 7140 |
| acccctatca | ccatctttaa | tacatgccca | attgtttcct | agtctacagt | ttcttcggtc | 7200 |
| agccatccaa | catcaaaaga | aagtcattct | aattcaaaga | gagttctcaa | cctttggggg | 7260 |
| gttagcttaa | ctttataatc | ccctgcaaaa | cctttcttaa | agttttgtaa | catgcacttc | 7320 |
| aatggagtaa | gttttgatgg | actttccttc | tattccttcc | tttacggccc | agcacactca | 7380 |
| ctcttcctct | agtttcggcc | aactatacca | tctcctatta | cgggagtttt | cagaagctac | 7440 |
| ttggcttttgg | agagttcctt | attcctgcta | caactctgag | ctgtagggca | gctcctatta | 7500 |
| gccatacgca | gatcaccact | agtcttagtt | ggccccacac | tttgctcgga | gcacccagtc | 7560 |

```
cacactaaga gaattgtgac ttcccatttt gtggctgatc agcctaataa ggcttcttca    7620
tttacacact gttacacact tccccactcc cagttcctaa gttcctaatt agggtggtaa    7680
gccactctcg ccacctccag tttccttttc ctaatcgact tagcaaacca ttctcacatc    7740
ctgtgatggt tggggtgtga gtttcatcca aatcgacgag ccactctcgc tgcccccaac    7800
ccctctgggt cggactgtta ggcaccccgc aagaagtgat cagcctcccc ttccatccct    7860
atgggatggg tcctgccttg gtccccaaaa ggttactgtg gttcctgacg tacactgttt    7920
ctgaaatcat tctgtagctc cttttcaggtt ttgttgtgct gctgggtagg ggcgccggct    7980 cagggagag ctgatttctc ctccaggctg aagttcaccc agtggcacct gggggtcacag    8040 gtctcctgag gcccggggct ccagccccca gaggcaaagg aggcagtaaa cctaccgtct    8100 ctggtcccctt cgtggtcgcc aaaaatgctg cgggaaactg aggactggtg agaccgatac    8160
ggagaacagg aggattgttt attttaggtg caaaccggct cagtggactc gcatctaaaa    8220
agctgagcat gaaacaaaga cagagcgagg ttttttatgag cagacttaca aaagtaaaac    8280
agaggcagtt aattttagga taggtgacat aatttatagt atagcataac ttgtggcctt    8340
gcatagctgg tggccttgta gctgtatcaa aaggaaaaaa aaagaactgg ctaaatacag    8400
acatttgtaa aacatagtta tgcttaagaa gccaggaaa ggagtaacag taaaggaatt    8460 tgttttctt tcttgtttc cttcaacctt gctctggaag ggggtgtgtc tggagcctat    8520
tcctttggcc ttggctttt aaacagtatt atcttataac tgtccttgaa gtgagccttg    8580
ctaagcagag gaaaagttgt tctttttta acccttttcct tgcctgttac ttttcttgga    8640
gtgaatgaat gcatatttat ttttaaattt ctgcctcagt tggggatgaa gaatccgaga    8700
gctctaggtc tgtgggagga aggggcagga gggtctcagg gccaggaggg caccacccca    8760
aaccctgctc ccatgcaggg aagctggagc atggggagg acttggcctg ggggctgccc    8820
tgggagctgg cgtcgctgcc ctgctcgctt tctgttcctg ccttgtcgtc ttcaggtaag    8880
catcggaggg caggcaatgc agggtgtggg aagggtgagg gttctagaat cccagacagt    8940
cccagctgca ggaatctaga tggggcagtg ggtgtgagaa ctaggccttg ggcaagagga    9000
tcagagcagg ggtctgctcc agagccctga tctgggccat ctatgagggt ccccagttct    9060
cactatggaa gtcaccccgt ggatatgtcc ccaccccact gggctctgca gccttccagc    9120
ctctgctaag ccatgtgggt agcagttttcc ccaggctctg gaccagcctg gaggctgaag    9180
ggcactgcct cctccctcag ggtgaagatc tgcaggaagg aagctcgcaa gagggcagca    9240
gctgagcagg acgtgccctc caccctggga cccatctccc aggtgagagc ccagcctctg    9300
tctgctgggg ccctgcctgt tccccttttcc ttgatggcca tgggtagtcc tcttggtgac    9360
ttgcagaatc attgtgcccc aaatagggtt ttgctcctgg gtccccatca atgcagtccc    9420
aagtcccatg atctgggagg caccctcccc actgctccct acatcccctc ccagaaccaa    9480 gggccccca ggcctgtcca tactctgcct gtgctcagat ccagtggacc ctccacctcc    9540
cactcctcat ttcctcctgc atcccgact cctttgccct ccctcctatc tctcctcctc    9600
aacacaggat gccagagagt cctttcctca gatgactatt gtctactaca aagctaaggg    9660
tccccatcct cacttctgac accaaccaca gttgtggggt cccacgacc actctgaggt    9720 tggataaccc cctaggactc gcaggactca ctgagagctg tgatcctcgt ggtgatggtt    9780
tatagtgacc gatacagatg aaaatcatgg acaggaagag gtgctcaggg caggtccagg    9840
agataccaaa cccacagctt ccggtggcct ttcccagggg agccatgggg acagcaccca    9900
attctcccag caaggaagtg tgacagatgc acggagcatc agggcaccgc tcacctggga    9960
```

```
agctccacca aacctgggtc cagggttcac tgggggtggg tcacgcaggc atgggggact   10020
tgccactgac ttcagttcct cagcccctgc agagccaaac tgatgctacg taggccccgc   10080
cgtaagtccc agtgctggcg taaactatgt ggcctggctt gtggtcccag gtcaacaggg   10140
atgctcctac cagcaggata ttccaaggcc ctacattaga ggttccttcc cagcacctgg   10200
gcacaaacgg ttgaagcttt ctctgggcaa ggggaatcct ttacttccag taacctttct   10260
ttcttgagct cctagctcag tttcacaatt gtgtccgagt agatcttcca aggtctttga   10320
ggtcagtcca ggtccgagca aatccctgtc tttctcacac ctcctccttc ctgggcatcc   10380
acttataatt tgcaattaga tagtaacttc attgactata gctttaatgt gtctacttct   10440
tcttccatac tgcaagctgc ctgagatcag gggtggtgtc tccctagttc ccccgggaat   10500 atccagggc tggcacaggg gagctgttcc ataaggcagc gggcactgga gtcagagaaa   10560
cctggacgtg aatcctggcc tgaccgctac ttagatgtgc gggtttgggg tatttactca   10620
gccttcattt ctccatctga tcatggagac aatagtgtct ccccagtgga ttgtggtgag   10680
gattttatga gtctggattg tggtgaggat tttatgagtc tggcagtgaa ttaccaagag   10740
ctagatgtta ttgttctcaa atatttgctg aatgagtgaa tgaatgaatg agtgaatgaa   10800
tgagggccca gctgacettt gtggaatgag taggtgaaac aggaaatact caatttccag   10860
atcctcttgt gcatcctcct tgctctcgct tagcccccat gacccctaatt tgacccccatt   10920 tctcccctgc attcagggtc accagcatga atgctcggca ggcagctccc aagaccaccc   10980 gccccaggt gcagccacct acaccccggg gaagggggaa gagcaggagc tccactatgc   11040
ctccctcagc ttcagggcc tgaggctctg ggagcctgcg gaccaggagg cccccagcac   11100
caccgagtac tcggagatca agatccacac aggacagccc ctgaggggcc caggctttgg   11160
gcttcaattg gagagggaga tgtcagggat ggttccaaag tgaagaggtc tccatggcaa   11220
caggacacca gcaagtgtgt gggagtcgca ctggtgtgac ggccagaact ggactcagat   11280
ttcagcccca tccccaatga agagcttgag tttgaagatt atacttttttt tgagacaggg   11340 tctgactctg tcctccaggc cagagtccag tggtgcaatc tcagctcact gtagcctcaa   11400
cctgccaggt tgaagtgagc ctcccatttc agcctcccaa gtagctggga ctacaattgt   11460
gagccaccat gccaggctca ttgttatatt tttagtagag acagggtttt gccatgtttc   11520
cctggctggt ctcagactcc tgggctcaag caatctgccc gcctctgcct cccaaagtgc   11580
tgggattaca gacgtgagcc accacagctg gctgaagatt atactttcaa ttcagagcga   11640
gtttgaagat gacactttga ggcatcgtgt ctatggttca ttactacaga agcttctctg   11700
gatgtgtaaa gcacaggaaa ccaggcagag gaggcacagg gtgctctcca gaacgagaag   11760
ccagctcctg gagttgtttg ctgcaactgc cattccccgt tgatgaccat gctcttcctt   11820
cagaagaggg agagtgagag gaccaagtcc aagtggttcc catttgaaca tttaaaaaaa   11880
aaaaaaaggc tgggcatggt ggctcacgcc tgtaatctca cactttggg aggctgaagt   11940 gggtggatca caagtcagga gttcaagacc agcctgggca agatggtgaa accccatctc   12000
tactaaaaat acaaaaatta gccgggcatg gtggcgggcg cctaaaatcc cagctactcg   12060
ggagactagg cagagaattg gttgaacccg ggaggtggag gttgcagtga gccgagatcg   12120
tcccactgca ctccagcctg ggcaacagag tgagactctg tttctaaata aataaatgaa   12180
```

<210> SEQ ID NO 20
<211> LENGTH: 4327
<212> TYPE: DNA

<213> ORGANISM: Homo sapiens

<400> SEQUENCE: 20

```
actcaccctc cggcttcctg tcggggcttt ctcagcccca ccccacgttt ggacatttgg      60
agcatttcct tccctgacag ccggacctgg gactgggctg gggccctggc ggatggagac     120
atgctgcccc tgctgctgct gccctgctg tggggggtg agtgagctga gggaggaggg      180
acaggcacag gggtgagaag gggggctgga gctgcagctg agcttctgtg tcccccagg     240
gtccctgcag gagaagccag tgtacgagct gcaagtgcag aagtcggtga cggtgcagga    300
gggcctgtgc gtccttgtgc cctgctcctt ctcttacccc tggagatcct ggtattcctc    360
tcccccactc tacgtctact ggttccggga cggggagatc ccatactacg ctgaggttgt    420
ggccacaaac aacccagaca gaagagtgaa gccagagacc cagggccgat tccgcctcct    480
tggggatgtc cagaagaaga actgctccct gagcatcgga gatgccagaa tggaggacac    540
gggaagctat ttcttccgcg tggagagagg aagggatgta aaatatagct accaacagaa    600
taagctgaac ttggaggtga caggtatggc aggaaccccta ggagaggacc ctgggacgtg    660
gagaccccccg tatgagaaca gggacaggag ttgggcaggg gcggctggag gaggtgtagg   720
acttggggca ggtcggggcc tgaggcctgg ccactctcgg ggtcacacct tacgtcctca    780
agccctgggg gccaggtat ctccctgtct cctcctcagc cctgatagag aaacccgaca     840
tccactttct ggagcctctg gagtccggcc gcccacaag gctgagctgc agccttccag      900
gatcctgtga gcgggacca cctctcacat tcctggac ggggaatgcc ctcagccccc        960
tggaccccga ccacccgc tcctcggagc tcaccctcac ccccaggccc gaggaccatg     1020
gcaccaacct cacctgtcag gtgaaacgcc aaggagctca ggtgaccacg gagagaactg    1080
tccagctcaa tgtctcctgt gagtggtgct ggggacacag ctgagtcccc aagggcagtg    1140
ggagtgaggg gggtgtgtgt gtgtgtgtgt gtgtgtgtgt agaagagaga gagagaaaga    1200
gaatgataac cagggaaaac tcgtgtgtgg gcaggaagga cagcggtccc cacctggtgg    1260
gtttctgtgg cccctccttg ggtccctccc gggaccacgc ccatccctct tgtcacctct    1320
gaagctggtg ctgtatcttt ctatcccaga tgctccacag aacctcgcca tcagcatctt    1380
cttcagaaat ggcacaggca caggtaggaa agaccctctt ccctctgggg ctgtgatggg    1440
agccttctat tagctcaggg ttcagcattg ggagaggaga ccctccctca ccctcagcc     1500
cctgggtctg ggtccttcct gctcccaacc ccccaatccc agtcactaag atcttgcacg    1560
aacagaccta gtatttcttt tggcttctcc ctttttctctg ctctctttttt cagatttatt  1620
ttttcattgt gagaaaatac acatagcaca aaatttgtca tcttagccat tttaaagagt    1680
acagttcagc agtgttaaat gtgttcacat tgttgcaaaa ccaaactgca gagctccttt    1740
tatctggcaa aactgaaact ttgtacccac tgaacagcga cttttccactt ccccctcctg   1800
ccaccgagca gtcaccattc tacttttctg tctctgtgag tttgagtact caggacacgc    1860
tgttcccttt tcttgaattt ctgcctgctc cgatgtcctc tgatgcatgc cctgcttcat    1920
ctctaactga tcgtccttttt tgggagcctt cgactttccc acctcccaca gctctgtccc   1980
agaacccagt tcttcccctc cacattcctg agtaatccga tctctccttg acctgtcct    2040
gatgcctccc acaactttat atccagccct ttctctgagg cacagatctg cacatttagc   2100
cacctccctc ggatgcttct cggctcctcc ttccctgttg atcccagggc tgttctggac   2160
atcgctgtag acagcaccct ttctcatcag ctgtttcatg agtccgcaag tcttaacacc   2220
tttacttcac caatcatcac ttccctcctc atccccttgg ttccaggccc agctcaagtc   2280
```

```
tcgtgctcaa ccctggccca ttgccccagc ctcctcccag cctccctgcc tcctatccca    2340
cttctctcca gtccgggacc tacttggctc cagcaggatc tttctagatc cagtgctaac    2400
tctgtttccc ttgcttatag cccctcttg cttccagga taaagcccaa ggccctcaat     2460
ctggcaccca atgctccaaa agatctgagc ctgcttctac ctccattatc gtgtcttggg    2520
agctctgggt cctccctgac aggttgcgga tctaggagcc tctttcctcg tctgcctgtc    2580
tcagttcttg gcacgtctgc acctgagctg cccatccact tctccttaat gtgagaactc    2640
ctcctcatct gtcttttctc agctcagcca ccttctttct ggtagcctga cctgatcacc    2700
aagtcctcat cctttcaccc atgactagcc cattctcagc actcaccaca cagtcttgtc    2760
tttcttcttg cagctcagtg ggaggaatga gggagaattg ggcctcccag ctccactcac    2820
ctggctgtgc ttctctttcc cagccctgcg gatcctgagc aatggcatgt cggtgcccat    2880
ccaggagggc cagtccctgt cctcgcctg cacagttgac agcaacccc ctgcctcact      2940 gagctggttc cggagggaa aagccctcaa tccttcccag acctcaatgt ctgggaccct     3000
ggagctgcct aacataggag ctagagaggg agggaattc acctgccggg ttcagcatcc     3060
gctgggctcc cagcacctgt ccttcatcct ttctgtgcag agtgagttgc aggacaggtg    3120
ctgagggtag acagcccggt gaggtattca ggttggtggg agggactgag gcctggtaac    3180
agcaccttac cttctccttt ctcccaggaa gctcctcttc ctgcatatgt gtaactgaga    3240
aacagcaggg ctcctggccc ctcgtcctca ccctgatcag gggggctctc atgggggctg    3300
gcttcctcct cacctatggc ctcacctgga tctactatac caggtgagcc ggactgcctg    3360
tctccaggaa gctcctgagt tccaggtggg gctgagctgt cctgccccag acagctcag    3420 ccccacctgg aattagaact gaagtggctg gtgctgatct gaggcccatg ttggctctgc    3480
aggtgtggag gcccccagca gagcagggct gagaggcctg gctgagcccc tcccgctcaa    3540
gacagaactg aggtgtggac acttagcct gtgggacaca tgcaggacat cactgtcagc     3600
ttctttctgg aagctcacat cccactgact accctcttt tccttcctgc cccatacccc     3660
ttctacttat tcccctctgc ttgtgagtct tgccccacca cctgcatc ccatctgca       3720 ccccatcccc tctccacctg cccttctctt ccctctccat ccaccatctc cagccctgtg    3780
aagggaatgt actttcggtc ttataccccc attaccatt acccaaaagt tacctttttt     3840 ttttttttt ttttttgaga cagagtctca ctctgttgca caggctggag ttcagtggca    3900
caatctccgt tcactgcaac ctccacctct ggggttcaag caattctcct gcctcagcct    3960
ccctagtagc tgggattaca ggtgcctgcc accacatcca gttaatttt ttttttgta     4020 tgttagtaga gatggggttt taccatgttg gccaggtctc gaactcctga cctcaagcaa    4080
tccactgcat tggcctccca aagtgctggc attacaggta tgagccaccg tgcctggctg    4140
ccaaaagtta ccttcttaac acttgaattt ctggtctcct cagcttccct atccatatag    4200
gcacagagag gcagcatttg ttttccagtt aaaactctac ctcattgtga ttattatcca    4260
atacaattgt tacaaaataa gtaaaacttt tatgaaacaa tacaacataa ctgattttac    4320
tctttaa                                                              4327
```

<210> SEQ ID NO 21
<211> LENGTH: 3932
<212> TYPE: DNA
<213> ORGANISM: Homo sapiens

<400> SEQUENCE: 21

-continued

| | |
|---|---|
| actgcccctc caccaggctt cctgctggag gagtttcctt cccagccagg ccggcccaga | 60 |
| agccagatgg tcccgggaca ggcccagccc cagagcccag agatgctgct gctgcccctg | 120 |
| ctgctgcccg tgctgggggc gggtgagtgg gtcggtggct gggggtccca ggcagggggct | 180 |
| ggggctgccg ctgagcctct gcatctcccc agggtccctg aacaaggatc ccagttacag | 240 |
| tcttcaagtg cagaggcagg tgccggtgcc ggagggcctg tgtgtcatcg tgtcttgcaa | 300 |
| cctctcctac ccccgggatg gctgggacga gtctactgct gcttatggct actggttcaa | 360 |
| aggatggacc agcccaaaga cgggtgctcc tgtggccact aacaaccaga gtcgagaggt | 420 |
| ggaaatgagc acccgggacc gattccagct cactggggat cccggcaaag ggagctgctc | 480 |
| cttggtgatc agagacgcgc agagggagga tgaggcatgg tacttctttc gggtggagag | 540 |
| aggaagccgt gtgagacata gtttcgtgaa caatttgttc taaaagtaac aggtatggaa | 600 |
| tggggtggga acccctgcct gtcacactgg ggagggaccc tggggacagg ctatgggctg | 660 |
| agcagagagg gctttcaggg acccctgcag cacaagaatt ccccacccg gtctctgccc | 720 |
| cagcccctgac tcagaagcct gatgtctaca tccccgagac cctggagccc gggcagccgg | 780 |
| tgacggtcat ctgtgtgttt aactgggctt tcaagaaatg tccagcccct tctttctcct | 840 |
| ggacggggc tgccctctcc cctagaagaa ccagaccaag cacctcccac ttctcagtgc | 900 |
| tcagcttcac gcccagcccc caggaccacg acaccgacct cacctgccat gtggacttct | 960 |
| ccagaaaggg tgtgagcgca cagaggaccg tccgactccg tgtggcctgt gagtgtggcc | 1020 |
| tgggagggtg gggcgtgcag acagccccgg tgggtgggga ggtggaggag cccagcagga | 1080 |
| cagtgagtgg ctcccagctc aggagcatcc agggagagga agctgtgggg tcccaggatg | 1140 |
| ccggctcagc cctgggaggg ggatgggaat ggcgtctgat cctctgtcca catgtgtgag | 1200 |
| ccctggagct ggttgtcact tgtccatcct gggatgttcc cactttcttt tccctgaggg | 1260 |
| agttttttcc aggtgtgagg aacaaattgt ccctccctga agccagctca caatcttgtt | 1320 |
| gcagatgccc ccaaagacct tattatcagc atttcacatg acaacacgtc aggtactgag | 1380 |
| ggccttcggg ctggggctgg gccagtcctc tttagggatg aaaaggcttc aggggggtga | 1440 |
| ggggatgtgt tcctctttgc agcccccct cccacccatt ctctctctcc acccccaccc | 1500 |
| tctctctttc cctgtcttca gccctggaac tccagggaaa cgtcatatat ctggaagttc | 1560 |
| agaaaggcca gttcctgcgg ctcctctgtg ctgctgacag ccagccccct gccacgctga | 1620 |
| gctgggtcct gcaggacaga gtcctctcct cgtcccaccc ctggggcccc agaaccctgg | 1680 |
| ggctggagct gcgtggggta agggccgggg attcagggcg ctacacctgc cgagcggaga | 1740 |
| acaggcttgg ctcccagcag cgagccctgg acctctctgt gcagtgtgag tgtgcctagc | 1800 |
| aggggcctgg agtccattgg gagggcagag ggatacaggg gctgggctca gtgtcccaga | 1860 |
| gctgaggggg tcttgaaccc caggcctcgg ggactgacct tcttacctgt gtagaccctc | 1920 |
| atgcagtttg tgtctgggac tcagtgggtg attctgccct gcccttctat cccacccact | 1980 |
| tcccccacct cagtctccag gacgcttccc tttgcccaga gggaagtccc tggtccgtct | 2040 |
| agagccggtc cctgtctcc atttcagatc ctccagagaa cctgagagtg atggtttccc | 2100 |
| aagcaaacag gacaggtagg aaaggagaca gaggagccag ggcctctcag tgccaaattg | 2160 |
| ggggcccagg tgtctggagg gtccccatgc aggcgggtcc ctgagccctg agctgcacgt | 2220 |
| cgattctgcc tcttccttcc ctagtcctgg aaaacctgag gaacggcaca tccctccggg | 2280 |
| tcctggaggg ccaaagcctg cgtctggtct gtgtcacaca cagcagcccc ccagccaggc | 2340 |
| tgagctggac ccggtgggga cagaccgtgg gcccctccca gccctcagac cctggggtcc | 2400 |

-continued

```
tggagctgcc tcgggttcaa atggagcacg aaggagagtt cacctgccac gctcggcacc    2460
cgctgggctc ccagcgcgtc tctctcagct tctccgtgca ctgtgagtgg ggaaagggga    2520
cacctgggtc ccaggaaggg gcccctgctg agtcctgtcc tccctcccac agagccccc    2580 cagctgctgg gaccctcctg ctcctgggag gctgagggtc tgcactgcag ctgctcctcc    2640
caaggcagcc cggccccgtc tctgccctgg tggattggtg gggagctgcg agggaaaca    2700 gcagccagga ctacttcaag gtcaccccca gctcagccgg gccctgggcc aacagctccc    2760
tgatcctcca agggggggct tggctccaac ctcaggctca cctttgaggc ccagaacgtc    2820 catgggccc agagctctct gattcctggc ggacagtcag ggtataggt ggggaggcct    2880 gggctcacca ggtcctgcat ccagggatgt aggaagggcc tggagaacca agttgcaata    2940
agagaggaag gattcggaag tgtggtttag aaggtgaatg ggccttatcc cactttcca    3000 ggcaaatcag ggcccatgac gggggtggtt ctggtggctg ttggggaggt ggctatgaag    3060
atcctgcttc tctgcctctg cctcatcctc tcaggtgag ccctgcccca gggaccaagg    3120
ggaggggcgg agagggcaaa ggatacaccg ctgaatccca gaatctcaat cctgggggta    3180
cttggacagt taaagaggcc tgtggccagg cagaggctga gttgatcgtg atgattccac    3240
acgggccagt gttgtcagtc cccaactctg gaccaatgtc caggctgggg aggttcctgc    3300
ttgtatcagg gaggtcctgg gggctaggcc tgctctctct gcctcagtcc cctccaaccc    3360
cttagcaggg cacaggagg tgagtctgct gccctcttca cccccatcca gccacactca    3420
caggccctgg tctcttcacc cagagtgagg tcttgcagga ggaaggcagc aagggcagca    3480
ttgggcatgg aggctgcaga cgctgtcacg gactaatctc caggtgagtg tcgtgggcct    3540
cttaccctcc aacatcccgc tggacacctc ccctcgatg gccccaagga ctgctccact    3600
caacttggcc ataactgact catcacctcc ctttccaagc ccacttctct tgttgagagc    3660
cccatccctc tgatgacatg gtagcccat ctctaacgtc agaacccggg tgtgggtgtc    3720
caccttgacc tccctccctc ctccagatcc caaaaatcac tagcacttgt ccctcctcct    3780
aagtacaggt cacctggag cccttttctc catcctggcc ccggtcatgc ctgggcctca    3840
cctcttccct ggtcgctgaa cccacctcac ctcttgcctc catctctccc aacagactcc    3900
agactgcttc cagatgcctc ctcatccagt tc    3932
```

```
<210> SEQ ID NO 22
<211> LENGTH: 19
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 1
<223> OTHER INFORMATION: Xaa = Asp or Glu
<220> FEATURE:
<221> NAME/KEY: VARIANT
<222> LOCATION: 2, 3
<223> OTHER INFORMATION: Xaa = Any Amino Acid and up to 2 of them can be
      present or absent
<220> FEATURE:
<221> NAME/KEY: VARIANT
<222> LOCATION: 5, 6
<223> OTHER INFORMATION: Xaa = Any Amino Acid
<220> FEATURE:
<221> NAME/KEY: VARIANT
<222> LOCATION: 7
<223> OTHER INFORMATION: Xaa = Leu or Ile
<220> FEATURE:
<221> NAME/KEY: VARIANT
```

-continued

```
<222> LOCATION: 8, 9, 10, 11, 12, 13, 14, 15
<223> OTHER INFORMATION: Xaa = Any Amino Acid and up to 2 of them can be
      present or absent
<220> FEATURE:
<221> NAME/KEY: VARIANT
<222> LOCATION: 17, 18
<223> OTHER INFORMATION: Xaa = Any Amino Acid
<220> FEATURE:
<221> NAME/KEY: VARIANT
<222> LOCATION: 19
<223> OTHER INFORMATION: Xaa = Leu or Ile

<400> SEQUENCE: 22

Xaa Xaa Xaa Tyr Xaa Xaa Xaa Xaa Xaa Xaa Xaa Xaa Xaa Xaa Tyr
1               5                   10                  15

Xaa Xaa Xaa
```